(12) United States Patent
Qi

(10) Patent No.: US 12,325,681 B2
(45) Date of Patent: Jun. 10, 2025

(54) INHIBITORS OF NITRIC OXIDE SYNTHASES (NOS), PHARMACEUTICAL PRODUCTS THEREOF, AND METHODS THEREOF

(71) Applicant: Gacter Inc., Lewes, DE (US)

(72) Inventor: Wenxin Qi, Lewes, DE (US)

(73) Assignee: Gacter Inc., Middletown, DE (US)

( * ) Notice: Subject to any disclaimer, the term of this patent is extended or adjusted under 35 U.S.C. 154(b) by 0 days.

(21) Appl. No.: 18/182,234

(22) Filed: Mar. 10, 2023

(65) Prior Publication Data

US 2023/0286913 A1  Sep. 14, 2023

Related U.S. Application Data

(60) Provisional application No. 63/362,528, filed on Apr. 6, 2022, provisional application No. 63/362,527, filed
(Continued)

(51) Int. Cl.

| | | |
|---|---|---|
| *C07C 335/04* | (2006.01) | |
| *C07C 211/10* | (2006.01) | |
| *C07C 255/34* | (2006.01) | |
| *C07D 209/34* | (2006.01) | |
| *C07D 209/44* | (2006.01) | |
| *C07D 211/54* | (2006.01) | |
| *C07D 213/643* | (2006.01) | |
| *C07D 231/12* | (2006.01) | |
| *C07D 231/56* | (2006.01) | |
| *C07D 235/08* | (2006.01) | |
| *C07D 237/18* | (2006.01) | |
| *C07D 239/38* | (2006.01) | |
| *C07D 241/18* | (2006.01) | |
| *C07D 249/12* | (2006.01) | |
| *C07D 249/18* | (2006.01) | |
| *C07D 251/38* | (2006.01) | |
| *C07D 257/04* | (2006.01) | |
| *C07D 271/06* | (2006.01) | |

(Continued)

(52) U.S. Cl.
CPC .......... *C07C 335/04* (2013.01); *C07C 211/10* (2013.01); *C07C 255/34* (2013.01); *C07D 209/34* (2013.01); *C07D 209/44* (2013.01); *C07D 211/54* (2013.01); *C07D 213/643* (2013.01); *C07D 231/12* (2013.01); *C07D 231/56* (2013.01); *C07D 235/08* (2013.01); *C07D 237/18* (2013.01); *C07D 239/38* (2013.01); *C07D 241/18* (2013.01); *C07D 249/12* (2013.01); *C07D 249/18* (2013.01); *C07D 251/38* (2013.01); *C07D 257/04* (2013.01); *C07D 271/06* (2013.01); *C07D 277/36* (2013.01); *C07D 307/81* (2013.01); *C07D 311/60* (2013.01); *C07D 313/00* (2013.01); *C07D 313/08* (2013.01); *C07D 313/14* (2013.01); *C07D 313/20* (2013.01); *C07D 401/06* (2013.01); *C07D 401/12* (2013.01); *C07D 403/12* (2013.01); *C07D 471/04* (2013.01); *C07D 473/00* (2013.01); *C07D 473/36* (2013.01)

(58) Field of Classification Search
CPC ... C07C 335/04; C07C 211/10; C07D 209/34; C07D 209/44; C07D 211/54; C07D 213/643; C07D 231/12; C07D 231/56; C07D 235/08; C07D 237/18; C07D 239/38; C07D 241/18; C07D 249/12; C07D 249/18; C07D 251/38; C07D 257/04; C07D 271/06; C07D 277/36; C07D 307/81; C07D 311/60; C07D 313/00; C07D 313/08; C07D 313/14; C07D 313/20; C07D 401/06; C07D 401/12; C07D 403/12; C07D 471/04; C07D 473/00; C07D 473/36
See application file for complete search history.

(56) References Cited

U.S. PATENT DOCUMENTS 5,409,780 A * 4/1995 Schrier .............. G01N 33/0039
428/411.1

OTHER PUBLICATIONS

Wegener et al. Pharmaceuticals 2010, 3, 273-299; doi:10.3390/ph3010273). (Year: 2010).*
(Continued)

*Primary Examiner* — Clinton A Brooks
*Assistant Examiner* — Jerica Katlynn Wilson
(74) *Attorney, Agent, or Firm* — George Guosheng Wang; Upstream Research and Patent LLC

(57) ABSTRACT

The present invention provides NOS inhibitors such as iNOS inhibitors, or a pharmaceutically acceptable salt, ester, prodrug, complex, solvate, hydrate, or isomer thereof, in any crystalline form or in amorphous form. The inhibitors include 1,1 or 1,2 substituted-ethyl carbamimido thioates, cyclic compounds substituted with a carbamimidoyl sulfanylethylphenyl group and a carbamimidoylsulfanyl group, compounds substituted with a carbamimidoyl sulfanylethyl phenylmethyl group, bis-carbamimidoylsulfanylethyl substituted compounds, 2-propoxypyridine derivatives, alkylamine or heteroalkylamine derivatives, n-aminoethyl n-phenyl amine derivatives, and saturated heterocyclic fused benzene derivatives. Pharmaceutical products comprising the NOS inhibitors such as iNOS inhibitors and the applications thereof in prophylaxis and/or treatment of inflammatory diseases, and proliferative diseases such as cancer including gastro-intestinal, colorectal, gynecological, pancreatic, head and neck, esophageal, breast, lung, and central nervous system tumors, among others, are also provided.

19 Claims, 22 Drawing Sheets

Related U.S. Application Data on Apr. 6, 2022, provisional application No. 63/362,526, filed on Apr. 6, 2022, provisional application No. 63/362,529, filed on Apr. 6, 2022, provisional application No. 63/269,171, filed on Mar. 10, 2022, provisional application No. 63/269,174, filed on Mar. 10, 2022, provisional application No. 63/269,173, filed on Mar. 10, 2022, provisional application No. 63/269,170, filed on Mar. 10, 2022.

(51) Int. Cl.

| | | |
|---|---|---|
| *C07D 277/36* | (2006.01) | |
| *C07D 307/81* | (2006.01) | |
| *C07D 311/60* | (2006.01) | |
| *C07D 313/00* | (2006.01) | |
| *C07D 313/08* | (2006.01) | |
| *C07D 313/14* | (2006.01) | |
| *C07D 313/20* | (2006.01) | |
| *C07D 401/06* | (2006.01) | |
| *C07D 401/12* | (2006.01) | |
| *C07D 403/12* | (2006.01) | |
| *C07D 471/04* | (2006.01) | |
| *C07D 473/00* | (2006.01) | |
| *C07D 473/36* | (2006.01) | |

(56) References Cited

OTHER PUBLICATIONS

Horig et al. Journal of Translational Medicine 2004, 2(44) (Year: 2004).*
Schafer et al. Drug Discovery Today 2008, 13 (21/22), 913-916 (Year: 2008).*
Brooks. Curr Top Med Chem. 2011;11(7):760-70 (Year: 2011).*
Yirik et al. (J Cheminform. 2021; 13: 48) (Year: 2021).*
Napoli et al. JACC vol. 62, No. 2, 2013. 89-95 (Year: 2013).*

* cited by examiner

INHIBITORS OF NITRIC OXIDE SYNTHASES (NOS), PHARMACEUTICAL PRODUCTS THEREOF, AND METHODS THEREOF

CROSS-REFERENCE TO RELATED APPLICATIONS

This application expressly claims the benefit under 35 U.S.C. Section 119(e) and Article 4 of the Stockholm Act of the Paris Convention for the Protection of Industrial Property of U.S. Provisional Patent Application Nos. (A) 63/269,170 filed on Mar. 10, 2022, entitled "1,1 or 1,2 Substituted-Ethyl Carbamimidothioates, Pharmaceutical Compositions Comprising the Same, Preparation Thereof, and Their Use in Inhibiting Nitric Oxide Synthases"; (B) 63269171 filed on Mar. 10, 2022, entitled "Cyclic Compounds Substituted with a Carbamimidoyl sulfanylethyl phenyl Group and a Carbamimidoylsulfanyl Group, Pharmaceutical Composition Comprising the Same, Preparation Thereof, and Their Use in Inhibiting Nitric Oxide Synthases"; (C) 63269173 filed on Mar. 10, 2022, entitled "Compounds Substituted with a Carbamimidoyl sulfanylethyl phenylmethyl Group, Pharmaceutical Composition Comprising the Same, Preparation Thereof, and Their Use in Inhibiting Nitric Oxide Synthases"; (D) 63269174 filed on Mar. 10, 2022, entitled "Bis-carbamimidoylsulfanylethyl Substituted Compounds, Pharmaceutical Composition Comprising the Same, Preparation Thereof, and Their Use in Inhibiting Nitric Oxide Synthases"; (E) 63362526 filed on Apr. 6, 2022, entitled "2-Propoxypyridine Derivatives, Pharmaceutical Composition Comprising the Same, Preparation Thereof, and Their Use in Inhibiting Nitric Oxide Synthases"; (F) 63362527 filed on Apr. 6, 2022, entitled "Alkylamine or Heteroalkyl amine Derivatives, Pharmaceutical Composition Comprising the Same, Preparation Thereof, and Their Use in Inhibiting Nitric Oxide Synthases"; (G) 63362528 filed on Apr. 6, 2022, entitled "N-aminoethyl N-phenyl Amine Derivatives, Pharmaceutical Composition Comprising the Same, Preparation Thereof, and Their Use in Inhibiting Nitric Oxide Synthases"; and (H) 63362529 filed on Apr. 6, 2022, entitled "Saturated Heterocyclic Fused Benzene Derivatives, Pharmaceutical Composition Comprising the Same, Preparation Thereof, and Their Use in Inhibiting Nitric Oxide Synthases"; the entire disclosures of which are hereby incorporated by reference.

FIELD OF THE INVENTION

The present invention generally relates to inhibitors of nitric oxide synthases (NOS), pharmaceutical products thereof, productions thereof, and applications thereof. Although the invention will be illustrated, explained and exemplified by the application of a class of compounds in the prophylaxis and/or treatment of inflammatory diseases, and/or proliferative diseases, such as cancer, it should be appreciated that the present invention can also include applications of the compounds and derivatives thereof in prophylaxis and/or treatment of a broader range of disorders or diseases related to or mediated by the NOS, or associated with aberrant NOS activity.

BACKGROUND OF THE INVENTION

Nitric oxide (NO) is a small endogenous biological mediator. It exhibits a wide range of physiological and pathophysiological potentials. NO can undergo numerous reactions such as the formation of biologically reactive nitrogen oxide species, which may be carcinogenic through chemically altering DNA and enhancing the genotoxicity of other substances. The chemical reactions of NO can be divided into two categories, direct and indirect. Direct chemical reactions are those in which NO reacts with biological targets without any further modifications. The indirect effects of NO are associated with pathophysiological conditions, and thus, are responsible for the etiology of many diseases including cancer. Indirect chemical reactions are nitrosation and oxidation reactions that may result in nitrosative stress and oxidative stress, therefore, produces genotoxic effects.

NO is synthesized from L-arginine by a family of nitric oxide synthases (NOS), which have three isoforms: nNOS, eNOS, and iNOS. NOS have been classified into two categories, constitutive (nNOS and eNOS) and inducible (iNOS). These 3 NOS isozymes are involved in specific physiological functions in various cell types. Neuronal NOS (nNOS) controls neuronal signal transmission. Endothelial NOS (eNOS) is involved with blood vessel dilation. Inducible NOS (iNOS) is involved in immune response, such as cytotoxicity, pathogens and tumors. nNOS and eNOS are calcium- and calmodulin-dependent and produce only a low level of NO. iNOS is calcium- and calmodulin-independent and generates a high concentration of NO. iNOS is usually absent in resting cells, however, after stimulation by cytokines and bacterial cell wall products such as the interleukins, tumor necrosis factor alpha (TNFα) and endotoxin lipopolysaccharide (LPS), iNOS can be upregulated and generates a high concentration of NO.

Numerous experimental and clinical reports indicate that iNOS is associated with chronic inflammatory diseases as well as cancer, including gastro-intestinal, colorectal, gynecological, pancreatic, head and neck, esophageal, breast, lung, and central nervous system tumors. Therefore, the selective inhibitor of iNOS could have anti-inflammatory and anti-cancer potential.

WO/1994/012165 discloses isothiourea derivatives and their use in medicine, particularly in the treatment of conditions where there is an advantage in inhibiting inducible nitric oxide synthase. For example, S,S'-1,4-phenylene-bis (1,2-ethanediyl)bis-isothiourea (PBIT) inhibits production of NO from NOS by binding at the site of the natural substrate L-arginine. However, PBIT does not exhibit necessary selectivity as compared to its inhibition on iNOS to eNOS. This selectivity factor is a very important consideration. eNOS activity must be kept intact because of its role in maintaining normal blood pressure and flow. In addition, it was reported that it is acutely toxic in mice and rats at doses as low as 10 mg/kg.

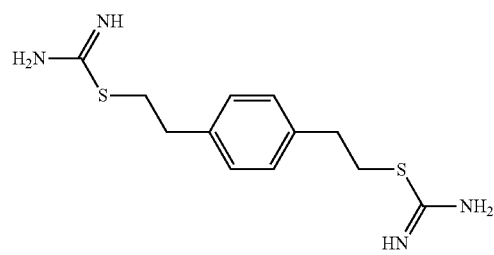

PBIT

WO/2001/062704 by AstraZeneca (AZ) discloses some phenylheteroalkylamine derivatives for the treatment or prophylaxis of diseases or conditions in which inhibition of inducible nitric oxide synthase activity is beneficial. AZ compound 6b below is an example of the iNOS inhibitors in WO/2001/062704.

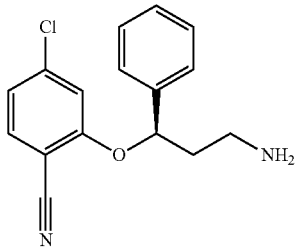

Structure of AZ

However, the state of the prior art is not satisfactory, and there remains a need to identify small molecules with novel structure that show higher potency, better selective inhibition of iNOS vs. eNOS and nNOS, less toxicity, and enhanced overall anti-inflammatory and anti-cancer efficacies.

SUMMARY OF THE INVENTION

One aspect of the present invention provides a compound represented by anyone of Formula (I-1)~Formula (I-8) [collectively Formula (I)], or a pharmaceutically acceptable salt, ester, prodrug, complex, solvate, hydrate, or isomer thereof, in any crystalline form or in amorphous form. Formula (I) is a collection of the following Formulas:

(1) 1,1 or 1,2 substituted-ethyl carbamimidothioates of Formula (I-1) wherein R is any monovalent non-hydrogen group:

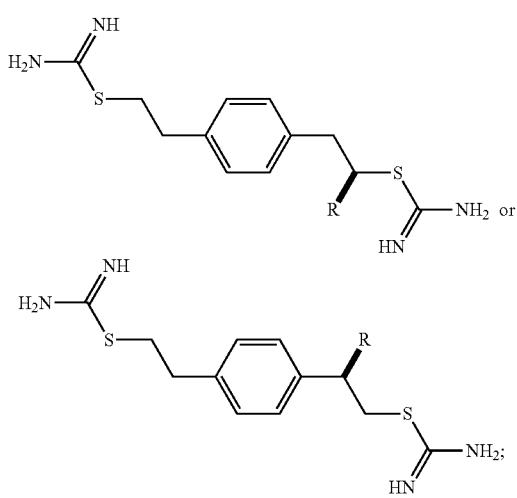

(2) cyclic compounds substituted with a carbamimidoylsulfanylethylphenyl group and a carbamimidoylsulfanyl group as represented by Formula (I-2) wherein R is any non-ethylene bivalent group:

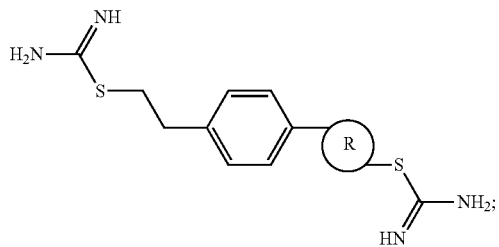

(3) compounds substituted with a carbamimidoylsulfanylethylphenylmethyl group as represented by Formula (I-3) wherein R is any monovalent non-hydrogen group except group of Formula (Ix) (i.e. carbamimidoylsulfanylmethyl):

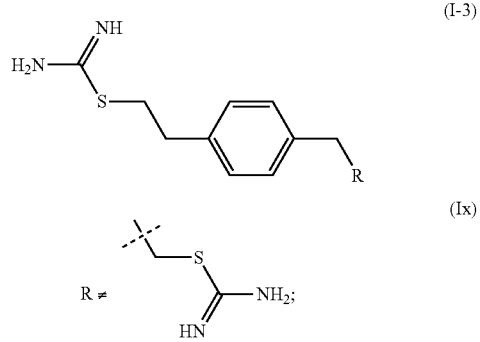

(4) bis-carbamimidoylsulfanylethyl substituted compounds as represented by Formula (I-4) wherein R is any bivalent group except Formula (Ix) group (i.e. 1,4-phenylene):

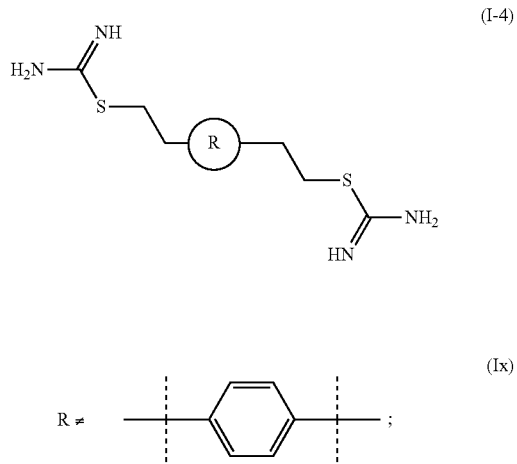

(5) 2-propoxypyridine derivatives as represented by Formula (I-5), wherein R1, R2, R3 and R4 are independent of each other any monovalent non-hydrogen group with a proviso that R1, R2, R3 and R4 are not amino, phenyl, chloro and cyano groups respectively at the same time:

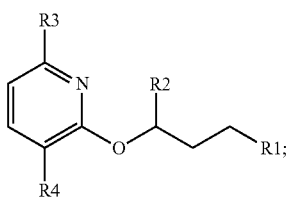

(I-5)

(6) alkylamine or heteroalkylamine derivatives as represented by Formula (I-6), wherein the waved line represents an alkyl chain or a heteroalkyl chain; R1, R3 and R4 are independent of each other any monovalent group including hydro and non-hydrogen group; and R2 is any bivalent group or two hydro groups, with a proviso that R1, R2, R3 and R4 are not hydro, two hydro groups, phenyl and 2-cyano-5-cholrophenoxy respectively at the same time:

(I-6)

(7) N-aminoethyl N-phenyl amine derivatives as represented by Formula (I-7), wherein R1 is a monovalent non-hydrogen group, and R2 is any monovalent non-hydrogen group:

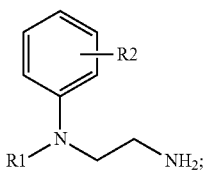

(I-7)

and (8) saturated heterocyclic fused benzene derivatives as represented by Formula (I-8), wherein R is a phenyl group or a fused benzene ring:

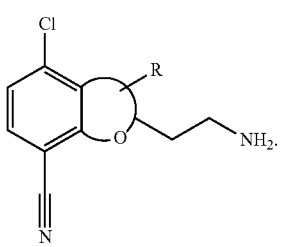

(I-8)

Another aspect of the invention provides pharmaceutical composition, a kit, or a packaged pharmaceutical product comprising a therapeutically effective amount of the compound of above Formula (I), or a pharmaceutically acceptable salt, ester, prodrug, complex, solvate, isomer, or hydrate thereof, in any crystalline form or in amorphous form, and a pharmaceutically acceptable carrier or excipient.

Still another aspect of the invention provides a method of inhibiting one or more members selected from the family of nitric oxide synthases (NOS) including three isoforms inducible NOS (iNOS), endothelial NOS (eNOS), and neuronal NOS (nNOS), comprising contacting the NOS with an effective amount of a compound of above Formula (I), or a pharmaceutically acceptable salt, ester, prodrug, complex, solvate, isomer, or hydrate thereof, in any crystalline form or in amorphous form.

A further aspect of the invention provides a method for prophylaxis and/or treatment of a disorder or disease mediated by one or more members in the family of nitric oxide synthases (NOS) such as iNOS or associated with aberrant NOS activity such as iNOS activity, comprising administering to a subject in need thereof a therapeutically effective amount of a compound of above Formula (I), or a pharmaceutically acceptable salt, ester, prodrug, complex, solvate, isomer, or hydrate thereof, in any crystalline form or in amorphous form; or a pharmaceutical composition thereof.

The above features and advantages and other features and advantages of the present invention are readily apparent from the following detailed description of the best modes for carrying out the invention when taken in connection with the accompanying drawings.

BRIEF DESCRIPTION OF THE SEVERAL VIEWS OF THE DRAWINGS

The present invention is illustrated by way of example, and not by way of limitation, in the figures of the accompanying drawings and in which like reference numerals refer to similar elements. All the figures are schematic and generally only show parts which are necessary in order to elucidate the invention. For simplicity and clarity of illustration, elements shown in the figures and discussed below have not necessarily been drawn to scale. Well-known structures and devices are shown in simplified form, omitted, or merely suggested, in order to avoid unnecessarily obscuring the present invention.

DETAILED DESCRIPTION OF THE PREFERRED EMBODIMENT

Figure 1:
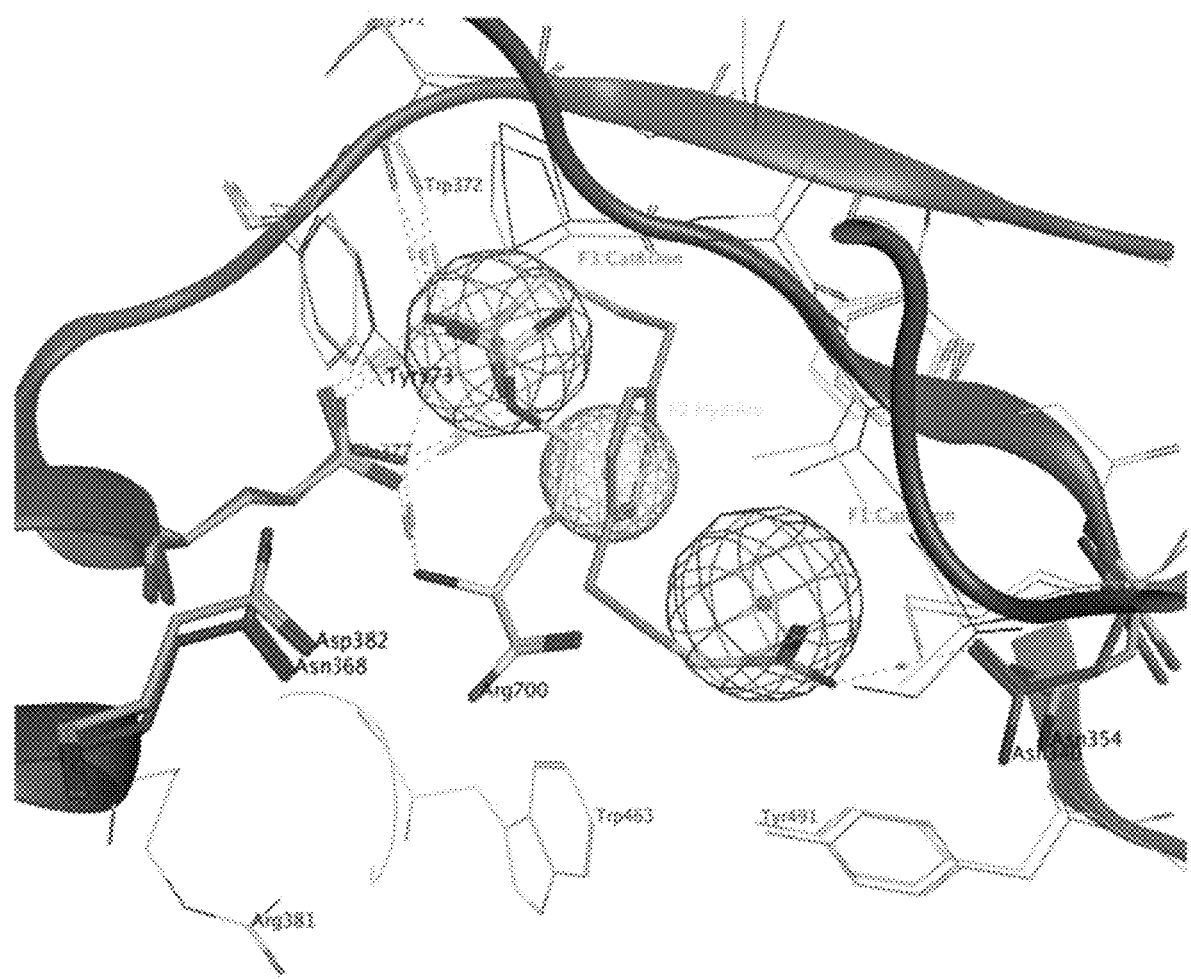
FIG. 1 shows alignment of PDB 1D1X bovine eNOS with PBIT bound against PDB 1NSI human iNOS with L-Arg.

In the following description, for the purposes of explanation, numerous specific details are set forth in order to provide a thorough understanding of the present invention. It is apparent, however, to one skilled in the art that the present invention may be practiced without these specific details or with an equivalent arrangement.

At various places in the present specification, substituents of compounds of the invention are disclosed in groups or in ranges. It is specifically intended that the invention include each and every individual sub-combination of the members of such groups and ranges. For example, the term "$C_{1-6}$ alkyl" is specifically intended to include $C_1$ alkyl (methyl), $C_2$ alkyl (ethyl), $C_3$ alkyl, $C_4$ alkyl, $C_5$ alkyl, and $C_6$ alkyl. Where a numerical range is disclosed herein, unless otherwise specified, such range is continuous, inclusive of both the minimum and maximum values of the range as well as every value between such minimum and maximum values. Still further, where a range refers to integers, only the integers from the minimum value to and including the maximum value of such range are included. In addition, where multiple ranges are provided to describe a feature or characteristic, such ranges can be combined.

The present invention provides a compound represented by Formula (I), or a pharmaceutically acceptable salt, ester, prodrug, complex, solvate, hydrate, or isomer thereof, in any crystalline form or in amorphous form. Formula (I) is a collection of the following Formulas:
(1) 1,1 or 1,2 substituted-ethyl carbamimidothioates of Formula (I-1) wherein R is any monovalent non-hydrogen group:

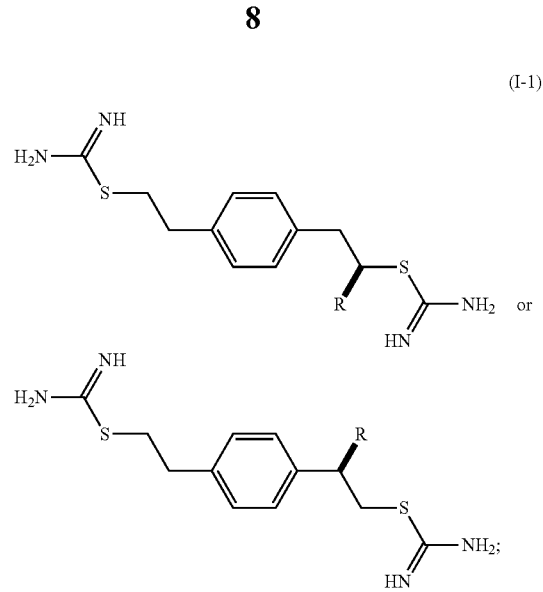

(2) cyclic compounds substituted with a carbamimidoylsulfanylethylphenyl group and a carbamimidoylsulfanyl group as represented by Formula (I-2) wherein R is any non-ethylene bivalent group:

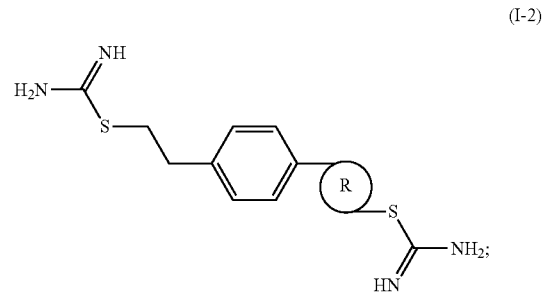

(3) compounds substituted with a carbamimidoylsulfanylethylphenylmethyl group as represented by Formula (I-3) wherein R is any monovalent non-hydrogen group except group of Formula (Ix) (i.e. carbamimidoylsulfanylmethyl):

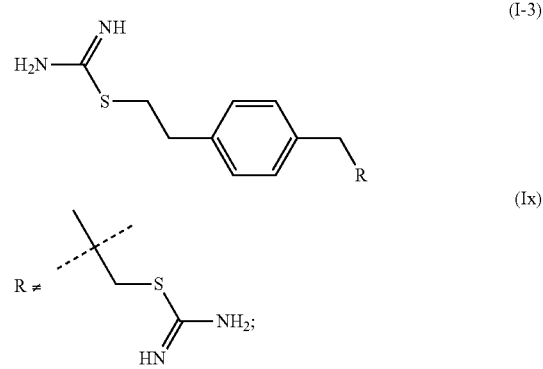

(4) bis-carbamimidoylsulfanylethyl substituted compounds as represented by Formula (I-4) wherein R is any bivalent group except Formula (Ix) group (i.e. 1,4-phenylene):

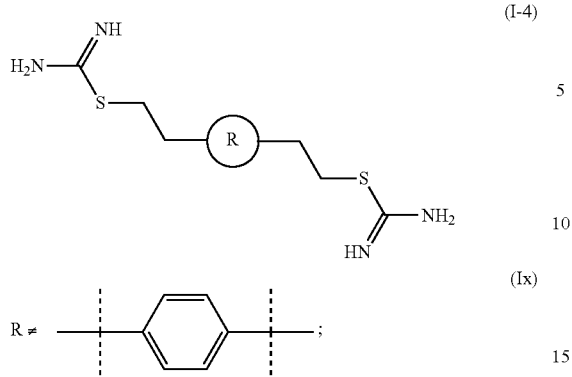

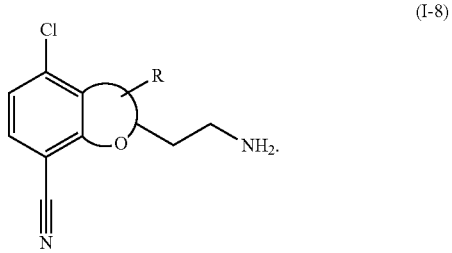

(5) 2-propoxypyridine derivatives as represented by Formula (I-5), wherein R1, R2, R3 and R4 are independent of each other any monovalent non-hydrogen group with a proviso that R1, R2, R3 and R4 are not amino, phenyl, chloro and cyano groups respectively at the same time:

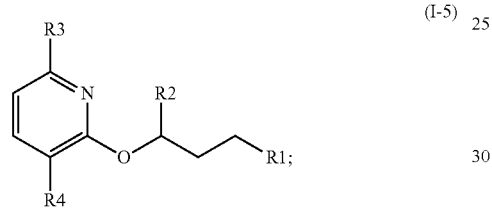

(6) alkylamine or heteroalkylamine derivatives as represented by Formula (I-6), wherein the waved line represents an alkyl chain or a heteroalkyl chain; R1, R3 and R4 are independent of each other any monovalent group including hydro and non-hydrogen group; and R2 is any bivalent group or two hydro groups, with a proviso that R1, R2, R3 and R4 are not hydro, two hydro groups, phenyl and 2-cyano-5-cholrophenoxy respectively at the same time:

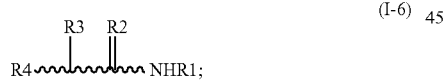

(7) N-aminoethyl N-phenyl amine derivatives as represented by Formula (I-7), wherein R1 is a monovalent non-hydrogen group, and R2 is any monovalent non-hydrogen group:

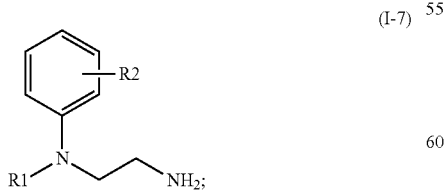

and (8) saturated heterocyclic fused benzene derivatives as represented by Formula (I-8), wherein R is a phenyl group or a fused benzene ring:

The term "monovalent non-hydrogen group", as used Formulas (I-1), (I-3), (I-5), (I-6) and (I-7), may include, but is not limited to, groups in the following 8 classes.

Class (1): Halo or halogen group, i.e. —F, —Cl, —Br or —I; —CN, —$NO_2$, —$N_3$, —$SO_2H$, —$SO_3H$, —OH, —OR, —$ONR_2$, —$NR_2$, —$NR_3^+X^-$, —N(OR)R, —SH, —SR, —SSR, —C(=O)R, —$CO_2H$, —CHO, —C(OR)$_2$, —$CO_2R$, —OC(=O)R, —$OCO_2R$, —C(=O)$NR_2$, —OC(=O)$NR_2$, —NRC(=O)R, —$NRCO_2R$, —NRC(=O)$NR_2$, —C(=NR)R, —C(=NR)OR, —OC(=NR)R, —OC(=NR)OR, —C(=NR)$NR_2$, —OC(=NR)$NR_2$, —NRC(=NR)$NR_2$, —C(=O)$NRSO_2R$, —$NRSO_2R$, —$SO_2NR_2$, —$SO_2R$, —$SO_2OR$, —$OSO_2R$, —S(=O)R, —OS(=O)R, —$SiR_3$, —$OSiR_3$, —C(=S)$NR_2$, —C(=O)SR, —C(=S)SR, —SC(=S)SR, —SC(=O)SR, —OC(=O)SR, —SC(=O)OR, —SC(=O)R, —P(=O)$_2$R, —OP(=O)$_2$R, —P(=O)$R_2$, —OP(=O)$R_2$, —OP(=O)(OR)$_2$, —P(=O)$NR_2$, —OP(=O)$_2NR_2$, —P(=O)(NR)$_2$, —OP(=O)(NR)$_2$, —NRP(=O)(OR)$_2$, —NRP(=O)(NR)$_2$, —$PR_2$, —$PR_3$, —$OPR_2$, —$OPR_3$, —$BR_2$, —B(OR)$_2$, —BR(OR), and the like. R is independently of each other any suitable group e.g. alkyl group. For example, —OR may be an alkoxy or alkyloxy group, i.e. an —O-alkyl group. The term $C_{1-6}$ alkoxy/alkyloxy is an —O—($C_{1-6}$ alkyl) group. Examples of alkoxy include methoxy, ethoxy, propoxy (e.g., n-propoxy and isopropoxy), tert-butoxy, and the like. The alkoxy or alkyloxy group optionally can be substituted by 1 or more (e.g., 1 to 5) suitable substituents.

Class (2): Alkyl group, i.e. saturated aliphatic hydrocarbon including straight chains and branched chains. In some embodiments, the alkyl group has 1 to 20 carbon atoms, 1 to 10 carbon atoms, 1 to 6 carbon atoms, or 1 to 4 carbon atoms. For example, the term "$C_1$-6 alkyl" refers to linear or branched radicals of 1 to 6 carbon atoms (e.g., methyl, ethyl, n-propyl, isopropyl, n-butyl, isobutyl, sec-butyl, tert-butyl, n-pentyl, or n-hexyl). An alkyl group optionally can be substituted by one or more (e.g., 1 to 5) suitable substituents.

Class (3): Alkenyl group, i.e. aliphatic hydrocarbon having at least one carbon-carbon double bond, including straight chains and branched chains having at least one carbon-carbon double bond. In some embodiments, the alkenyl group has 2 to 20 carbon atoms, 2 to 10 carbon atoms, 2 to 6 carbon atoms, 3 to 6 carbon atoms, or 2 to 4 carbon atoms. For example, the term "$C_{2-6}$ alkenyl" includes straight or branched chain unsaturated radicals (having at least one carbon-carbon double bond) of 2 to 6 carbon atoms, including, but not limited to, ethenyl, 1-propenyl, 2-propenyl (allyl), isopropenyl, 2-methyl-1-propenyl, 1-butenyl, 2-butenyl, and the like. An alkenyl group optionally can be substituted by one or more (e.g., 1 to 5) suitable substituents. The alkenyl group may exist as the pure E form, the pure Z form, or any mixture thereof.

Class (4): Alkynyl group, i.e. aliphatic hydrocarbons having at least one carbon-carbon triple bond, including straight chains and branched chains having at least one carbon-carbon triple bond. In some embodiments, the alkynyl group has 2 to 20, 2 to 10, 2 to 6, or 3 to 6 carbon atoms. For example, "$C_{2-6}$ alkynyl" includes straight or branched hydrocarbon chain alkynyl radicals as defined above, having 2 to 6 carbon atoms. An alkynyl group optionally can be substituted by one or more (e.g., 1 to 5) suitable substituents.

Class (5): Cycloalkyl group may be saturated or unsaturated, non-aromatic, monocyclic or polycyclic (such as bicyclic) hydrocarbon rings (e.g., monocyclics such as cyclopropyl, cyclobutyl, cyclopentyl, cyclohexyl, cycloheptyl, cyclooctyl, cyclononyl, or bicyclics including spiro, fused, or bridged systems (such as bicyclo[1.1.1]pentanyl, bicyclo[2.2.1]heptanyl, bicyclo [3.2.1]octanyl or bicyclo[5.2.0]nonanyl, decahydronaphthalenyl, etc.). The cycloalkyl group has 3 to 15 carbon atoms. In some embodiments the cycloalkyl may optionally contain one, two or more non-cumulative non-aromatic double or triple bonds and/or one to three oxo groups. In some embodiments, the bicycloalkyl group has 6 to 14 carbon atoms. For example, "$C_3$-14 cycloalkyl" includes saturated or unsaturated, non-aromatic, monocyclic or polycyclic (such as bicyclic) hydrocarbon rings of 3 to 14 ring-forming carbon atoms (e.g., cyclopropyl, cyclobutyl, cyclopentyl, cyclohexyl, bicyclo[1.1.1]pentanyl, or cyclodecanyl). The cycloalkyl group optionally can be substituted by 1 or more (e.g., 1 to 5) suitable substituents.

Class (6): Aryl group, i.e. all-carbon monocyclic or fused-ring polycyclic aromatic groups having a conjugated pi-electron system. The aryl group may have 6 or 10 carbon atoms in the ring(s). Most commonly, the aryl group has 6 carbon atoms in the ring. For example, $C_6$-10 aryl is an aromatic radical containing from 6 to 10 carbon atoms such as phenyl or naphthyl. The aryl group optionally can be substituted by 1 or more (e.g., 1 to 5) suitable substituents.

Class (7): Heteroaryl group, i.e. monocyclic or fused-ring polycyclic aromatic heterocyclic groups with one or more heteroatom ring members (ring-forming atoms) each independently selected from O, S and N in at least one ring. The heteroaryl group has 5 to 14 ring-forming atoms, including 1 to 13 carbon atoms, and 1 to 8 heteroatoms selected from 0, S, and N. In some embodiments, the heteroaryl group has 5 to 10 ring-forming atoms including one to four heteroatoms. The heteroaryl group can also contain one to three oxo or thiono (i.e., =S) groups. In some embodiments, the heteroaryl group has 5 to 8 ring-forming atoms including one, two or three heteroatoms. For example, 5-membered heteroaryl group is a monocyclic heteroaryl group as defined above with 5 ring-forming atoms in the monocyclic heteroaryl ring; 6-membered heteroaryl is a monocyclic heteroaryl group as defined above with 6 ring-forming atoms in the monocyclic heteroaryl ring; 5-10-membered heteroaryl is a monocyclic or bicyclic heteroaryl group as defined above with 5, 6, 7, 8, 9 or 10 ring-forming atoms in the monocyclic or bicyclic heteroaryl ring. A heteroaryl group optionally can be substituted by 1 or more (e.g., 1 to 5) suitable substituents. Examples of monocyclic heteroaryls include those with 5 ring-forming atoms including one to three heteroatoms or those with 6 ring-forming atoms including one, two or three nitrogen heteroatoms. Examples of fused bicyclic heteroaryls include two fused 5- and/or 6-membered monocyclic rings including one to four heteroatoms. Examples of heteroaryl groups include pyridinyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl (e.g., pyrazol-1-yl, pyrazol-3-yl, pyrazol-4-yl), tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, 1H-imidazo[4,5-c]pyridinyl, imidazo[1,2-a]pyridinyl, 1H-pyrrolo[3,2-c]pyridinyl, imidazo[1,2-a]pyrazinyl, imidazo[2,1-c][1,2,4]triazinyl, imidazo[1,5-a]pyrazinyl, imidazo[1,2-a]pyrimidinyl, 1H-indazolyl, 9H-purinyl, imidazo[1,2-a]pyrimidinyl, [1,2,4]triazolo[1,5-a]pyrimidinyl, [1,2,4]triazolo[4,3-b]pyridazinyl, isoxazolo[5,4-c]pyridazinyl, isoxazolo[3,4-c]pyridazinyl, pyridone, pyrimidone, pyrazinone, pyrimidinone, 1H-imidazol-2(3H)-one, 1H-pyrrole-2,5-dione, 3-oxo-2H-pyridazinyl, 1H-2-oxo-pyrimidinyl, 1H-2-oxo-pyridinyl, 2,4(1H,3H)-dioxo-pyrimidinyl, 1H-2-oxo-pyrazinyl, and the like.

Class (8): Heterocycloalkyl group, i.e. monocyclic or polycyclic (including 2 or more rings that are fused together, including spiro, fused, or bridged systems, for example, a bicyclic ring system), saturated or unsaturated, non-aromatic 4- to 15-membered ring system including 1 to 14 ring-forming carbon atoms and 1 to 10 ring-forming heteroatoms each independently selected from O, S, N, P and B. The heterocycloalkyl group can also optionally contain one or more oxo (i.e., =O) or thiono (i.e., =S) groups. For example, 4- to 12-membered heterocycloalkyl is a monocyclic or polycyclic, saturated or unsaturated, non-aromatic 4- to 12-membered ring system that comprises one or more ring-forming heteroatoms. Examples of such heterocycloalkyl rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, quinuclidinyl, chromanyl, isochromanyl, benzoxazinyl, 2-oxaspiro[3.3]heptyl {e.g., 2-oxaspiro[3.3]hept-6-yl}, 7-azabicyclo[2.2.1]heptan-1-yl, 7-azabicyclo[2.2.1]heptan-2-yl, 7-azabicyclo[2.2.1] heptan-7-yl, 2-azabicyclo[2.2.1]heptan-3-on-2-yl, 3-azabicyclo[3.1.0]hexanyl, 3-azabicyclo[4.1.0]heptanyl and the like. Further examples of heterocycloalkyl rings include tetrahydrofuran-2-yl, tetrahydrofuran-3-yl, tetrahydropyranyl (e.g., tetrahydro-2H-pyran-4-yl), imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,3-oxazolidin-3-yl, 1,4-oxazepan-1-yl, isothiazolidinyl, 1,3-thiazolidin-3-yl, 1,2-pyrazolidin-2-yl, 1,2-tetrahydrothiazin-2-yl, 1,3-thiazinan-3-yl, 1,2-tetrahydrodiazin-2-yl, 1,3-tetrahydrodiazin-1-yl, 1,4-oxazin-4-yl, oxazolidinonyl, 2-oxo-piperidinyl (e.g., 2-oxo-piperidin-1-yl), 2-oxoazepan-3-yl, and the like. Some examples of aromatic-fused heterocycloalkyl groups include indolinyl, isoindolinyl, isoindolin-1-one-3-yl, 5,7-dihydro-6H-pyrrolo[3,4-b]pyridin-6-yl, 6,7-dihydro-5H-pyrrolo[3,4-d]pyrimidin-6-yl, 4,5,6,7-tetrahydrothieno[2,3-c]pyridine-5-yl, 5,6-dihydrothieno[2,3-c]pyridin-7(4H)-one-5-yl, 1,4,5,6-tetrahydropyrrolo[3,4-c]pyrazol-5-yl, and 3,4-dihydroisoquinolin-1(2H)-one-3-yl groups. The heterocycloalkyl group is optionally substituted by 1 or more (e.g., 1 to 5) suitable substituents. Examples of heterocycloalkyl groups include 5- or 6-membered monocyclic rings and 9- or 10-membered fused bicyclic rings.

The term "monovalent non-hydrogen group" may include a combination of any number of groups selected from the above 8 classes. By a combination of two groups, it means that one group (G1) is substituted with another group (G2) to form a new group -G1-G2. By combination of three groups, it means that a first group (G1) is substituted with a second group (G2) which is substituted with a third group (G3), forming a new group -G1-G2-G3. For example, a group from Classes (2)-(8) may be substituted with a group from Class (1): (i) Haloalkyl group such as fluoroalkyl, i.e. an alkyl group having one or more halogen substituents such as F (up to perhaloalkyl, i.e., every hydrogen atom of the alkyl group has been replaced by a halogen atom). For example, C1-6 haloalkyl is a C1-6 alkyl group having one or more halogen substituents (up to perhaloalkyl, i.e., every hydrogen atom of the alkyl group has been replaced by a halogen atom). C1 haloalkyl is a methyl group having one, two, or three halogen substituents. (ii) Hydroxylalkyl or hydroxyalkyl, i.e. an alkyl group having one or more (e.g., 1, 2, or 3) OH substituents. (iii) Cyanoalkyl group, i.e an alkyl group having one or more (e.g., 1, 2, or 3) —CN substituents. A group from Class (1) may be substituted with another group from Class (1), e.g. haloalkoxy group such as fluoroalkoxy, i.e. an —O-haloalkyl group. C1-6 haloalkoxy refers to an —O—(C1-6 haloalkyl) group.

The term "monovalent non-hydrogen group" may also be any group selected from the above 8 classes and combination of any number of groups selected from the above 8 classes, that are substituted with one or more bivalent groups, i.e. two germinal hydrogens on a same atom are replaced with a group such as =O, =S, =NNR$_2$, =NNRC(=O)R, =NNRC(=O)OR, =NNRS(=O)$_2$R, =NR, =NOR, or the like.

Generally, the point of attachment of the monovalent non-hydrogen group can be from any suitable position. For example, piperidinyl can be piperidin-1-yl (attached through the N atom of the piperidinyl), piperidin-2-yl (attached through the C atom at the 2-position of the piperidinyl), piperidin-3-yl (attached through the C atom at the 3-position of the piperidinyl), or piperidin-4-yl (attached through the C atom at the 4-position of the piperidinyl). For another example, pyridinyl (or pyridyl) can be 2-pyridinyl (or pyridin-2-yl), 3-pyridinyl (or pyridin-3-yl), or 4-pyridinyl (or pyridin-4-yl). The point of attachment of the non-hydrogen monovalent group can be specified to indicate the position where the non-hydrogen monovalent group is attached to another moiety. For example, "—C$_{1-2}$ alkyl-(C$_{3-4}$ cycloalkyl)" means the point of attachment occurs at the "C$_{1-2}$ alkyl" part. For another example, "(C$_{3-4}$ cycloalkyl)-C$_{1-2}$ alkyl-" also means the point of attachment occurs at the "C$_{1-2}$ alkyl" part. When a bond to a substituent is shown to cross a bond connecting two atoms in a ring, then such substituent may be bonded to any of the ring-forming atoms in that ring that are substitutable (i.e., one or more hydrogen atoms), unless otherwise specified or otherwise implicit from the context.

In some exemplary embodiments, the 1,1 or 1,2 substituted-ethyl carbamimidothioate of Formula (I-1) is selected from the following compounds:

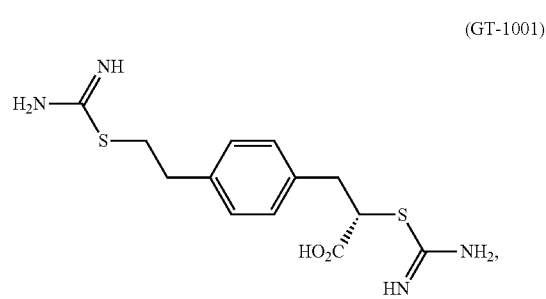

(GT-1001)

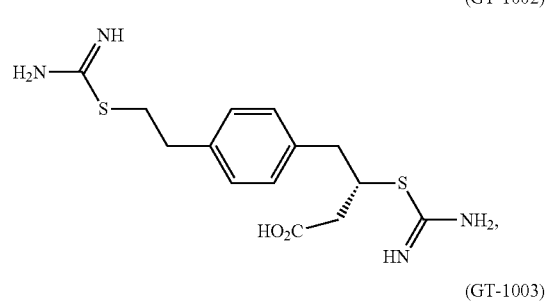

(GT-1002)

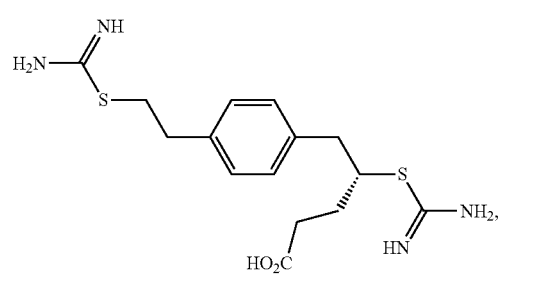

(GT-1003)

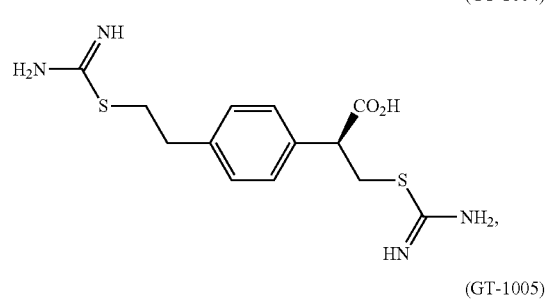

(GT-1004)

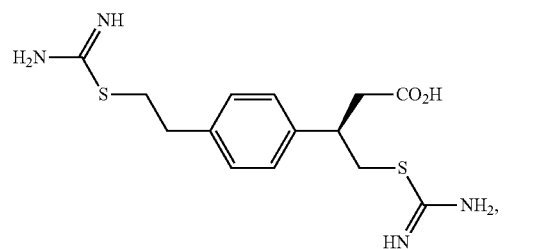

(GT-1005)

(GT-1006)
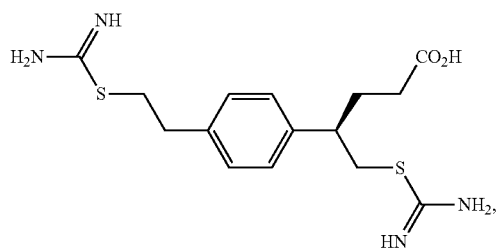
(GT-1007)
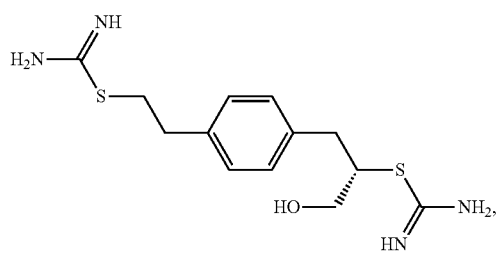
(GT-1008)
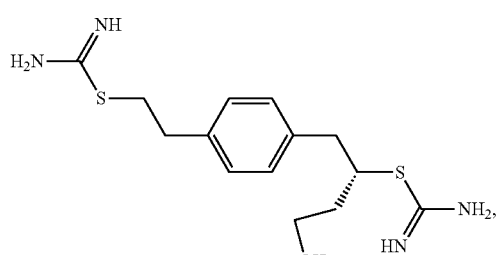
(GT-1009)
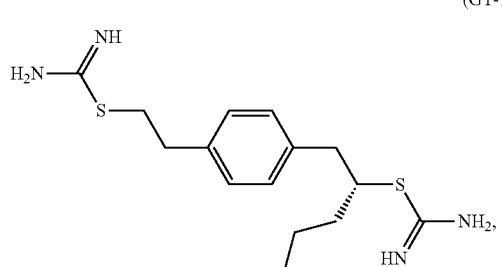
(GT-1010)
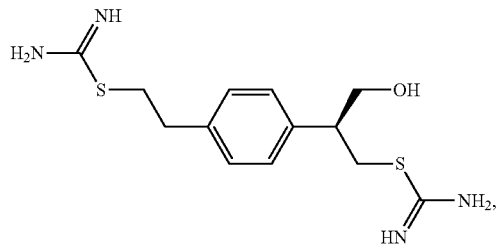
(GT-1011)
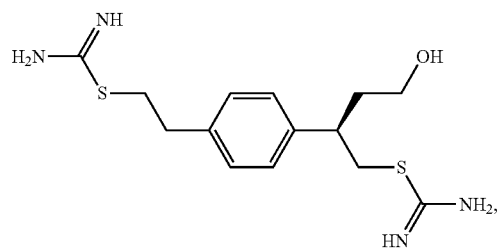
(GT-1012)
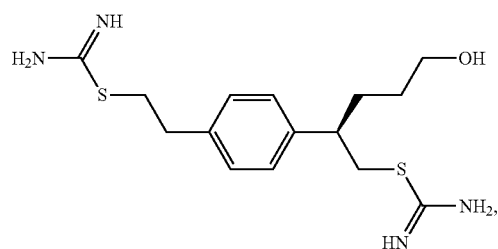
(GT-1013)
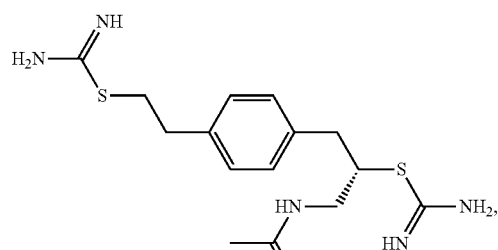
(GT-1014)
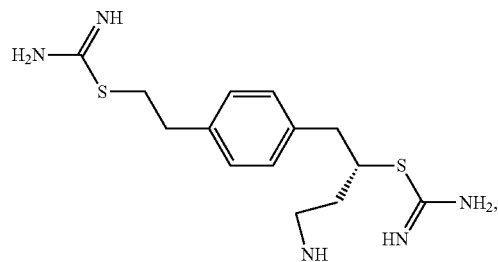
(GT-1015)
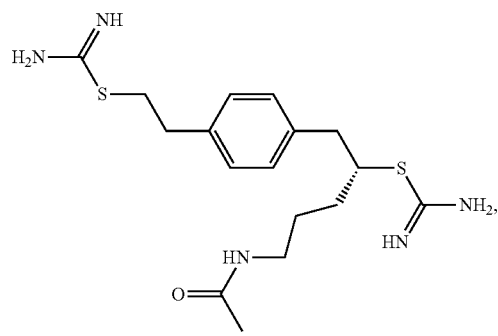

(GT-1016)
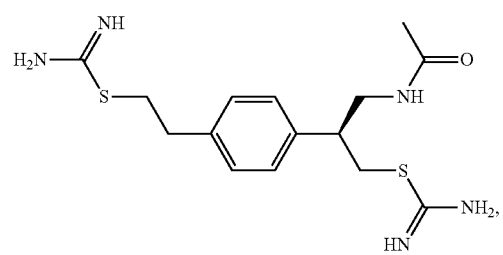
(GT-1017)
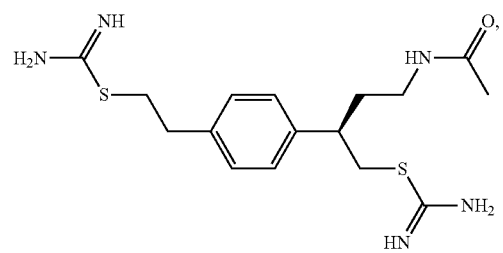
(GT-1018)
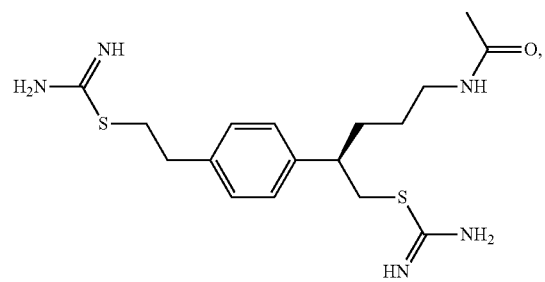
(GT-1019)
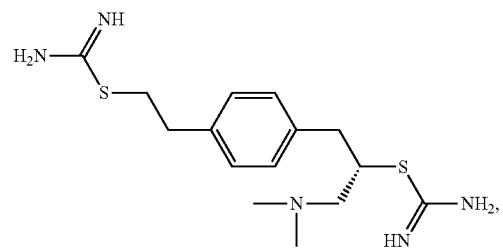
(GT-1020)
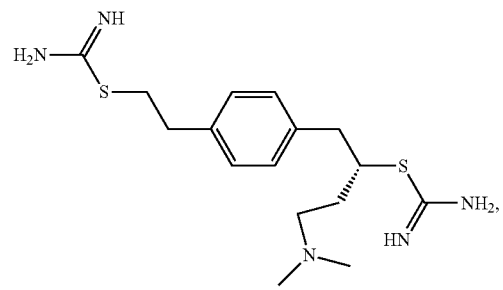
(GT-1021)
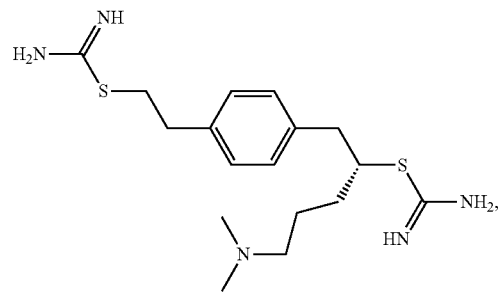
(GT-1022)
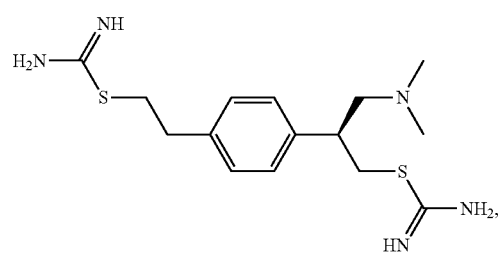
(GT-1023)
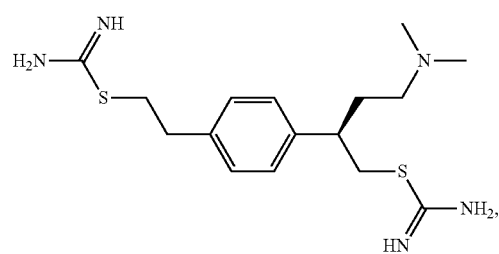
(GT-1024)
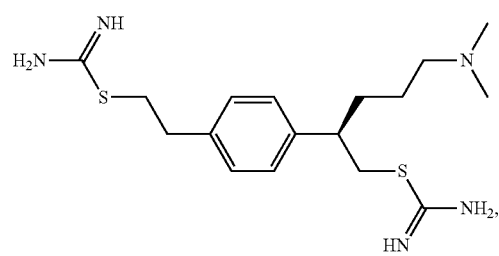
(GT-1025)
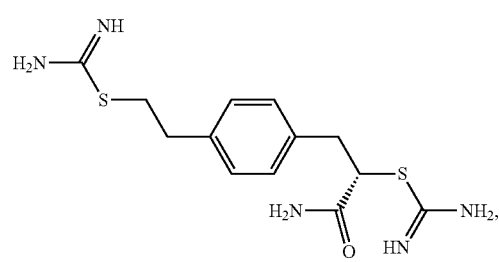

(GT-1026)
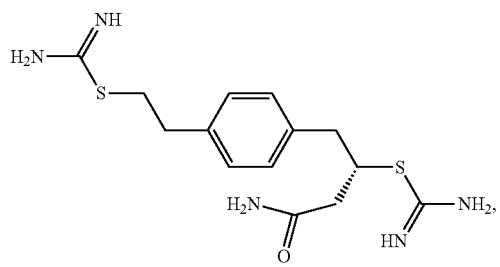
(GT-1027)
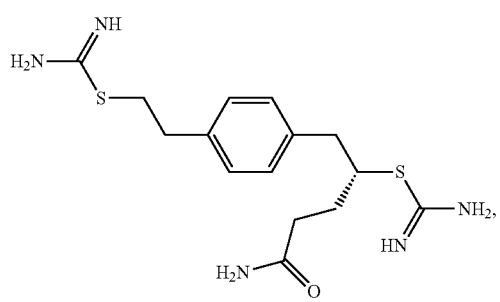
(GT-1028)
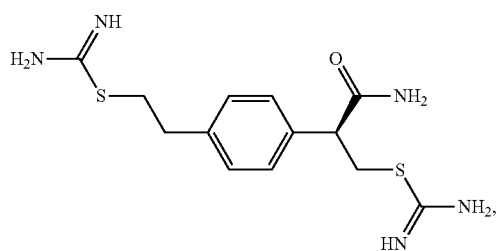
(GT-1029)
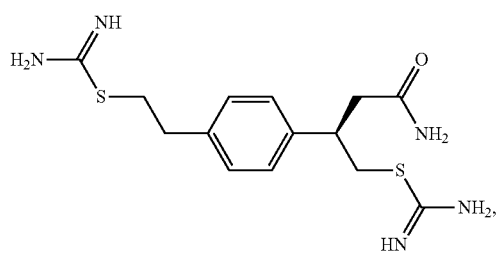
(GT-1030)
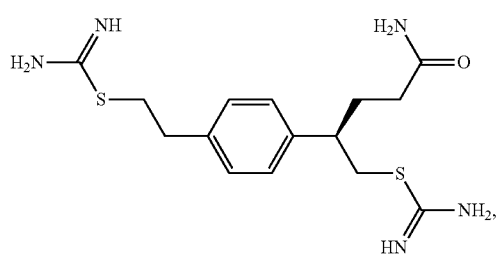
(GT-1031)
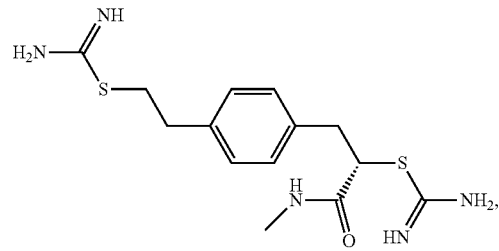
(GT-1032)
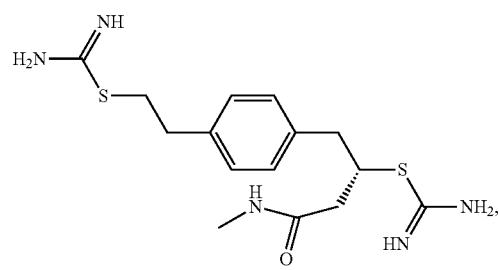
(GT-1033)
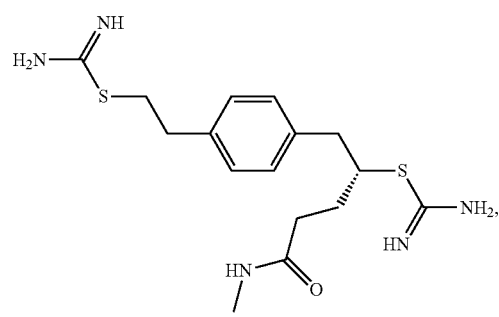
(GT-1034)
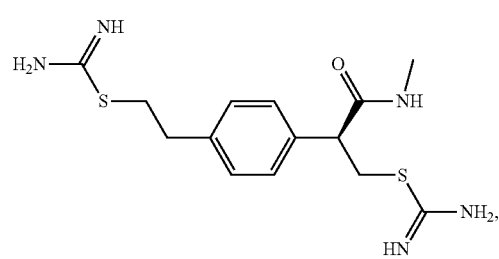
(GT-1035)
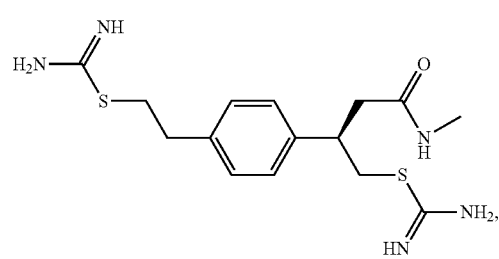

(GT-1036)
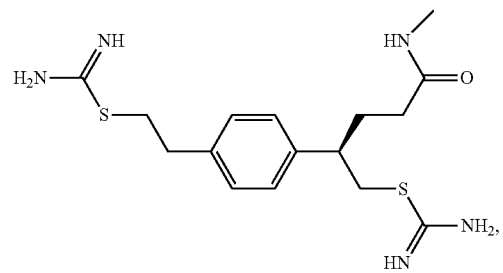
(GT-1037)
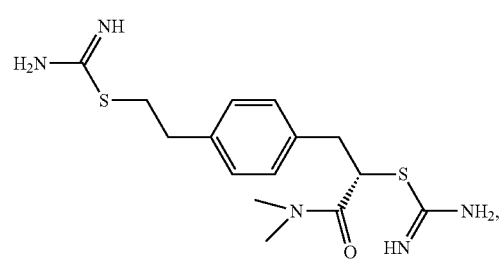
(GT-1038)
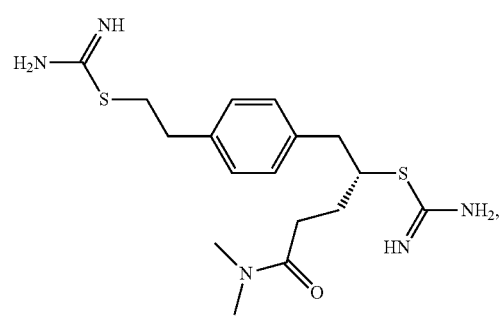
(GT-1039)
(GT-1040)
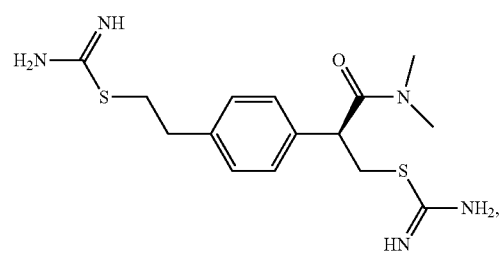
(GT-1041)
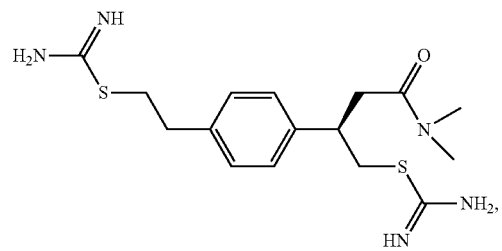
(GT-1042)
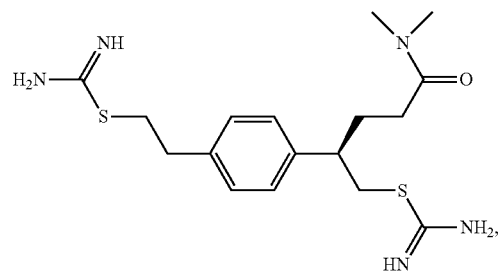
(GT-1043)
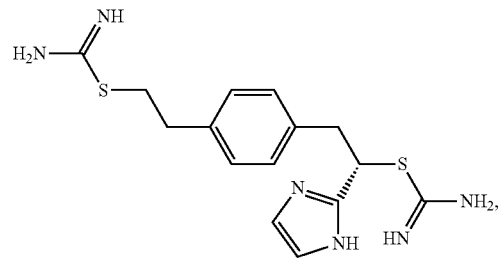
(GT-1044)
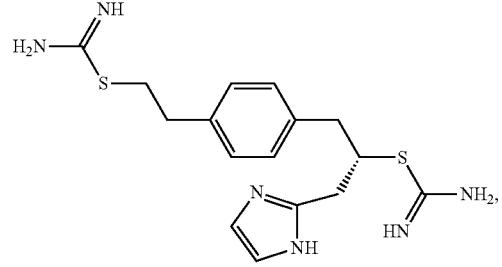
(GT-1045)
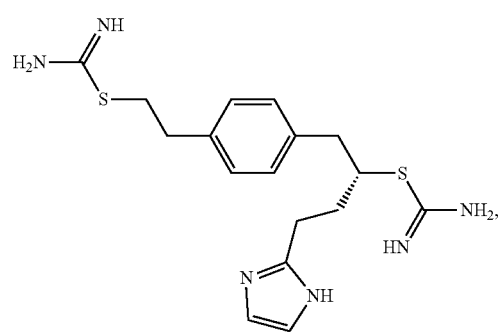

(GT-1046)
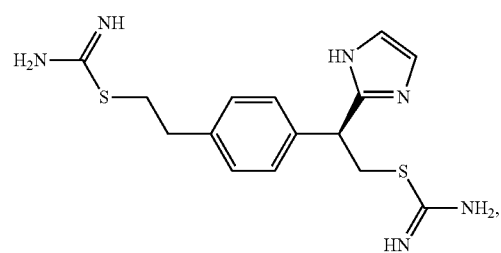
(GT-1047)
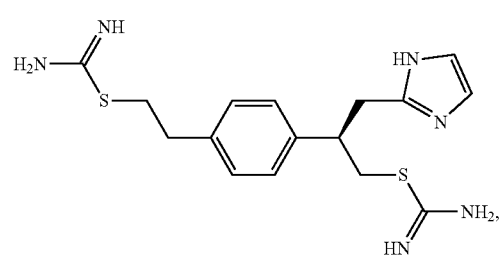
(GT-1048)
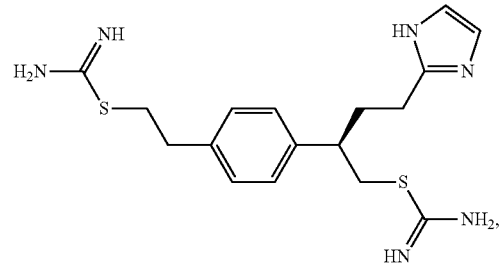
(GT-1049)
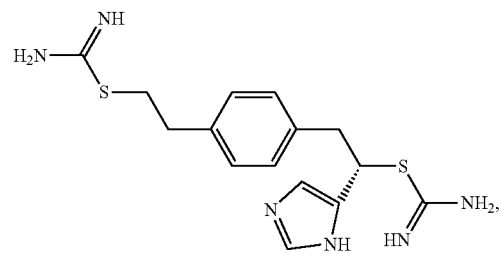
(GT-1050)
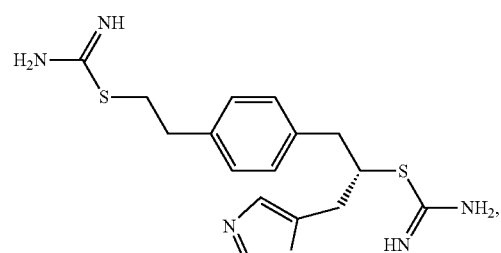
(GT-1051)
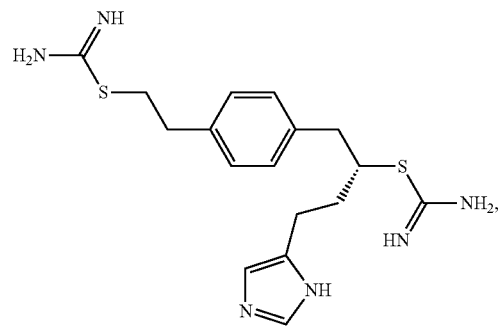
(GT-1052)
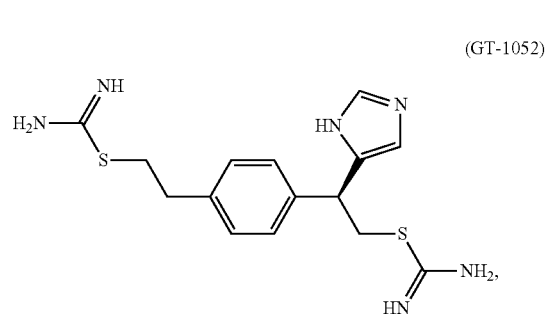
(GT-1053)
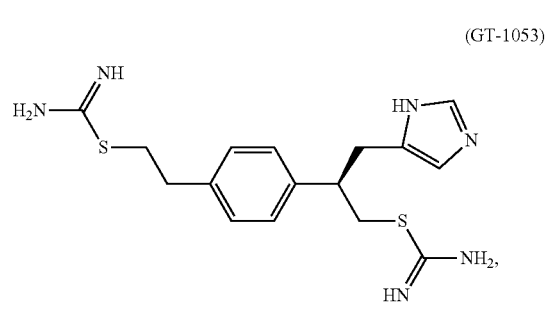
(GT-1054)
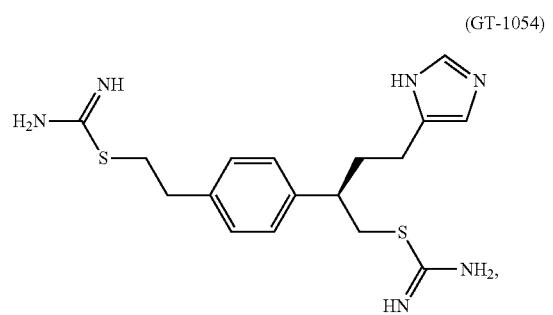
(GT-1055)
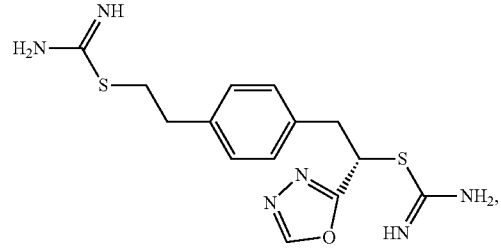

(GT-1056)
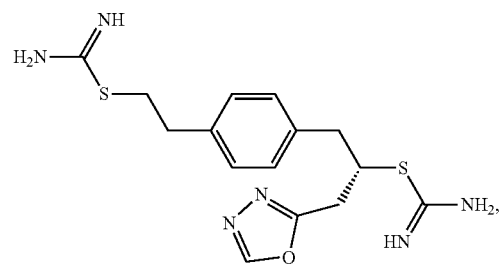
(GT-1057)
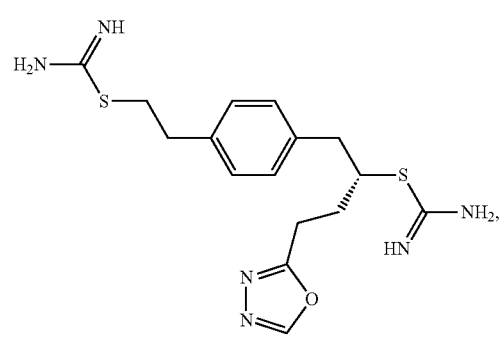
(GT-1058)
(GT-1059)
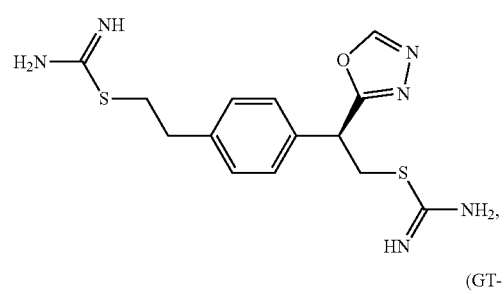
(GT-1060)
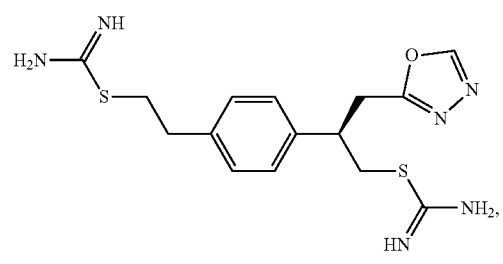
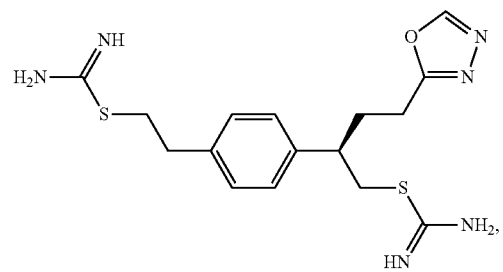
(GT-1061)
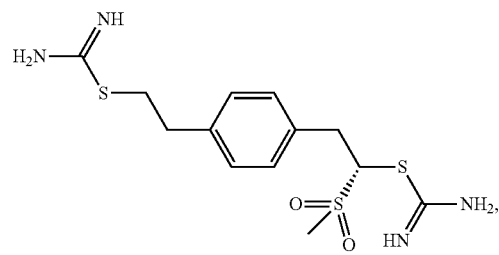
(GT-1062)
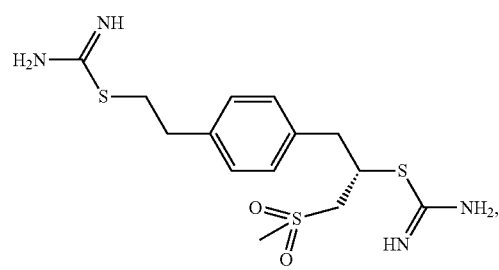
(GT-1063)
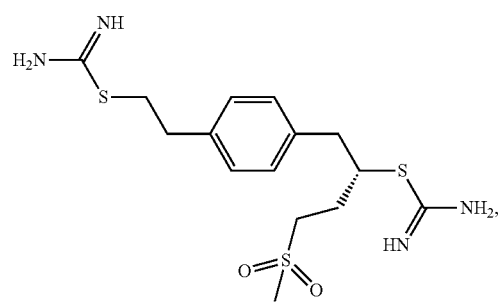
(GT-1064)
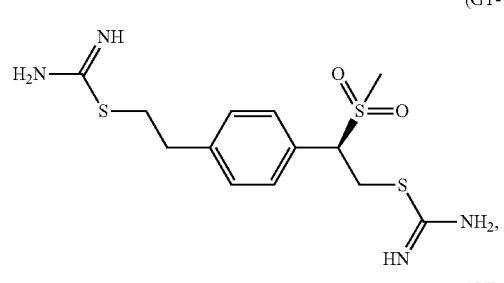
(GT-1065)
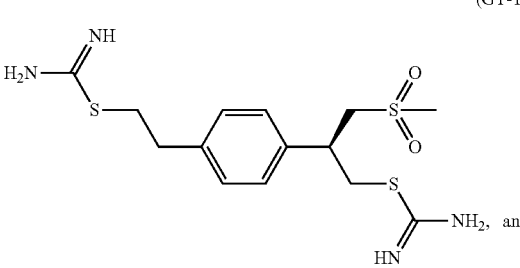

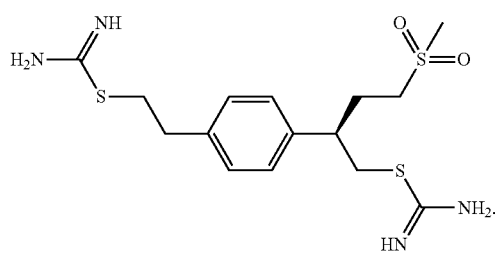
(GT-1066)
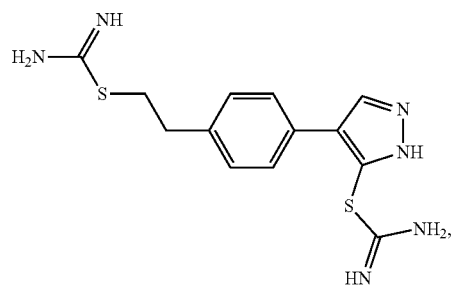
(GT-2005)
In some exemplary embodiments, the cyclic compound substituted with a carbamimidoylsulfanylethylphenyl group and a carbamimidoylsulfanyl group as represented by Formula (I-2) is selected from the following compounds:
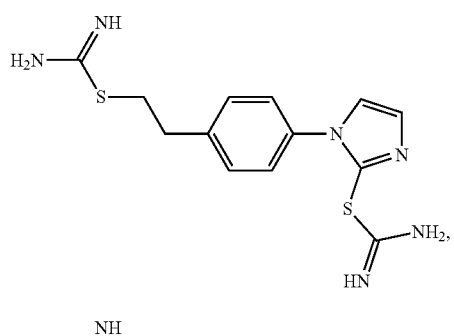
(GT-2001)
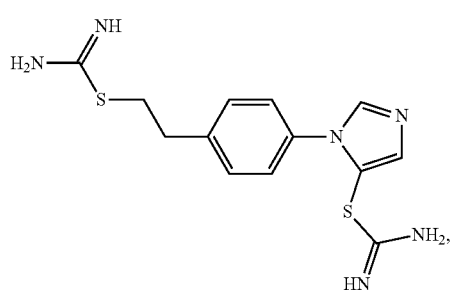
(GT-2002)
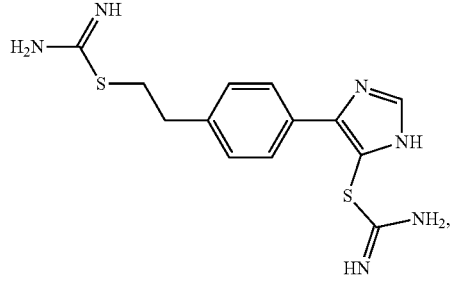
(GT-2003)
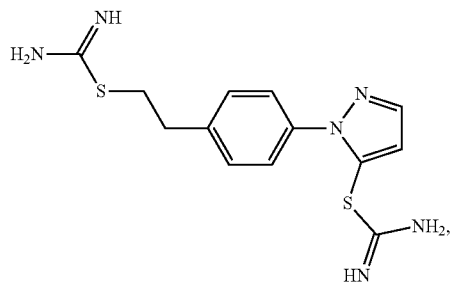
(GT-2004)
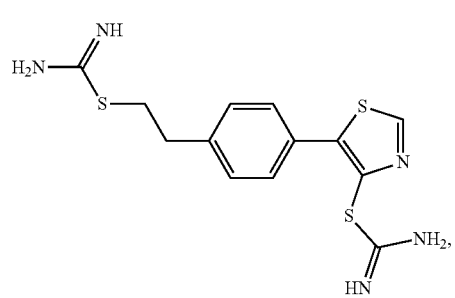
(GT-2006)
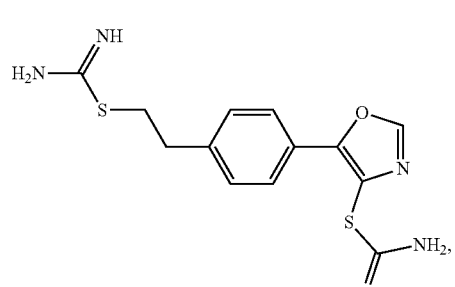
(GT-2007)
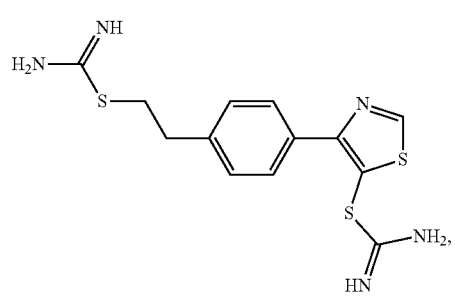
(GT-2008)
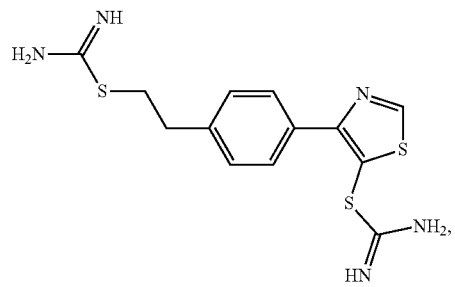
(GT-2009)
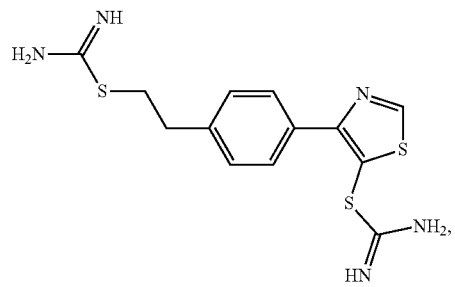

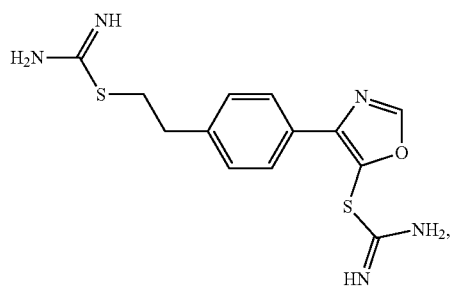
(GT-2010)
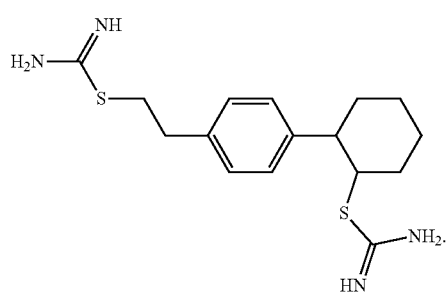
(GT-2015)
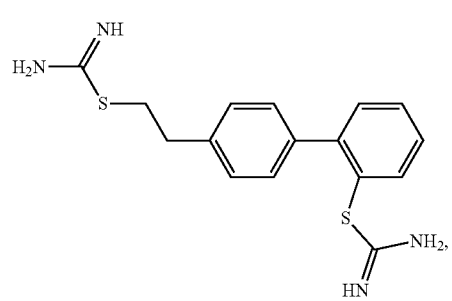
(GT-2011)
In some exemplary embodiments, the compound substituted with a carbamimidoyl sulfanylethylphenylmethyl group as represented by Formula (I-3) is selected from the following compounds:
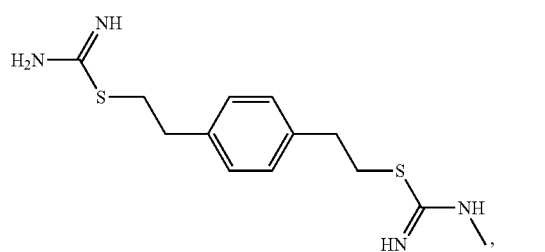
(GT-3001)
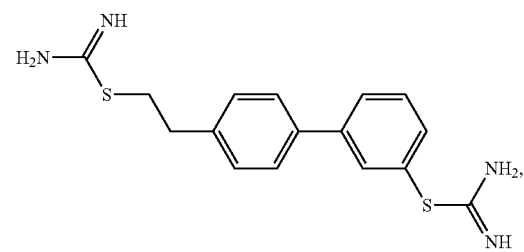
(GT-2012)
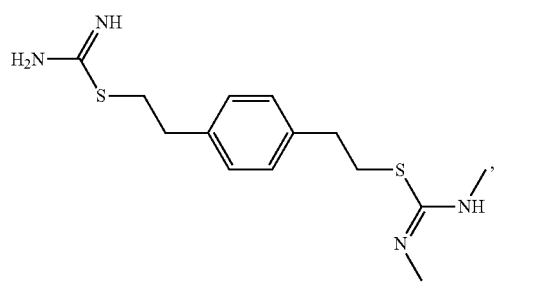
(GT-3002)
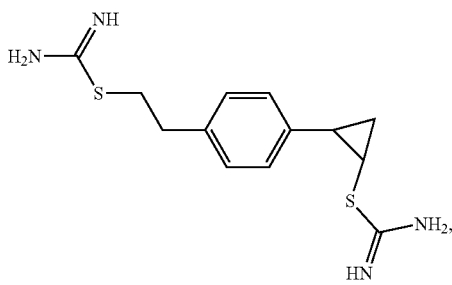
(GT-2013)
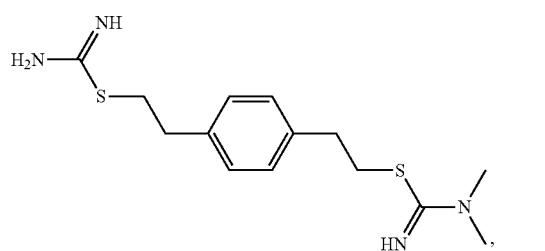
(GT-3003)
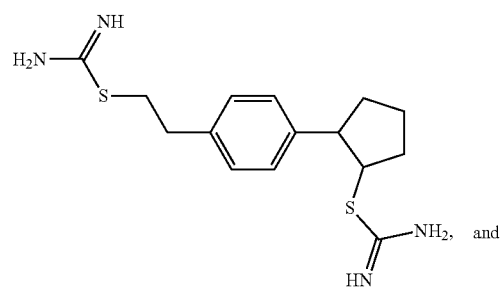
(GT-2014) and
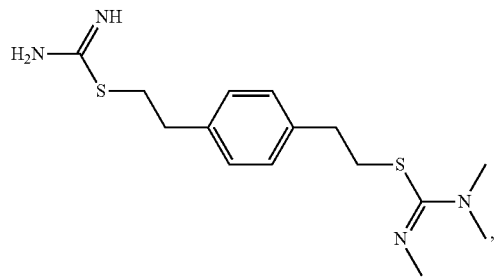
(GT-3004)

(GT-3005)
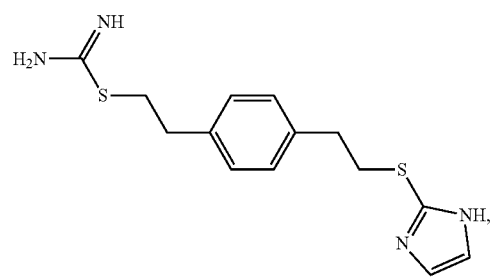
(GT-3006)
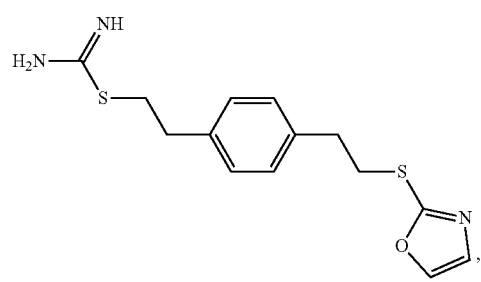
(GT-3007)
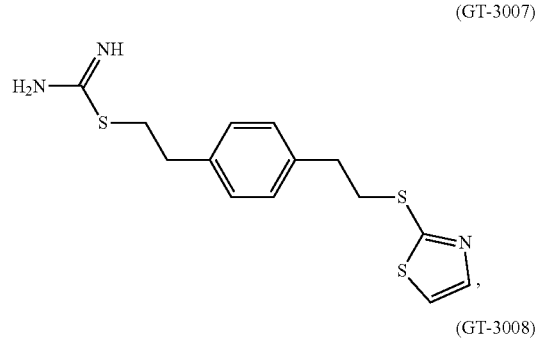
(GT-3008)
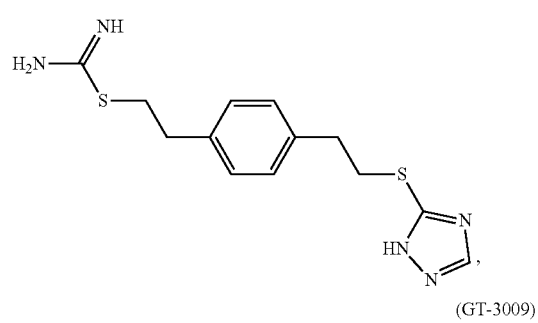
(GT-3009)
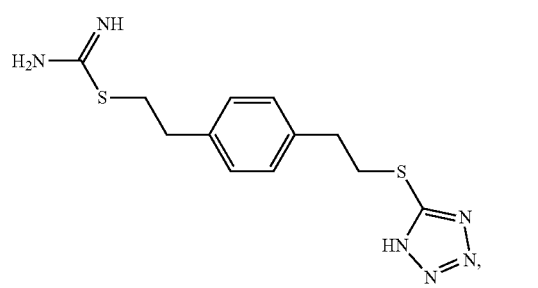
(GT-3010)
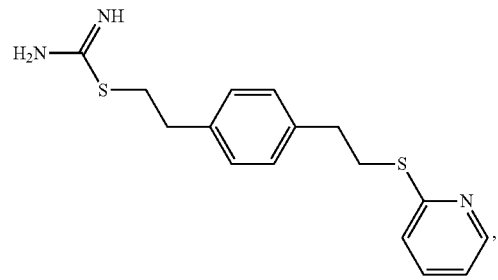
(GT-3011)
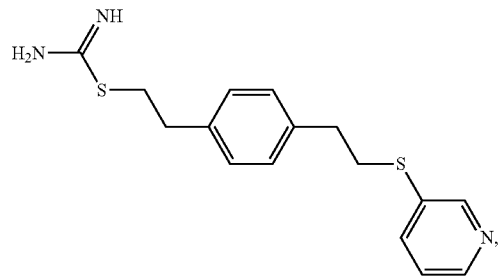
(GT-3012)
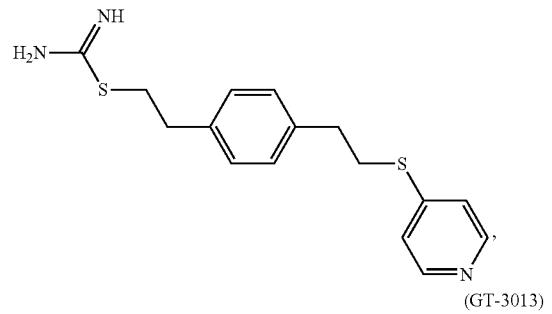
(GT-3013)
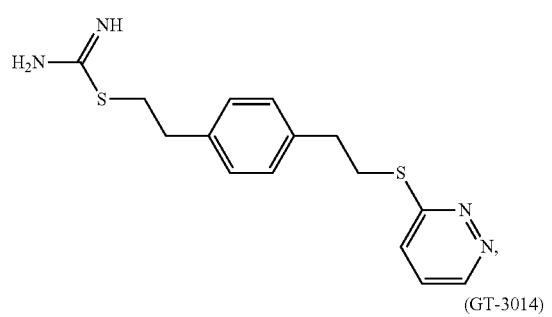
(GT-3014)
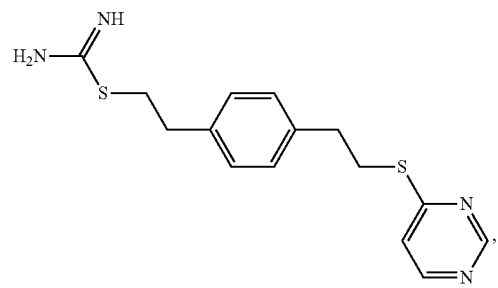

(GT-3015)
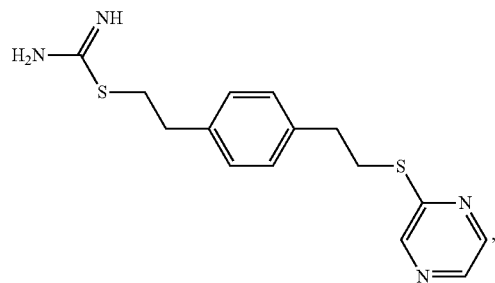
(GT-3016)
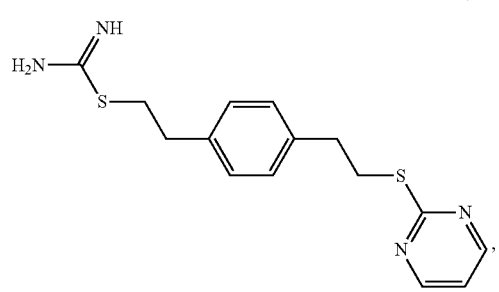
(GT-3017)
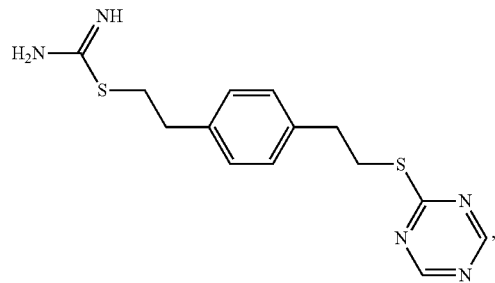
(GT-3018)
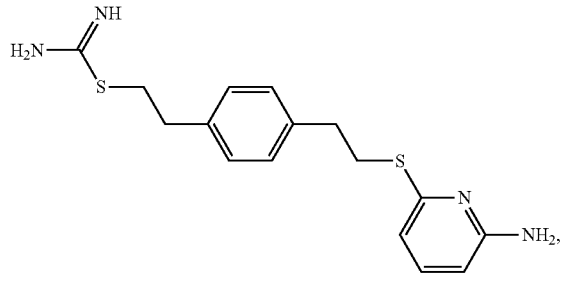
(GT-3019)
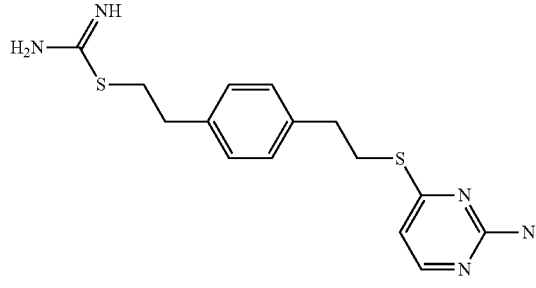
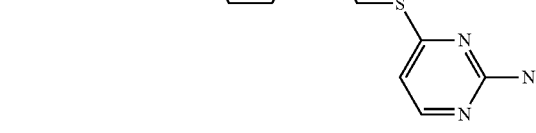
(GT-3020)
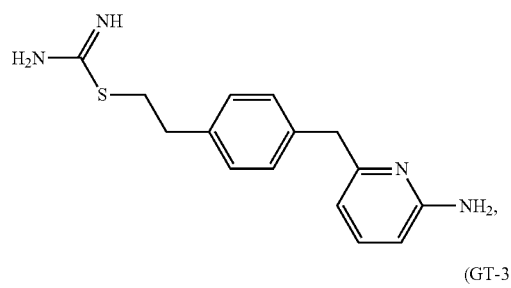
(GT-3021)
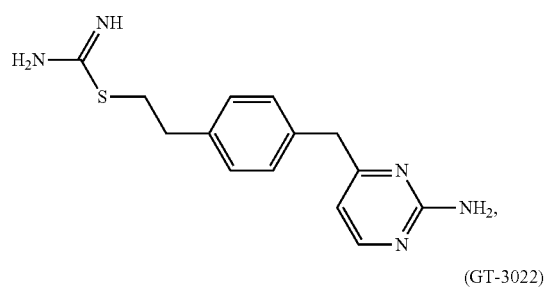
(GT-3022)
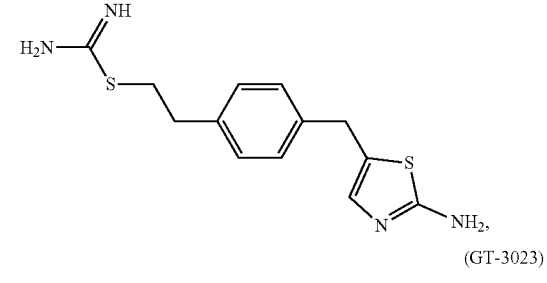
(GT-3023)
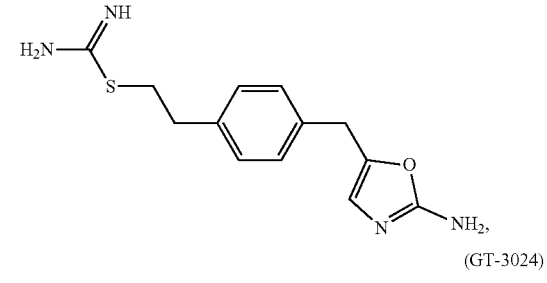
(GT-3024)
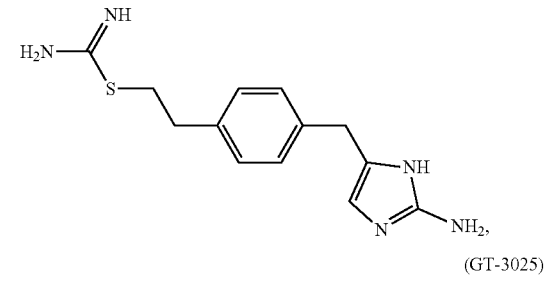
(GT-3025)
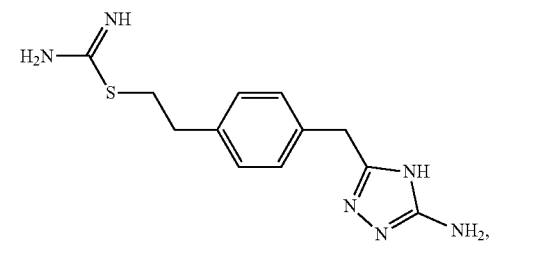

In some exemplary embodiments, the bis-carbamimidoylsulfanylethyl substituted compound as represented by Formula (I-4) is selected from the following compounds:

(GT-4008)
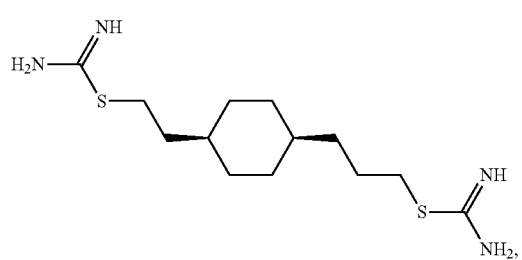
(GT-4009)
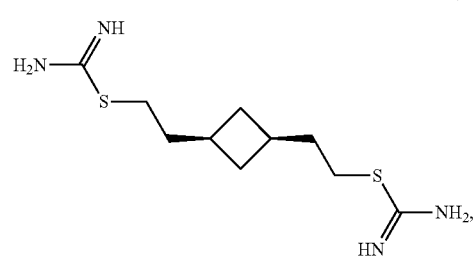
(GT-4010)
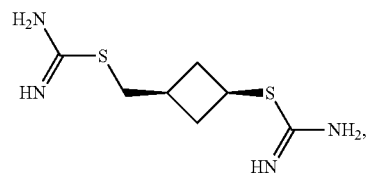
(GT-4011)
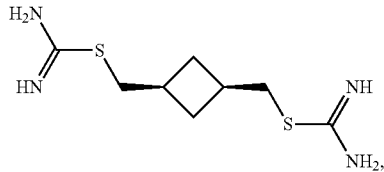
(GT-4012)
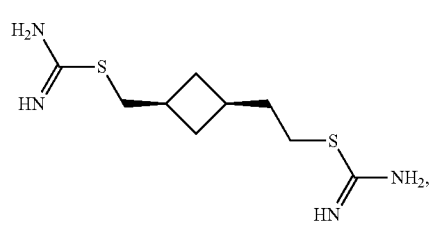
(GT-4013)
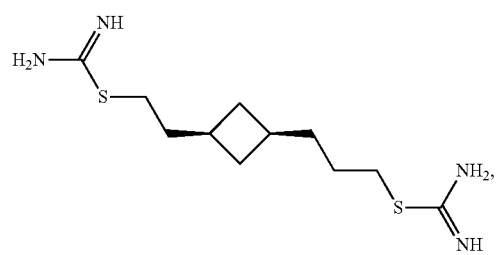
(GT-4014)
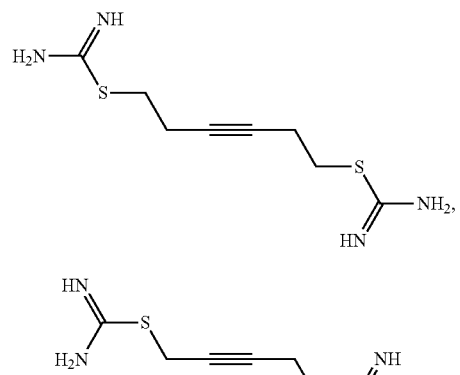
(GT-4015)
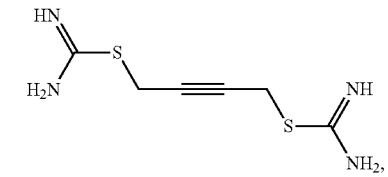
(GT-4016)
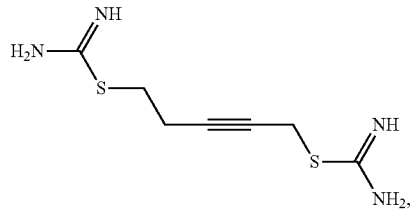
(GT-4017)
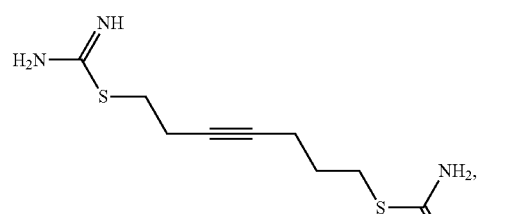
(GT-4018)
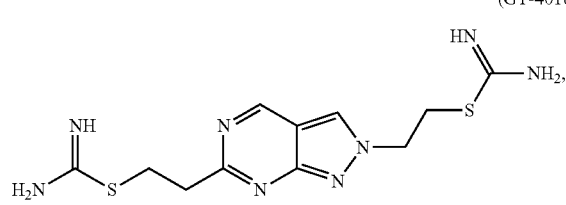
(GT-4019)
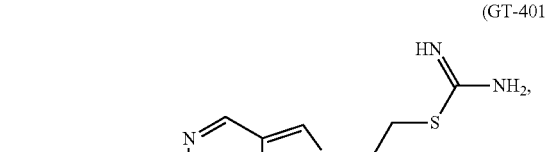
(GT-4020)
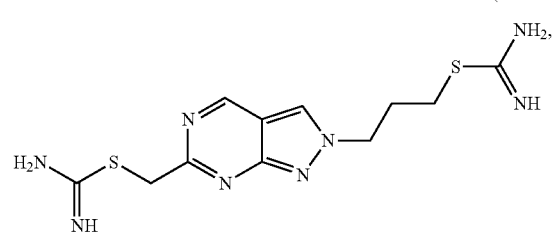

-continued
(GT-4021)
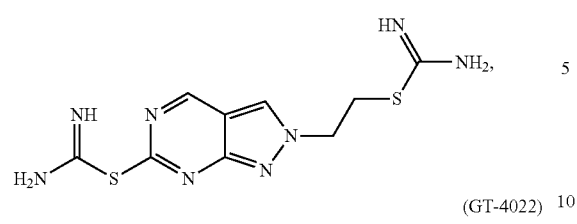
(GT-5001)
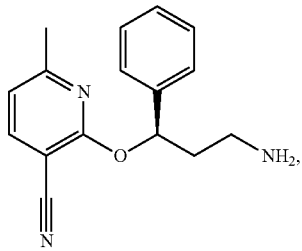
(GT-4022)
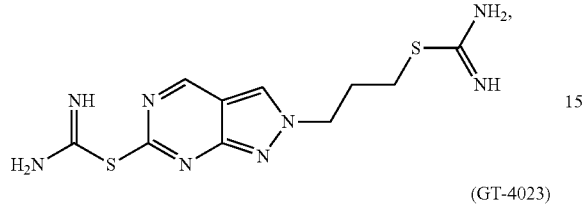
(GT-5002)
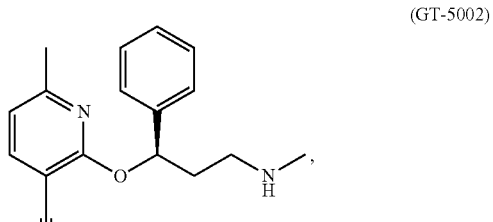
(GT-4023)
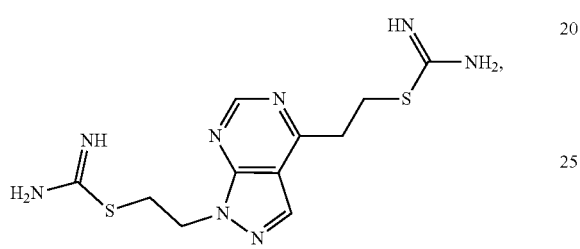
(GT-5003)
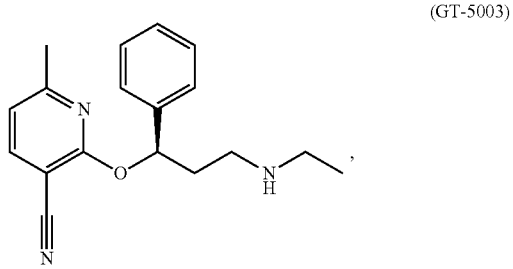
(GT-4024)
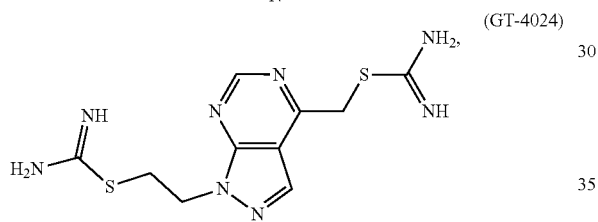
(GT-5004)
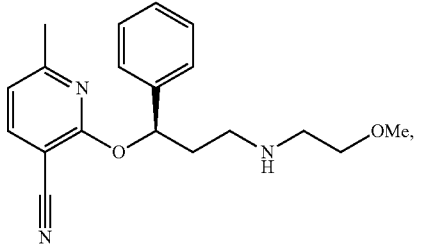
(GT-4025)
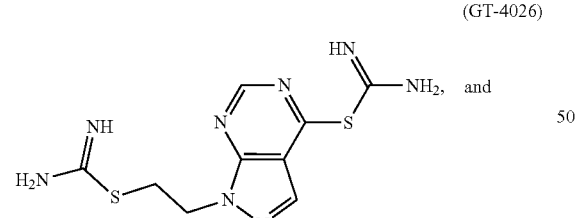
(GT-5005)
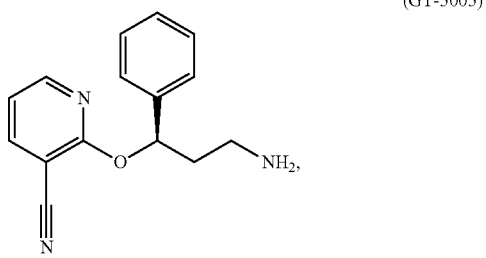
(GT-4026) and
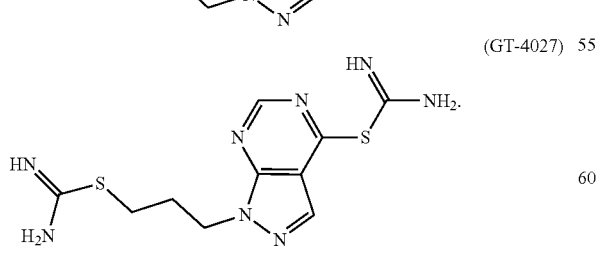
(GT-4027)
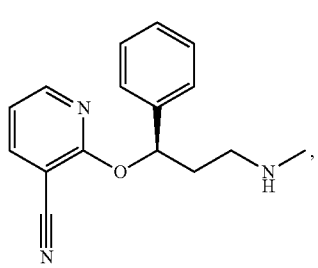
(GT-5006)
In some exemplary embodiments, the 2-propoxypyridine derivative as represented by Formula (I-5) is selected from the following compounds:

(GT-5007) 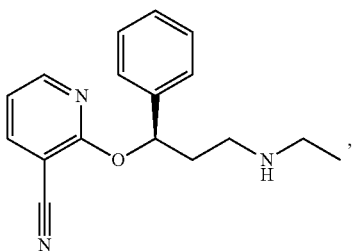
(GT-5013) 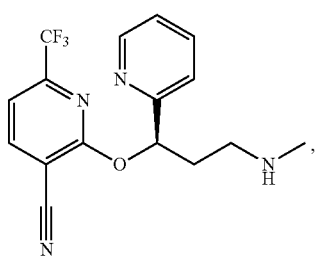
(GT-5008) 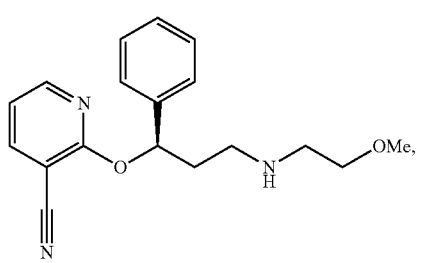
(GT-5014) 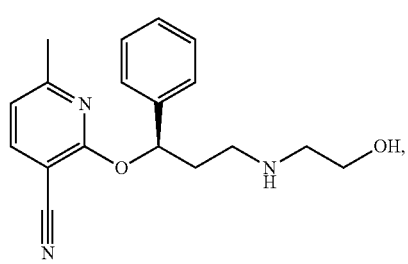
(GT-5009) 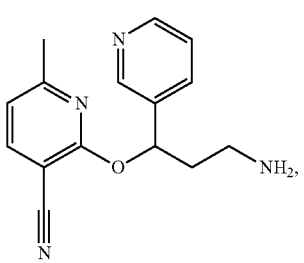
(GT-5015) 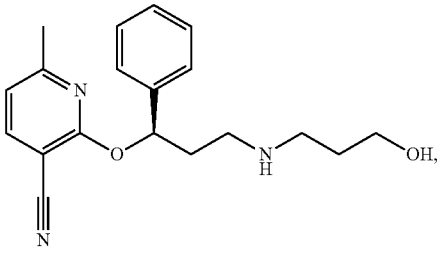
(GT-5010) 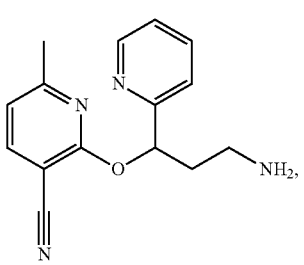
(GT-5016) 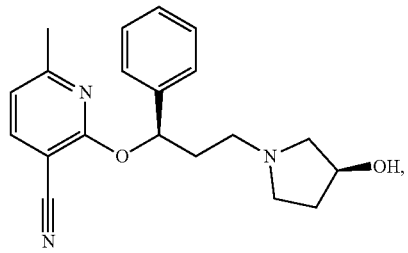
(GT-501) 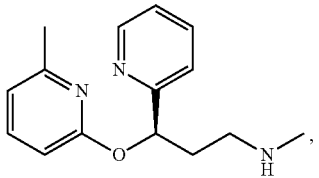
(GT-5017) 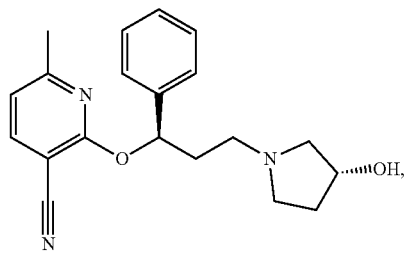
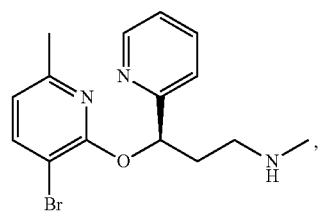
(GT-5018) 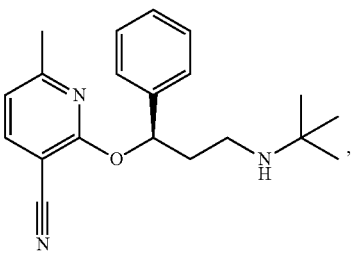

(GT-5019)
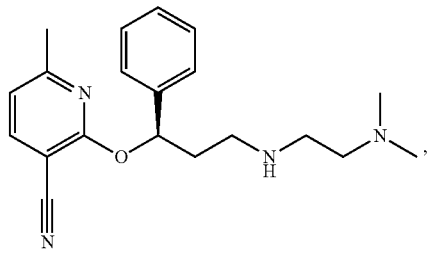
(GT-5020)
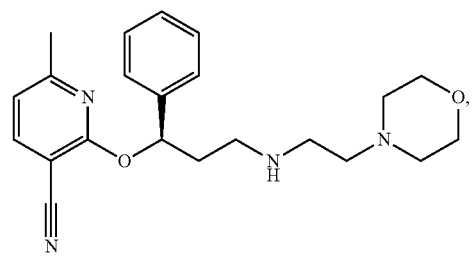
(GT-5021)
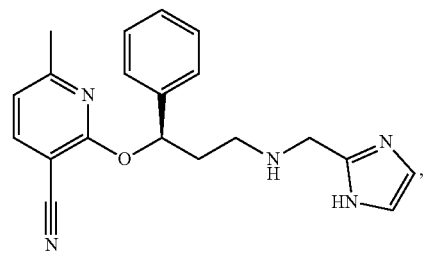
(GT-5022)
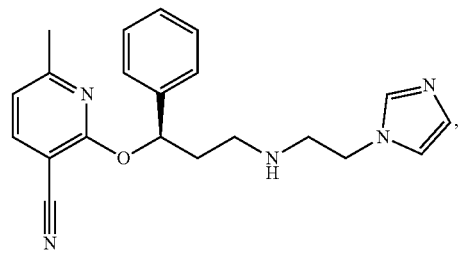
(GT-5023)
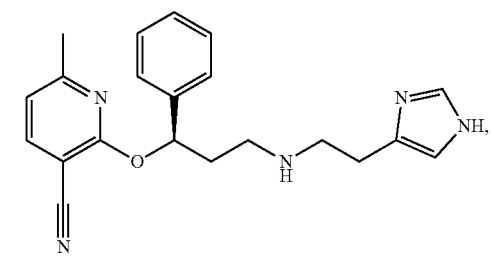
(GT-5024)
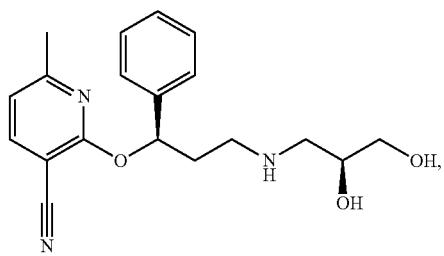
(GT-5025)
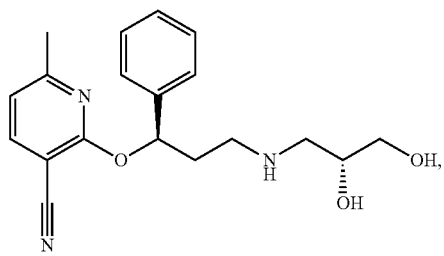
(GT-5026)
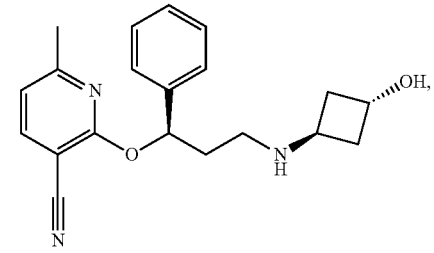
(GT-5027)
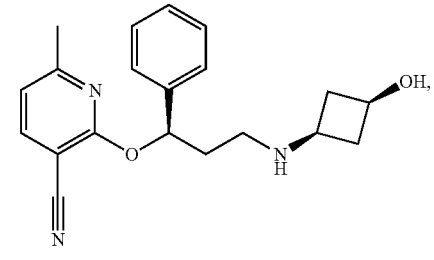
(GT-5028)
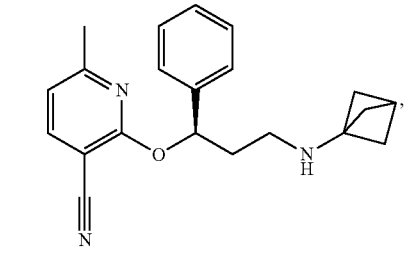
(GT-5029)
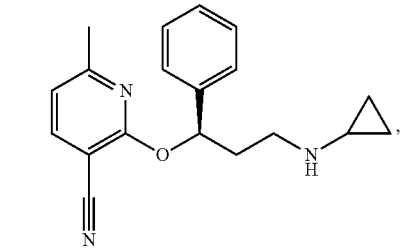
(GT-5030)
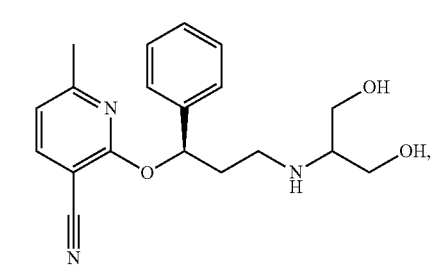
and

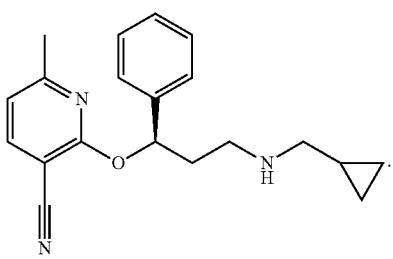
(GT-5031)

In preferred embodiments, the 2-propoxypyridine derivative as represented by Formula (I-5) is selected from the following compounds listed by increasing IC50 as will be described in more details: (GT-5002), (GT-5001), (GT-5015), (GT-5014), (GT-5024), (GT-5025), (GT-5016), (GT-5031), (GT-5018), (GT-5023), (GT-5017), (GT-5020), (GT-5019), (GT-5013), and (GT-5012).

In some exemplary embodiments, the alkylamine or heteroalkylamine derivatives as represented by Formula (I-6) is selected from the following compounds:

(GT-6001)

(GT-6002)

(GT-6003)

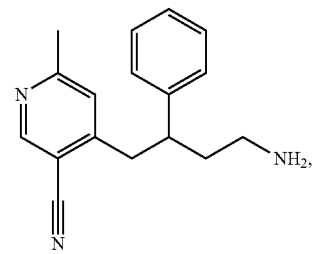

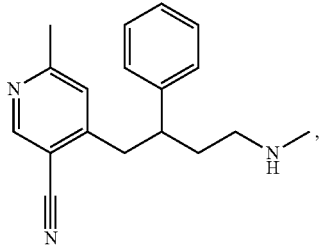
(GT-6004)

(GT-6005)
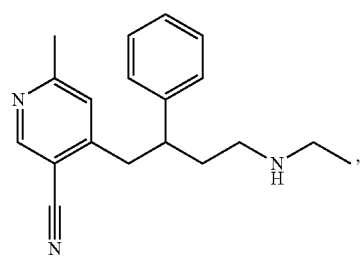

(GT-6006)
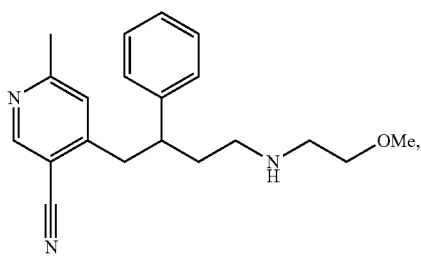

(GT-6007)
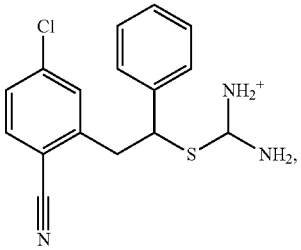

(GT-6008)
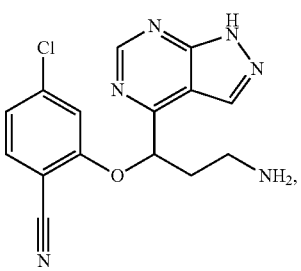

(GT-6009)
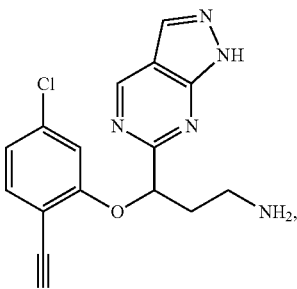

(GT-6010)
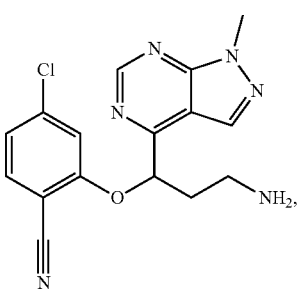

(GT-6011)
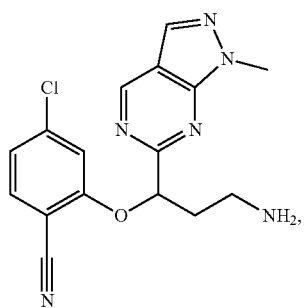
(GT-6016)
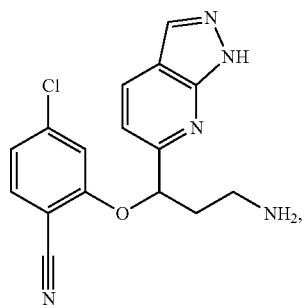
(GT-6012)
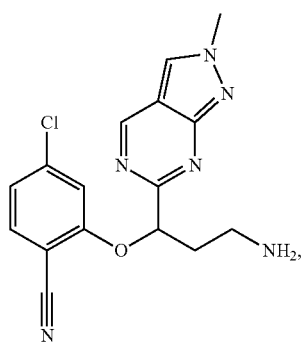
(GT-6017)
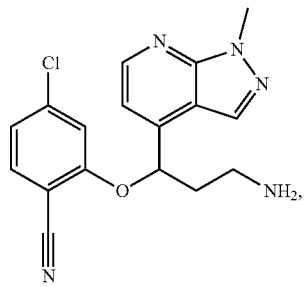
(GT-6013)
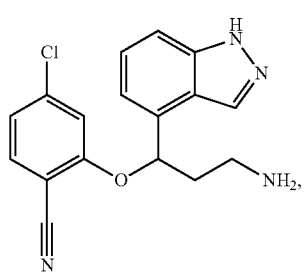
(GT-6016)
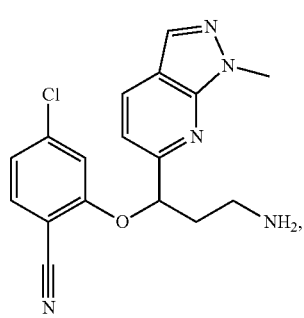
(GT-6014)
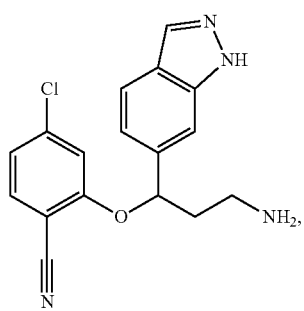
(GT-6019)
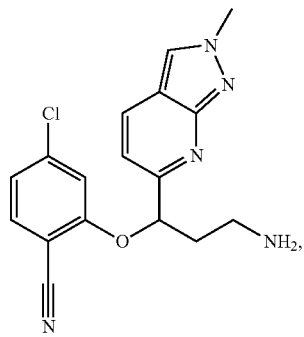
(GT-6015)
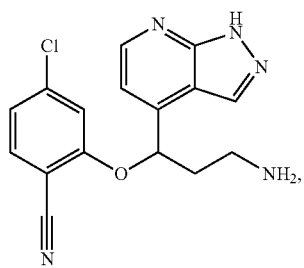
(GT-6020)
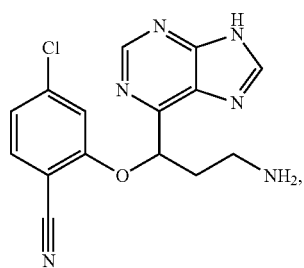

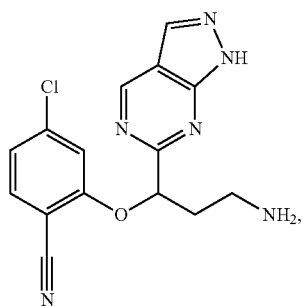
(GT-6021)
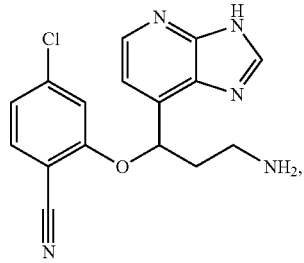
(GT-6026)
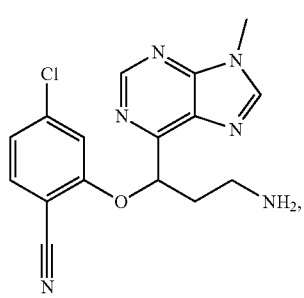
(GT-6022)
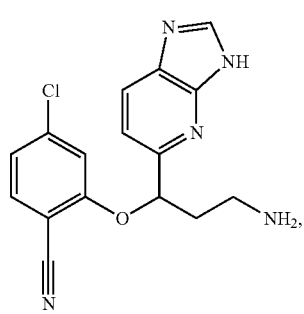
(GT-6027)
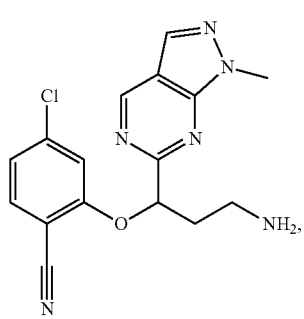
(GT-6023)
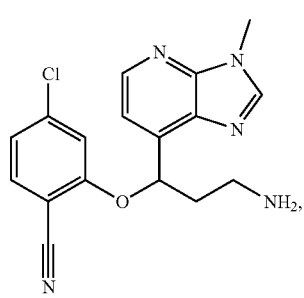
(GT-6028)
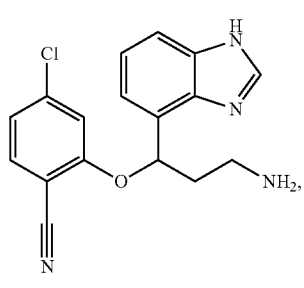
(GT-6024)
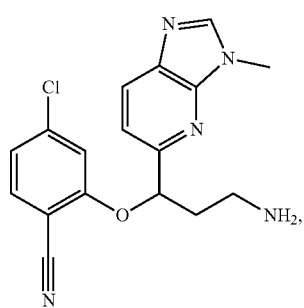
(GT-6029)
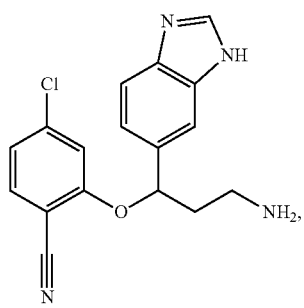
(GT-6025)
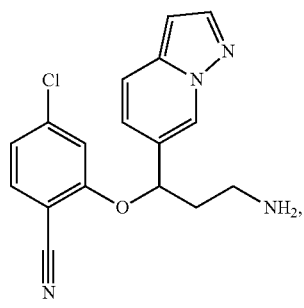
(GT-6030)

-continued
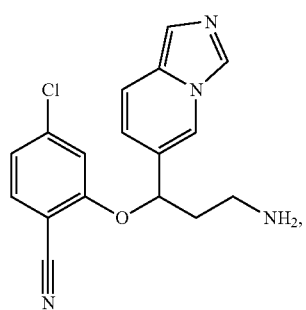
(GT-6031)
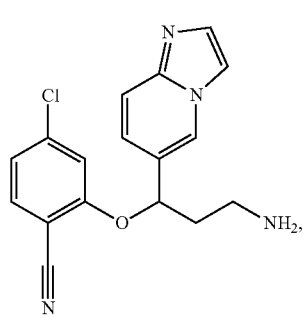
(GT-6032)
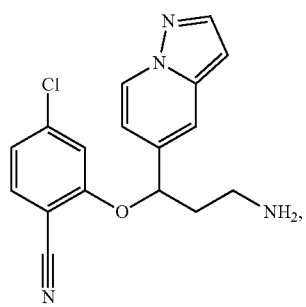
(GT-6033)
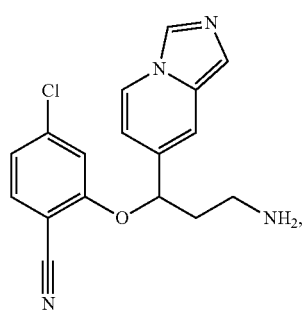
(GT-6034)
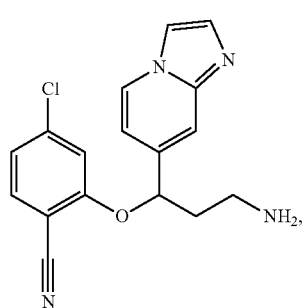
(GT-6035)
-continued
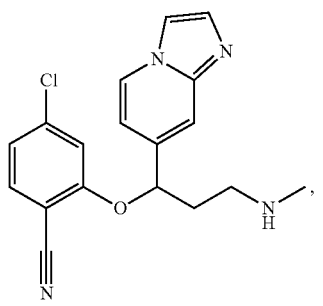
(GT-6036)
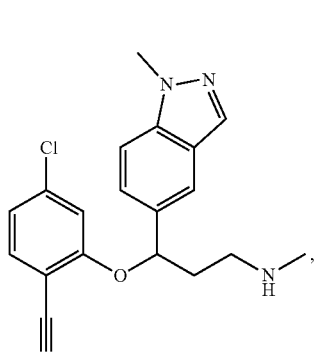
(GT-6037)
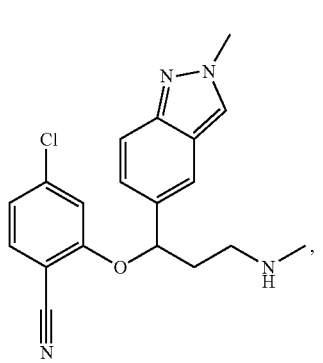
(GT-6038)
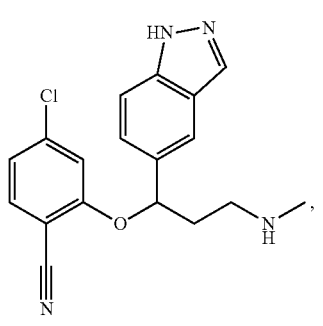
(GT-6039)
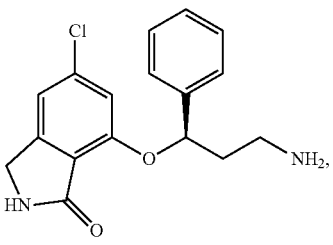
(GT-6040)

(GT-6041)
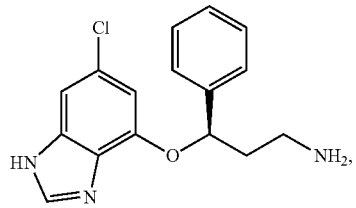
(GT-6042)
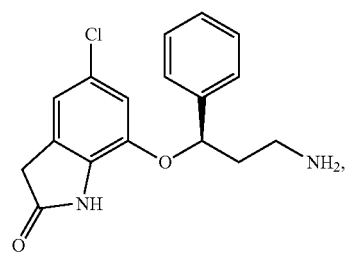
(GT-6043)
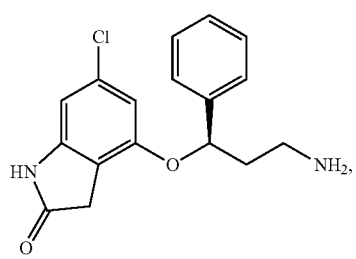
(GT-6044)
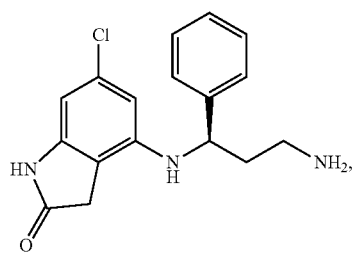
(GT-6045)
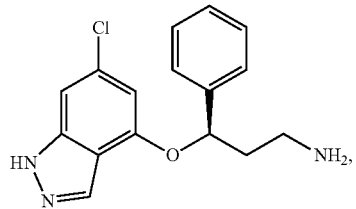
(GT-6046)
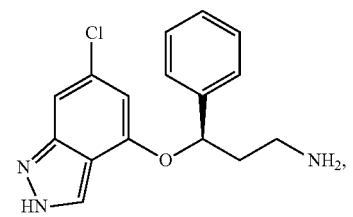
(GT-6047)
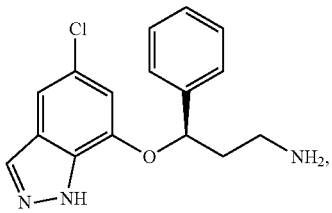
(GT-6048)
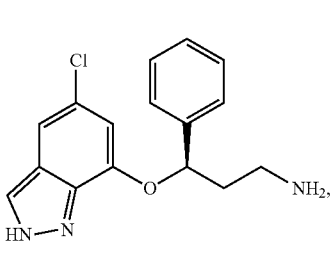
(GT-6049)
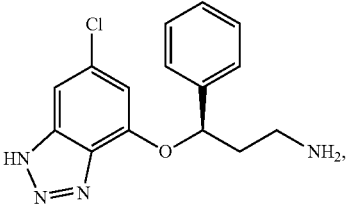
(GT-6050)
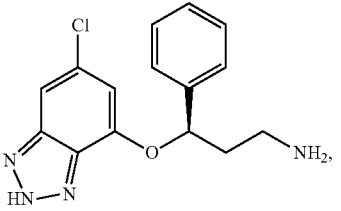
(GT-6051)
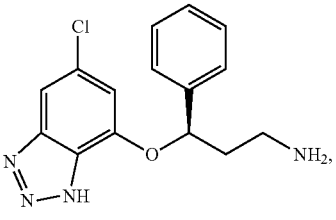
(GT-6052)
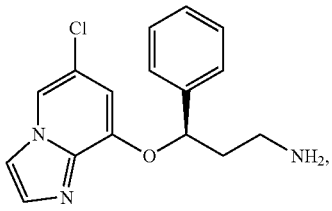
(GT-6053)
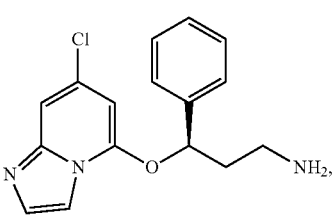

(GT-6054) 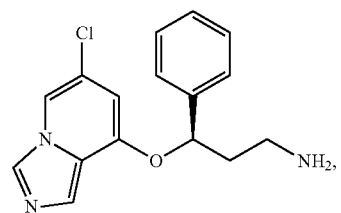
(GT-6055) 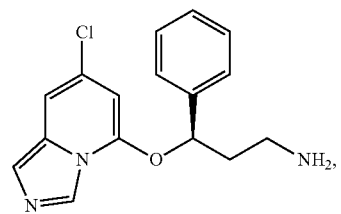
(GT-6056) 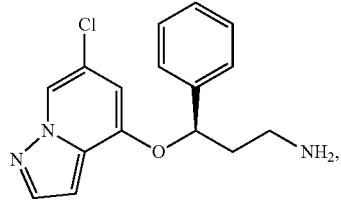
(GT-6057) 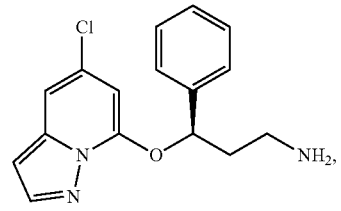
(GT-6058) 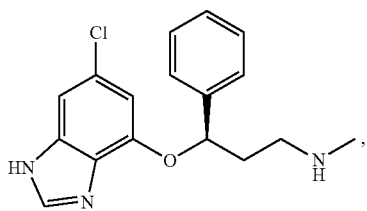
(GT-6059) 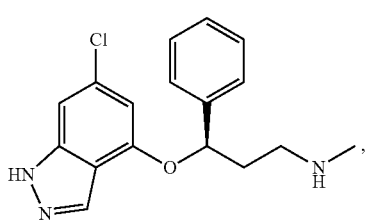
(GT-6060) 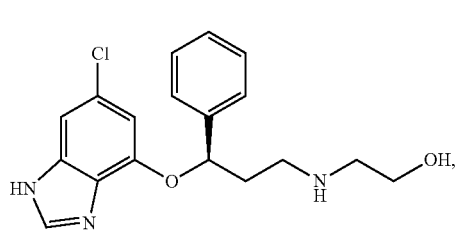
(GT-6061) 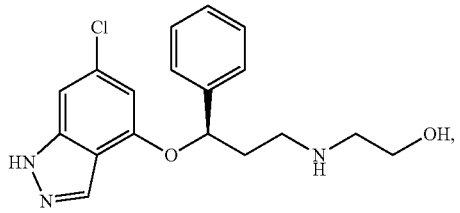
(GT-6062) 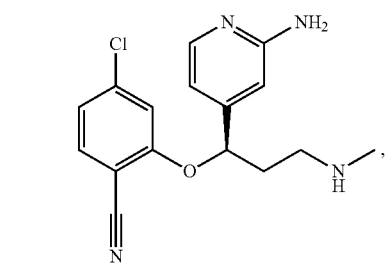
(GT-6063) 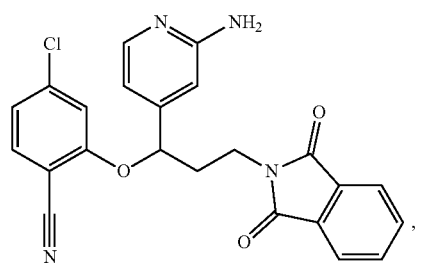
(GT-6064) 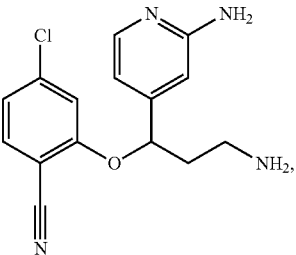
(GT-6065) 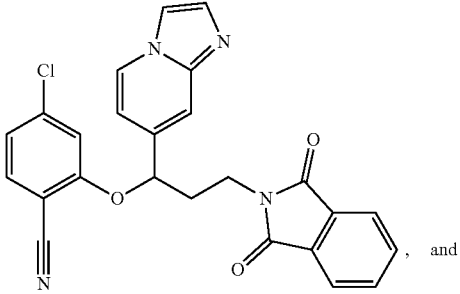
and
(GT-6066) 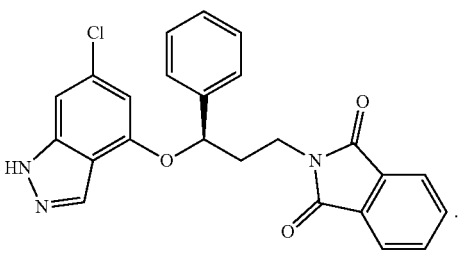
In preferred embodiments, the alkylamine or heteroalkylamine derivatives as represented by Formula (I-6) is selected from the following compounds listed by increasing IC50: (GT-6064), (GT-6065), (GT-6041), (GT-6045), (GT-6059), (GT-6066), (GT-6060), and (GT-6058).

In more preferred embodiments, the alkylamine or heteroalkylamine derivatives as represented by Formula (I-6) is selected from the following compounds listed by increasing IC50: (GT-6064) and (GT-6065).

In some exemplary embodiments, the N-aminoethyl N-phenyl amine derivative as represented by Formula (I-7) is selected from the following compounds:

(GT-7001)
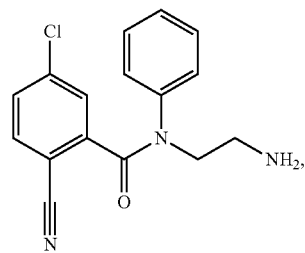

(GT-7002)
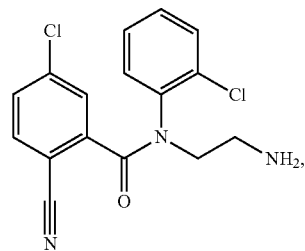

(GT-7003)
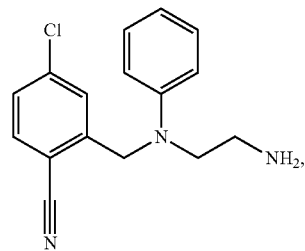

(GT-7004)
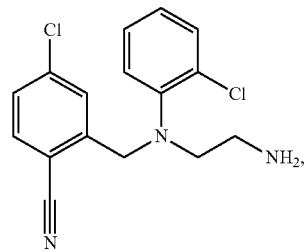

(GT-7005)
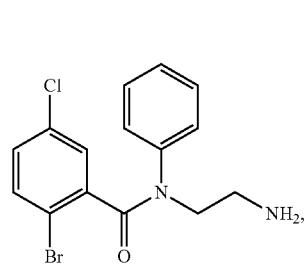

-continued (GT-7006)
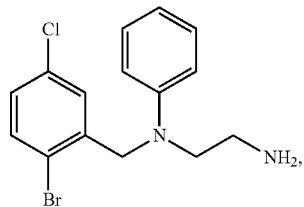

(GT-7007)
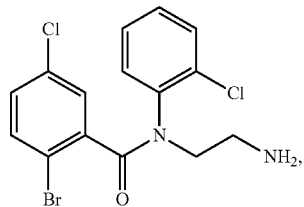

(GT-7008)
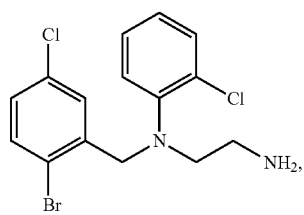

(GT-7009)
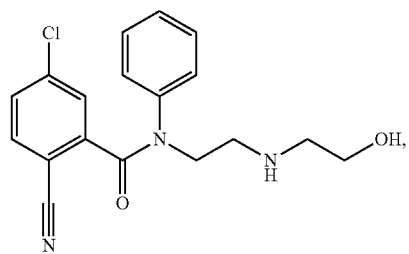

(GT-7010)
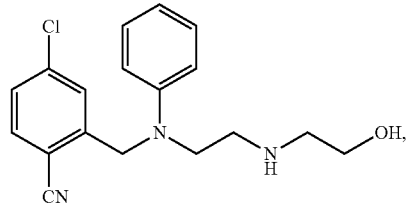

(GT-7011)
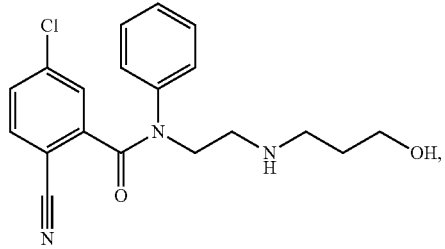

(GT-7012)
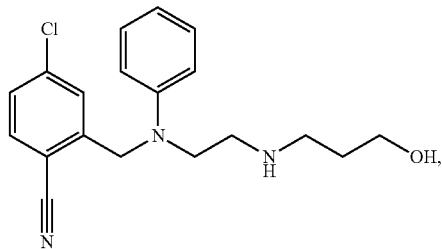
(GT-7013)
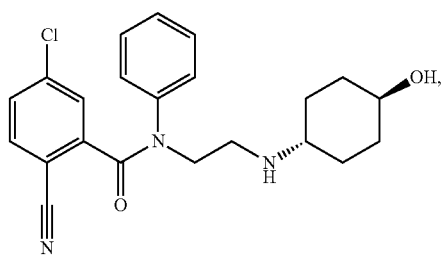
(GT-7014)
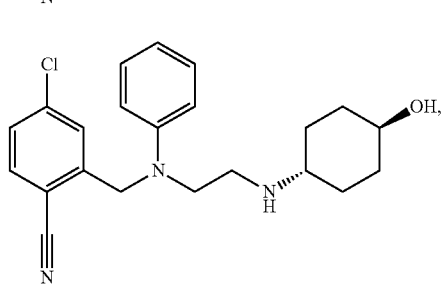
(GT-7015)
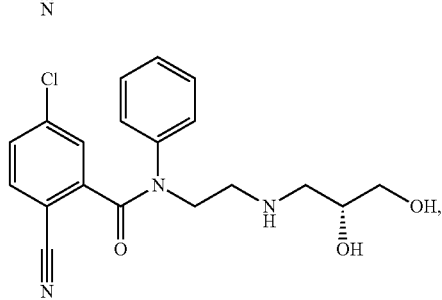
(GT-7016)
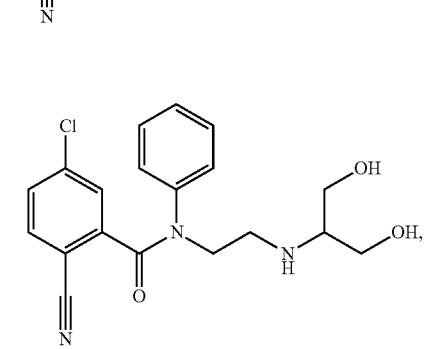
(GT-7017)
(GT-7018)
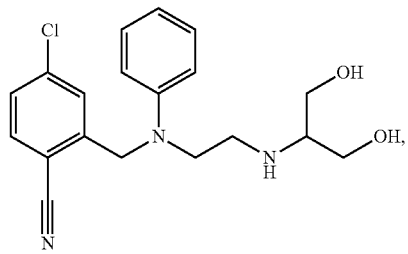
(GT-7019)
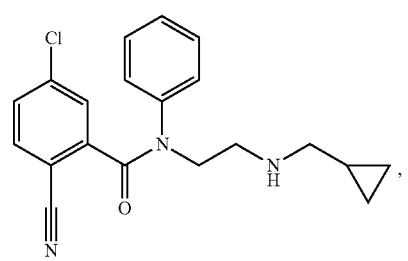
(GT-7020)
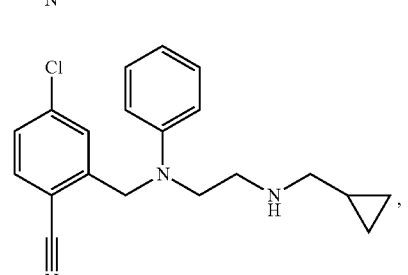
(GT-7021)
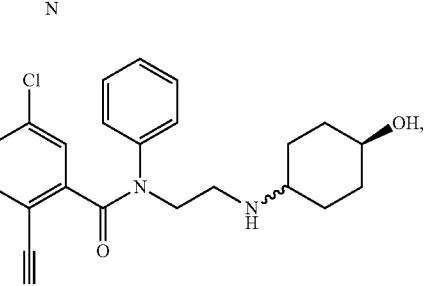
(GT-7022)
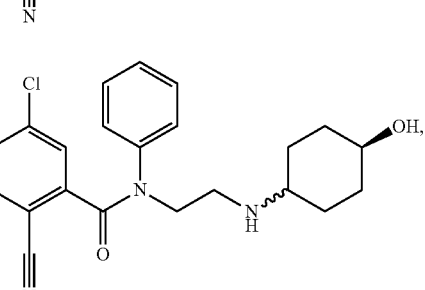
(GT-7023)
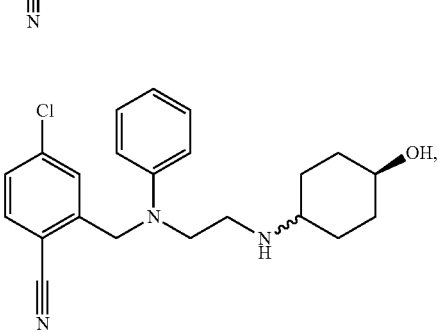
and (GT-7024)

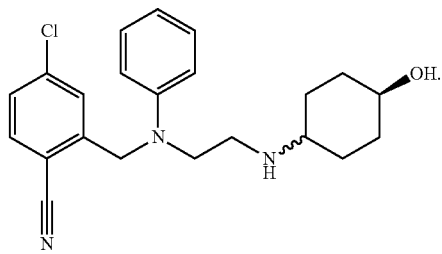

In preferred embodiments, the N-aminoethyl N-phenyl amine derivative as represented by Formula (I-7) is selected from the following compounds listed by increasing IC50: (GT-7003), (GT-7007), (GT-7002), (GT-7009), (GT-7011), (GT-7019), (GT-7017), (GT-7008), (GT-7004), (GT-7016), (GT-7010), (GT-7023), (GT-7024), (GT-7020), (GT-7018), and (GT-7006).

In more preferred embodiments, the N-aminoethyl N-phenyl amine derivative as represented by Formula (I-7) is selected from the following compounds listed by increasing IC50: (GT-7003), (GT-7007), (GT-7002), (GT-7009), (GT-7011), and (GT-7019).

In even more preferred embodiments, the N-aminoethyl N-phenyl amine derivative as represented by Formula (I-7) is selected from (GT-7003) and (GT-7007).

In some exemplary embodiments, the saturated heterocyclic fused benzene derivative as represented by Formula (I-8) is selected from the following compounds:

(GT-8001)

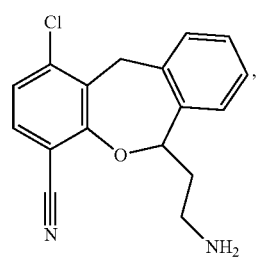

(GT-8002)

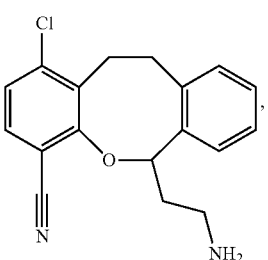

(GT-8003)

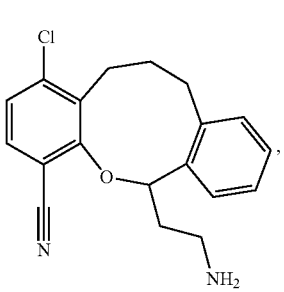

(GT-8004)

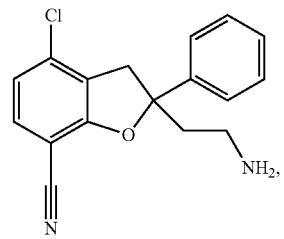

(GT-8005)

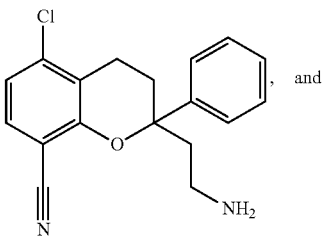

(GT-8006)

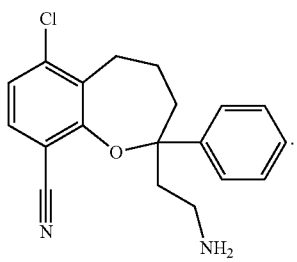

The present invention may include all pharmaceutically acceptable isotopically labelled compounds of Formulas (I-1)~(I-8) or salts thereof, wherein one or more atoms are replaced by atoms having the same atomic number, but an atomic mass or mass number different from the atomic mass or mass number which predominates in nature. Examples of isotopes suitable for inclusion in the compounds of the invention include isotopes of hydrogen, such as 2H and 3H, carbon, such as $^{11}$C $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as 32P, and sulfur, such as 35S. Certain isotopically labelled compounds of Formulas (I-1)~(I-8), for example, those incorporating a radioactive isotope, are useful in drug and/or substrate tissue distribution studies. The radioactive isotopes tritium, i.e., $^{3}$H, and carbon-14, i.e., 14C, are particularly useful for this purpose in view of their ease of incorporation and detection. Substitution with heavier isotopes such as deuterium, i.e., $^{2}$H, may afford certain therapeutic advantages resulting from greater metabolic stability, for example, increased in vivo half-life or reduced dosage requirements, and hence may be preferred in some circumstances. Substitution with positron-emitting isotopes, such as $^{11}$C, $^{18}$F, $^{15}$O and $^{13}$N, can be useful in Positron Emission Topography (PET) studies for examining substrate receptor occupancy. Isotopically labeled compounds of Formula (I) can generally be prepared by conventional techniques known to those skilled in the art using an appropriate isotopically labeled reagent in place of the non-labeled reagent previously employed.

Regarding iosmers, some compounds of Formulas (I-1)~(I-8) may include stereoisomers and tautomers, all of which are included within the scope of the invention. Stereoisomers of Formulas (I-1)~(I-8) include cis and trans isomers, optical isomers such as R and S enantiomers, diastereomers, geometric isomers, rotational isomers, atropisomers, and conformational isomers of the compounds of Formulas (I-1)~(I-8), including compounds exhibiting more than one type of isomerism; and mixtures thereof (such as racemates and diastereomeric pairs).

The compounds of Formulas (I-1)~(I-8) may exist in the form of pharmaceutically acceptable salts such as acid addition salts and/or base salts thereof. Suitable acid addition salts are formed from acids which form non-toxic salts e.g. hydrochloride/chloride. Suitable base salts are formed from bases which form non-toxic salts such as calcium and sodium salts. Hemisalts of acids and bases may also be formed, for example, hemisulfate and hemicalcium salts.

The compounds of Formulas (I-1)~(I-8) or a pharmaceutically acceptable salt thereof include all forms of the compound of Formulas (I-1)~(I-8) or pharmaceutically salt thereof, including hydrates, solvates, isomers (e.g. rotational stereoisomers), crystalline and non-crystalline forms, isomorphs, polymorphs, metabolites, and prodrugs thereof. Compounds of Formulas (I-1)~(I-8) may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions.

The compounds of Formulas (I-1)~(I-8) may exist in a continuum of solid states ranging from fully amorphous to fully crystalline. The term "amorphous" refers to a state in which the material lacks long-range order at the molecular level and, depending upon temperature, may exhibit the physical properties of a solid or a liquid. Typically, such materials do not give distinctive X-ray diffraction patterns and, while exhibiting the properties of a solid, are more formally described as a liquid. Upon heating, a change from apparent solid to a material with liquid properties occurs, which is characterized by a change of state, typically second order ("glass transition"). The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point"). The compounds of the invention may also exist in a mesomorphic state (mesophase or liquid crystal) when subjected to suitable conditions. The mesomorphic state is intermediate between the true crystalline state and the true liquid state (either melt or solution).

The invention also relates to prodrugs of the compounds of Formulas (I-1)~(I-8). Some compounds of Formulas (I-1)~(I-8) may have little or no pharmacological activity themselves, but they can, when administered into or onto the body, be converted into compounds of Formulas (I-1)~(I-8) having the desired activity, for example, by hydrolytic cleavage. Such derivatives are referred to as "prodrugs". Prodrugs in accordance with the invention can, for example, be produced by replacing appropriate functionalities present in the compounds of Formulas (I-1)~(I-8) with certain moieties known to those skilled in the art as "pro-moieties". In some embodiments, certain compounds of Formulas (I-1)~(I-8) may themselves act as prodrugs of other compounds of Formulas (I-1)~(I-8). Metabolites of compounds of Formulas (I-1)~(I-8) formed in vivo upon administration of the drug are also included within the scope of the invention.

Preparation of Formulas (I-1)~(I-8) Compounds

Starting materials and intermediates useful for making the compounds of the present invention can be obtained from chemical vendors or can be made according to methods described in the chemical art.

Compounds of the invention, including salts of the compounds, can be prepared using known organic synthesis techniques and can be synthesized according to any of numerous possible synthetic routes. The reactions for preparing compounds of the invention can be carried out in suitable solvents, which can be readily selected by one of skill in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention may involve the protection and deprotection of various chemical groups. The need for protection and deprotection, and the selection of appropriate protecting groups, can be readily determined by one skilled in the art. For example, a —CN group can be hydrolyzed to afford an amide group; a carboxylic acid can be converted to an amide; a carboxylic acid can be converted to an ester, which in turn can be reduced to an alcohol, which in turn can be further modified. For another example, an OH group can be converted into a better leaving group such as a methanesulfonate, which in turn is suitable for nucleophilic substitution, such as by a cyanide ion. For another example, an —S— can be oxidized to —S($=$O)— and/or —S($=$O)$_2$—. For yet another example, an unsaturated bond such as C$=$C double bond or C—C triple bond can be reduced to a saturated bond by hydrogenation.

Functional (reactive) groups can be protected/deprotected in the course of the synthetic scheme, if appropriate and/or desired. For example, an OH group can be protected by a benzyl, methyl, or acetyl group, which can be deprotected and converted back to the OH group in a later stage of the synthetic process. For another example, an NH$_2$ group can be protected by a benzyloxycarbonyl (Cbz) or BOC group; conversion back to the NH$_2$ group can be carried out at a later stage of the synthetic process via deprotection.

Reactions can be monitored according to any suitable method known in the art. For example, product formation can be monitored by spectroscopic means, such as LCMS, nuclear magnetic resonance spectroscopy (e.g., $^1$H or $^{13}$C), infrared spectroscopy, spectrophotometry (e.g., UV-visible), mass spectrometry, or by chromatographic methods such as high-performance liquid chromatography (HPLC) or thin layer chromatography (TLC).

In some embodiments, the compounds of may exist as stereoisomers, such as atropisomers, racemates, enantiomers, or diastereomers. Conventional techniques for the preparation/isolation of individual enantiomers include chiral synthesis from a suitable optically pure precursor or resolution of the racemate using, for example, chiral high-performance liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization, and one or both of the diastereoisomers converted to the corresponding pure enantiomer(s) by means well known to one skilled in the art. Chiral compounds (and chiral precursors thereof) may be obtained in enantiomerically enriched form using chromatography, typically HPLC, on an asymmetric resin with a mobile phase consisting of a hydrocarbon, typically heptane or hexane, containing from 0% to 50% 2-propanol, typically from 2% to 20%, and from 0% to 5% of an alkylamine, typically 0.1% diethylamine. Concentration of the eluate affords the enriched mixture. Stereoisomeric conglomerates may be separated by conventional techniques known to those skilled in the art. Suitable stereoselective techniques are well known to those of ordinary skill in the art. For a compound of Formula (I) that contains an alkenyl or alkenylene group, geometric cis/trans (or Z/E) isomers are possible. Cis/trans isomers may be separated by conventional techniques well known to those skilled in the art, for example, chromatography and fractional crystallization.

Pharmaceutical Composition and Administration

The present invention also provides a pharmaceutical composition comprising a therapeutically effective amount of the compound of Formulas (I-1)~(I-8), or a pharmaceutically acceptable salt, ester, prodrug, complex, solvate, isomer, or hydrate thereof, in any crystalline form or in amorphous form, a pharmaceutically acceptable carrier or excipient, and optionally comprising at least one additional medicinal or pharmaceutical agent.

The pharmaceutically acceptable carrier or excipient may comprise any conventional pharmaceutical carrier or excipient. Suitable pharmaceutical carriers include inert diluents or fillers, water and various organic solvents such as hydrates and solvates. The pharmaceutical compositions may, if desired, contain additional ingredients such as flavorings, binders, excipients and the like.

The term "therapeutically effective amount" as used herein refers to that amount of the compound (including a pharmaceutically acceptable salt thereof) being administered which will relieve to some extent one or more of the symptoms of the disorder being treated. In reference to the prophylaxis and/or treatment of a disorder or disease mediated by NOS or associated with aberrant NOS activity, a therapeutically effective amount refers to that amount which has the effect of relieving to some extent or eliminating one or more symptoms associated with the NOS-mediated disease or disorder. The term "treating"/"treatment", as used herein, unless otherwise indicated, means reversing, alleviating, inhibiting the progress of, or preventing the disorder or condition to which such term applies, or one or more symptoms of such disorder or condition. The term "treating"/"treatment" also includes adjuvant and neo-adjuvant treatment of a subject.

Administration of the compounds of Formulas (I-1)~(I-8) (including salts thereof) may be effected by any method that enables delivery of the compounds to the site of action. These methods include, for example, enteral routes (e.g., oral routes, buccal routes, sublabial routes, and sublingual routes), oral routes, intranasal routes, inhaled routes, intraduodenal routes, parenteral injection (including intravenous, subcutaneous, intramuscular, intravascular or infusion), intrathecal routes, epidural routes, intracerebral routes, intracerbroventricular routes, topical, and rectal administration. In one embodiment of the present invention, the compounds of Formulas (I-1)~(I-8) may be administered/effected by parenteral injection routes (e.g., intravenous injection route). In one embodiment of the present invention, the compounds of Formulas (I-1)~(I-8) may be administered or effected by oral routes.

Dosage of the compounds of Formulas (I-1)~(I-8) may be adjusted to provide the desired response. It is to be noted that dosage values may vary with the type and severity of the condition to be alleviated, and they may include single or multiple doses.

Kit or Packaged Pharmaceutical Product

The present invention provides a kit or packaged pharmaceutical product comprising a compound of Formulas (I-1)~(I-8), or a pharmaceutically acceptable salt, ester, prodrug, complex, solvate, isomer, or hydrate thereof, in any crystalline form or in amorphous form, and instructions for use thereof.

The kits (e.g., pharmaceutical packs) may include a provided pharmaceutical composition or compound and a container (e.g., a vial, ampule, bottle, syringe, and/or dispenser package, or other suitable containers). In some embodiments, the kits may optionally further include a second container comprising a pharmaceutical excipient for dilution or suspension of the pharmaceutical composition or compound. In some embodiments, a pharmaceutical composition or compound is provided in two containers, and when it is needed, the contents in the two containers are combined to form one unit dosage form.

Applications

The present invention provides a method of inhibiting one or more members selected from the family of nitric oxide synthases (NOS) including three isoforms inducible NOS (iNOS), endothelial NOS (eNOS), and neuronal NOS (nNOS), comprising contacting the NOS with an effective amount of a compound of Formulas (I-1)~(I-8), or a pharmaceutically acceptable salt, ester, prodrug, complex, solvate, isomer, or hydrate thereof, in any crystalline form or in amorphous form. In preferred embodiments, the present invention provides a method of selectively inhibiting (iNOS) over eNOS and/or nNOS.

The step of inhibiting may be carried out in vitro or in vivo. "In vitro" refers to procedures performed in an artificial environment such as, e.g., without limitation, in a test tube or culture medium. "In vivo" refers to procedures performed within a living organism such as, without limitation, a human, a mouse, dog, rat or rabbit.

As used herein, the term "IC50" refers to the half maximal inhibitory concentration of an inhibitor in inhibiting biological or biochemical function. This quantitative measure indicates how much of a particular inhibitor is needed to inhibit a given biological process (or component of a process, i.e. an enzyme, cell, cell receptor or microorganism) by half. In other words, it is the half maximal (50%) inhibitory concentration (IC) of a substance (50% IC, or IC50). EC50 refers to the plasma concentration required for obtaining 50%> of a maximum effect in vivo.

In some embodiments, the method of the invention utilizes the NOS inhibitor of Formulas (I-1)~(I-8) with an IC50 value of about or less than a predetermined value, as ascertained in an in vitro assay. In some embodiments, the inhibitor inhibits NOS (e.g. iNOS) with an IC50 value of about 0.01 µM or less, 0.02 µM or less, 0.03 µM or less, 0.04 µM or less, 0.05 µM or less, 0.06 µM or less, 0.07 µM or less, 0.08 µM or less, 0.09 µM or less, 0.1 µM or less, 0.2 µM or less, 0.4 µM or less, 0.6 µM or less, 0.8 µM or less, 1 µM or less, 2 µM or less, 3 µM or less, 4 µM or less, 5 µM or less, 10 µM or less, 15 µM or less, 20 µM or less, or 25 µM or less (or a number in the range defined by and including any two numbers above).

The present invention provides a method for prophylaxis and/or treatment of a disorder or disease mediated by NOS such as iNOS or associated with aberrant NOS such as iNOS activity, comprising administering to a subject in need thereof a therapeutically effective amount of a compound of Formulas (I-1)~(I-8), or a pharmaceutically acceptable salt, ester, prodrug, complex, solvate, isomer, or hydrate thereof, in any crystalline form or in amorphous form; or a pharmaceutical composition thereof.

As used herein, the term "NOS-mediated disorder" such as "iNOS-mediated disorder" means any disease, disorder, or other pathological condition in which NOS such as iNOS is known to play a role. Accordingly, in some embodiments, the present invention relates to treating or lessening the severity of one or more diseases in which NOS such as iNOS is known to play a role. The methods of the invention are useful for treating a disease condition associated with NOS such as iNOS. Any disease condition that results directly or indirectly from an abnormal activity or expression level of NOS such as iNOS can be an intended disease condition. Different disease conditions associated with NOS such as iNOS have been reported.

The disorder or disease includes inflammatory diseases, and proliferative diseases such as cancer including gastrointestinal, colorectal, gynecological, pancreatic, head and neck, esophageal, breast, lung, and central nervous system tumors.

Compounds of Formulas (I-1)~(I-8), as well as pharmaceutical compositions comprising them, can be administered to treat any of the described diseases, alone or in combination with a medical therapy. Medical therapies include, for example, surgery and radiotherapy (e.g. gamma-radiation, neutron beam radiotherapy, electron beam radiotherapy, proton therapy, brachytherapy, systemic radioactive isotopes).

The invention will be described in greater detail by way of specific examples. The following examples are offered for illustrative purposes, and are not intended to limit the invention in any manner. Those of skill in the art will readily recognize a variety of non-critical parameters that can be changed or modified to yield essentially the same results. Additional compounds within the scope of this invention may be prepared using the methods illustrated in these Examples, either alone or in combination with techniques generally known in the art.

EXAMPLES

Formulas (I-1)~(I-4): Molecular Design

Inducible nitric oxide synthase (iNOS) plays key roles in variety of diseases including inflammatory diseases and cancer. Selective iNOS inhibitors could have anti-inflammatory and anti-cancer potential. S,S'-1,4-phenylene-bis(1, 2-ethanediyl)bis-isothiourea (PBIT) inhibits iNOS, but does not exhibit necessary selectivity comparing its inhibition on iNOS to endothelial NOS (eNOS), which could increase risk factors for atherosclerosis.

With toxicity being a concern, iNOS inhibition selectivity vs. eNOS is an important factor in selective inhibitor design. To this end, active site comparison as shown in FIG. 1 revealed an important structural difference. FIG. 1 shows alignment of PDB 1D1X bovine eNOS with PBIT (stick model in green for carbon atoms) bound against PDB 1NSI human iNOS with L-Arg (yellow stick for carbon atoms). ASP382 (iNOS) and ASN368 (eNOS) are marked with a red circle. The residue in the region of iNOS which binds the carboxylic acid of L-arginine is ASP382. The residue which overlaps the same position in bovine eNOS is ASN368 (in human it is ASN366, PDB 6AV6). These 2 residues are very different. The one the inventors were targeting has a hydrogen bond (H-bond) acceptor (iNOS with ASP382) and the one the inventors want to avoid has a H-bond donor (eNOS with ASN368). As compared to PBIT, compounds of the present invention show more potency, selective inhibition of iNOS vs. eNOS and nNOS, less toxicity and overall anti-inflammatory and anti-cancer efficacies.

Two steps of modeling procedures were carried out in the CADD process to assign binding scores for the proposed molecules. First, a "ligand based" pharmacophore model was developed based on the key features and the bound conformation of PBIT defined in the x-ray (bovine eNOS PDB 1D1X). The three-feature pharmacophore model of FIG. 1 was developed to capture the isothiourea warhead interactions with Glu377 as well as hydrophobic interactions with the aliphatic central linker. The second step was to keep the pharmacophore model in place and apply docking to predict binding affinity of each designed molecule in terms of a binding score.

CADD is carried out using Molecular Operating Environment (MOE) software, one of the top leading modeling software developed by Chemical Computing Group (https://www.chemcomp.com/).

The docking score (S) from induced fit docking (IFD) with the guidance of certain pharmacophore (F) for the target protein (iNOS or eNOS). The inventors used 3 features pharmacophore model (F3). The S are calculated based on the procedures of very complicated yet sophisticated mathematics process. Basically, sample the possible conformations of both small molecules as well as receptors, followed by ranking by scoring process. All the theories are hard coded into the process of the module the inventors employed for the estimations.

In addition, the differences between the S from iNOS docking and that from eNOS docking are calculated. The negative meaning the compound shows more favorable score in iNOS than that in eNOS, based on calculation. This is our defined function to assess the potential selectivity from computational estimation.

Formula (I-1)

Figure 2:
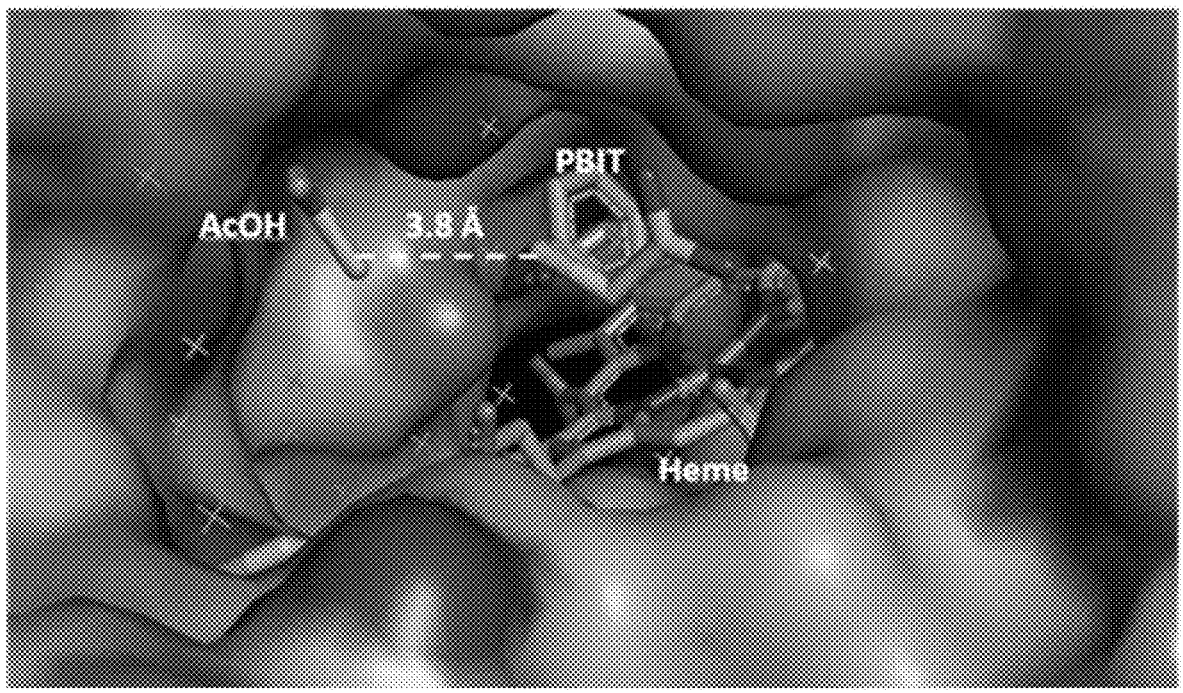
FIG. 2 shows the iNOS-PBIT crystal structure with an acetic acid (AcOH) molecule in proximity to the PBIT.
Figure 3:
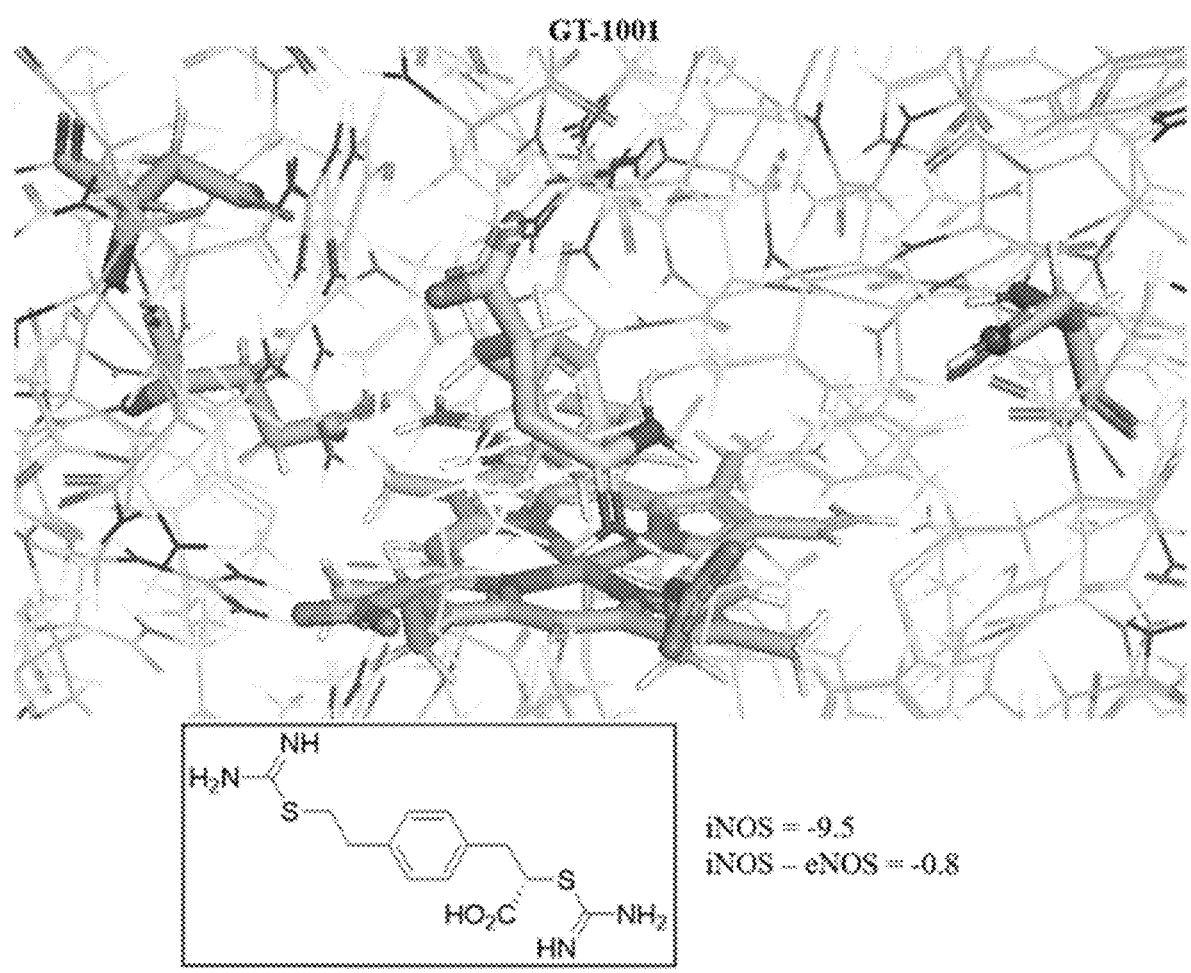
FIG. 3 illustrates the binding image of a compound of Formula (I-1) to iNOS or eNOS in accordance with an exemplary embodiment of the present invention.
Figure 4:
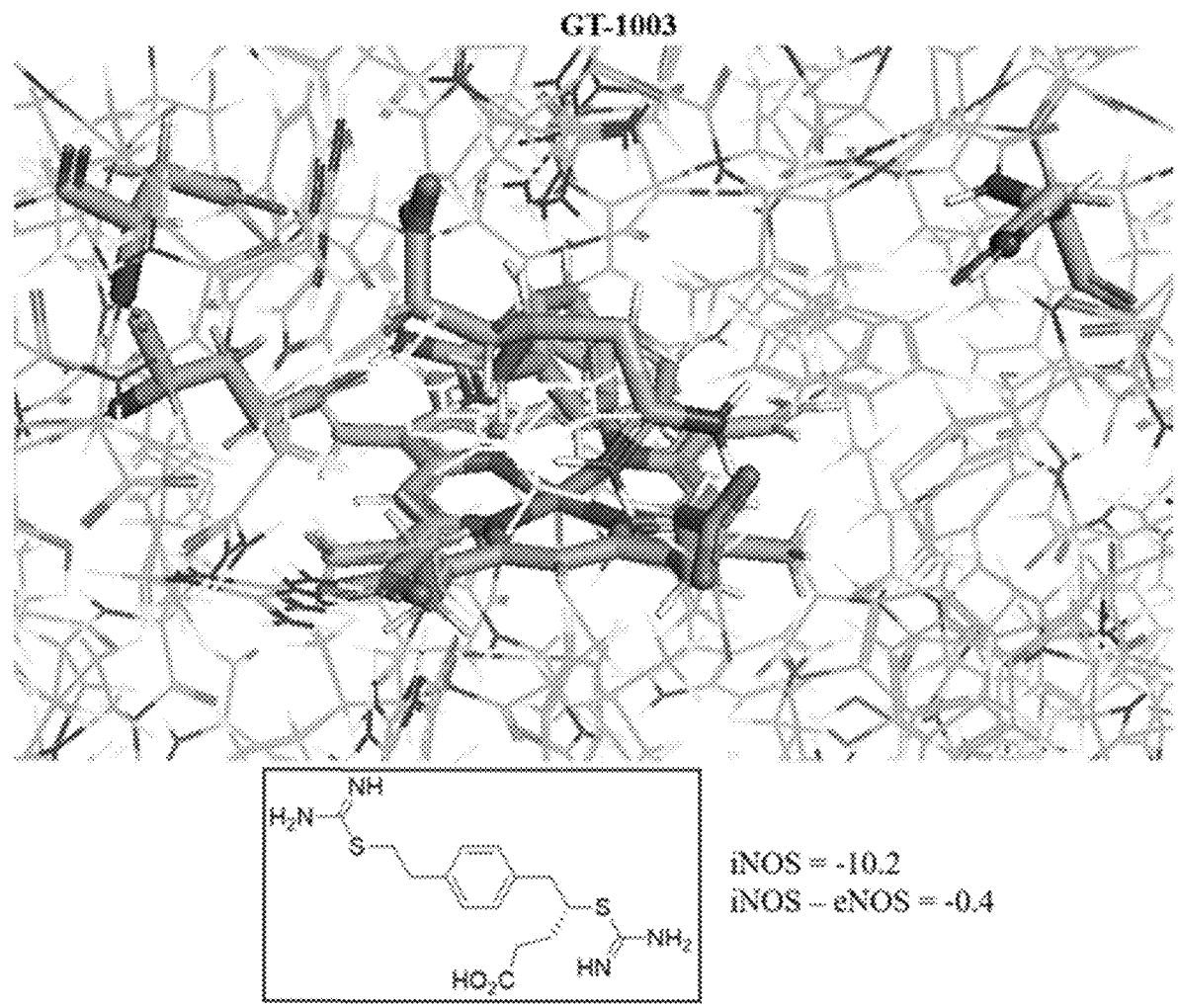
FIG. 4 illustrates the binding image of another compound of Formula (I-1) to iNOS or eNOS in accordance with an exemplary embodiment of the present invention.
Figure 5:
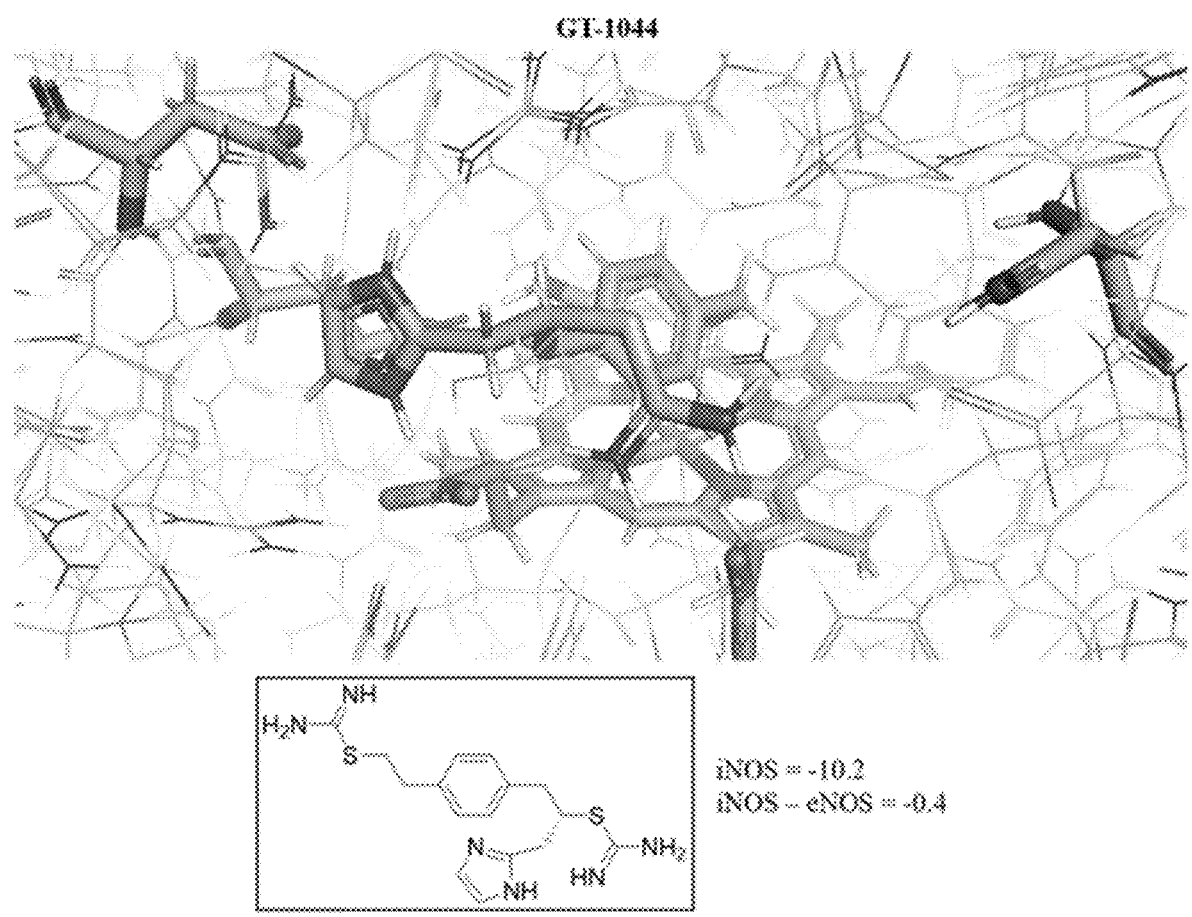
FIG. 5 illustrates the binding image of still another compound of Formula (I-1) to iNOS or eNOS in accordance with an exemplary embodiment of the present invention.
Figure 6:
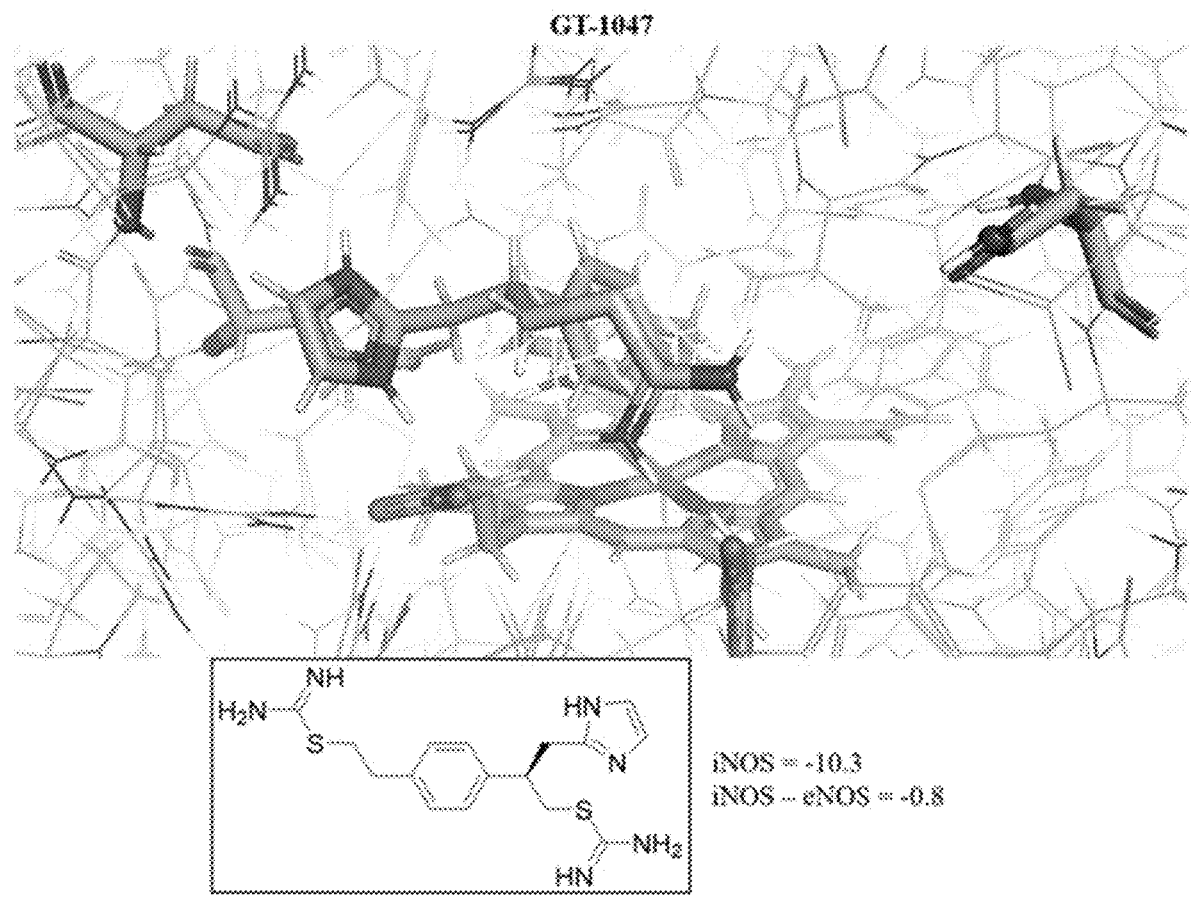
FIG. 6 illustrates the binding image of still another compound of Formula (I-1) to iNOS or eNOS in accordance with an exemplary embodiment of the present invention.
Figure 7:
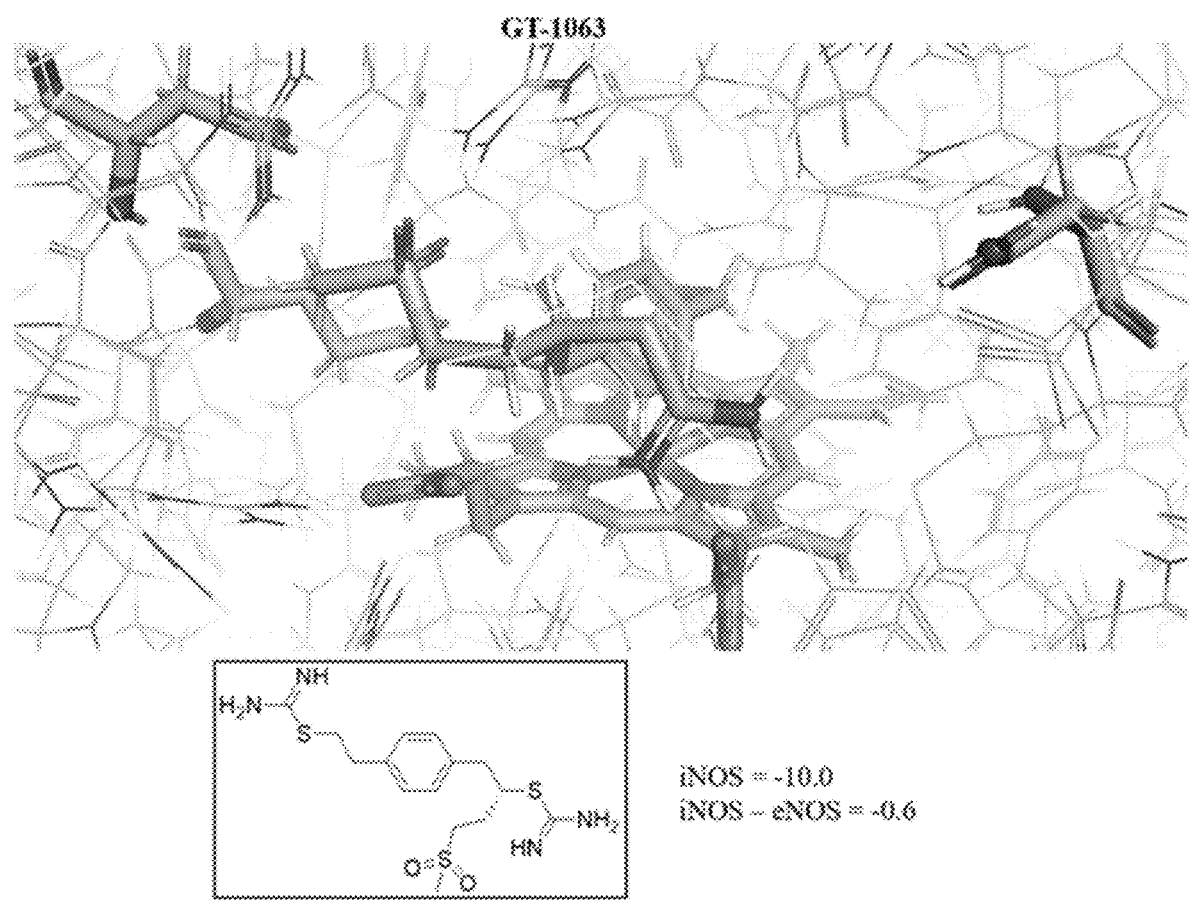
FIG. 7 illustrates the binding image of still another compound of Formula (I-1) to iNOS or eNOS in accordance with an exemplary embodiment of the present invention.

Referring to FIG. 2, in the iNOS-PBIT crystal structure, there is an acetic acid (AcOH) molecule in proximity to the PBIT. FIG. 2 is a view of PBIT 3.8A in proximity to acetic acid (AcOH) also bound to iNOS.

In the embodiments of Formula (I-1), a sidechain is added to replace the acetic acid in PBIT. In specific embodiments, the new NOS inhibitors below have some groups designed to replace the acetic acid as shown in FIG. 2.

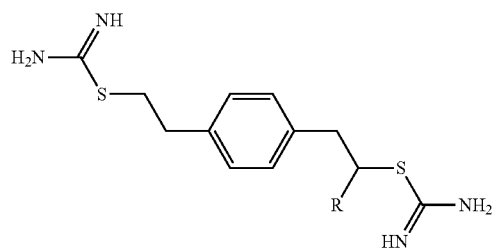

In exemplary embodiments, a class of compounds represented by Formula (I-1) is listed in the tables below. The compound ID, SMILES code, MW, CD clogP and CD TPSA are listed in Table I-1-1. Their calculated induced fit docking (IFD) scores for binding to iNOS and eNOS are shown in Table I-1-2. The extra sidechain R-group is intended to provide for additional binding selectivity and potency. A sidechain R to interact with iNOS selectively vs. eNOS is shown below, in which a side chain R is to interact with iNOS selectively vs. eNOS. "n=0-3" indicates that the group in the parentheses is repeated 1, 2 or 3 times. The n is variable.

TABLE I-1-1

| GT-ID | SMILES Code | MW | CD clogP | CD TPSA |
|---|---|---|---|---|
| GT-1001 | NC(S[C@H](C(O)=O)CC1=CC=C(CCSC(N)=N)C=C1)=N | 326 | 1.2 | 137 |
| GT-1002 | NC(S[C@H](CC(O)=O)CC1=CC=C(CCSC(N)=N)C=C1)=N | 340 | 1.4 | 137 |
| GT-1003 | NC(S[C@H](CCC(O)=O)CC1=CC=C(CCSC(N)=N)C=C1)=N | 354 | 1.8 | 137 |
| GT-1004 | NC(SC[C@H](C(O)=O)C1=CC=C(CCSC(N)=N)C=C1)=N | 326 | 1.1 | 137 |
| GT-1005 | NC(SC[C@H](CC(O)=O)C1=CC=C(CCSC(N)=N)C=C1)=N | 340 | 1.4 | 137 |
| GT-1006 | NC(SC[C@H](CCC(O)=O)C1=CC=C(CCSC(N)=N)C=C1)=N | 354 | 1.6 | 137 |
| GT-1007 | NC(S[C@H](CO)CC1=CC=C(CCSC(N)=N)C=C1)=N | 312 | 1 | 120 |
| GT-1008 | NC(S[C@H](CCO)CC1=CC=C(CCSC(N)=N)C=C1)=N | 326 | 1.4 | 120 |
| GT-1009 | NC(S[C@H](CCCO)CC1=CC=C(CCSC(N)=N)C=C1)=N | 340 | 1.4 | 120 |
| GT-1010 | NC(SC[C@H](CO)C1=CC=C(CCSC(N)=N)C=C1)=N | 312 | 1 | 120 |
| GT-1011 | NC(SC[C@H](CCO)C1=CC=C(CCSC(N)=N)C=C1)=N | 326 | 1 | 120 |
| GT-1012 | NC(SC[C@H](CCCO)C1=CC=C(CCSC(N)=N)C=C1)=N | 340 | 1.5 | 120 |
| GT-1013 | NC(S[C@H](CNC(C)=O)CC1=CC=C(CCSC(N)=N)C=C1)=N | 353 | 0.97 | 129 |
| GT-1014 | NC(S[C@H](CCNC(C)=O)CC1=CC=C(CCSC(N)=N)C=C1)=N | 368 | 1.3 | 129 |
| GT-1015 | NC(S[C@H](CCCNC(C)=O)CC1=CC=C(CCSC(N)=N)C=C1)=N | 381 | 1.1 | 129 |
| GT-1016 | NC(SC[C@H](CNC(C)=O)C1=CC=C(CCSC(N)=N)C=C1)=N | 353 | 0.85 | 129 |
| GT-1017 | NC(SC[C@H](CCNC(C)=O)C1=CC=C(CCSC(N)=N)C=C1)=N | 368 | 0.68 | 129 |
| GT-1018 | NC(SC[C@H](CCCNC(C)=O)C1=CC=C(CCSC(N)=N)C=C1)=N | 381 | 1.2 | 129 |
| GT-1019 | NC(S[C@H](CN(C)C)CC1=CC=C(CCSC(N)=N)C=C1)=N | 340 | 2 | 103 |
| GT-1020 | NC(S[C@H](CCN(C)C)CC1=CC=C(CCSC(N)=N)C=C1)=N | 354 | 2.3 | 103 |
| GT-1021 | NC(S[C@H](CCCN(C)C)CC1=CC=C(CCSC(N)=N)C=C1)=N | 367 | 2.2 | 103 |
| GT-1022 | NC(SC[C@H](CN(C)C)C1=CC=C(CCSC(N)=N)C=C1)=N | 340 | 1.9 | 103 |
| GT-1023 | NC(SC[C@H](CCN(C)C)C1=CC=C(CCSC(N)=N)C=C1)=N | 354 | 1.8 | 103 |
| GT-1024 | NC(SC[C@H](CCCN(C)C)C1=CC=C(CCSC(N)=N)C=C1)=N | 368 | 2.3 | 103 |
| GT-1025 | NC(S[C@H](C(N)=O)CC1=CC=C(CCSC(N)=N)C=C1)=N | 325 | 0.39 | 143 |
| GT-1026 | NC(S[C@H](CC(N)=O)CC1=CC=C(CCSC(N)=N)C=C1)=N | 339 | 0.75 | 143 |
| GT-1027 | NC(S[C@H](CCC(N)=O)CC1=CC=C(CCSC(N)=N)C=C1)=N | 354 | 1.1 | 143 |
| GT-1028 | NC(SC[C@H](C(N)=O)C1=CC=C(CCSC(N)=N)C=C1)=N | 325 | 0.37 | 143 |
| GT-1029 | NC(SC[C@H](CC(N)=O)C1=CC=C(CCSC(N)=N)C=C1)=N | 339 | 0.67 | 143 |
| GT-1030 | NC(SC[C@H](CCC(N)=O)C1=CC=C(CCSC(N)=N)C=C1)=N | 354 | 0.64 | 143 |
| GT-1031 | NC(S[C@H](C(NC)=O)CC1=CC=C(CCSC(N)=N)C=C1)=N | 339 | 0.66 | 129 |
| GT-1032 | NC(S[C@H](CC(NC)=O)CC1=CC=C(CCSC(N)=N)C=C1)=N | 354 | 0.97 | 129 |
| GT-1033 | NC(S[C@H](CCC(NC)=O)CC1=CC=C(CCSC(N)=N)C=C1)=N | 368 | 1.3 | 129 |
| GT-1034 | NC(SC[C@H](C(NC)=O)C1=CC=C(CCSC(N)=N)C=C1)=N | 339 | 0.74 | 129 |
| GT-1035 | NC(SC[C@H](CC(NC)=O)C1=CC=C(CCSC(N)=N)C=C1)=N | 354 | 0.85 | 129 |
| GT-1036 | NC(SC[C@H](CCC(NC)=O)C1=CC=C(CCSC(N)=N)C=C1)=N | 368 | 0.68 | 129 |
| GT-1037 | NC(S[C@H](C(N(C)C)=O)CC1=CC=C(CCSC(N)=N)C=C1)=N | 354 | 1.1 | 120 |
| GT-1038 | NC(S[C@H](CC(N(C)C)=O)CC1=CC=C(CCSC(N)=N)C=C1)=N | 368 | 1.4 | 120 |
| GT-1039 | NC(S[C@H](CCC(N(C)C)=O)CC1=CC=C(CCSC(N)=N)C=C1)=N | 382 | 1.7 | 120 |
| GT-1040 | NC(SC[C@H](C(N(C)C)=O)C1=CC=C(CCSC(N)=N)C=C1)=N | 354 | 1.1 | 120 |
| GT-1041 | NC(SC[C@H](CC(N(C)C)=O)C1=CC=C(CCSC(N)=N)C=C1)=N | 368 | 1.2 | 120 |
| GT-1042 | NC(SC[C@H](CCC(N(C)C)=O)C1=CC=C(CCSC(N)=N)C=C1)=N | 382 | 0.96 | 120 |
| GT-1043 | NC(S[C@H](C1=NC=CN1)CC2=CC=C(CCSC(N)=N)C=C2)=N | 349 | 0.73 | 124 |
| GT-1044 | NC(S[C@H](CC1=NC=CN1)CC2=CC=C(CCSC(N)=N)C=C2)=N | 363 | 1.53 | 124 |
| GT-1045 | NC(S[C@H](CCC1=NC=CN1)CC2=CC=C(CCSC(N)=N)C=C2)=N | 377 | 1.9 | 124 |
| GT-1046 | NC(SC[C@H](C1=NC=CN1)C2=CC=C(CCSC(N)=N)C=C2)=N | 348 | 1.5 | 124 |
| GT-1047 | NC(SC[C@H](CC1=NC=CN1)C2=CC=C(CCSC(N)=N)C=C2)=N | 362 | 1.5 | 124 |
| GT-1048 | NC(SC[C@H](CCC1=NC=CN1)C2=CC=C(CCSC(N)=N)C=C2)=N | 377 | 2 | 124 |
| GT-1049 | NC(S[C@H](C1=CN=CN1)CC2=CC=C(CCSC(N)=N)C=C2)=N | 348 | 0.73 | 124 |
| GT-1050 | NC(S[C@H](CC1=CN=CN1)CC2=CC=C(CCSC(N)=N)C=C2)=N | 363 | 1.5 | 124 |
| GT-1051 | NC(S[C@H](CCC1=CN=CN1)CC2=CC=C(CCSC(N)=N)C=C2)=N | 377 | 1.91 | 124 |
| GT-1052 | NC(SC[C@H](C1=CN=CN1)C2=CC=C(CCSC(N)=N)C=C2)=N | 348 | 1.5 | 124 |
| GT-1053 | NC(SC[C@H](CC1=CN=CN1)C2=CC=C(CCSC(N)=N)C=C2)=N | 362 | 1.47 | 124 |
| GT-1054 | NC(SC[C@H](CCC1=CN=CN1)C2=CC=C(CCSC(N)=N)C=C2)=N | 377 | 2 | 124 |
| GT-1055 | NC(S[C@H](C1=NN=CO1)CC2=CC=C(CCSC(N)=N)C=C2)=N | 350 | −0.65 | 134 |
| GT-1056 | NC(S[C@H](CC1=NN=CO1)CC2=CC=C(CCSC(N)=N)C=C2)=N | 364 | 0.153 | 134 |
| GT-1057 | NC(S[C@H](CCC1=NN=CO1)CC2=CC=C(CCSC(N)=N)C=C2)=N | 379 | 0.53 | 134 |
| GT-1058 | NC(SC[C@H](C1=NN=CO1)C2=CC=C(CCSC(N)=N)C=C2)=N | 350 | 0.093 | 134 |
| GT-1059 | NC(SC[C@H](CC1=NN=CO1)C2=CC=C(CCSC(N)=N)C=C2)=N | 364 | 0.093 | 134 |
| GT-1060 | NC(SC[C@H](CCC1=NN=CO1)C2=CC=C(CCSC(N)=N)C=C2)=N | 379 | 0.62 | 134 |
| GT-1061 | NC(S[C@H](S(=O)(C)=O)CC1=CC=C(CCSC(N)=N)C=C1)=N | 361 | 0.37 | 134 |
| GT-1062 | NC(S[C@H](CS(=O)(C)=O)CC1=CC=C(CCSC(N)=N)C=C1)=N | 375 | 0.66 | 134 |
| GT-1063 | NC(S[C@H](CCS(=O)(C)=O)CC1=CC=C(CCSC(N)=N)C=C1)=N | 389 | 0.96 | 134 |
| GT-1064 | NC(SC[C@H](S(=O)(C)=O)C1=CC=C(CCSC(N)=N)C=C1)=N | 361 | 0.43 | 134 |
| GT-1065 | NC(SC[C@H](CS(=O)(C)=O)C1=CC=C(CCSC(N)=N)C=C1)=N | 374 | 0.52 | 134 |
| GT-1066 | NC(SC[C@H](CCS(=O)(C)=O)C1=CC=C(CCSC(N)=N)C=C1)=N | 389 | 0.26 | 134 |

TABLE I-1-1-continued

| GT-ID | SMILES Code | MW | CD clogP | CD TPSA |
|---|---|---|---|---|

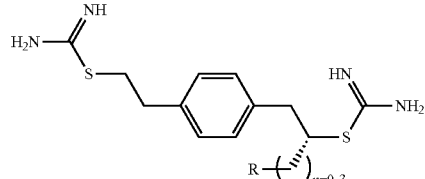

| cmpd | R |
|---|---|
| GT-1001 to GT-1006 | —$CO_2H$ |
| GT-1007 to GT-1012 | —OH |
| GT-1013 to GT-1018 | —HNAc |
| GT-1019 to GT-1024 | —$NMe_2$ |
| GT-1026 to GT-1030 | —$C(O)NH_2$ |
| GT-1031 to GT-10036 | —$C(O)NHMe_2$ |
| GT-1037 to GT-1042 | —$C(O)NMe_2$ |
| OT-1043 to GT-1048 | imidazol-2-yl |
| GT-1049 to GT-1054 | imidazol-4-yl |
| GT-1055 to GT-1060 | 1,3,4-oxadiazol-2-yl |
| GT-1061 to GT-1066 | —$SO_2Me$ |

Table I-1-2 is a list of compounds and their calculated induced fit docking (IFD) scores for binding to iNOS and eNOS. As shown in Table I-1-2, a more negative score indicates better binding energy. These energy values are provided under the column headers labeled "S_IFD_F3_iNOS" and "S_IFD_F3_eNOS". The column header "iNOS-eNOS" describes the difference in binding between iNOS and eNOS. The values <−0.4 indicate favorable binding to iNOS as compared to eNOS. Further comparison with consideration for the 3D-fit within the binding site resulted in the diverse set of compounds.

TABLE I-1-2

| GT-ID | S_IFD_F3_iNOS | S_IFD_F3_eNOS | iNOS-eNOS |
|---|---|---|---|
| GT-1001 | −9.5 | −8.7 | −0.8 |
| GT-1002 | −9.0 | −9.6 | 0.5 |
| GT-1003 | −10.2 | −9.7 | −0.4 |
| GT-1004 | −8.6 | −8.6 | −0.1 |
| GT-1005 | −9.1 | −9.5 | 0.4 |
| GT-1006 | −10.3 | −10.4 | 0.1 |
| GT-1007 | −8.7 | −8.2 | −0.4 |
| GT-1008 | −9.4 | −8.9 | −0.4 |
| GT-1009 | −9.5 | −9.4 | −0.1 |
| GT-1010 | −8.9 | −8.9 | 0.0 |
| GT-1011 | −9.7 | −9.5 | −0.1 |
| GT-1012 | −10.1 | −10.2 | 0.1 |
| GT-1013 | −9.7 | −9.3 | −0.5 |
| GT-1014 | −9.6 | −10.1 | 0.5 |
| GT-1015 | −10.5 | −10.0 | −0.5 |
| GT-1016 | −9.8 | −9.4 | −0.5 |
| GT-1017 | −10.1 | −10.2 | 0.1 |
| GT-1018 | −10.3 | −10.1 | −0.3 |
| GT-1019 | −9.5 | −9.5 | 0.0 |
| GT-1020 | −9.7 | −9.5 | −0.2 |
| GT-1021 | −9.7 | −10.1 | 0.4 |
| GT-1022 | −9.5 | −9.2 | −0.3 |
| GT-1023 | −9.7 | −9.9 | 0.2 |
| GT-1024 | −9.8 | −10.4 | 0.6 |
| GT-1025 | −8.7 | −8.8 | 0.1 |
| GT-1026 | −9.1 | −9.4 | 0.3 |
| GT-1027 | −9.5 | −9.8 | 0.3 |
| GT-1028 | −8.8 | −9.0 | 0.2 |
| GT-1029 | −9.4 | 9.6 | 0.2 |
| GT-1030 | −9.7 | −9.5 | −0.2 |
| GT-1031 | −8.9 | −9.3 | 0.4 |
| GT-1032 | −9.7 | −9.8 | 0.1 |
| GT-1033 | −9.9 | −10.2 | 0.3 |

TABLE I-1-2-continued

| GT-ID | S_IFD_F3_iNOS | S_IFD_F3_eNOS | iNOS-eNOS |
|---|---|---|---|
| GT-1034 | −9.2 | −8.8 | −0.4 |
| GT-1035 | −9.4 | −9.6 | 0.3 |
| GT-1036 | −8.8 | −9.5 | 0.8 |
| GT-1037 | −9.5 | −9.2 | −0.3 |
| GT-1038 | −9.9 | −10.1 | 0.2 |
| GT-1039 | −10.1 | −10.0 | −0.2 |
| GT-1040 | −9.8 | −9.3 | −0.5 |
| GT-1041 | −9.8 | −10.1 | 0.3 |
| GT-1042 | −10.2 | −9.9 | −0.3 |
| GT-1043 | −8.9 | −9.3 | 0.4 |
| GT-1044 | −10.2 | −9.7 | −0.4 |
| GT-1045 | −9.5 | −9.8 | 0.3 |
| GT-1046 | −9.8 | −9.6 | −0.1 |
| GT-1047 | −10.3 | −9.5 | −0.8 |
| GT-1048 | −10.3 | −10.2 | −0.2 |
| GT-1049 | −9.1 | −9.2 | 0.1 |
| GT-1050 | −9.8 | −9.3 | −0.4 |
| GT-1051 | −9.1 | −9.8 | 0.8 |
| GT-1052 | −9.8 | −9.6 | −0.2 |
| GT-1053 | −9.9 | −10.0 | 0.1 |
| GT-1054 | −9.2 | −9.5 | 0.3 |
| GT-1055 | −8.9 | −9.1 | 0.2 |
| GT-1056 | −9.7 | −9.6 | −0.2 |
| GT-1057 | −10.0 | −9.6 | −0.3 |
| GT-1058 | −9.2 | −9.6 | 0.3 |
| GT-1059 | −10.2 | −9.8 | −0.4 |
| GT-1060 | −10.2 | −10.1 | −0.1 |
| GT-1061 | −9.4 | −9.4 | 0.0 |
| GT-1062 | −9.8 | −9.4 | −0.4 |
| GT-1063 | −10.0 | −9.4 | −0.6 |
| GT-1064 | −9.4 | −8.9 | −0.5 |
| GT-1065 | −10.4 | −10.4 | 0.1 |
| GT-1066 | −9.8 | −9.3 | −0.5 |

A list of compounds with both optimal binding energy and selectivity is provided in Table I-1-3 below.

TABLE I-1-3

| GT-ID | S_IFD_F3_iNOS | S_IFD_F3_eNOS | iNOS-eNOS |
|---|---|---|---|
| GT-1001 | −9.5 | −8.7 | −0.8 |
| GT-1003 | −10.2 | −9.7 | −0.4 |
| GT-1007 | −8.7 | −8.2 | −0.4 |
| GT-1008 | −9.4 | −8.9 | −0.4 |
| GT-1013 | −9.7 | −9.3 | −0.5 |

TABLE I-1-3-continued

| GT-ID | S_IFD_F3_iNOS | S_IFD_F3_eNOS | iNOS-eNOS |
|---|---|---|---|
| GT-1015 | −10.5 | −10.0 | −0.5 |
| GT-1016 | −9.8 | −9.4 | −0.5 |
| GT-1034 | −9.2 | −8.8 | −0.4 |
| GT-1040 | −9.8 | −9.3 | −0.5 |
| GT-1044 | −10.2 | −9.7 | −0.4 |
| GT-1047 | −10.3 | −9.5 | −0.8 |
| GT-1050 | −9.8 | −9.3 | −0.4 |
| GT-1059 | −10.2 | −9.8 | −0.4 |
| GT-1062 | −9.8 | −9.4 | −0.4 |
| GT-1063 | −10.0 | −9.4 | −0.6 |
| GT-1064 | −9.4 | −8.9 | −0.5 |
| GT-1066 | −9.8 | −9.3 | −0.5 |

Binding images of some top binders GT-1001, GT-1003, GT-1044, GT-1047 and GT-1063 are shown in FIGS. 3, 4, 5, 6 and 7, respectively.

Formula (I-2)

Figure 8:
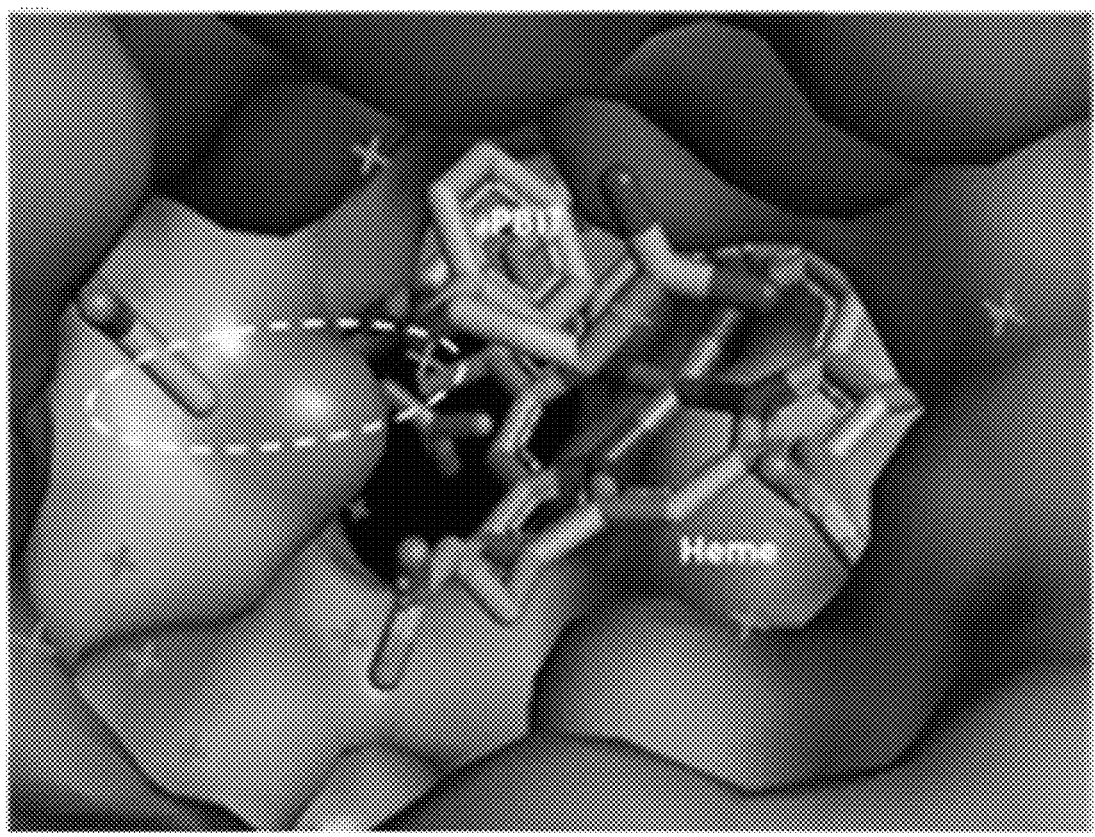
FIG. 8 shows a space in the binding site that is filled with a small ring structure in the iNOS-PBIT crystal structure.

Referring again to FIG. 2, in the iNOS-PBIT crystal structure, there is an acetic acid (AcOH) molecule in proximity to the PBIT. FIG. 2 is a view of PBIT 3.8A in proximity to acetic acid (AcOH) also bound to iNOS. Referring now to FIG. 8, the white dashed oval represents space in the binding site that is filled with a small ring structure. In the embodiments of Formula (I-2), a ring X (or ring R in Formula (I-2)) is introduced between the isothiourea and the core benzene ring of PBIT, to explore the small cavity near the bound AcOH group.

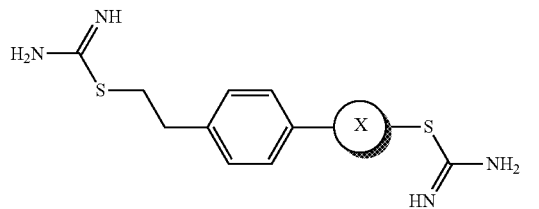

A class of such compounds is listed in Tables I-2-1 and I-2-2. The compound ID, SMILES code, MW, CD clogP and CD TPSA are listed in Table I-2-1. Their calculated induced fit docking (IFD) scores for binding to iNOS and eNOS are shown in Table I-2-2. Adding a ring between the isothiourea and the core benzene ring of PBIT will restrict the freedom of rotation of the 2-carbon chain connecting to the isothiourea and hence improve potency by getting the molecule closer to the binding conformation in its ground state. Restricting rotatable bonds with a ring is shown below, in which n=1, 3 or 4, indicating that the group in the parentheses is repeated 1, 3 or 4 times.

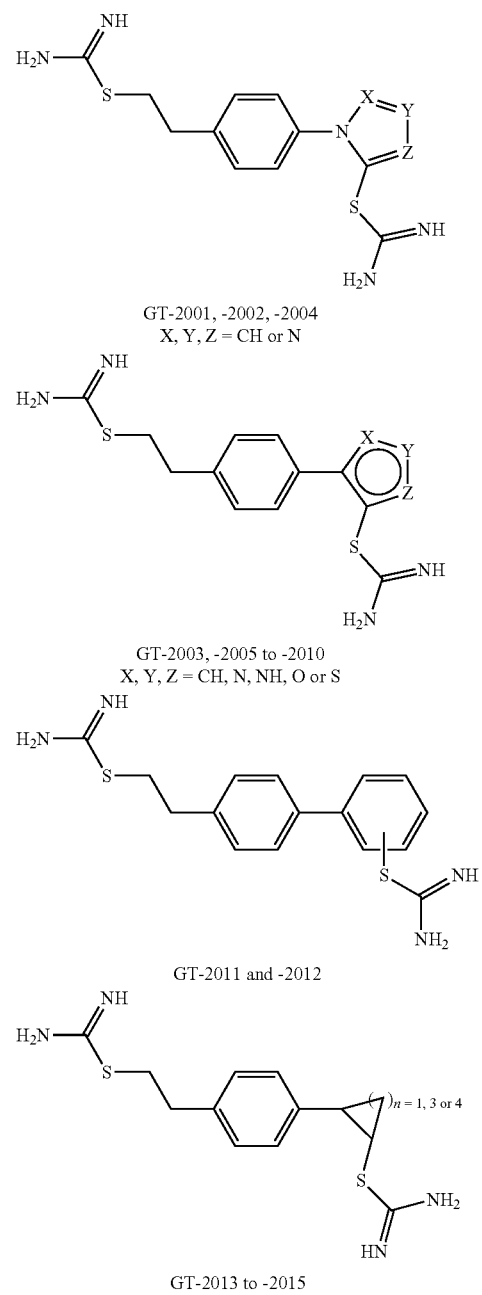

GT-2001, -2002, -2004
X, Y, Z = CH or N

GT-2003, -2005 to -2010
X, Y, Z = CH, N, NH, O or S

GT-2011 and -2012

GT-2013 to -2015

In Table I-2-1, some compound physical property calculations are provided including molecular weight (MW), cLogP, and TPSA. These are metrics for the desired properties of a drug.

TABLE I-2-1

| GT-ID | SMILES Code | MW | CD clogP | CD TPSA |
|---|---|---|---|---|
| GT-2001 | NC(SCCC1=CC=C(N2C=CN=C2SC(N)=N)C=C1)=N | 320 | 0.78 | 115 |
| GT-2002 | NC(SCCC1=CC=C(N2C=NC=C2SC(N)=N)C=C1)=N | 320 | 0.78 | 115 |
| GT-2003 | NC(SCCC1=CC=C(C2=C(SC(N)=N)NC=N2)C=C1)=N | 320 | 0.77 | 124 |
| GT-2004 | NC(SCCC1=CC=C(N2N=CC=C2SC(N)=N)C=C1)=N | 320 | 0.9 | 115 |
| GT-2005 | NC(SCCC1=CC=C(C2=C(SC(N)=N)NN=C2)C=C1)=N | 320 | 0.9 | 124 |
| GT-2006 | NC(SCCC1=CC=C(C2=NNC=C2SC(N)=N)C=C1)=N | 320 | 1 | 124 |
| GT-2007 | NC(SCCC1=CC=C(C2=C(SC(N)=N)N=CS2)C=C1)=N | 337 | 1.3 | 112 |
| GT-2008 | NC(SCCC1=CC=C(C2=C(SC(N)=N)N=CO2)C=C1)=N | 321 | 0.62 | 121 |

TABLE I-2-1-continued

| GT-ID | SMILES Code | MW | CD clogP | CD TPSA |
|---|---|---|---|---|
| GT-2009 | NC(SCCC1=CC=C(C2=C(SC(N)=N)SC=N2)C=C1)=N | 337 | 1.3 | 112 |
| GT-2010 | NC(SCCC1=CC=C(C2=C(SC(N)=N)OC=N2)C=C1)=N | 321 | 0.62 | 121 |
| GT-2011 | NC(SCCC1=CC=C(C2=C(C=CC=C2)SC(N)=N)C=C1)=N | 330 | 2.7 | 100 |
| GT-2012 | NC(SCCC1=CC=C(C2=CC(SC(N)=N)=CC=C2)C=C1)=N | 330 | 2.7 | 100 |
| GT-2013 | NC(SCCC1=CC=C(C2C(C2)SC(N)=N)C=C1)=N | 294 | 2.1 | 100 |
| GT-2014 | NC(SCCC1=CC=C(C2C(CCC2)SC(N)=N)C=C1)=N | 322 | 3 | 100 |
| GT-2015 | NC(SCCC1=CC=C(C2C(CCCC2)SC(N)=N)C=C1)=N | 336 | 3.5 | 100 |

As shown in Table I-2-2, a more negative score indicates better binding energy. These energy values are provided under the column headers labeled "S_IFD_F3_iNOS", and "S_IFD_F3_eNOS". The column header "iNOS-eNOS" describes the difference in binding and values <−0.4 indicate favorable binding to iNOS compared to eNOS. Further comparison with consideration for the 3D-fit within the binding site resulted in the diverse set of compounds.

TABLE I-2-2

| GT-ID | S_IFD_F3_iNOS | S_IFD_F3_eNOS | iNOS-eNOS |
|---|---|---|---|
| GT-2001 | −9.3 | −9.1 | −0.2 |
| GT-2002 | −9.1 | −9.1 | 0.0 |
| GT-2003 | −8.9 | −9.1 | 0.2 |
| GT-2004 | −9.0 | −8.8 | −0.2 |
| GT-2005 | −9.1 | −8.9 | −0.2 |
| GT-2006 | −9.2 | −8.9 | −0.3 |
| GT-2007 | −8.6 | −9.2 | 0.6 |
| GT-2008 | −8.6 | −8.9 | 0.3 |
| GT-2009 | −9.1 | −8.8 | −0.3 |
| GT-2010 | −9.1 | −9.0 | −0.1 |
| GT-2011 | −9.2 | −9.2 | 0.0 |
| GT-2012 | −8.3 | −9.3 | 0.9 |
| GT-2013 | −7.6 | −8.1 | 0.5 |
| GT-2014 | −9.4 | −9.4 | −0.1 |
| GT-2015 | −9.6 | −9.1 | −0.4 |

Figure 9:
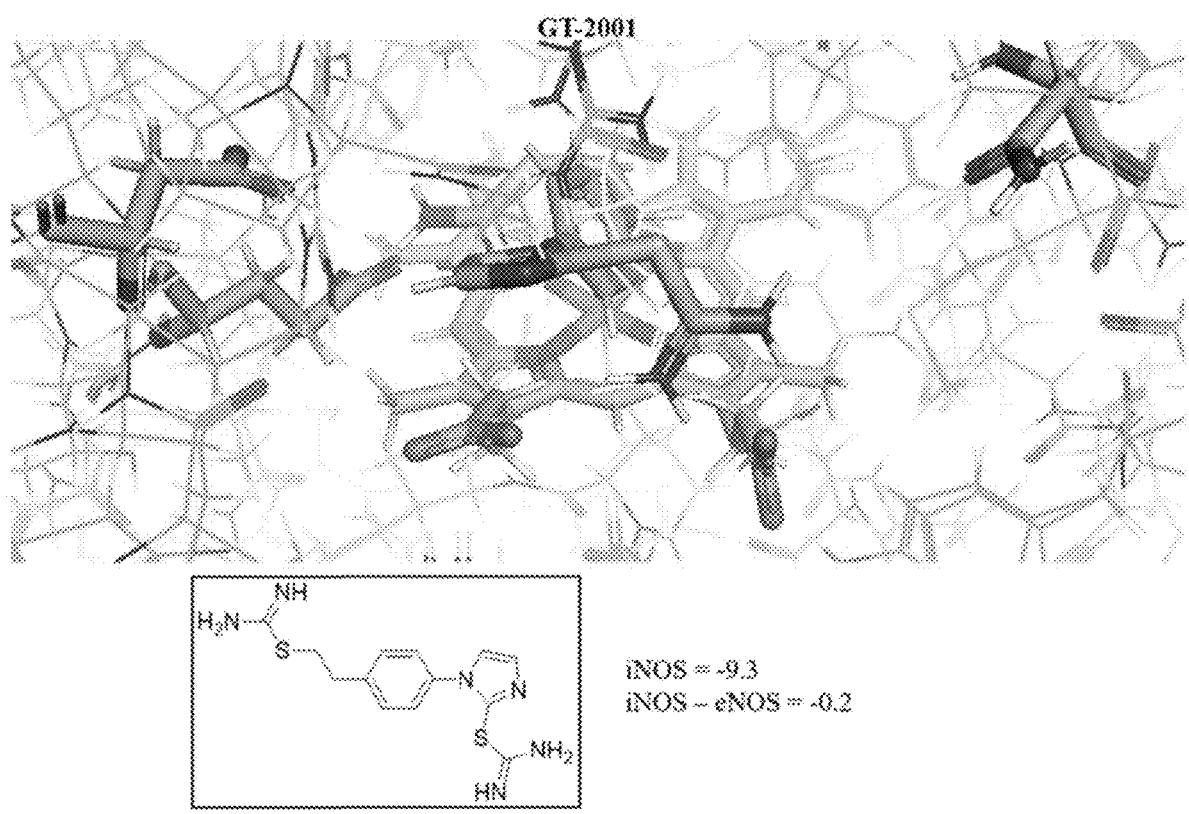
FIG. 9 illustrates the binding image of a compound of Formula (I-2) to iNOS or eNOS in accordance with an exemplary embodiment of the present invention.
Figure 10:
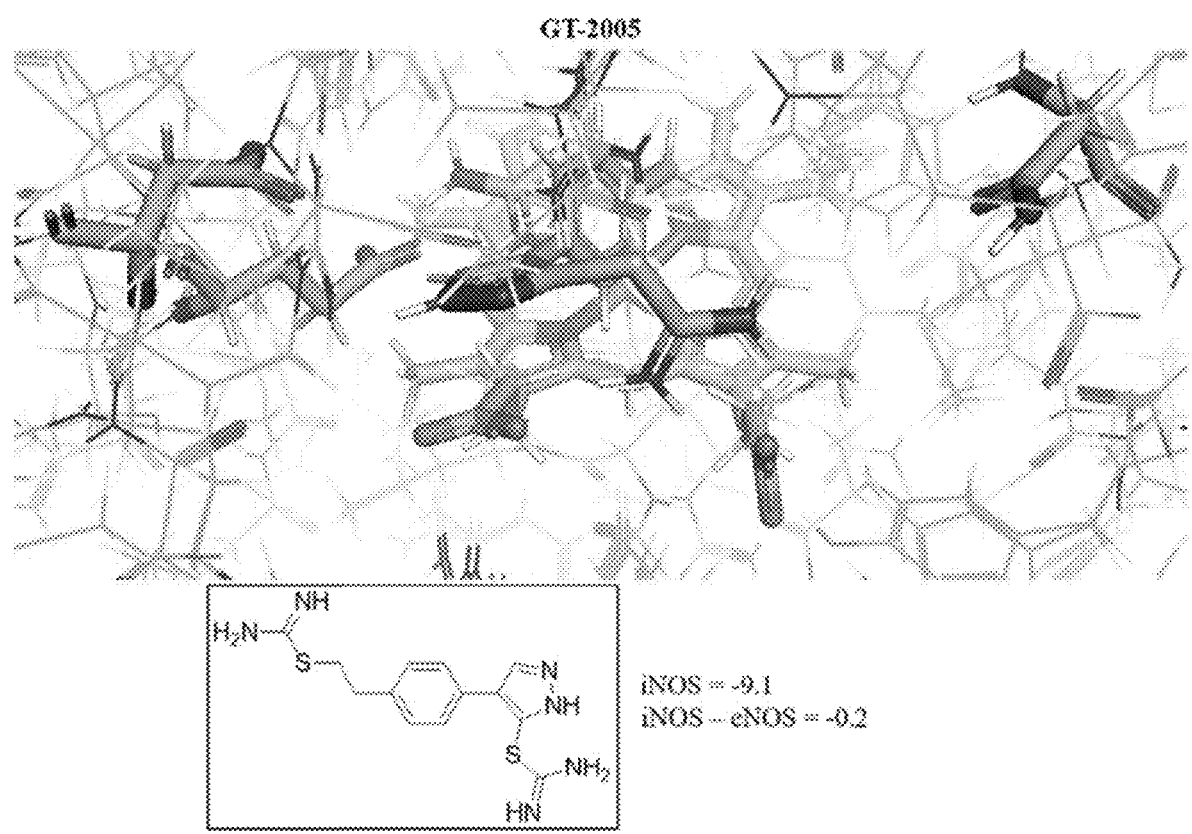
FIG. 10 illustrates the binding image of another compound of Formula (I-2) to iNOS or eNOS with an exemplary embodiment of the present invention.
Figure 11:
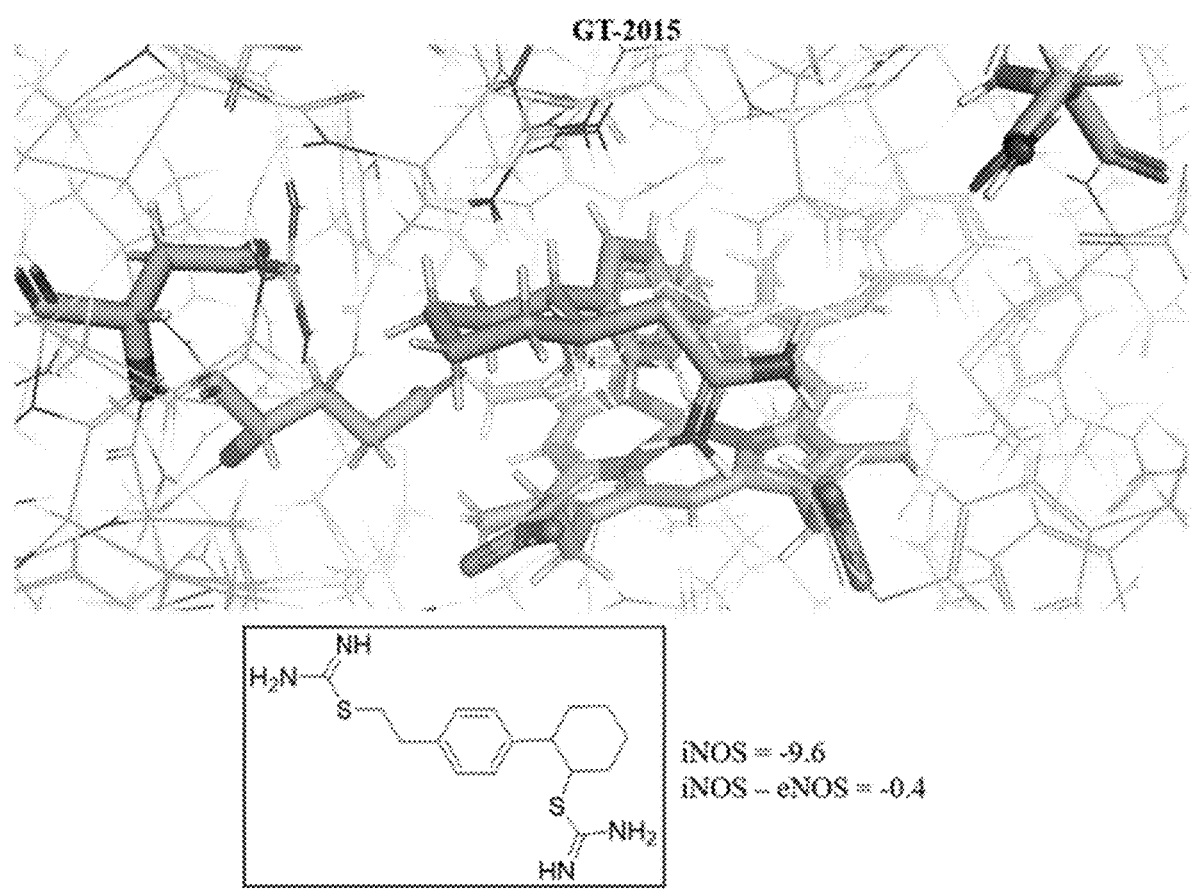
FIG. 11 illustrates the binding image of still another compound of Formula (I-2) to iNOS or eNOS in accordance with an exemplary embodiment of the present invention.

Binding images of some top binders GT-2001, GT-2005, and GT-2015 are shown in FIGS. 9, 10 and 11, respectively.

Formula (I-3)

Figure 12:
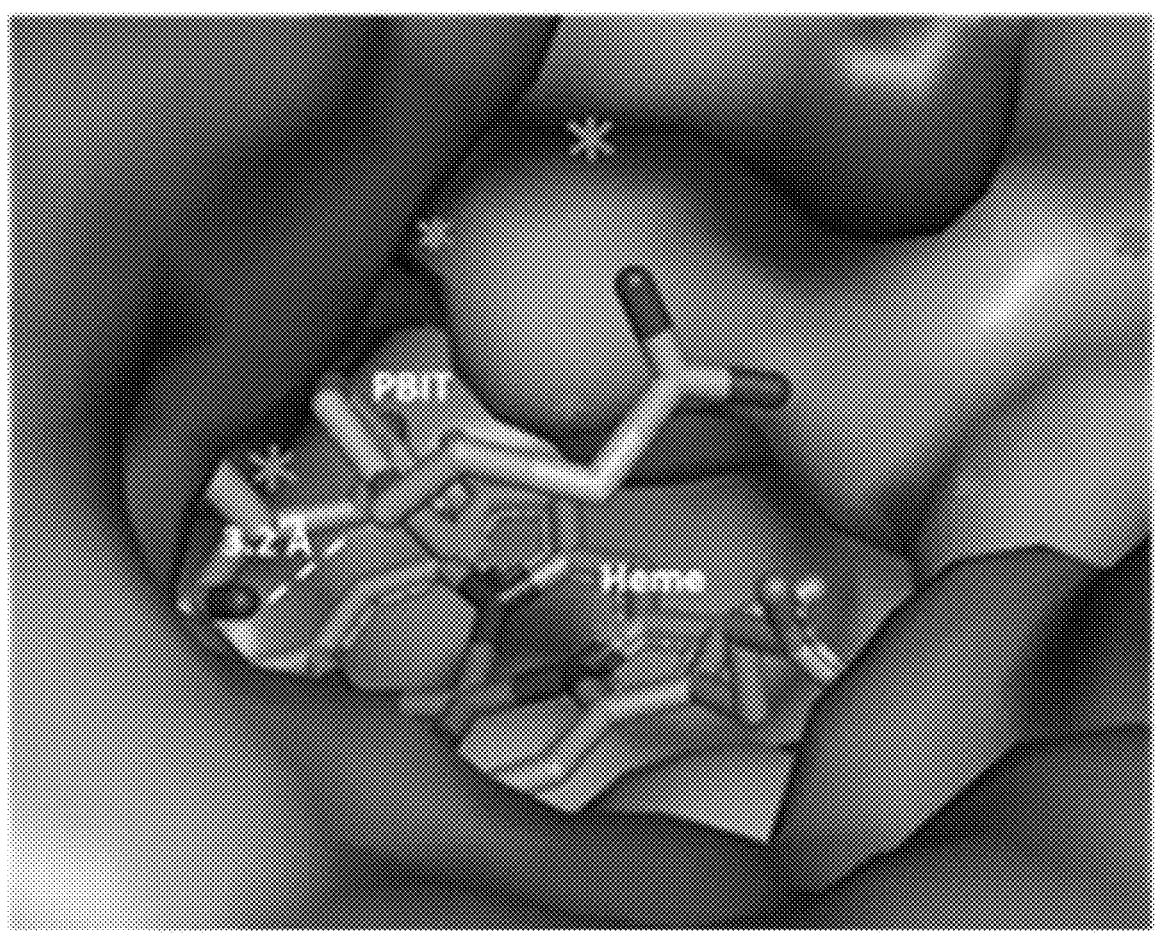
FIG. 12 is a view of the internal isothiourea in PBIT showing the close proximity of the C═NH bending back to the —SCH2 part of the molecule deep inside the iNOS.
Figure 13:
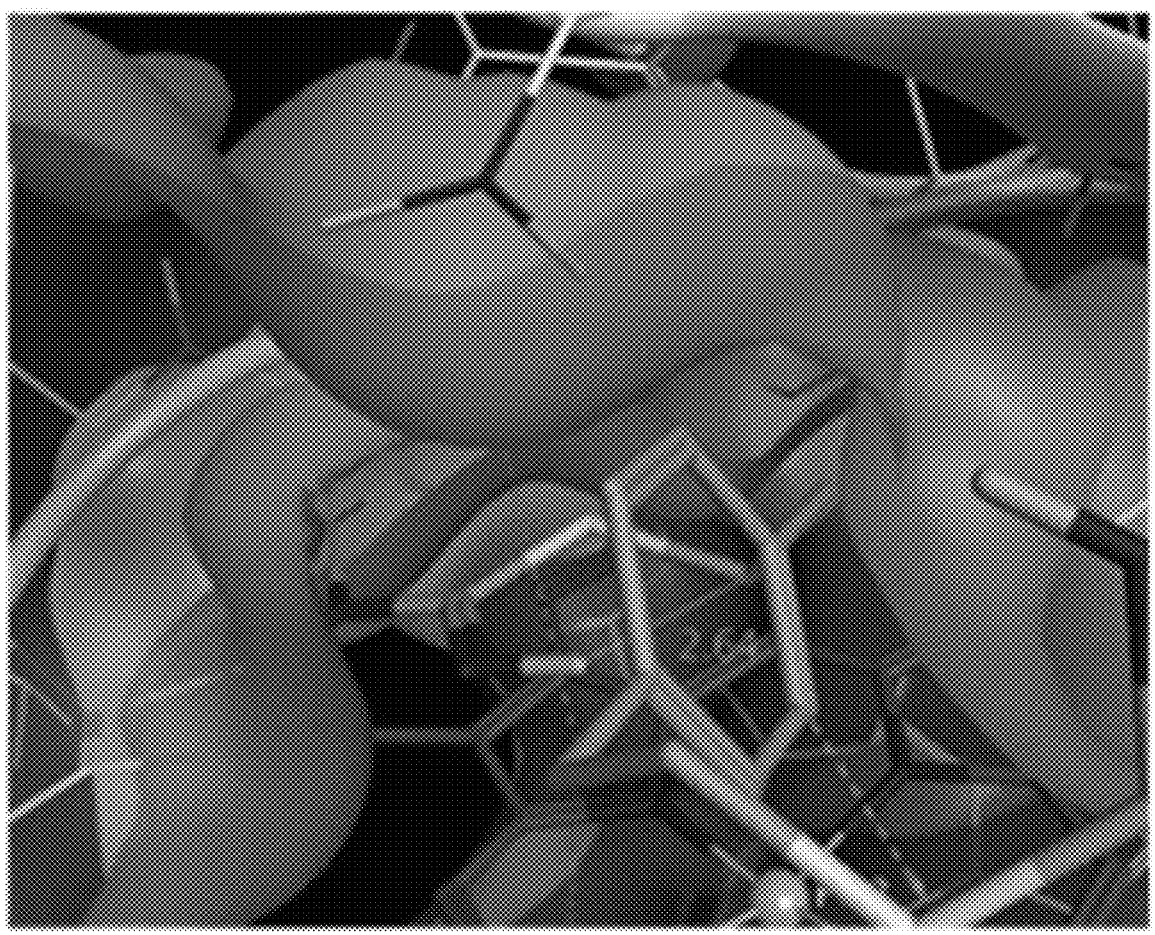
FIG. 13 is another view with some surface area removed to show more of the internal isothiourea of FIG. 12 with the C═NH bending back to the —SCH2 part of the molecule deep inside the iNOS.

In the internal part of the PBIT binding, the isothiourea group bends back to point the C=NH group towards the —S-CH2- group that it is connected to, and a ring can be imagined where the N and C are connected, as shown in FIGS. 12 and 13. FIG. 12 is a view of the internal isothiourea showing the close proximity of the C=NH bending back to the —SCH2 part of the molecule deep inside the iNOS. FIG. 13 is another view with some surface area removed to show more of the internal isothiourea with the C=NH bending back to the —SCH2 part of the molecule deep inside the iNOS.

A less polar group was added to replace the isothiourea in PBIT, and one new cyclic structure is shown below. A class of such compounds is listed in Tables I-3-1 and I-3-2. By exploring alternatives to the isothiourea, a less polar group is desired to lower the overall polar surface area of the molecule and hence make it to have more "drug-like" properties.

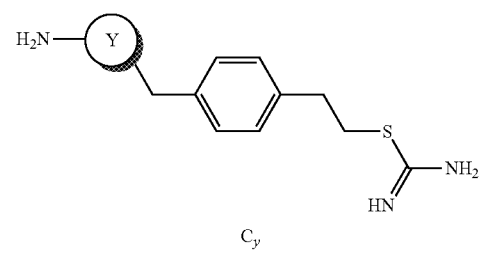

$C_y$

The compound ID, SMILES code, MW, CD clogP and CD TPSA are listed in Table I-3-1. Their calculated induced fit docking (IFD) scores for binding to iNOS and eNOS are shown in Table I-3-2. As indicated below, a less polar group is added to replace the isothiourea on one side, which lowers the overall polar surface area of the new molecule.

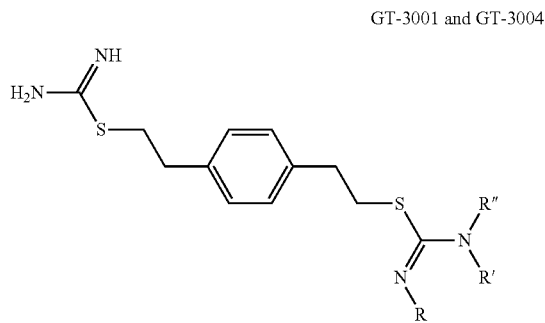

GT-3001 and GT-3004

R, R', R″ = H or Me

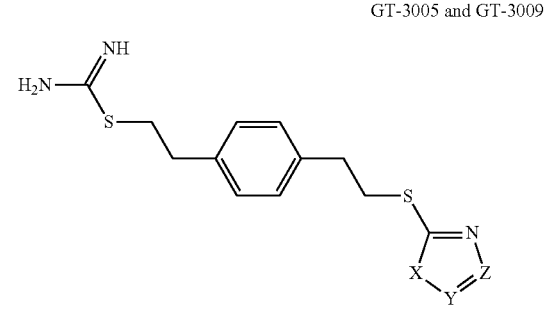

GT-3005 and GT-3009

N = NH, O or S; Y = CH, N; Z = CH, N

-continued

GT-3018 and GT-3019

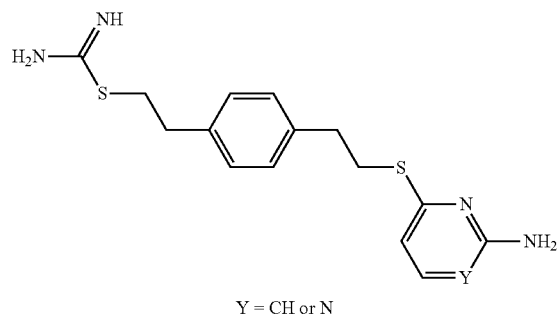

Y = CH or N

GT-3022 and GT-3025

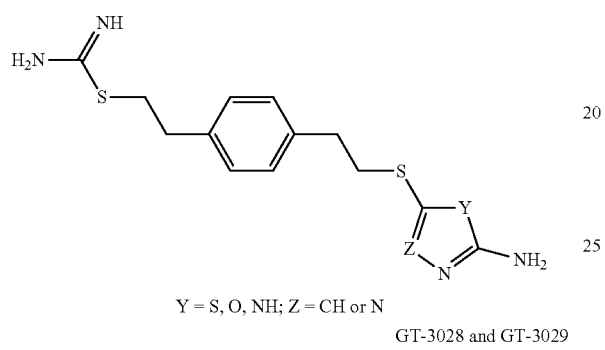

Y = S, O, NH; Z = CH or N

GT-3028 and GT-3029

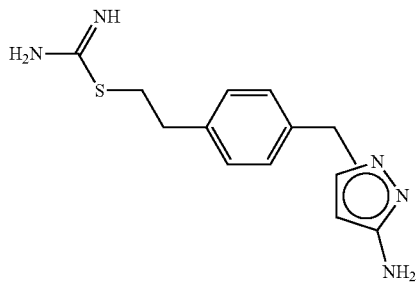

-continued

GT-3010 to GT-3017

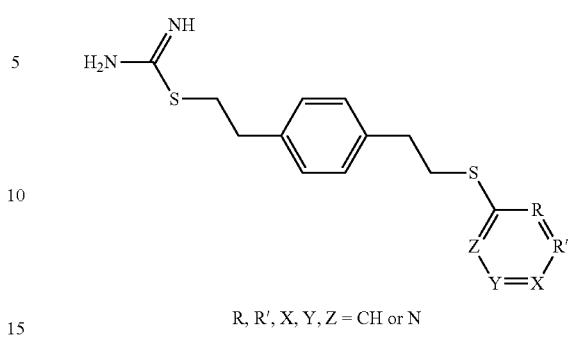

R, R', X, Y, Z = CH or N

GT-3026 and GT-3027

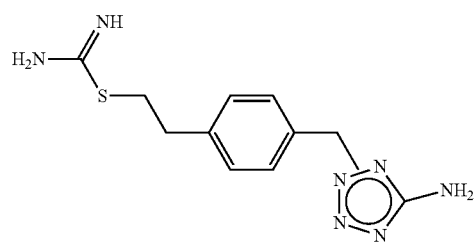

In Table I-3-1, some compound physical property calculations are provided including molecular weight (MW), cLogP, and TPSA. These are metrics for the desired properties of a drug.

TABLE I-3-1

| GT-ID | SMILES Code | MW | CD clogP | CD TPSA |
|---|---|---|---|---|
| GT-3001 | N=C(NC)SCCC1=CC=C(CCSC(N)=N)C=C1 | 296 | 2.2 | 86 |
| GT-3002 | NC(SCCC1=CC=C(CCS/C(NC)=N/C)C=C1)=N | 310 | 1.5 | 74 |
| GT-3003 | N=C(N(C)C)SCCC1=CC=C(CCSC(N)=N)C=C1 | 310 | 1.9 | 77 |
| GT-3004 | NC(SCCC1=CC=C(CCS/C(N(C)C)=N/C)C=C1)=N | 324 | 2.2 | 65 |
| GT-3005 | NC(SCCC1=CC=C(CCSC2=NC=CN2)C=C1)=N | 306 | 3.1 | 74 |
| GT-3006 | NC(SCCC1=CC=C(CCSC2=NC=CO2)C=C1)=N | 307 | 2.9 | 71 |
| GT-3007 | NC(SCCC1=CC=C(CCSC2=NC=CS2)C=C1)=N | 323 | 3.6 | 62 |
| GT-3008 | NC(SCCC1=CC=C(CCSC2=NC=NN2)C=C1)=N | 307 | 2.9 | 87 |
| GT-3009 | NC(SCCC1=CC=C(CCSC2=NN=NN2)C=C1)=N | 308 | 2.1 | 99 |
| GT-3010 | NC(SCCC1=CC=C(CCSC2=CC=CC=N2)C=C1)=N | 317 | 3.8 | 62 |
| GT-3011 | NC(SCCC1=CC=C(CCSC2=CC=CN=C2)C=C1)=N | 317 | 3.4 | 62 |
| GT-3012 | NC(SCCC1=CC=C(CCSC2=CC=NC=C2)C=C1)=N | 317 | 3.4 | 62 |
| GT-3013 | NC(SCCC1=CC=C(CCSC2=CC=CN=N2)C=C1)=N | 318 | 2.2 | 75 |
| GT-3014 | NC(SCCC1=CC=C(CCSC2=CC=NC=N2)C=C1)=N | 318 | 2.9 | 75 |
| GT-3015 | NC(SCCC1=CC=C(CCSC2=CN=CC=N2)C=C1)=N | 318 | 2.9 | 75 |
| GT-3016 | NC(SCCC1=CC=C(CCSC2=NC=CC=N2)C=C1)=N | 318 | 2.9 | 75 |
| GT-3017 | NC(SCCC1=CC=C(CCSC2=NC=NC=N2)C=C1)=N | 319 | 1.9 | 87 |
| GT-3018 | NC(SCCC1=CC=C(CCSC2=CC=CC(N)=N2)C=C1)=N | 332 | 3.4 | 88 |
| GT-3019 | NC(SCCC1=CC=C(CCSC2=CC=NC(N)=N2)C=C1)=N | 333 | 2.9 | 100 |
| GT-3020 | NC1=CC=CC(CC2=CC=C(CCSC(N)=N)C=C2)=N1 | 286 | 2.4 | 88 |
| GT-3021 | NC1=NC=CC(CC2=CC=C(CCSC(N)=N)C=C2)=N1 | 287 | 1.8 | 101 |
| GT-3022 | NC(SCCC1=CC=C(CC2=CN=C(N)S2)C=C1)=N | 292 | 2.3 | 88 |
| GT-3023 | NC(SCCC1=CC=C(CC2=CN=C(N)O2)C=C1)=N | 276 | 1.6 | 97 |
| GT-3024 | NC(SCCC1=CC=C(CC2=CN=C(N)N2)C=C1)=N | 275 | 1.7 | 100 |
| GT-3025 | NC(SCCC1=CC=C(CC2=NN=C(N)N2)C=C1)=N | 276 | 1.3 | 112 |

TABLE I-3-1-continued

| GT-ID | SMILES Code | MW | CD clogP | CD TPSA |
|---|---|---|---|---|
| GT-3026 | NC(SCCC1=CC=C(CN2N=NC(N)=N2)C=C1)=N | 277 | 0.16 | 116 |
| GT-3027 | NC(SCCC1=CC=C(CN2N=NN=C2N)C=C1)=N | 277 | 1.2 | 116 |
| GT-3028 | NC(SCCC1=CC=C(CN2C=CC(N)=N2)C=C1)=N | 275 | 1.5 | 91 |
| GT-3029 | NC(SCCC1=CC=C(CC2=NNC(N)=C2)C=C1)=N | 275 | 2 | 100 |

As shown in Table I-3-2, a more negative score indicates better binding energy. These energy values are provided under the column headers labeled "S_IFD_F3_iNOS", "S_IFD_F2_iNOS", "S_IFD_F3_eNOS", and "S_IFD_F2_eNOS". The column header "iNOS-eNOS" describes the difference in binding and values <−0.4 indicate favorable binding to iNOS compared to eNOS. Further comparison with consideration for the 3D-fit within the binding site resulted in the diverse set of compounds.

TABLE I-3-2

| GT-ID | S_IFD_F3_iNOS | S_IFD_F2_iNOS | S_IFD_F3_eNOS | S_IFD_F2_eNOS | iNOS-eNOS |
|---|---|---|---|---|---|
| GT-3001 | −8.5 | | −8.9 | | 0.4 |
| GT-3002 | −8.8 | | −8.9 | | 0.1 |
| GT-3003 | −9.0 | | −8.7 | | −0.3 |
| GT-3004 | −8.4 | | −8.8 | | 0.4 |
| GT-3005 | −8.7 | | −8.6 | | −0.1 |
| GT-3006 | | −7.6 | | −8.3 | 0.8 |
| GT-3007 | | −7.6 | | −8.6 | 0.9 |
| GT-3008 | | −8.6 | | −8.8 | 0.2 |
| GT-3009 | | −8.6 | | −8.7 | 0.1 |
| GT-3010 | | −8.3 | | −8.6 | 0.3 |
| GT-3011 | | −8.5 | | −8.7 | 0.2 |
| GT-3012 | −8.2 | | −8.7 | | 0.4 |
| GT-3013 | | −8.0 | | −8.5 | 0.5 |
| GT-3014 | | −8.0 | | −8.8 | 0.8 |
| GT-3015 | | −8.5 | | −8.4 | −0.1 |
| GT-3016 | | −8.0 | | −8.7 | 0.8 |
| GT-3017 | | −8.2 | | −8.7 | 0.5 |
| GT-3018 | | −8.2 | | −8.2 | 0.0 |
| GT-3019 | | −8.2 | | −8.9 | 0.7 |
| GT-3020 | | −7.8 | | −7.7 | −0.1 |
| GT-3021 | | −8.3 | | −8.4 | 0.1 |
| GT-3022 | | −8.3 | | −8.5 | 0.2 |
| GT-3023 | | −8.2 | | −8.1 | −0.1 |
| GT-3024 | −9.1 | | −8.1 | | −1.1 |
| GT-3025 | | −7.9 | | −8.3 | 0.4 |
| GT-3026 | | −7.9 | | −8.2 | 0.3 |
| GT-3027 | | −7.7 | | −8.3 | 0.6 |
| GT-3028 | | −7.6 | | 8.3 | 0.7 |
| GT-3029 | | −8.2 | | −8.4 | 0.2 |

Figure 14:
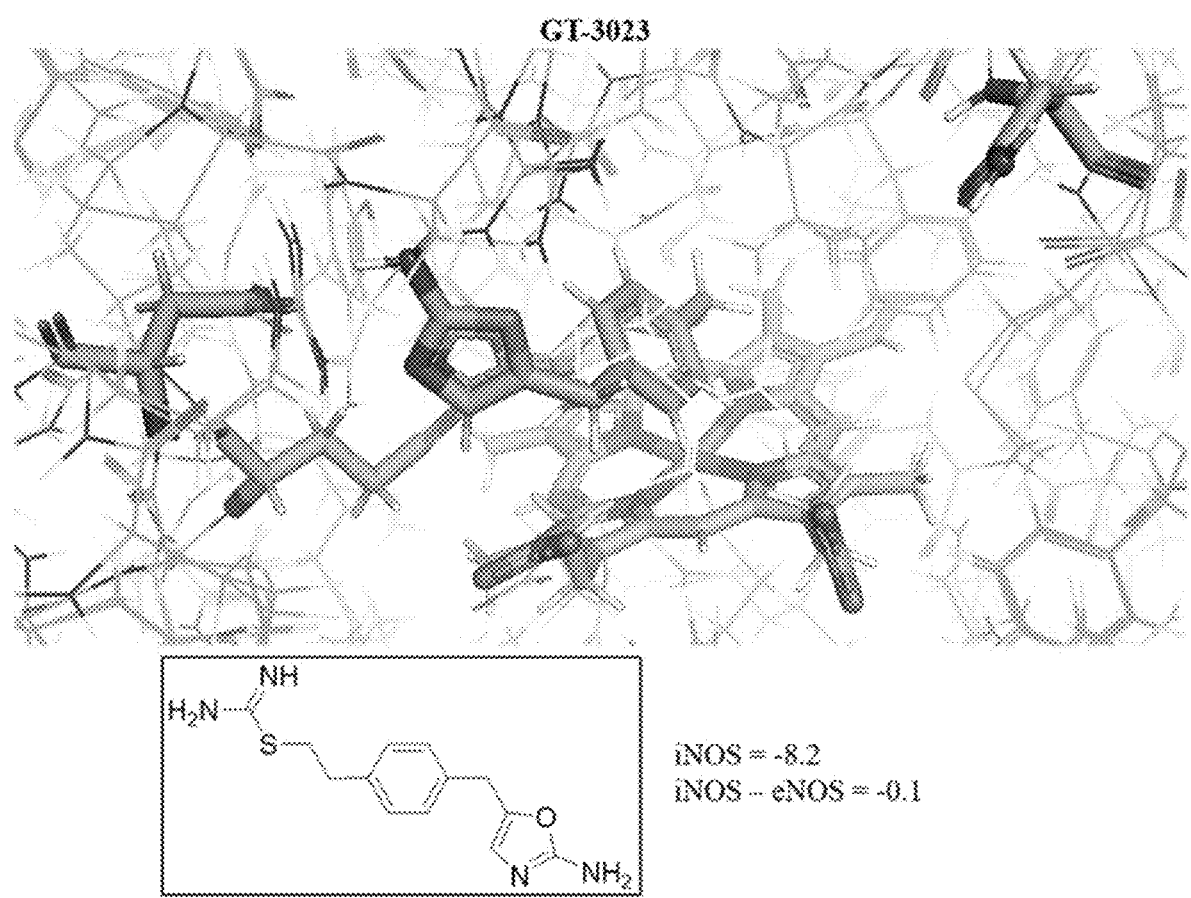
FIG. 14 illustrates the binding image of a compound of Formula (I-3) to iNOS or eNOS in accordance with an exemplary embodiment of the present invention.
Figure 15:
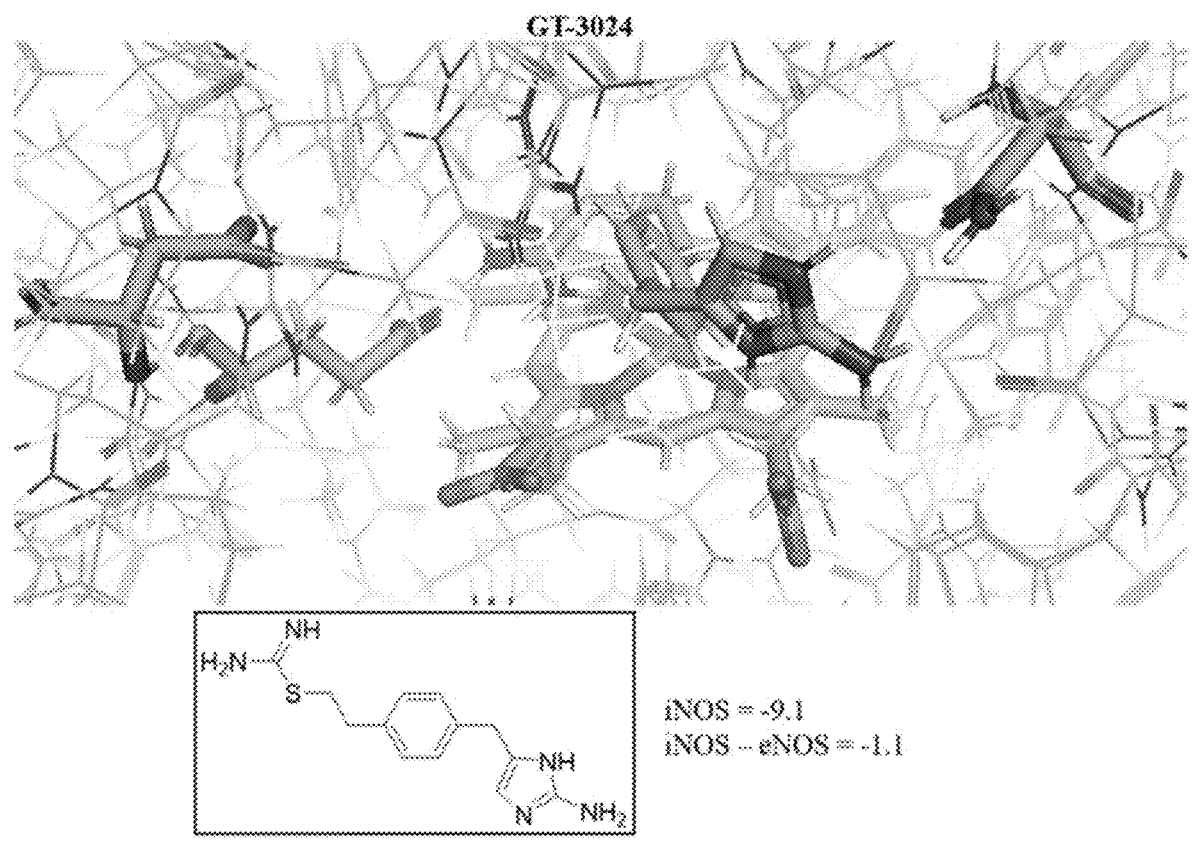
FIG. 15 illustrates the binding image of another compound of Formula (I-3) to iNOS or eNOS in accordance with an exemplary embodiment of the present invention.
Figure 16:
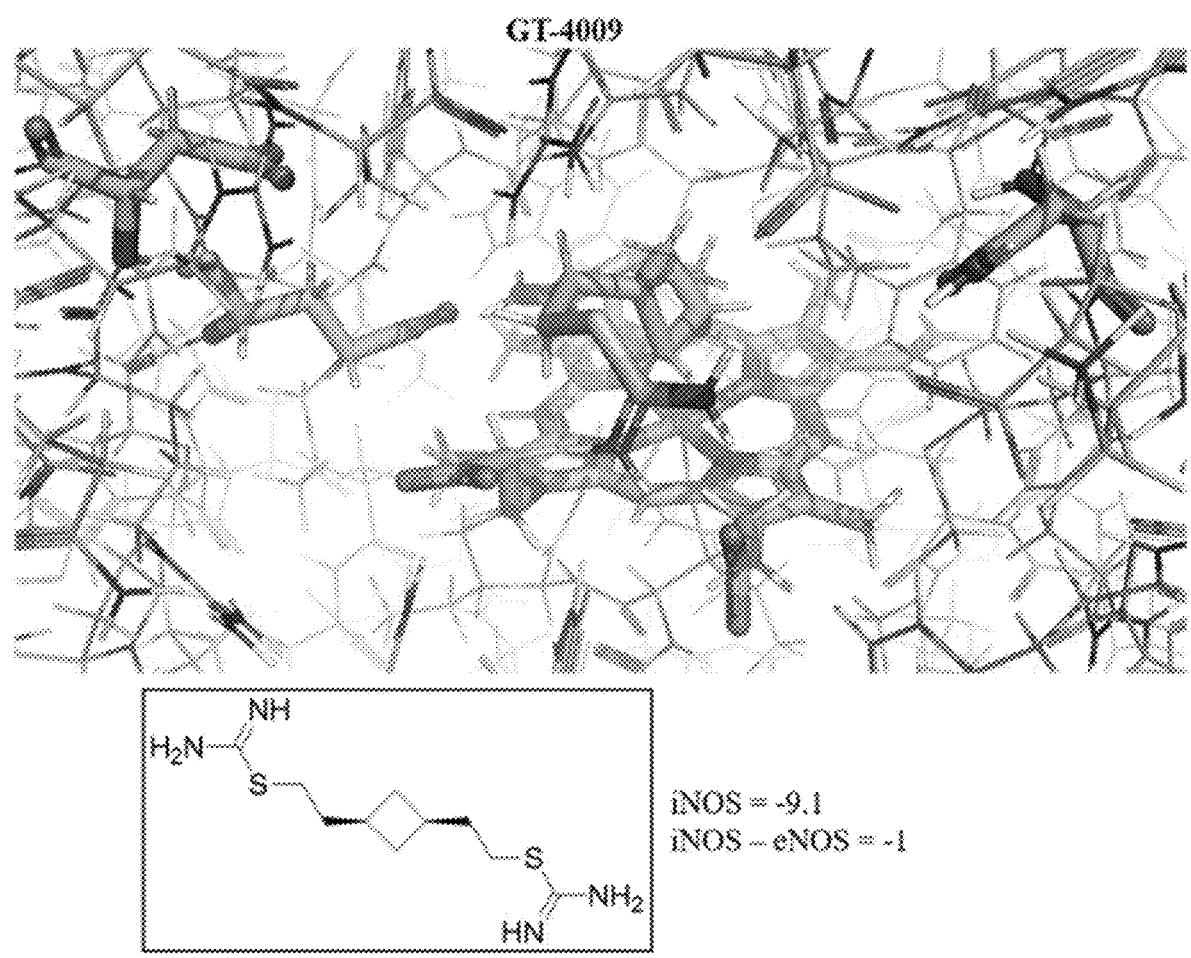
FIG. 16 illustrates the binding image of a compound of Formula (I-4) to iNOS or eNOS in accordance with an exemplary embodiment of the present invention.
Figure 17:
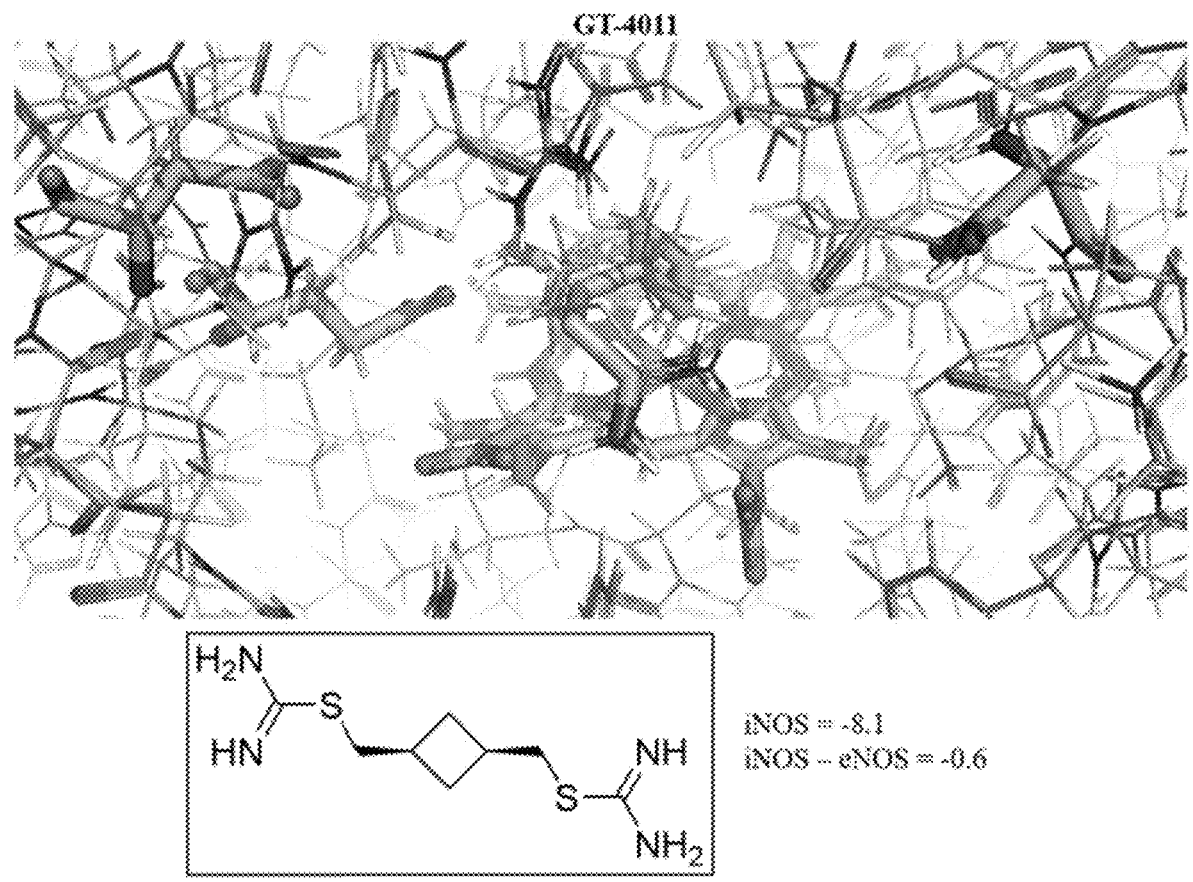
FIG. 17 illustrates the binding image of another compound of Formula (I-4) to iNOS or eNOS in accordance with an exemplary embodiment of the present invention.
Figure 18:
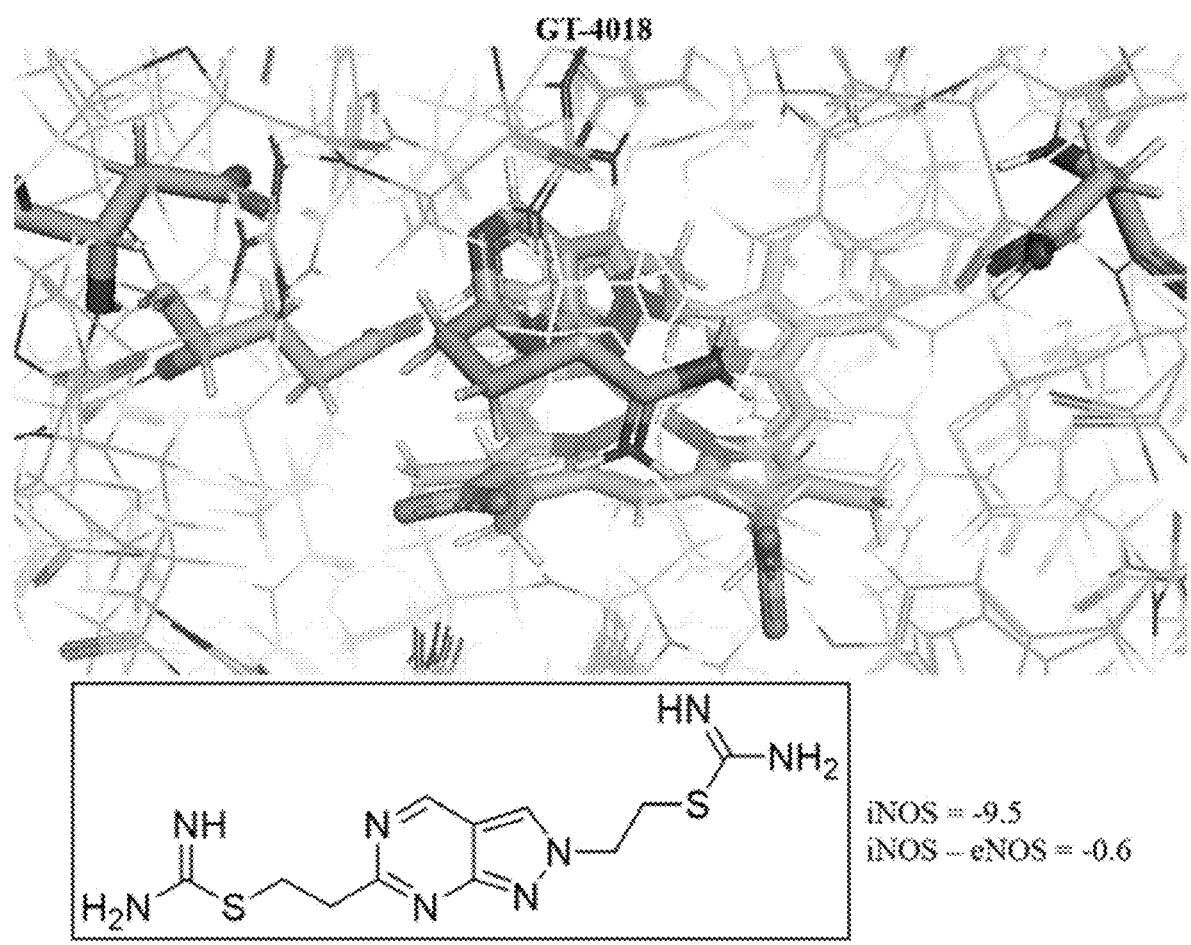
FIG. 18 illustrates the binding image of still another compound of Formula (I-4) to iNOS or eNOS in accordance with an exemplary embodiment of the present invention.
Figure 19:
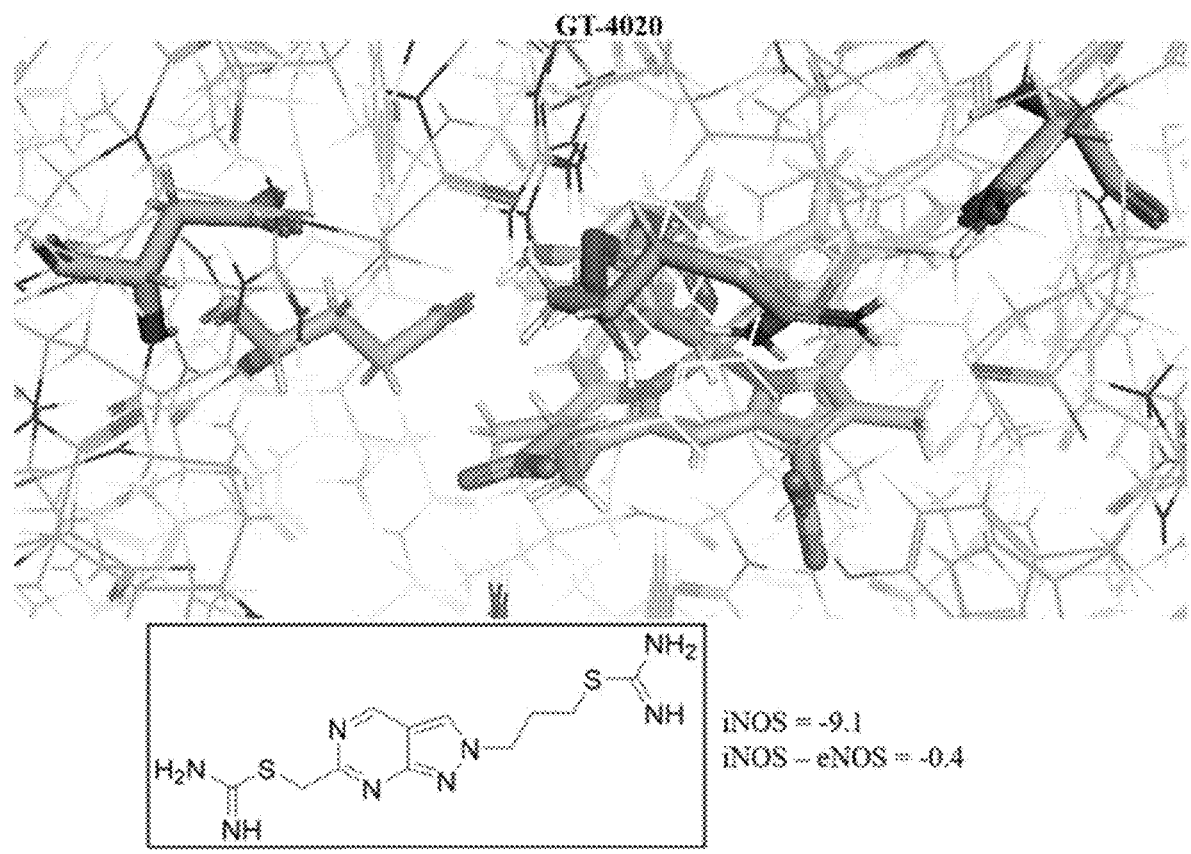
FIG. 19 illustrates the binding image of still another compound of Formula (I-4) to iNOS or eNOS in accordance with an exemplary embodiment of the present invention.

Binding images of some top binders GT-3023 and GT-3024 are shown in FIGS. 14 and 15, respectively.

Formula (I-4)

Rigid-structure substitutions are used to replace the core benzene ring in PBIT. The inventors have introduced a more complex ring system to replace benzene, which is in between two isothioureas, as indicated below. These compounds increase binding potency and selectivity.

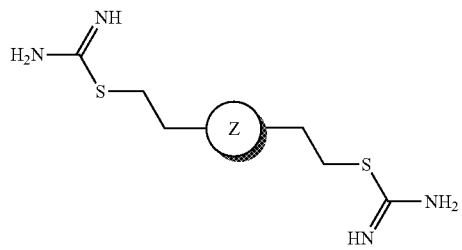

A class of such compounds is listed in Tables I-4-1 and I-4-2. The compound ID, SMILES code, MW, CD clogP and CD TPSA are listed in Table I-4-1. Their calculated induced fit docking (IFD) scores for binding to iNOS and eNOS are shown in Table I-4-2. The compounds below represent rigid-structure substitutions for the core benzene ring in PBIT. This was explored to determine if an alternative central element in the structure could lead to better binding and better physical properties than the benzene ring.

GT-4001 to GT-4017

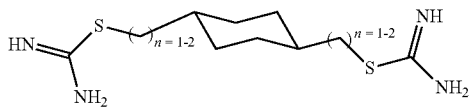

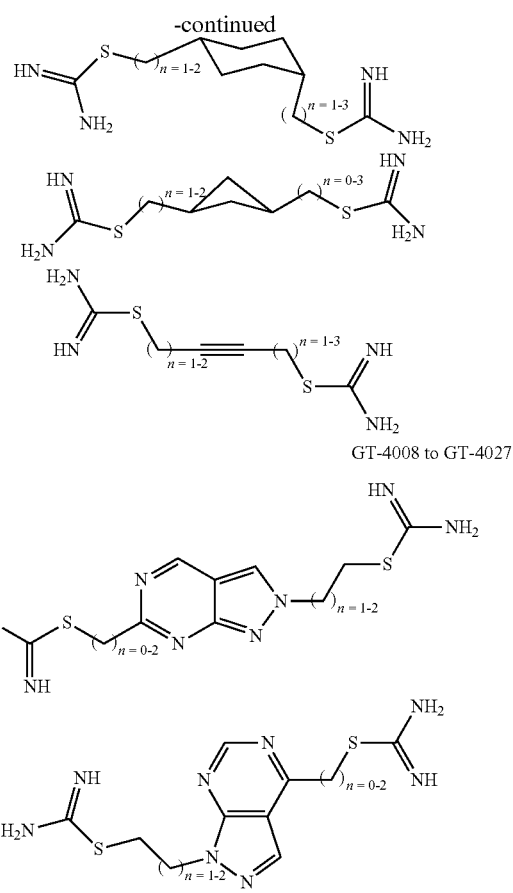

GT-4008 to GT-4027

In Table I-4-1, some compound physical property calculations are provided including molecular weight (MW), cLogP, and TPSA. These are metrics for the desired properties of a drug.

TABLE I-4-1

| GT-ID | SMILES Code | MW | CD clogP | CD TPSA |
| --- | --- | --- | --- | --- |
| GT-4001 | NC(SCC[C@H]1CC[C@H](CCSC(N)=N)CC1)=N | 288 | 3.20 | 100 |
| GT-4002 | NC(SCC[C@H]1CC[C@@H](CCSC(N)=N)CC1)=N | 288 | 3.20 | 100 |
| GT-4003 | NC(SC[C@H]1CC[C@H](CSC(N)=N)CC1)=N | 260 | 2.1 | 100 |
| GT-4004 | NC(SC[C@H]1CC[C@@H](CSC(N)=N)CC1)=N | 260 | 2.1 | 100 |
| GT-4005 | NC(SC[C@@H]1CC[C@@H](CCSC(N)=N)CC1)=N | 274 | 2.6 | 100 |
| GT-4006 | NC(SC[C@H]1CC[C@@H](CCSC(N)=N)CC1)=N | 274 | 2.6 | 100 |
| GT-4007 | NC(SCC[C@@H]1CC[C@@H](CCCSC(N)=N)CC1)=N | 302 | 3.7 | 100 |
| GT-4008 | NC(SCC[C@H]1CC[C@@H](CCCSC(N)=N)CC1)=N | 302 | 3.7 | 100 |
| GT-4009 | N=C(N)SCC[C@H]1C[C@@H](CCSC(N)=N)C1 | 260 | 2 | 100 |
| GT-4010 | NC(SC[C@H]1C[C@@H](SC(N)=N)C1)=N | 218 | 0.36 | 100 |
| GT-4011 | NC(SC[C@H]1C[C@@H](CSC(N)=N)C1)=N | 232 | 0.98 | 100 |
| GT-4012 | NC(SC[C@H]1C[C@@H](CCSC(N)=N)C1)=N | 246 | 1.6 | 100 |
| GT-4013 | N=C(N)SCC[C@H]1C[C@@H](CCCSC(N)=N)C1 | 274 | 2.6 | 100 |
| GT-4014 | N=C(N)SCCC#CCCSC(N)=N | 230 | 0.9 | 100 |
| GT-4015 | NC(SCC#CCSC(N)=N)=N | 202 | −0.042 | 100 |
| GT-4016 | N=C(N)SCCC#CCSC(N)=N | 216 | 0.44 | 100 |
| GT-4017 | N=C(N)SCCC#CCCCSC(N)=N | 244 | 1.2 | 100 |
| GT-4018 | NC(SCCC1=NC2=NN(CCSC(N)=N)C=C2C=N1)=N | 324 | −0.48 | 140 |
| GT-4019 | NC(SCC1=NC2=NN(CCSC(N)=N)C=C2C=N1)=N | 310 | −1.5 | 140 |
| GT-4020 | NC(SCC1=NC2=NN(CCCSC(N)=N)C=C2C=N1)=N | 324 | −1.2 | 140 |
| GT-4021 | NC(SCCN1N=C2N=C(SC(N)=N)N=CC2=C1)=N | 296 | −1.8 | 140 |
| GT-4022 | NC(SC1=NC2=NN(CCCSC(N)=N)C=C2C=N1)=N | 310 | −1.5 | 140 |
| GT-4023 | NC(SCCC1=NC=NC2=C1C=NN2CCSC(N)=N)=N | 324 | −0.48 | 140 |
| GT-4024 | NC(SCC1=NC=NC2=C1C=NN2CCSC(N)=N)=N | 310 | −1.5 | 140 |
| GT-4025 | NC(SCC1=NC=NC2=C1C=NN2CCCSC(N)=N)=N | 324 | −1.2 | 140 |
| GT-4026 | NC(SC1=NC=NC2=C1C=NN2CCSC(N)=N)=N | 296 | −1.8 | 140 |
| GT-4027 | NC(SC1=NC=NC2=C1C=NN2CCCSC(N)=N)=N | 310 | −1.5 | 140 |

As shown in Table I-4-2, a more negative score indicates better binding energy. These energy values are provided under the column headers labeled "S_IFD_F3_iNOS", and "S_IFD_F3_eNOS". The column header "iNOS—eNOS" describes the difference in binding and values <−0.4 indicate favorable binding to iNOS compared to eNOS. Further comparison with consideration for the 3D-fit within the binding site resulted in the diverse set of compounds.

TABLE I-4-2

| GT-ID | S_IFD_F3_iNOS | S_IFD_F3_eNOS | iNOS-eNOS |
|---|---|---|---|
| GT-4001 | −8.1 | −8.6 | 0.6 |
| GT-4002 | −9.0 | −8.8 | −0.2 |
| GT-4003 | −7.9 | −8.2 | 0.3 |
| GT-4004 | −8.0 | −7.8 | −0.2 |
| GT-4005 | −8.6 | −8.5 | −0.1 |
| GT-4006 | −8.1 | −8.4 | 0.2 |
| GT-4007 | −8.8 | −8.7 | 0.0 |
| GT-4008 | −8.6 | −9.2 | 0.7 |
| GT-4009 | −9.1 | −8.1 | −1.0 |
| GT-4010 | −7.6 | −7.5 | −0.2 |
| GT-4011 | −8.1 | −7.4 | −0.6 |
| GT-4012 | −8.1 | −8.2 | 0.1 |
| GT-4013 | −8.3 | −8.5 | 0.1 |
| GT-4014 | −7.9 | −8.1 | 0.2 |
| GT-4015 | −7.3 | −7.2 | −0.1 |
| GT-4016 | −7.8 | −7.5 | −0.3 |
| GT-4017 | −8.3 | −8.6 | 0.3 |
| GT-4018 | −9.5 | −8.9 | −0.6 |
| GT-4019 | −8.9 | −8.9 | 0.0 |
| GT-4020 | −9.1 | −8.8 | −0.4 |
| GT-4021 | −8.4 | −8.3 | −0.1 |
| GT-4022 | −8.3 | −8.4 | 0.1 |
| GT-4023 | −9.2 | −9.0 | −0.1 |
| GT-4024 | −8.7 | −9.1 | 0.4 |
| GT-4025 | −8.8 | −9.2 | 0.4 |
| GT-4026 | −8.1 | −8.1 | 0.1 |
| GT-4027 | −8.0 | −8.4 | 0.3 |

Binding images of some top binders GT-4009, GT-4011, GT4018 and GT-4020 are shown in FIGS. 16, 17, 18 and 19, respectively.

Formulas (I-5)~(I-8): Molecular Design

Figure 20:
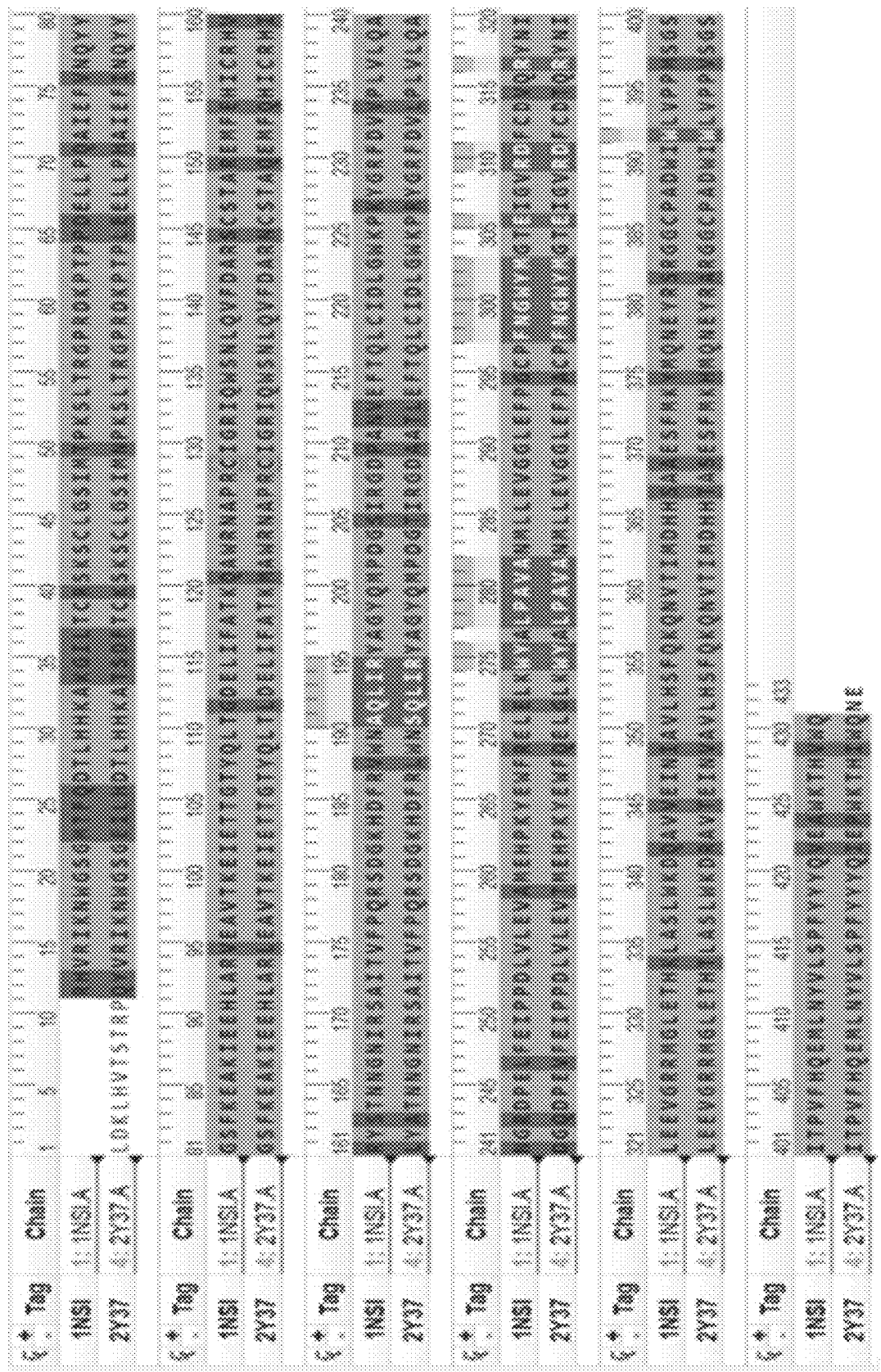
FIG. 20 demonstrates a homology comparison between mouse iNOS (PDB 2Y37) and human iNOS (PDB 1NSI).

A crystal structure has been published with AZ 6b bound to mouse iNOS (PDB 2Y37). The inventors have compared mouse iNOS (PDB 2Y37) to human iNOS (PDB 1NSI). The inventors found that there is significant homology between this mouse iNOS or miNOS (PDB 2Y37) and published human iNOS or hiNOS (PDB 1NSI) with 22 of 23 residues in the active site binding region being identical (blue colored) as shown in FIG. 20, in which green parts are identical; red parts are different; and blue parts are highlighted pocket resides in both. The mouse iNOS PDB structure information was considered useful for being predictive in scoring designed inhibitors.

To rationally prioritize the molecular designs, a set of computational modeling procedures were carried out to estimate the potential binding affinity of the proposed molecules against the iNOS. Molecular docking is used to determine a binding affinity estimation in terms of docking score (S). The energy difference between the ground state conformation of the molecule vs. the predicted bound state (i.e. docked conformation) was estimated as well (dE).

CADD is carried out using Molecular Operating Environment (MOE) software, one of the top leading modeling software developed by Chemical Computing Group (https://www.chemcomp.com/). Both rigid receptors docking as well as induced fit docking (IFD) were conducted to each of the molecules, and a pharmacophore model was developed and applied to efficiently guide the docking procedure. The receptor template is described by the crystal complex with 6b bound in the pocket (PDB 2Y37). It was prepared by adding missing atoms and residues followed by fixing any bad contacts so that it is ready for the docking process.

Figure 21:
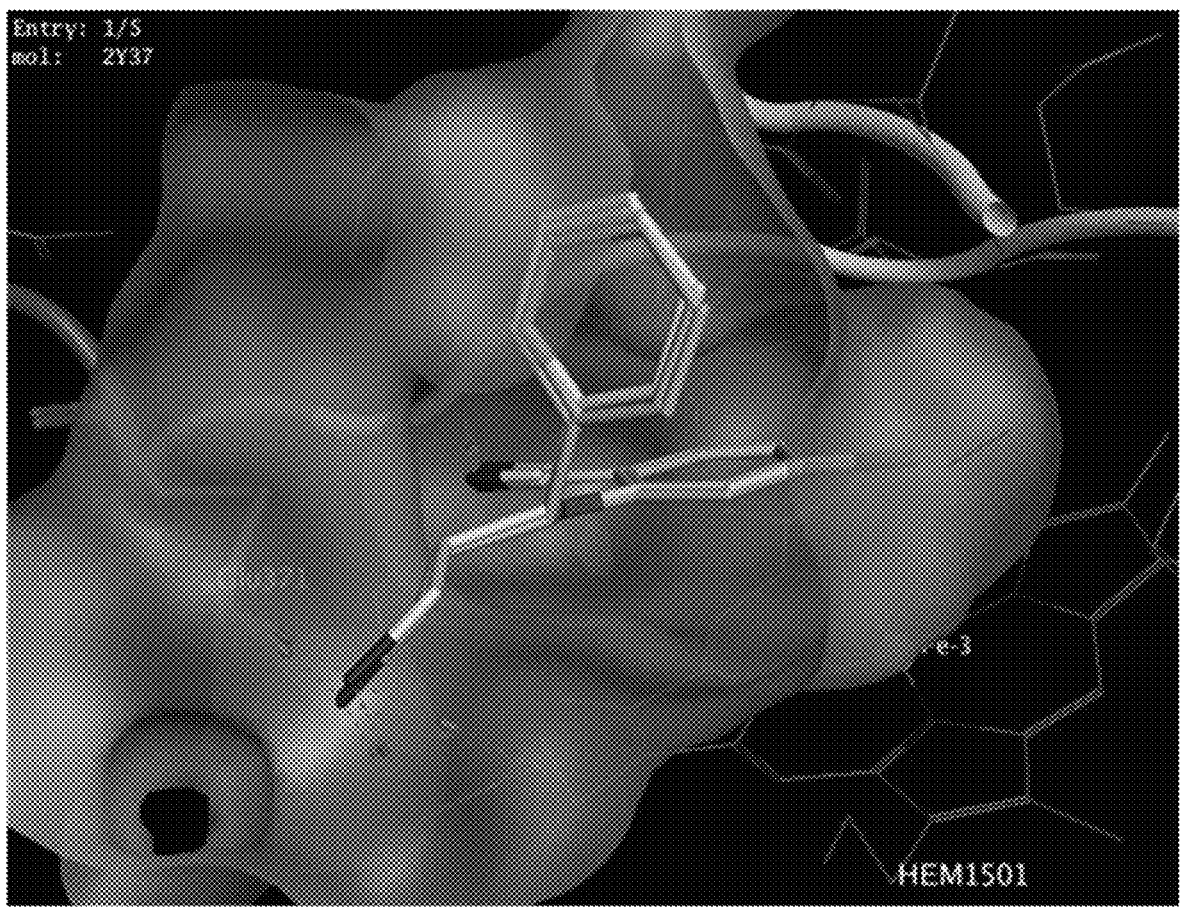
FIG. 21 shows compound AZ 6b as observed in mouse iNOS (PDB 2Y37) overlayed with a computationally guided induced fir docking (IFD) pose of AZ 6b.

The docking method was validated when the binding poses of AZ 6b observed in mouse iNOS (PDB 2Y37) was reproduced with an induced fit docking (IFD) operation on compound AZ 6b. FIG. 21 is compound AZ 6b as observed in published mouse iNOS PDB 2Y37 (cyan colored) overlayed with a computationally guided induced fir docking (IFD) pose of AZ 6b (yellow colored). The IFD binding energy S calculated for AZ 6b is −9.5 kcal. If designed molecules are near this binding energy, then they are hypothesized to bind nearly as well as AZ 6b and are candidates for synthesis and testing.

The docking score (S) from induced fit docking (IFD) with the guidance of a certain pharmacophore (F) for iNOS. The inventors used 3 features of the pharmacophore model (F3). The S are calculated based on the procedures of a very complicated yet sophisticated mathematics process. Basically, sample the possible conformations of both small molecules as well as receptors, followed by score ranking. All the theories are hard coded into the process of the module the inventors employed for the estimations.

As compared to compound AZ 6b, compounds of the invention show more potency, selective inhibition of iNOS vs. eNOS and nNOS, less toxicity and overall anti-inflammatory and anti-cancer efficacies.

Formula (I-5)

In these embodiments, N-atom is added to within the all-carbon benzene ring claimed in WO2001062704 as indicated below.

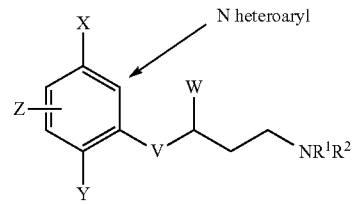

WO2001062704

A list of compound IDs and their SMILES codes are shown in Table I-5-1.

TABLE I-5-1

| GT-ID | SMILES Code |
|---|---|
| GT-5001 | NCC[C@H](C1═CC═CC═C1)OC2═C(C#N)C═CC(C)═N2 |
| GT-5002 | CC1═NC(O[C@@H](C2═CC═CC═C2)CCNC)═C(C#N)C═C1 |
| GT-5003 | N#CC1═C(O[C@@H](C2═CC═CC═C2)CCNCC)N═C(C)C═C1 |
| GT-5004 | N#CC1═C(O[C@@H](C2═CC═CC═C2)CCNCCOC)N═C(C)C═C1 |
| GT-5005 | NCC[C@H](C1═CC═CC═C1)OC2═C(C#N)C═CC═N2 |
| GT-5006 | N#CC1═C(O[C@@H](C2═CC═CC═C2)CCNC)N═CC═C1 |
| GT-5007 | N#CC1═C(O[C@@H](C2═CC═CC═C2)CCNCC)N═CC═C1 |

TABLE I-5-1-continued

| GT-ID | SMILES Code |
|---|---|
| GT-5008 | N#CC1=C(O[C@@H](C2=CC=CC=C2)CCNCCOC)N=CC=C1 |
| GT-5009 | NCCC(C1=CC=CC=N1)OC2=C(C#N)C=CC(C)=N2 |
| GT-5010 | NCCC(C1=CC=CN=C1)OC2=C(C#N)C=CC(C)=N2 |
| GT-5011 | CC1=NC(O[C@@H](C2=CC=CC=C2)CCNC)=CC=C1 |
| GT-5012 | CC1=NC(O[C@@H](C2=CC=CC=C2)CCNC)=C(Br)C=C1 |
| GT-5013 | CNCC[C@H](C1=CC=CC=C1)OC2=C(C#N)C=CC(C(F)(F)F)=N2 |
| GT-5014 | CC1=NC(O[C@@H](C2=CC=CC=C2)CCNCCO)=C(C#N)C=C1 |
| GT-5015 | CC1=NC(O[C@@H](C2=CC=CC=C2)CCNCCCO)=C(C#N)C=C1 |
| GT-5016 | CC1=NC(O[C@@H](C2=CC=CC=C2)CCN3CC[C@H](O)C3)=C(C#N)C=C1 |
| GT-5017 | CC1=NC(O[C@@H](C2=CC=CC=C2)CCN3CC[C@@H](O)C3)=C(C#N)C=C1 |
| GT-5018 | CC1=NC(O[C@@H](C2=CC=CC=C2)CCNC(C)(C)C)=C(C#N)C=C1 |
| GT-5019 | CC1=NC(O[C@@H](C2=CC=CC=C2)CCNCCN(C)C)=C(C#N)C=C1 |
| GT-5020 | CC1=NC(O[C@@H](C2=CC=CC=C2)CCNCCN3CCOCC3)=C(C#N)C=C1 |
| GT-5021 | CC1=NC(O[C@@H](C2=CC=CC=C2)CCNCC3=NC=CN3)=C(C#N)C=C1 |
| GT-5022 | CC1=NC(O[C@@H](C2=CC=CC=C2)CCNCN3C=CN=C3)=C(C#N)C=C1 |
| GT-5023 | CC1=NC(O[C@@H](C2=CC=CC=C2)CCNCCC3=CNC=N3)=C(C#N)C=C1 |
| GT-5024 | CC1=NC(O[C@@H](C2=CC=CC=C2)CCNC[C@H](O)CO)=C(C#N)C=C1 |
| GT-5025 | CC1=NC(O[C@@H](C2=CC=CC=C2)CCNC[C@@H](O)CO)=C(C#N)C=C1 |
| GT-5026 | CC1=NC(O[C@@H](C2=CC=CC=C2)CCN[C@@H]3C[C@@H](O)C3)=C(C#N)C=C1 |
| GT-5027 | CC1=NC(O[C@@H](C2=CC=CC=C2)CCN[C@@H]3C[C@H](O)C3)=C(C#N)C=C1 |
| GT-5028 | CC1=NC(O[C@@H](C2=CC=CC=C2)CCNC3(C4)CC4C3)=C(C#N)C=C1 |
| GT-5029 | CC1=NC(O[C@@H](C2=CC=CC=C2)CCNC3CC3)=C(C#N)C=C1 |
| GT-5030 | CC1=NC(O[C@@H](C2=CC=CC=C2)CCNC(CO)CO)=C(C#N)C=C1 |
| GT-5031 | CC1=NC(O[C@@H](C2=CC=CC=C2)CCNCC3CC3)=C(C#N)C=C1 |

As shown in Table I-5-1, compounds GT-5001, -5002 and -5011 are to check if —CH3 can substitute for the Cl in 6b. Compounds GT-5006 and -5013 examine the scope of this —Cl replacement with —H and —CF3 (the CF3 group was reported to provide a near equivalent inhibitor in the AZ paper). Compounds GT-5002, -5006, -5011, -5012 and -5013 examine the NMe substituent alternative (the —NMe substituent is within the AZ patent). Finally, GT-5011 and -5012 test the importance of the —CN group with replacements of —H and —Br.

The compound physical property calculations including molecular weight (MW), cLogP, TPSA, as well as energy values "S_IFD_F3_iNOS" and "dE iNOS binding conf—ground state conf" are provided in Table I-5-2.

TABLE I-5-2

| GT-ID | MW | CD clogP | CD TPSA | Binding energy (S_IFD_F3_iNOS) (kcal) | dE iNOS binding conf–ground state conf (kcal) |
|---|---|---|---|---|---|
| GT-5001 | 267 | 2.2 | 71 | −9.3 | 7.9 |
| GT-5002 | 281 | 2.5 | 57 | −9 | 6.8 |
| GT-5003 | | | | −9.5 | 10.9 |
| GT-5004 | 325 | 2.8 | 67 | −9.8 | 8.9 |
| GT-5005 | | | | −8.6 | 7.4 |
| GT-5006 | 267 | 2 | 57 | −8.6 | 6.0 |
| GT-5007 | | | | −8.9 | 6.3 |
| GT-5008 | | | | −9.4 | 8.6 |
| GT-5009 | | | | −9 | 4.7 |
| GT-5010 | | | | −8.8 | 6.8 |
| GT-5011 | 256 | 2.9 | 34 | −8.2 | 6.4 |
| GT-5012 | 335 | 3.6 | 34 | −8.8 | 6.9 |
| GT-5013 | 335 | 2.9 | 57 | −9.7 | 5.7 |
| GT-5014 | 311 | 2 | 78 | −9.4 | 10.6 |
| GT-5015 | 325 | 2.3 | 77.6 | −9.3 | 10.0 |
| GT-5016 | 337 | 2.5 | 69 | −9.1 | 11.5 |
| GT-5017 | 337 | 2.5 | 69 | −9.3 | 7.7 |
| GT-5018 | 323 | 3.8 | 57 | −9.4 | 6.2 |
| GT-5019 | 338 | 3 | 61 | −9.7 | 13.1 |
| GT-5020 | 380 | 3 | 70 | −10.0 | 19.7 |
| GT-5021 | 347 | 2.3 | 82 | −10.1 | 11.4 |
| GT-5022 | 361 | 2.6 | 73 | −10.3 | 14.8 |
| GT-5023 | 361 | 2.2 | 82 | −9.9 | 15.1 |
| GT-5024 | 341 | 2 | 98 | | |
| GT-5025 | 341 | 2 | 98 | | |
| GT-5026 | 337 | 2.7 | 78 | | |
| GT-5027 | 337 | 2.7 | 78 | | |
| GT-5028 | 333 | 3.2 | 57 | | |
| GT-5029 | 307 | 3.1 | 57 | | |
| GT-5030 | 341 | 2 | 98 | | |
| GT-5031 | 321 | 3.5 | 57 | | |

Formula (I-6)

In these embodiments, the inventors used a fused aromatic ring system to replace the "W" group within the patent WO2001062704 as indicated below. Claims in the patent WO2001062704 define the W-group as a single aromatic ring.

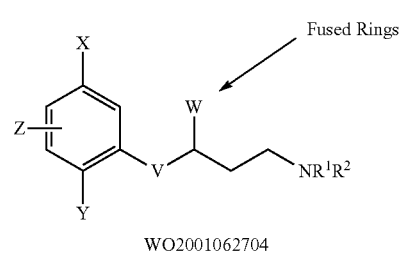

WO2001062704

A list of compound IDs and their SMILES codes are shown in Table I-6-1.

TABLE I-6-1

| GT-ID | SMILES Code |
|---|---|
| GT-6001 | NCCC(C1=CC=CC=C1)CC2=C(C#N)C=NC(OC)=C2 |
| GT-6002 | NCCC(C1=CC=CC=C1)CC2=C(C#N)C=NC(C(F)(F)F)=C2 |
| GT-6003 | NCCC(C1=CC=CC=C1)CC2=C(C#N)C=NC(C)=C2 |
| GT-6004 | CC1=CC(CC(C2=CC=CC=C2)CCNC)=C(C#N)C=N1 |
| GT-6005 | CC1=CC(CC(C2=CC=CC=C2)CCNCC)=C(C#N)C=N1 |
| GT-6006 | CC1=CC(CC(C2=CC=CC=C2)CCNCOC)=C(C#N)C=N1 |
| GT-6007 | NC(SC(C1=CC=CC=C1)CC2=C(C#N)C=CC(Cl)=C2)=[NH2+] |
| GT-6008 | NCCC(C1=C(C=NN2)C2=NC=N1)OC3=C(C#N)C=CC(Cl)=C3 |
| GT-6009 | NCCC(C1=NC(NN=C2)=C2C=N1)OC3=C(C#N)C=CC(Cl)=C3 |
| GT-6010 | NCCC(C1=C(C=NN2C)C2=NC=N1)OC3=C(C#N)C=CC(Cl)=C3 |
| GT-6011 | NCCC(C1=NC(N(C)N=C2)=C2C=N1)OC3=C(C#N)C=CC(Cl)=C3 |
| GT-6012 | NCCC(C1=NC2=NN(C)C=C2C=N1)OC3=C(C#N)C=CC(Cl)=C3 |
| GT-6013 | NCCC(C1=C(C=NN2)C2=CC=C1)OC3=C(C#N)C=CC(Cl)=C3 |
| GT-6014 | NCCC(C1=CC(NN=C2)=C2C=C1)OC3=C(C#N)C=CC(Cl)=C3 |
| GT-6015 | NCCC(C1=C(C=NN2)C2=NC=C1)OC3=C(C#N)C=CC(Cl)=C3 |
| GT-6016 | NCCC(C1=NC(NN=C2)=C2C=C1)OC3=C(C#N)C=CC(Cl)=C3 |
| GT-6017 | NCCC(C1=C(C=NN2C)C2=NC=C1)OC3=C(C#N)C=CC(Cl)=C3 |
| GT-6018 | NCCC(C1=NC(N(C)N=C2)=C2C=C1)OC3=C(C#N)C=CC(Cl)=C3 |
| GT-6019 | NCCC(C1=NC2=NN(C)C=C2C=C1)OC3=C(C#N)C=CC(Cl)=C3 |
| GT-6020 | NCCC(C1=C(N=CN2)C2=NC=N1)OC3=C(C#N)C=CC(Cl)=C3 |
| GT-6021 | NCCC(C1=NC(NC=N2)=C2C=N1)OC3=C(C#N)C=CC(Cl)=C3 |
| GT-6022 | NCCC(C1=C(N=CN2C)C2=NC=N1)OC3=C(C#N)C=CC(Cl)=C3 |
| GT-6023 | NCCC(C1=NC(N(C)C=N2)=C2C=N1)OC3=C(C#N)C=CC(Cl)=C3 |
| GT-6024 | NCCC(C1=C(N=CN2)C2=CC=C1)OC3=C(C#N)C=CC(Cl)=C3 |
| GT-6025 | NCCC(C1=CC(NC=N2)=C2C=C1)OC3=C(C#N)C=CC(Cl)=C3 |
| GT-6026 | NCCC(C1=C(N=CN2)C2=NC=C1)OC3=C(C#N)C=CC(Cl)=C3 |
| GT-6027 | NCCC(C1=NC(NC=N2)=C2C=C1)OC3=C(C#N)C=CC(Cl)=C3 |
| GT-6028 | NCCC(C1=C(N=CN2C)C2=NC=C1)OC3=C(C#N)C=CC(Cl)=C3 |
| GT-6029 | NCCC(C1=NC(N(C)C=N2)=C2C=C1)OC3=C(C#N)C=CC(Cl)=C3 |
| GT-6030 | NCCC(C1=CN2C(C=C1)=CC=N2)OC3=C(C#N)C=CC(Cl)=C3 |
| GT-6031 | NCCC(C1=CN2C(C=C1)=CN=C2)OC3=C(C#N)C=CC(Cl)=C3 |
| GT-6032 | NCCC(C1=CN2C(C=C1)=NC=C2)OC3=C(C#N)C=CC(Cl)=C3 |
| GT-6033 | NCCC(C1=CC2=CC=NN2C=C1)OC3=C(C#N)C=CC(Cl)=C3 |
| GT-6034 | NCCC(C1=CC2=CN=CN2C=C1)OC3=C(C#N)C=CC(Cl)=C3 |
| GT-6035 | NCCC(C1=CC2=NC=CN2C=C1)OC3=C(C#N)C=CC(Cl)=C3 |
| GT-6036 | N#CC1=C(OC(C2=CC3=NC=CN3C=C2)CCNC)=C(Cl)C=C1 |
| GT-6037 | N#CC1=C(OC(C2=CC(C=NN3C)=C3C=C2)CCNC)=C(Cl)C=C1 |
| GT-6038 | N#CC1=C(OC(C2=CC3=CN(C)N=C3C=C2)CCNC)=C(Cl)C=C1 |
| GT-6039 | N#CC1=C(OC(C2=CC(C=NN3)=C3C=C2)CCNC)=C(Cl)C=C1 |
| GT-6040 | NCC[C@H](C1=CC=CC=C1)OC2=C3C(CNC3=O)=CC(Cl)=C2 |
| GT-6041 | NCC[C@H](C1=CC=CC=C1)OC2=C3C(NC=N3)=CC(Cl)=C2 |
| GT-6042 | NCC[C@H](C1=CC=CC=C1)OC2=C3C(CC(N3)=O)=CC(Cl)=C2 |
| GT-6043 | NCC[C@H](C1=CC=CC=C1)OC2=C3C(NC(C3)=O)=CC(Cl)=C2 |
| GT-6044 | NCC[C@H](C1=CC=CC=C1)NC2=C3C(NC(C3)=O)=CC(Cl)=C2 |
| GT-6045 | NCC[C@H](C1=CC=CC=C1)OC2=C3C(NN=C3)=CC(Cl)=C2 |
| GT-6046 | NCC[C@H](C1=CC=CC=C1)OC2=CC(Cl)=CC3=NNC=C32 |
| GT-6047 | NCC[C@H](C1=CC=CC=C1)OC2=C3C(C=NN3)=CC(Cl)=C2 |
| GT-6048 | NCC[C@H](C1=CC=CC=C1)OC2=CC(Cl)=CC3=CNN=C32 |
| GT-6049 | NCC[C@H](C1=CC=CC=C1)OC2=C3C(NN=N3)=CC(Cl)=C2 |
| GT-6050 | NCC[C@H](C1=CC=CC=C1)OC2=CC(Cl)=CC3=NNN=C32 |
| GT-6051 | NCC[C@H](C1=CC=CC=C1)OC2=C3C(N=NN3)=CC(Cl)=C2 |
| GT-6052 | NCC[C@H](C1=CC=CC=C1)OC2=CC(Cl)=CN3C2=NC=C3 |
| GT-6053 | NCC[C@H](C1=CC=CC=C1)OC2=CC(Cl)=CC3=NC=CN32 |
| GT-6054 | NCC[C@H](C1=CC=CC=C1)OC2=CC(Cl)=CN3C2=CN=C3 |
| GT-6055 | NCC[C@H](C1=CC=CC=C1)OC2=CC(Cl)=CC3=CN=CN32 |
| GT-6056 | NCC[C@H](C1=CC=CC=C1)OC2=CC(Cl)=CN3C2=CC=N3 |
| GT-6057 | NCC[C@H](C1=CC=CC=C1)OC2=CC(Cl)=CC3=CC=NN32 |
| GT-6058 | C1C1=CC(O[C@@H](C2=CC=CC=C2)CCNC)=C3C(NC=N3)=C1 |
| GT-6059 | C1C1=CC(O[C@@H](C2=CC=CC=C2)CCNC)=C3C(NN=C3)=C1 |
| GT-6060 | C1C1=CC(O[C@@H](C2=CC=CC=C2)CCNCCO)=C3C(NC=N3)=C1 |
| GT-6061 | C1C1=CC(O[C@@H](C2=CC=CC=C2)CCNCCO)=C3C(NN=C3)=C1 |
| GT-6062 | C1C1=CC(OC(C2=CC(N)=NC=C2)CCNC)=C(C#N)C=C1 |
| GT-6063 | N#CC1=C(OC(C2=CC(N)=NC=C2)CCN3C(C(C=CC=C4)=C4C3=O)=O)C=C(Cl)C=C1 |
| GT-6064 | NCCC(C1=CC(N)=NC=C1)OC2=C(C#N)C=CC(Cl)=C2 |
| GT-6065 | N#CC1=C(OC(C2=CC3=NC=CN3C=C2)CCN4C(C(C=CC=C5)=C5C4=O)=O)C=C(Cl)C=C1 |
| GT-6066 | C1C1=CC(O[C@@H](C2=CC=CC=C2)CCN3C(C(C=CC=C4)=C4C3=O)=O)=C5C(NN=C5)=C1 |

The compound physical property calculations including molecular weight (MW), cLogP, TPSA, as well as energy values "S_IFD_F3_iNOS" and "dE iNOS binding conf—ground state conf" are provided in Table I-6-2.

TABLE I-6-2

| GT-ID | MW | CD clogP | CD TPSA | Binding energy (S_IFD_F3_iNOS) (kcal) | dE iNOS binding conf-ground state conf (kcal) |
|---|---|---|---|---|---|
| GT-6001 | | | | −9.3 | 9.4 |
| GT-6002 | | | | −9.7 | 10.0 |
| GT-6003 | | | | −9.2 | 9.2 |
| GT-6004 | | | | −9.5 | 10.1 |
| GT-6005 | | | | −9.6 | 13.2 |
| GT-6006 | | | | −10.0 | 17.8 |
| GT-6007 | | | | −9.1 | 10.2 |
| GT-6008 | | | | −9.3 | 5.6 |
| GT-6009 | | | | −9.2 | 4.1 |
| GT-6010 | | | | −9.5 | 7.3 |
| GT-6011 | | | | −9.7 | 5.4 |
| GT-6012 | | | | −9.9 | 4.3 |
| GT-6013 | | | | −9.3 | 5.3 |
| GT-6014 | | | | −9.5 | 8.6 |
| GT-6015 | | | | −9.3 | 5.3 |
| GT-6016 | | | | −9.4 | 8.2 |
| GT-6017 | | | | −9.9 | 7.0 |
| GT-6018 | 341 | 2.1 | 87 | −9.9 | 5.5 |
| GT-6019 | | | | −9.2 | 4.4 |
| GT-6020 | | | | −9 | 5.0 |
| GT-6021 | | | | −9.6 | 9.2 |
| GT-6022 | | | | −9.5 | 4.1 |
| GT-6023 | | | | −9.6 | 6.9 |
| GT-6024 | | | | −9.3 | 8.8 |
| GT-6025 | | | | −9.7 | 8.2 |
| GT-6026 | | | | −9.2 | 8.3 |
| GT-6027 | | | | −8.9 | 5.8 |
| GT-6028 | | | | −9.8 | 8.4 |
| GT-6029 | | | | −9.2 | 7.3 |
| GT-6030 | | | | −9.5 | 8.8 |
| GT-6031 | | | | −9.6 | 5.0 |
| GT-6032 | | | | −9.6 | 6.9 |
| GT-6033 | | | | −9.5 | 5.4 |
| GT-6034 | | | | −9.5 | 5.1 |
| GT-6035 | 327 | 3 | 75 | −9.7 | 3.4 |
| GT-6036 | 340 | 3.2 | 61 | −9.7 | 4.4 |
| GT-6037 | 354 | 3.5 | 61 | −9.9 | 4.7 |
| GT-6038 | 354 | 3.5 | 61 | −9.9 | 7.3 |
| GT-6039 | 341 | 3.4 | 69 | −9.6 | 7.8 |
| GT-6040 | 317 | 3 | 64 | −8.3 | 12.2 |
| GT-6041 | 302 | 3.7 | 60 | −8.6 | 9.7 |
| GT-6042 | 317 | 2.8 | 64 | −8.4 | 6.3 |
| GT-6043 | 317 | 2.8 | 64 | −8.6 | 7.7 |
| GT-6044 | 316 | 2.2 | 67 | −8.4 | 13.6 |
| GT-6045 | 302 | 3.9 | 60 | −9.2 | 4.9 |
| GT-6046 | 302 | 3.9 | 60 | −8.3 | 7.3 |
| GT-6047 | 302 | 3.9 | 60 | −8.6 | 3.5 |
| GT-6048 | 302 | 3.9 | 60 | −8.5 | 9.2 |
| GT-6049 | 303 | 3.5 | 72 | −8.7 | 4.7 |
| GT-6050 | 303 | 3.2 | 72 | −8.3 | 6.1 |
| GT-6051 | 303 | 3.5 | 72 | −8.6 | 3.1 |

TABLE I-6-2-continued

| GT-ID | MW | CD clogP | CD TPSA | Binding energy (S_IFD_F3_iNOS) (kcal) | dE iNOS binding conf-ground state conf (kcal) |
|---|---|---|---|---|---|
| GT-6052 | 302 | 3.5 | 51 | −8.6 | 10.2 |
| GT-6053 | 302 | 3.5 | 51 | −8.6 | 3 |
| GT-6054 | 302 | 3.5 | 51 | −9 | 18.3 |
| GT-6055 | 302 | 3.5 | 51 | −8.7 | 7.3 |
| GT-6056 | 302 | 3.5 | 51 | −8.1 | 3 |
| GT-6057 | 302 | 3.5 | 51 | −8.7 | 8.5 |
| GT-6058 | 316 | 4 | 46 | | |
| GT-6059 | 316 | 4.2 | 46 | | |
| GT-6060 | 346 | 3.5 | 66 | | |
| GT-6061 | 346 | 3.7 | 66 | | |
| GT-6062 | 316 | 2.1 | 83 | | |
| GT-6063 | 432 | 3.9 | 109 | | |
| GT-6064 | 302 | 1.9 | 97 | | |
| GT-6065 | 456 | 5 | 86 | | |
| GT-6066 | 431 | 5.9 | 71 | | |

GT-6035, -6036, -6037, -6038 and -6039 test whether a fused aromatic ring will work as a replacement for the single aromatic ring in the patent WO2001062704. Notably, compound GT-6035 had the most optimal energetic calculations for all designed molecules with the IFD energy of binding determined to be −9.7 kcal and the difference from ground state to bound state, dE calculated at 3.3 kcal. Low values in the latter indicate a low energy barrier for the molecule to assume the bound conformation and hence might be an indication of a favorable inhibitor. The other members of this class test small changes to the molecule to see where potency might be further improved.

Formula (I-7)

In these embodiments, the inventors inserted an achiral N-atom center to replace a chiral C-center atom defined in the patent WO2001062704 as indicated below. This change would remove the complexity introduced by having a chiral center in the molecule.

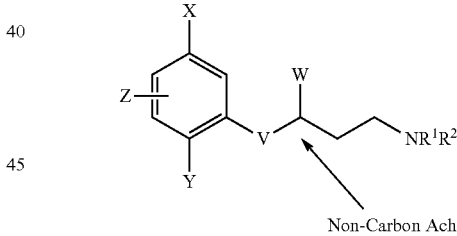

Non-Carbon Achiral-center
WO2001062704

A list of compound IDs and their SMILES codes are shown in Table I-7-1.

TABLE I-7-1

| GT-ID | SMILES Code |
|---|---|
| GT-7001 | NCCN(C1=CC=CC=C1)C(C2=C(C#N)C=CC(Cl)=C2)=O |
| GT-7002 | NCCN(C1=C(Cl)C=CC=C1)C(C2=C(C#N)C=CC(Cl)=C2)=O |
| GT-7003 | NCCN(C1=CC=CC=C1)CC2=C(C#N)C=CC(Cl)=C2 |
| GT-7004 | NCCN(C1=C(Cl)C=CC=C1)CC2=C(C#N)C=CC(Cl)=C2 |
| GT-7005 | NCCN(C1=CC=CC=C1)C(C2=C(Br)C=CC(Cl)=C2)=O |
| GT-7006 | NCCN(C1=CC=CC=C1)CC2=C(Br)C=CC(Cl)=C2 |
| GT-7007 | NCCN(C1=C(Cl)C=CC=C1)C(C2=C(Br)C=CC(Cl)=C2)=O |
| GT-7008 | NCCN(C1=C(Cl)C=CC=C1)CC2=C(Br)C=CC(Cl)=C2 |
| GT-7009 | ClC1=CC(C(N(C2=CC=CC=C2)CCNCCO)=O)=C(C#N)C=C1 |
| GT-7010 | ClC1=CC(CN(C2=CC=CC=C2)CCNCCO)=C(C#N)C=C1 |
| GT-7011 | ClC1=CC(C(N(C2=CC=CC=C2)CCNCCCO)=O)=C(C#N)C=C1 |
| GT-7012 | ClC1=CC(CN(C2=CC=CC=C2)CCNCCCO)=C(C#N)C=C1 |

TABLE I-7-1-continued

| GT-ID | SMILES Code |
|---|---|
| GT-7013 | ClC1=CC(C(N(C2=CC=CC=C2)CCN[C@H]3CC[C@H](O)CC3)=O)=C(C#N)C=C1 |
| GT-7014 | ClC1=CC(CN(C2=CC=CC=C2)CCN[C@H]3CC[C@H](O)CC3)=C(C#N)C=C1 |
| GT-7015 | ClC1=CC(C(N(C2=CC=CC=C2)CCNC[C@@H](O)CO)=O)=C(C#N)C=C1 |
| GT-7016 | ClC1=CC(CN(C2=CC=CC=C2)CCNC[C@@H](O)CO)=C(C#N)C=C1 |
| GT-7017 | ClC1=CC(C(N(C2=CC=CC=C2)CCNC(CO)CO)=O)=C(C#N)C=C1 |
| GT-7018 | ClC1=CC(CN(C2=CC=CC=C2)CCNC(CO)CO)=C(C#N)C=C1 |
| GT-7019 | ClC1=CC(C(N(C2=CC=CC=C2)CCNCC3CC3)=O)=C(C#N)C=C1 |
| GT-7020 | ClC1=CC(CN(C2=CC=CC=C2)CCNCC3CC3)=C(C#N)C=C1 |
| GT-7021 | ClC1=CC(C(N(C2=CC=CC=C2)CCNC3CC[C@H](O)CC3)=O)=C(C#N)C=C1 |
| GT-7022 | ClC1=CC(C(N(C2=CC=CC=C2)CCNC3CC[C@H](O)CC3)=O)=C(C#N)C=C1 |
| GT-7023 | ClC1=CC(CN(C2=CC=CC=C2)CCNC3CC[C@H](O)CC3)=C(C#N)C=C1 |
| GT-7024 | ClC1=CC(CN(C2=CC=CC=C2)CCNC3CC[C@H](O)CC3)=C(C#N)C=C1 |

The compound physical property calculations including molecular weight (MW), cLogP, TPSA, as well as energy values "S_IFD_F3_iNOS" and "dE iNOS binding conf—ground state conf" are provided in Table I-7-2.

TABLE I-7-2

| GT-ID | MW | CD clogP | CD TPSA | Binding energy (S_IFD_F3_iNOS) (kcal) | dE iNOS binding conf-ground state conf (kcal) |
|---|---|---|---|---|---|
| GT-7001 | 300 | 2.3 | 70 | −9.0 | 7.0 |
| GT-7002 | 334 | 2.6 | 70 | −9.2 | 7.3 |
| GT-7003 | 287 | 3.6 | 53 | −9.1 | 14.7 |
| GT-7004 | 320 | 4.5 | 53 | −9.1 | 19.6 |
| GT-7005 | 353 | 3.6 | 46 | −8.5 | 10.5 |
| GT-7006 | 340 | 4.9 | 29 | −8.3 | 14.1 |
| GT-7007 | 388 | 4 | 46 | −8.8 | 13.0 |
| GT-7008 | 374 | 5.8 | 29 | −8.3 | 14.8 |
| GT-7009 | 344 | 2.1 | 76 | −8.9 | 15.2 |
| GT-7010 | 330 | 3.5 | 59 | −8.6 | 21.4 |
| GT-7011 | 358 | 2.4 | 76 | | |
| GT-7012 | 344 | 3.8 | 59 | | |
| GT-7013 | 398 | 2.6 | 76 | | |
| GT-7014 | 384 | 3.9 | 59 | | |
| GT-7015 | 374 | 2.1 | 97 | | |
| GT-7016 | 360 | 3.4 | 80 | | |
| GT-7017 | 374 | 2.1 | 97 | | |
| GT-7018 | 360 | 3.4 | 80 | | |
| GT-7019 | 353 | 3.6 | 56 | | |
| GT-7020 | 340 | 4.9 | 39 | | |
| GT-7021 | 398 | 2.6 | 76 | | |
| GT-7022 | 398 | 2.6 | 76 | | |
| GT-7023 | 384 | 3.9 | 59 | | |
| GT-7024 | 384 | 3.9 | 59 | | |

GT-7001, -7002, -7003 and -7004 test whether the carbon chiral center is necessary to binding efficiency. The new C(O) group which will replace the 0-linker atom, though rigid and enforcing a flat geometry to this portion of the molecule, still allows all groups to reasonably overlap with AZ 6b and have favorable interactions with the protein. Compound GT-7002 has IFD S=−9.2 kcal and dE=7.3 KCal/Mol. Both are reasonable to expect potent binding in the in vitro inhibition assay. These molecules represent a promising simplification being achiral compared to the chiral AZ 6b. The simplification represents ease of synthesis, expanded diversity potential, favorable physical properties such as solubility. Also, the group adds polarity which could prevent penetration into the CNS, hence eliminating concerns about toxicity related to nNOS inhibition.

Formula (I-8)

Figure 22:
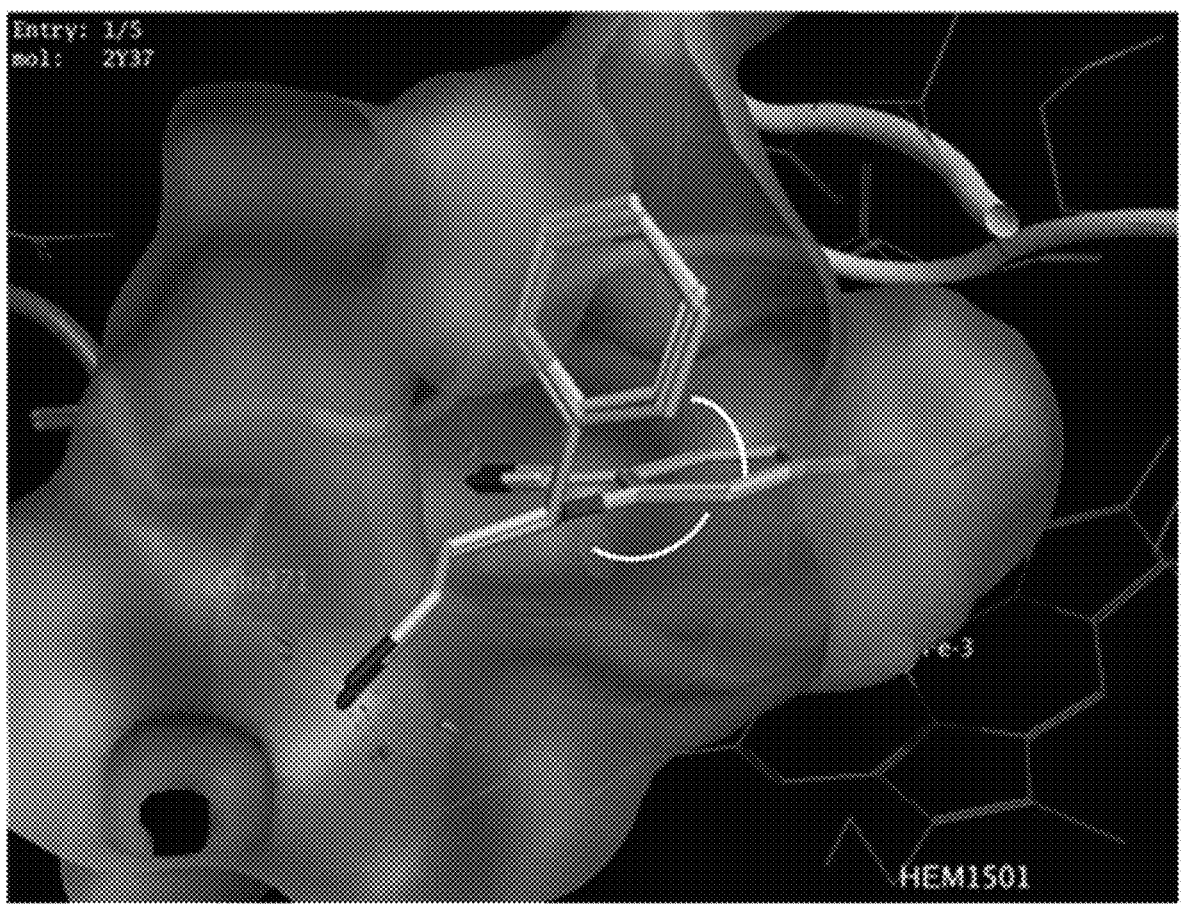
FIG. 22 schematically illustrates a strategy to cyclize different regions of the compound AZ 6b in accordance with an exemplary embodiment of the present invention.

In these embodiments, the inventors' strategy is to cyclize different regions of the AZ 6b as shown in FIG. 22. Potential cyclic AZ 6b analogues are implied by the white arcs which connect different regions of the lead molecule AZ 6b. Cyclization can result in multiple positive attributes for the molecules such as improved potency since the molecule is conformationally locked into a favorable binding orientation. Cyclization also can enhance selectivity since they are in mainly one conformation and improve drug-like physical properties and patentability from the underexplored cyclic molecule type.

A list of compound IDs and their SMILES codes are shown in Table I-8-1.

TABLE I-8-1

| GT-ID | SMILES Code |
|---|---|
| GT-8001 | ClC1=CC=C(C#N)C2=C1CC3=C(C=CC=C3)C(CCN)O2 |
| GT-8002 | ClC1=C2C(OC(CCN)C(C=CC=C3)=C3CC2)=C(C#N)C=C1 |
| GT-8003 | ClC1=C2CCCC3=C(C=CC=C3)C(CCN)OC2=C(C#N)C=C1 |
| GT-8004 | ClC1=C2C(OC(C3=CC=CC=C3)(CCN)C2)=C(C#N)C=C1 |
| GT-8005 | ClC1=C(CC2)C(OC2(C3=CC=CC=C3)CCN)=C(C#N)C=C1 |
| GT-8006 | ClC1=C2C(OC(C3=CC=CC=C3)(CCN)CCC2)=C(C#N)C=C1 |

The compound physical property calculations including molecular weight (MW), cLogP, TPSA, as well as energy values "S_IFD_F3_iNOS" and "dE iNOS binding conf—ground state conf" are provided in Table I-8-2.

TABLE I-8-2

| GT-ID | MW | CD clogP | CD TPSA | Binding energy (S_IFD_F3_iNOS) (kcal) | dE iNOS binding conf-ground state conf (kcal) |
|---|---|---|---|---|---|
| GT-8001 | 298 | 4 | 59 | −9.1 | 6.3 |
| GT-8002 | 313 | 4.4 | 59 | −9.2 | 7.3 |
| GT-8003 | 327 | 5 | 59 | −8.9 | 8.8 |
| GT-8004 | 299 | 3.9 | 59 | −9.1 | 9.9 |
| GT-8005 | 313 | 4.3 | 59 | −7.3 | 9.6 |
| GT-8006 | 327 | 4.9 | 59 | −9.3 | 7 |

Compounds GT-8001, -8002 and -8006 have the most favorable binding energetics.

Synthesis of Formula (I) Compounds

Some compounds of the invention identified by the following ID codes GT-XXXX are also identified by ID codes CPG-YYY, as listed in Table S-1.

TABLE S-1

| GT-XXXX | CPG-YYY |
|---|---|
| AZ 6b | CPG-6B |
| GT-5001 | CPG-157 |
| GT-5002 | CPG-158 |
| GT-5006 | CPG-162 |
| GT-6035 | CPG-195 |
| GT-6065 | CPG-264 |
| GT-7001 | CPG-196 |
| GT-7002 | CPG-197 |
| GT-7003 | CPG-198 |
| GT-7004 | CPG-199 |
| GT-6036 | CPG-200 |
| GT-5011 | CPG-201 |
| GT-5012 | CPG-202 |
| GT-5013 | CPG-203 |
| GT-7005 | CPG-207 |
| GT-7006 | CPG-208 |
| GT-7007 | CPG-209 |
| GT-7008 | CPG-210 |
| GT-5014 | CPG-211 |
| GT-5016 | CPG-213 |
| GT-5017 | CPG-214 |
| GT-7009 | CPG-215 |
| GT-7010 | CPG-216 |
| GT-5018 | CPG-217 |
| GT-5019 | CPG-218 |
| GT-5020 | CPG-219 |
| GT-5021 | CPG-220 |
| GT-5022 | CPG-221 |
| GT-5023 | CPG-222 |
| GT-6041 | CPG-224 |
| GT-7011 | CPG-237 |
| GT-7016 | CPG-242 |
| GT-5024 | CPG-243 |
| GT-5025 | CPG-244 |
| GT-5026 | CPG-245 |
| GT-5027 | CPG-246 |
| GT-5028 | CPG-247 |
| GT-5029 | CPG-248 |
| GT-5030 | CPG-249 |
| GT-7017 | CPG-250 |
| GT-7018 | CPG-251 |
| GT-5031 | CPG-252 |
| GT-7019 | CPG-253 |
| GT-7020 | CPG-254 |
| GT-6058 | CPG-255 |
| GT-6059 | CPG-256 |
| GT-6060 | CPG-257 |

TABLE S-1-continued

| GT-XXXX | CPG-YYY |
|---|---|
| GT-6061 | CPG-258 |
| GT-7021 | CPG-259 |
| GT-7022 | CPG-260 |
| GT-6064 | CPG-263 |
| GT-6066 | CPG-265 |
| GT-7023 | CPG-266 |
| GT-7024 | CPG-267 |

Synthesis of (R)-2-(3-amino-1-phenylpropoxy)-4-chlorobenzonitrile (CPG-6B)

Step 1: Synthesis of (R)-3-azido-1-phenylpropan-1-ol (2)

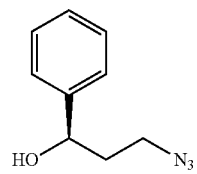

2

A mixture of (R)-3-chloro-1-phenylpropan-1-ol (5 g, 29.4 mmol) and NaN3 (3.22 g, 33 mmol) in DMSO (30 mL) was stirred at 40 degrees for 1.5 h. LCMS was used to monitor this reaction. The reaction mixture was partitioned between water (30 mL) and EtOAc (50 mL). The organic phase was separated, washed with water (20 mL) and brine (20 mL), dried over anhydrous Na2SO4 and concentrated to get the crude product, which was purified by column chromatography on silica gel (EA/.PE from 0/100 to 1/1) to get the pure (R)-3-azido-1-phenylpropan-1-ol (4.1 g, 78% yield) as a colorless oil. LCMS: m/z 178.1 [M+H]+.

Step 2. Synthesis of (R)-2-(3-azido-1-phenyl-propoxy)-4-chlorobenzonitrile (3)

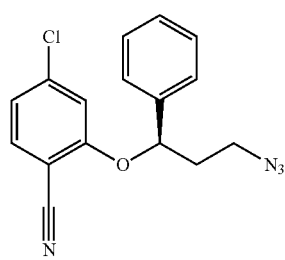

3

To a solution of (R)-3-azido-1-phenylpropan-1-ol (1 g, 5.65 mmol) and 4-chloro-2-fluorobenzonitrile (0.88 g, 5.65 mmol) in dried THF (20 mL) was treated with NaH (60%, 5.65 mmol, 0.226 g) at room temperature under $N_2$ atmosphere. The mixture was stirred at 60° C. for 1.5 h. LCMS was used to monitor this reaction. The reaction mixture was partitioned between water (30 mL) and EtOAc (50 mL). The organic phase was separated, washed with water (20 mL) and brine (20 mL), dried over anhydrous Na2SO4 and concentrated to get the crude product, which was purified by column chromatography on silica gel (EA/.PE from 0/100 to 1/10) to get the pure (R)-2-(3-azido-1-phenylpropoxy)-4-chlorobenzonitrile (1.41 g, 80% yield) as a colorless oil. LCMS: m/z 313.1 [M+H]+.

Step 3. Synthesis of (R)-2-(3-amino-1-phenyl-propoxy)-4-chlorobenzonitrile (4)

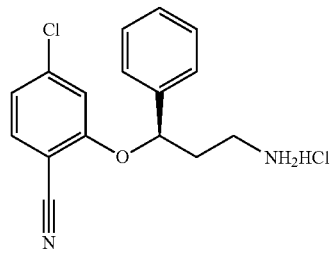

(4)

To a solution of (R)-2-(3-azido-1-phenylpropoxy)-4-chlorobenzonitrile (500 mg, 1.6 mmol) in THF (10 mL) and water (0.1 mL) was added PPh3 (226 mg) in portions. The reaction solution was stirred at room temperature overnight. The solvent was evaporated, and the residue was purified by column chromatography on silica gel (EA, then 10% 7N NH3 in MeOH/DCM). The oil obtained was converted into HCl salt using 1 eq. aq. HCl to afford the pure (R)-2-(3-amino-1-phenyl propoxy)-4-chlorobenzonitrile (258 mg, 50% yield) as a white solid. LCMS: m/z 287.1 [M+H]+. 1H NMR (400 MHz, DMSO) δ 7.96 (s, 3H), 7.79 (d, J=8.3 Hz, 1H), 7.47-7.39 (m, 4H), 7.39-7.31 (m, 1H), 7.21 (d, J=1.7 Hz, 1H), 7.16 (dd, J=8.3, 1.8 Hz, 1H), 5.86 (dd, J=8.1, 4.7 Hz, 1H), 2.95-2.85 (m, 2H), 2.35-2.23 (m, 1H), 2.22-2.02 (m, 1H).

Synthesis of (R)-2-(3-amino-1-phenylpropoxy)-6-methylnicotinonitrile (CPG-157)

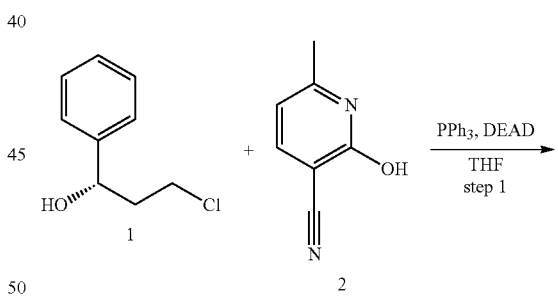

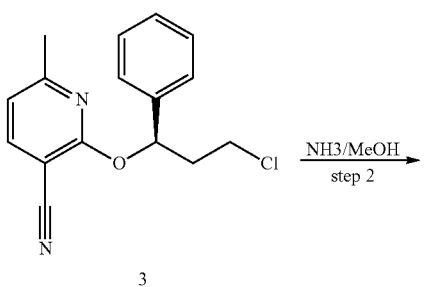

3

-continued

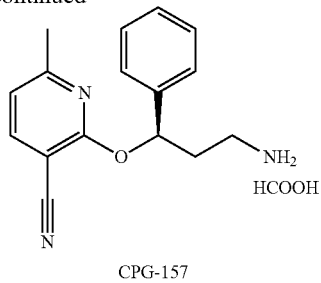

CPG-157

Step 1. Synthesis of (R)-2-(3-chloro-1-phenyl-propoxy)-6-methylnicotinonitrile (3)

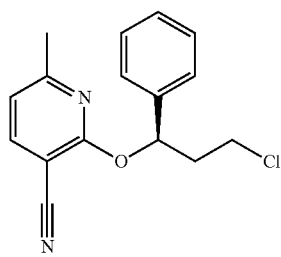

3

To a solution of (S)-3-chloro-1-phenylpropan-1-ol (2 g, 11.8 mmol), 2-hydroxy-6-methylnicotinonitrile (1.58 g, 11.8 mmol) and PPh3 (3.1 g, 11.8 mmol) in THF (50 mL) was added DEAD (2.05 g, 11.8 mmol) dropwise at 0° C. under N2 balloon. The reaction was allowed to warm to room temperature and stirred overnight. The reaction solution was purified by column chromatography on silica gel (EA/PE=1/10) to afford the pure (R)-2-(3-chloro-1-phenyl propoxy)-6-methylnicotinonitrile (2.36 g, 70% yield) as a viscous oil. LCMS: m/z 287.1 [M+H]+.

Step 2. Synthesis of (R)-2-(3-amino-1-phenyl-propoxy)-6-methylnicotinonitrile (CPG-157)

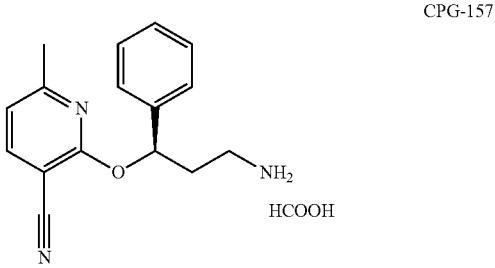 [SMILES: Cc1ccc(C#N)c(O[C@H](CCN)c2ccccc2)n1 ; "HCOOH"]

A mixture of (R)-2-(3-chloro-1-phenylpropoxy)-6-methylnicotinonitrile (200 mg, 0.7 mmol) and NaI (10 mg, 0.07 mmol) and NH3/MeOH (7 N, 0.5 mL, 3.5 mmol) in MeOH (5 mL) was stirred at 60° C. overnight. LCMS was used to monitor this reaction. The solvent was evaporated, and the residue was purified by Prep-HPLC (0.1% formic acid/MeCN) to get (R)-2-(3-amino-1-phenylpropoxy)-6-methylnicotinonitrile (60 mg, 32% yield) as formic acid salt as pale solid. LCMS: m/z 268.1 [M+H]+. 1H NMR (400 MHz, MeOD) δ 8.51 (s, 1H), 8.24 (dd, J=25.9, 7.8 Hz, 1H), 7.41 (d, J=7.3 Hz, 2H), 7.35 (t, J=7.5 Hz, 2H), 7.28 (dd, J=10.0, 4.4 Hz, 1H), 6.92 (dd, J=11.4, 7.9 Hz, 1H), 4.84 (dd, J=9.5, 3.0 Hz, 1H), 4.43 (d, J=7.1 Hz, 2H), 2.74-2.58 (m, 3H), 2.35-2.25 (m, 1H), 2.17-1.99 (m, 1H).

Synthesis of (R)-6-methyl-2-(3-(methylamino)-1-phenylpropoxy)nicotinonitrile (CPG-158)

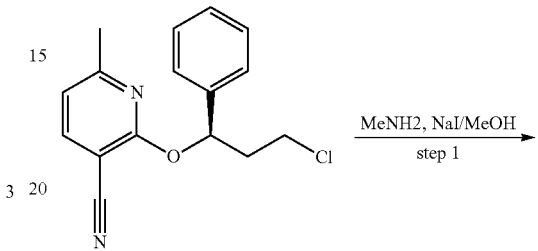

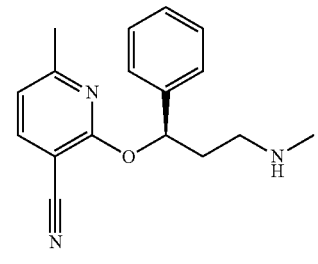

CPG-158

Step 1. Synthesis of (R)-6-methyl-2-(3-(methyl-amino)-1-phenylpropoxy)nicotinonitrile (CPG-158)

The exact method as described for the synthesis of (R)-2-(3-amino-1-phenylpropoxy)-6-methylnicotinonitrile (CPG-157) was applied with substitution of methylamine for ammonia to provide the product (R)-6-methyl-2-(3-(methylamino)-1-phenylpropoxy)nicotinonitrile (CPG-158, 30% yield) as formic acid salt as pale solid. LCMS: m/z 282.2.3 [M+H]+. 1H NMR (400 MHz, MeOD) δ 8.53 (s, 1H), 7.92 (t, J=8.9 Hz, 1H), 7.53-7.42 (m, 2H), 7.41-7.32 (m, 2H), 7.32-7.24 (m, 1H), 6.93 (d, J=7.7 Hz, 1H), 6.37-6.28 (m, 1H), 3.22-3.05 (m, 2H), 2.69 (s, 3H), 2.55-2.42 (m, 1H), 2.41 (d, J=6.3 Hz, 3H), 2.36-2.24 (m, 1H).

Synthesis of (R)-2-(3-amino-1-phenylpropoxy)-6-methylnicotinonitrile (CPG-162)

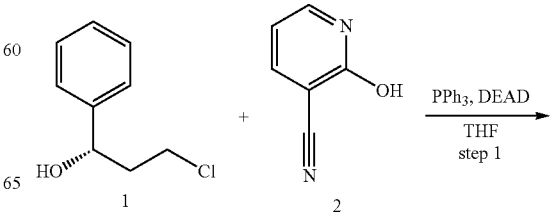

-continued

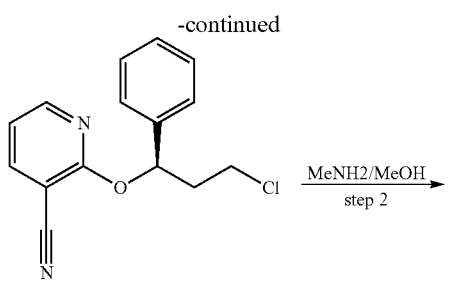

Step 1. Synthesis of (R)-2-(3-chloro-1-phenyl-propoxy)nicotinonitrile (3)

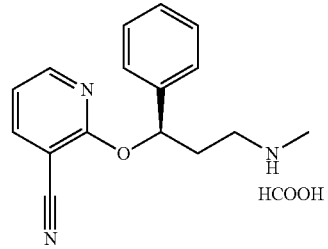

To a solution of (S)-3-chloro-1-phenylpropan-1-ol (2 g, 11.8 mmol), 2-hydroxy nicotinonitrile (1.42 g, 11.8 mmol) and PPh3 (3.1 g, 11.8 mmol) in THF (50 mL) was added DEAD (2.05 g, 11.8 mmol) dropwise at 0° C. under $N_2$ balloon. The reaction was allowed to warm to room temperature and stirred overnight. The reaction solution was purified by column chromatography on silica gel (EA/PE=1/10) to afford the pure (R)-2-(3-chloro-1-phenylpropoxy)nicotinonitrile (2.36 g, 74% yield) as a viscous oil. LCMS: m/z 273.1 [M+H]+.

Step 2. Synthesis of (R)-2-(3-(methylamino)-1-phenylpropoxy)nicotinonitrile (CPG-162)

A mixture of (R)-2-(3-chloro-1-phenylpropoxy) nicotinonitrile (190 mg, 0.7 mmol) and NaI (10 mg, 0.07 mmol) and MeNH2/MeOH (30%, 0.35 g, 3.5 mmol) in MeOH (5 mL) was stirred at 60° C. overnight. LCMS was used to monitor this reaction. The solvent was evaporated, and the residue was purified by Prep-HPLC (0.1% formic acid/MeCN) to get (R)-2-(3-(methyl amino)-1-phenylpropoxy)nicotinonitrile (60 mg, 32% yield) as formic acid salt as pale solid. LCMS: m/z 268.1 [M+H]+. 1H NMR (400 MHz, MeOD) δ 8.53 (s, 1H), 7.92 (t, J=8.9 Hz, 1H), 7.53-7.42 (m, 2H), 7.41-7.32 (m, 2H), 7.32-7.24 (m, 1H), 6.93 (d, J=7.7 Hz, 1H), 6.37-6.28 (m, 1H), 3.22-3.05 (m, 2H), 2.69 (s, 3H), 2.55-2.42 (m, 1H), 2.41 (d, J=6.3 Hz, 3H), 2.36-2.24 (m, 1H).

Synthesis of 2-(3-amino-1-(imidazo[1,2-a]pyridin-7-yl)propoxy)-4-chlorobenzonitrile (CPG-195)

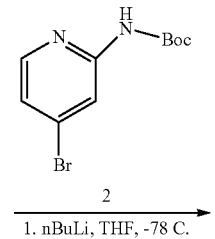

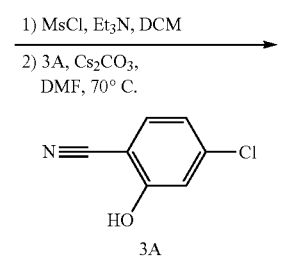

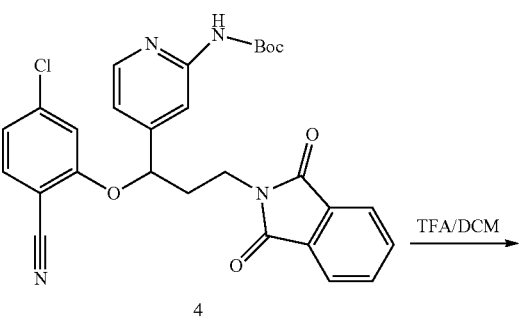

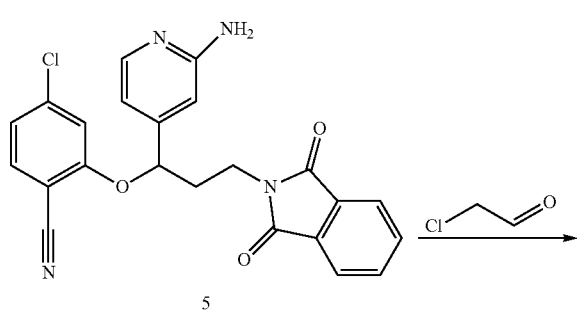

-continued

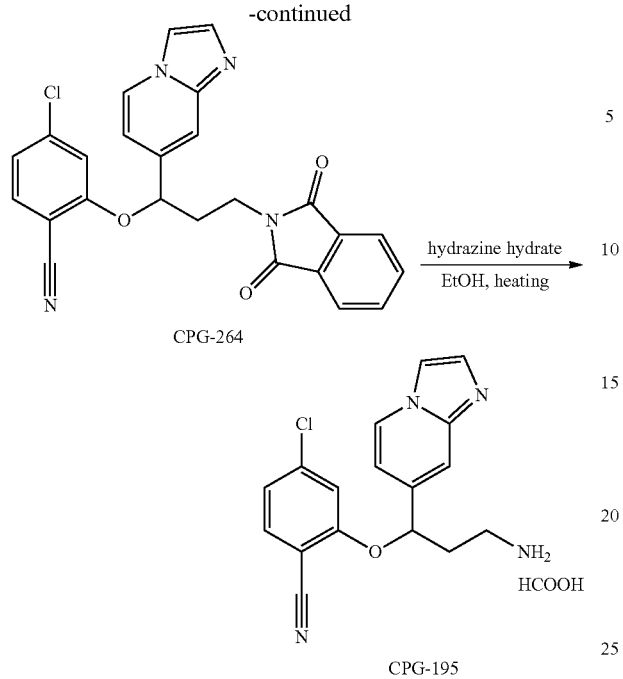

Step 1. Synthesis of tert-butyl (4-(3-(1,3-dioxoisoindolin-2-yl)-1-hydroxypropyl) pyridin-2-yl)carbamate (3)

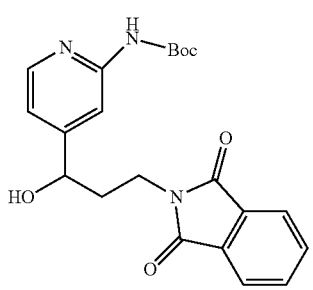

To a solution of tert-butyl (4-bromopyridin-2-yl)carbamate (1.34 g, 4.92 mmol) in THF (15 mL) was added n-BuLi (2.5 M, 3.94 mL, 9.85 mmol) at −78° C. and the mixture was stirred at −78° C. for 30 min. Then a solution of 3-(1,3-dioxoisoindolin-2-yl)propanal (1.0 g, 4.92 mmol) in THF (5 mL) was added dropwise to the above mixture at −78° C. and the mixture was stirred at room temperature for 12 hrs. Sat. NaCl solution (20 mL) was added to the mixture and the mixture was extracted with EA (20 mL×3). The organic layer was washed with brine (15 mL), dried over anhydrous Na2SO4, filtered and concentrated. The residue was purified by silica gel column (EA in PE=0% to 30%) to give tert-butyl (4-(3-(1,3-dioxoisoindolin-2-yl)-1-hydroxypropyl)pyridin-2-yl) carbamate (3) (556 mg, 1.4 mmol, 28.5% yield) as colorless oil. LCMS: m/z 398.3 [M+H]+ 1H NMR (400 MHz, CDCl$_3$) δ 8.18 (d, J=5.2 Hz, 1H), 7.89-7.84 (m, 3H), 7.75 (dd, J=5.6, 3.2 Hz, 3H), 7.02 (d, J=5.2 Hz, 1H), 4.69-4.61 (m, 1H), 3.99-3.92 (m, 2H), 3.43 (d, J=4.4 Hz, 1H), 2.14-2.03 (m, 1H), 1.98-1.96 m, 1H), 1.55-1.48 (m, 9H).

Step 2. Synthesis of tert-butyl (4-(1-(5-chloro-2-cyanophenoxy)-3-(1,3-dioxoisoindolin-2-yl)propyl) pyridin-2-yl)carbamate (4)

To a solution of tert-butyl(4-(3-(1,3-dioxoisoindolin-2-yl)-1-hydroxypropyl)pyridin-2-yl) carbamate (449 mg, 1.13 mmol), Et3N (228 mg, 2.26 mmol) in DCM (20 mL) was added MSCl (155 mg, 1.356 mmol) at 0° C. and the mixture was stirred at room temperature for 2 h. The solvent was removed to give 1-(2-((tert-butoxycarbonyl)amino)pyridin-4-yl)-3-(1,3-dioxo isoindolin-2-yl)propyl methanesulfonate (990 mg, crude) as yellow oil. A solution of 1-(2-((tert-butoxycarbonyl) amino)pyridin-4-yl)-3-(1,3-dioxoisoindolin-2-yl)propyl methanesulfonate (990 mg, crude) in DMF (2 mL) was added to a mixture of 4-chloro-2-hydroxybenzonitrile (174 mg, 1.13 mmol) and Cs2CO3 (441 mg, 1.356 mmol) in DMF (8 mL) at 70° C. and the mixture was stirred at 70° C. for 12 hrs. Water (100 mL) was added to the reaction mixture at 0° C. and the suspension was stirred for 30 min. The suspension mixture was filtered to give tert-butyl(4-(1-(5-chloro-2-cyanophenoxy)-3-(1,3-dioxoisoindolin-2-yl)propyl)pyridin-2-yl)carbamate (530 mg, crude) as a yellow solid. LCMS: m/z 533.1 [M+H]+.

Step 3. Synthesis of 2-(1-(2-aminopyridin-4-yl)-3-(1,3-dioxoisoindolin-2-yl)propoxy)-4-chlorobenzonitrile (5)

To a solution of tert-butyl (4-(1-(5-chloro-2-cyanophenoxy)-3-(1,3-dioxoisoindolin-2-yl) propyl)pyridin-2-yl)carbamate (530 mg, 0.996 mmol) in DCM (15 mL) was added TFA (10 mL) at 0° C. and the mixture was stirred at room temperature for 12 hrs. The solvent was removed, and the residue was dissolved with DCM (10 mL) and pH of the mixture was adjusted to 8-9 with a solution of NH3 in MeOH (7 M). Then the solvent was removed, and the residue was purified by silica gel column chromatography (MeOH in DCM=0% to 15%) to give 2-(1-(2-amino pyridin- 4-yl)-3-(1,3-dioxoisoindolin-2-yl)propoxy)-4-chlorobenzonitrile (5) (400 mg, 0.926 mmol, 93% yield) as yellow oil. LCMS: m/z 433.1 [M+H]+. 1H NMR (400 MHz, CDCl₃) δ 8.03 (d, J=5.6 Hz, 1H), 7.83 (dd, J=5.6, 3.2 Hz, 2H), 7.72 (dd, J=5.6, 3.2 Hz, 2H), 7.57-7.55 (m, 1H), 6.98 (dd, J=8.4, 1.6 Hz, 1H), 6.70 (d, J=1.6 Hz, 1H), 6.62 (d, J=5.2 Hz, 1H), 6.49 (s, 1H), 5.12 (dd, J=8.8, 4.0 Hz, 1H), 4.53 (s, 2H), 4.03-3.93 (m, 2H), 2.52-2.39 (m, 1H), 2.24-2.17 (m, 1H).

Step 4. Synthesis of 4-chloro-2-(3-(1,3-dioxoisoindolin-2-yl)-1-(imidazo[1,2-a]pyridin-7-yl)propoxy) benzonitrile (CPG-264)

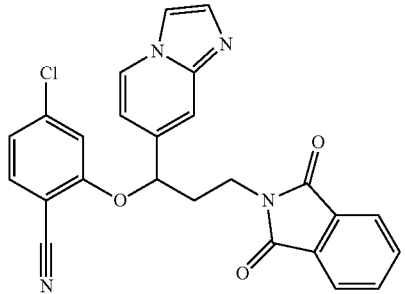

CPG-264

A mixture of 2-(1-(2-aminopyridin-4-yl)-3-(1,3-dioxoisoindolin-2-yl)propoxy)-4-chlorobenzonitrile (250 mg, 0.577 mmol), a solution of aqueous 2-chloroacetaldehyde (40% w/w, 6.1 mol/L, 0.11 mL, 0.693 mmol) in EtOH (10 mL) was stirred in a sealed tube at 70° C. for 12 hrs. The solvent was removed, and the residue was azeotroped with additional EtOH (10 mL) to remove the residual water to give 4-chloro-2-(3-(1,3-dioxoisoindolin-2-yl)-1-(imidazo[1,2-a]pyridin-7-yl)propoxy)benzonitrile (CPG-264) (264 mg, crude) as a white solid, which will be used in next step without further purification.

The crude product (100 mg) was purified by Prep-HPLC (Fluent with 0.2% FA and ACN) to give 4-chloro-2-(3-(1,3-dioxoisoindolin-2-yl)-1-(imidazo[1,2-a]pyridin-7-yl)propoxy) benzonitrile (CPG-264) (40.4 mg, 0.088 mmol, 38.5% yield) as a white solid, which has been delivered. LCMS: m/z 457.1[M+H]+. 1H NMR (400 MHz, MeOD) δ 8.21 (d, J=5.2 Hz, 1H), 7.91 (s, 1H), 7.64 (d, J=8.0 Hz, 1H), 7.11-6.96 (m, 3H), 5.53-5.49 (m, 1H), 3.58-3.55 (m, 1H), 3.51-3.48 (m, 1H), 2.86 (s, 3H), 2.28-2.23 (m, 2H), 1.53 (s, 9H), 1.43 (s, 9H).

Step 5. Synthesis of 2-(3-amino-1-(imidazo[1,2-a]pyridin-7-yl)propoxy)-4-chlorobenzonitrile (CPG-195)

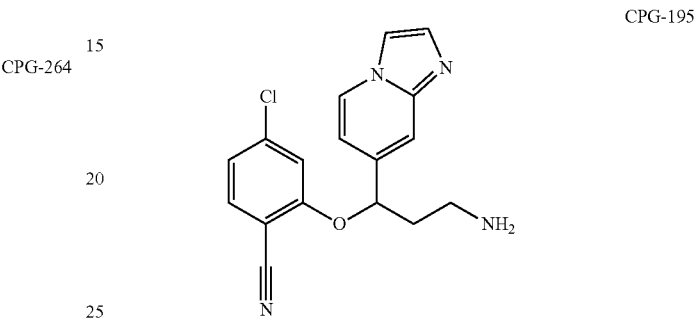

CPG-195

A mixture of 4-chloro-2-(3-(1,3-dioxoisoindolin-2-yl)-1-(imidazo[1,2-a]pyridin-7-yl) propoxy)benzonitrile (164 mg, crude) and hydrazine hydrate (0.52 mL, 10.77 mmol) in EtOH (10 mL) was stirred at 80° C. for 12 hrs. The solvent was removed under reduced pressure. The residue was purified by Prep-HPLC (Fluent with 10 mM NH4HCO3 and ACN) to give 2-(3-amino-1-(imidazo[1,2-a]pyridin-7-yl)propoxy)-4-chlorobenzonitrile (CPG-195) (12.8 mg, 0.039 mmol, 10.9% yield) as yellow oil. LCMS: m/z 327.0[M+H]+. 1HNMR (400 MHz, MeOD) δ 8.51 (d, J=7.2 Hz, 1H), 7.86 (s, 1H), 7.64 (d, J=8.4 Hz, 1H), 7.60 (s, 2H), 7.15 (s, 1H), 7.12-7.08 (m, 1H), 7.00 (d, J=7.2 Hz, 1H), 5.75 (dd, J=8.4, 4.0 Hz, 1H), 3.17-3.14 (m, 2H), 2.49-2.39 (m, 1H), 2.35-2.25 m, 1H).

Synthesis of N-(2-aminoethyl)-5-chloro-2-cyano-N-phenylbenzamide hydrochloride (CPG-196).

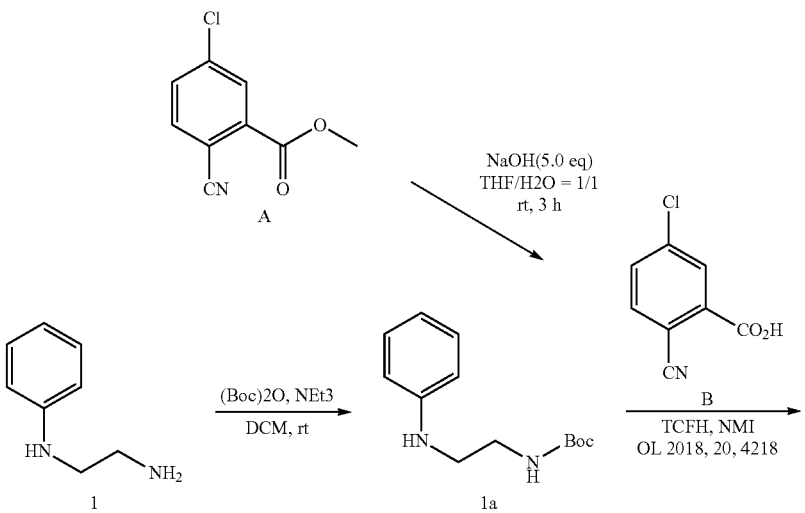

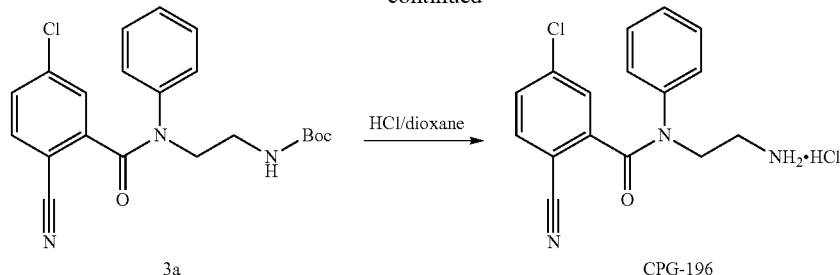

Step 1. Synthesis of 5-chloro-2-cyanobenzoic acid (B)

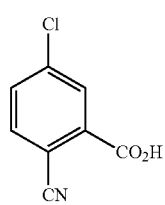

To a solution of methyl 5-chloro-2-cyanobenzoate (5.0 g, 0.026 mol) in THF/H2O=1/1 (60 mL) was added NaOH (5.1 g, 0.128 mol) at 0° C. and the mixture was stirred at room temperature for 3 h. When reaction was over, a white precipitate appeared. It was collected by filtration and washed by EA, and dried in vacuo to provide 5-chloro-2-cyanobenzoic acid (B) (4.0 g, 86% yield) as white solid. LCMS: m/z 181.9 [M+H]+.

Step 2. Synthesis of tert-butyl (2-(phenylamino)ethyl)carbamate (1a)

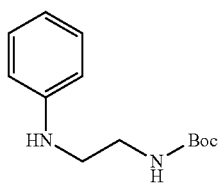

To a solution of N1-phenylethane-1,2-diamine (11 g, 0.08 mol), Et3N (24.2 g, 0.24 mol) in DCM (50 mL) was added (Boc)2O (21.0 g, 0.096 mol) at 0° C. and the mixture was stirred at room temperature for 2 h. The solvent was removed. The residue was purified by silica gel column (EA in PE=0% to 30%) to give tert-butyl (2-(phenylamino)ethyl) carbamate (1a) (20 g) as a white solid. LCMS: m/z 237.1 [M+H]+, 1H NMR (400 MHz, MeOD) δ 7.09 (dd, J=8.6, 7.3 Hz, 2H), 6.61 (dd, J=14.7, 7.5 Hz, 3H), 3.26-3.20 (m, 2H), 3.16 (dd, J=9.7, 3.5 Hz, 2H), 1.43 (s, 9H).

Step 3. Synthesis of tert-butyl(2-(5-chloro-2-cyano-N-phenylbenzamido) ethyl) carbamate (3a)

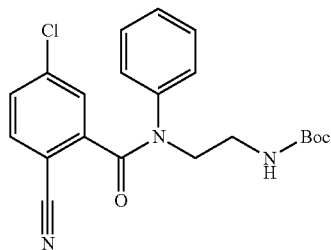

To a solution of tert-butyl (2-(phenylamino)ethyl)carbamate (2.77 g, 0.012 mol), 5-chloro-2-cyanobenzoic acid (2.34 g, 0.013 mol), in ACN (20 mL) was added TCFH (4.0 g, 0.014 mol), NMI (3.36 g, 0.042 mol), the mixture was stirred at room temperature for 16 hrs. Sat. NaCl solution (20 mL) was added to the mixture and the mixture was extracted with EA (20 mL×3). The organic layer was washed with brine (15 mL), dried over anhydrous Na2SO4, filtered and concentrated. The residue was purified by silica gel column (EA in PE=0% to 30%) to give tert-butyl (2-(5-chloro-2-cyano-N-phenylbenzamido)ethyl)carbamate (3a) (3.0 g, 0.0075 mmol, 62.5% yield) as colorless oil. LCMS: m/z 299.9 [M+H]+. 1H NMR (400 MHz, MeOD) δ 7.59 (d, J=8.4 Hz, 1H), 7.52 (d, J=1.7 Hz, 1H), 7.40 (dd, J=8.3, 1.7 Hz, 1H), 7.32-7.18 (m, 5H), 4.03 (t, J=5.9 Hz, 2H), 3.41 (t, J=5.8 Hz, 2H), 1.42 (s, 9H).

Step 4. Synthesis of N-(2-aminoethyl)-5-chloro-2-cyano-N-phenylbenzamide hydrochloride (CPG-196)

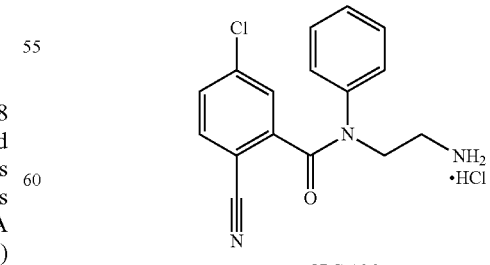

To a solution of (2-(5-chloro-2-cyano-N-phenylbenzamido)ethyl) carbamate (3.0 g, 0.0075 mol), 4M HCl in 1,4-Dioxane (30 mL) was added and the mixture was stirred at room temperature for 2 h. When reaction was over, the white precipitate was appeared, it was collected by filtration and washed by EA, dried in vacuo. To get N-(2-aminoethyl)-5-chloro-2-cyano-N-phenylbenzamide hydrochloride (CPG-196) (2.0 g, 0.006 mmol, 80% yield) as white solid. LCMS: m/z 299.9 [M+H]+. 1H NMR (400 MHz, MeOD) δ 7.68 (d, J=2.0 Hz, 1H), 7.61 (d, J=8.4 Hz, 1H), 7.45 (dd, J=8.4, 2.0 Hz, 1H), 7.34 (m, 4H), 7.31-7.24 (m, 1H), 4.27 (t, J=6.6 Hz, 2H), 3.28 (t, J=6.6 Hz, 2H).

Synthesis of N-(2-aminoethyl)-5-chloro-N-(2-chlorophenyl)-2-cyanobenzamide (CPG-197)

Step 2. Synthesis of N-(2-aminoethyl)-5-chloro-N-(2-chlorophenyl)-2-cyanobenzamide (CPG-197)

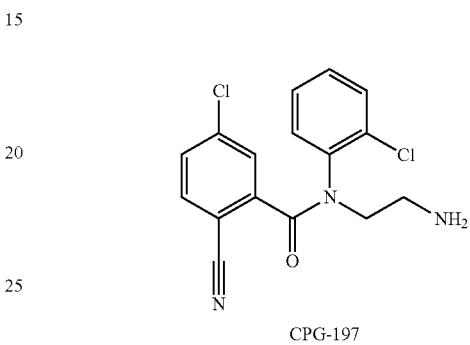

CPG-197

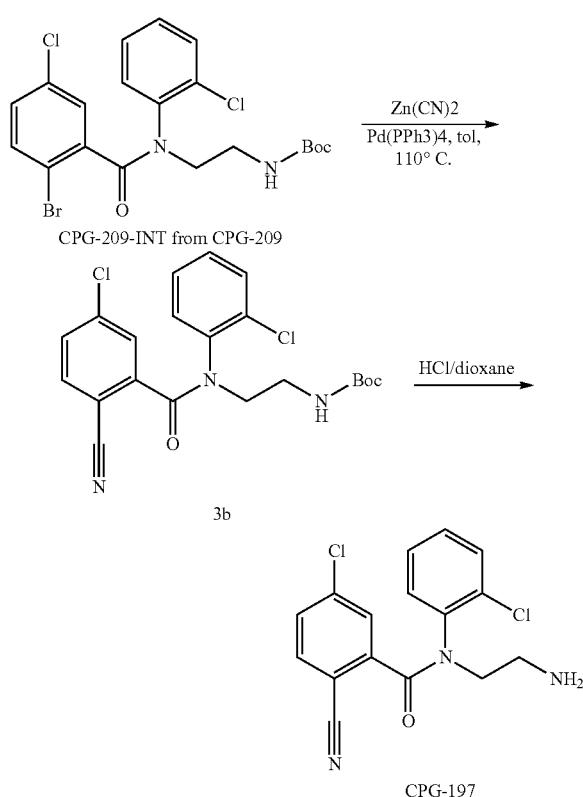

mmol), Zn(CN)2 (120 mg, 1.02 mmol) in Toluene (5.0 mL) was added Pd(PPh3)4 (150 mg, 0.15 mmol). The system was evacuated and then refilled with N2. The mixture was stirred at 110° C. for 16 hrs. Water (5.0 mL) was added to the mixture and the mixture was extracted with EA (10 mL×3). The organic layer dried over anhydrous Na2SO4, filtered and concentrated. The residue was purified by silica gel column (EA in PE=0% to 30%) to give tert-butyl (2-(5-chloro-N-(2-chlorophenyl)-2-cyanobenzamido) ethyl)carbamate (3b) (100 mg, 0.23 mmol, 23% yield) as white solid. LCMS: m/z 334.0 [M+H]+.

To a solution of tert-butyl (2-(5-chloro-N-(2-chlorophenyl)-2-cyanobenzamido)ethyl) carbamate (3b) (100 mg, 0.69 mmol), 4M HCl in 1,4-Dioxane (2.0 mL) was added and the mixture was stirred at room temperature for 2 h. When reaction was over, added aqueous saturated NaHCO3 solution, and the product was extracted with EA. The EA extract was dried (MgSO4). The solvent was removed. The residue was purified by Prep-HPLC (Fluent with 10 mM NH4HCO3 and ACN) to give N-(2-aminoethyl)-5-chloro-N-(2-chlorophenyl)-2-cyano benzamide (CPG-197) (20 mg, 0.06 mmol, 25% yield) as colorless oil. LCMS: m/z 334.0 [M+H]+. 1H NMR (400 MHz, MeOD) δ 7.69 (d, J=8.1 Hz, 1H), 7.61 (dd, J=8.1, 1.5 Hz, 1H), 7.44 (t, J=9.4 Hz, 3H), 7.40-7.27 (m, 2H), 4.36-4.15 (m, 1H), 3.77 (m, 1H), 3.04 (m, 2H).

Synthesis of 2-(((2-aminoethyl)(phenyl)amino)methyl)-4-chlorobenzonitrile hydrochloride (CPG-198)

Step 1. Synthesis of tert-butyl (2-(2-bromo-5-chloro-N-(2-chlorophenyl) benzamido)ethyl)carbamate (3b)

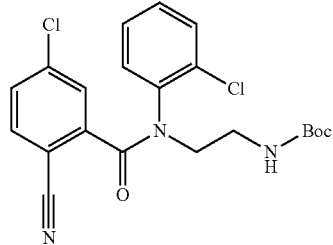

To a solution of tert-butyl (2-(2-bromo-5-chloro-N-(2-chlorophenyl)benzamido)ethyl) carbamate (500 mg, 1.02

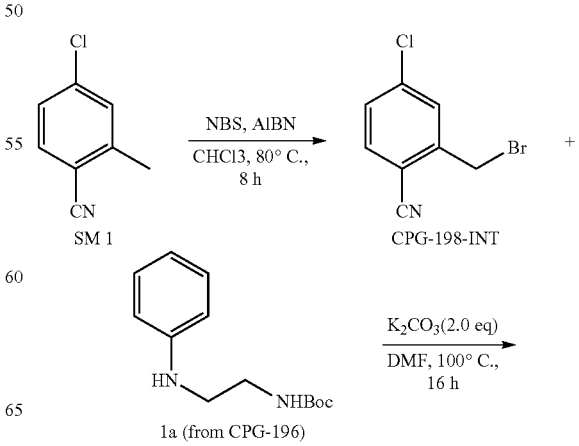

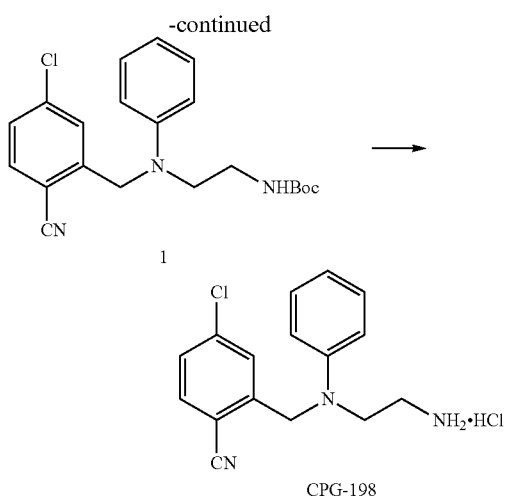

CPG-198

Step 1. Synthesis of 2-(bromomethyl)-4-chlorobenzonitrile (CPG-198-INT)

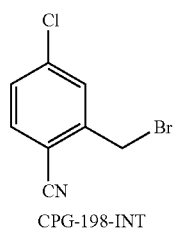 [SMILES: N#Cc1ccc(Cl)cc1CBr]

CPG-198-INT

To a solution of 4-chloro-2-methylbenzonitrile (5.0 g, 0.033 mmol), NBS (6.77 g, 0.38 mmol) in CHCl3 (50 mL) was added AIBN (0.27 g, 0.002 mmol) and the mixture was stirred at room temperature for 8 h. When reaction was over, water (20 mL) was added to the mixture and the mixture was extracted with EA (50 mL×3). The organic layer was dried over anhydrous Na2SO4, filtered and concentrated. The residue was purified by silica gel column (EA in PE=0% to 5%) to 2-(bromomethyl)-4-chlorobenzonitrile (CPG-198-INT) (3.5 g, 50%) as a white solid. LCMS: m/z 229.7 [M+H]+.

Step 2. Synthesis of tert-butyl (2-((5-chloro-2-cyanobenzyl)(phenyl)amino)ethyl) carbamate (1)

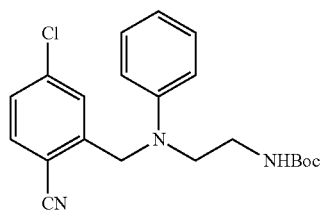

A solution of tert-butyl (2-(phenylamino)ethyl)carbamate (2.93 g, 0.013 mol), 2-(bromo methyl)-4-chlorobenzonitrile (2.7 g, 0.012 mol) and K2CO3 (3.4 g, 0.024 mol) in DMF (30 mL) and the mixture was stirred at 80° C. for 16 hrs. Water (20 mL) was added to the reaction mixture at room temperature and the mixture was extracted with EA (30 mL×3). The organic layer was dried over anhydrous Na2SO4, filtered and concentrated. The residue was purified by silica gel column (EA in PE=0% to 30%) to give tert-butyl (2-((5-chloro-2-cyanobenzyl)(phenyl)amino) ethyl)carbamate (2.1 g, 0.005 mmol, 40% yield) as white solid. LCMS: m/z 386.0 [M+H]+. 1H NMR (400 MHz, MeOD) δ 7.72 (d, J=8.2 Hz, 1H), 7.41 (d, J=8.2 Hz, 1H), 7.28 (s, 1H), 7.16 (dd, J=8.6, 7.4 Hz, 2H), 6.69 (dd, J=11.1, 7.9 Hz, 3H), 4.76 (s, 2H), 3.58 (t, J=6.7 Hz, 2H), 3.30 (t, J=6.7 Hz, 2H), 1.41 (s, 9H).

Step 3. Synthesis of 2-(((2-aminoethyl)(phenyl)amino)methyl)-4-chlorobenzonitrile hydrochloride (CPG-198)

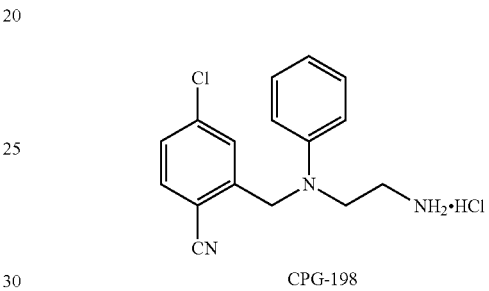

CPG-198

To a solution of tert-butyl (2-((5-chloro-2-cyanobenzyl)(phenyl)amino)ethyl)carbamate (2.1 g, 0.0054 mol), 4M HCl in 1,4-Dioxane (30 mL) was added and the mixture was stirred at room temperature for 2 h. When reaction was over, the white precipitate was appeared, it was collected by filtration and washed by EA, dried in vacuo, so to get 2-(((2-aminoethyl)(phenyl) amino)methyl)-4-chlorobenzonitrile hydrochloride as white solid (1.7 g, 0.0048 mmol, 96% yield, 214 nm: 98%). LCMS: m/z 286.0 [M+H]+. 1H NMR (400 MHz, MeOD) δ 7.74 (d, J=8.3 Hz, 1H), 7.45 (dd, J=8.3, 2.1 Hz, 1H), 7.34 (d, J=2.1 Hz, 1H), 7.25 (dd, J=8.3, 7.3 Hz, 2H), 6.91-6.81 (m, 3H), 4.81 (s, 2H), 3.81 (t, J=7.0 Hz, 2H), 3.20 (t, J=7.0 Hz, 2H).

Synthesis of 2-(((2-aminoethyl)(2-chlorophenyl)amino)methyl)-4-chlorobenzonitrile hydrochloride (CPG-199)

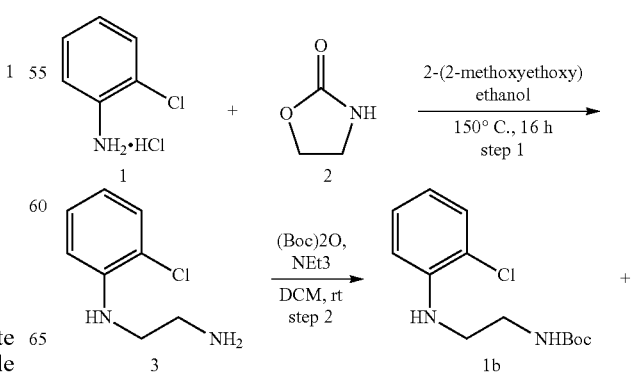

-continued

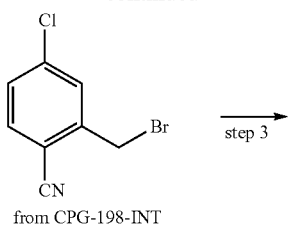

from CPG-198-INT

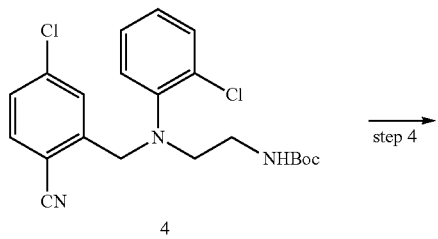

4

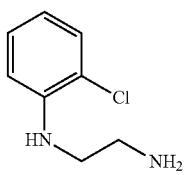

CPG-199

Step 1. Synthesis of N1-(2-chlorophenyl)ethane-1,2-diamine (3)

3

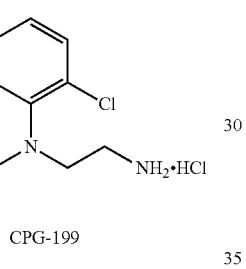

To a solution of oxazolidin-2-one (2.61 g, 0.03 mol), 2-chloroaniline hydrochloride (4.92 g, 0.03 mol) in 2-(2-methoxyethoxy)ethanol (10 mL) and the mixture was stirred at 150° C. for 16 h. When reaction was over, the heating bath was removed, and the dark reaction solution was allowed to cool to room temperature. The solution was concentrated in vacuo and the resulting dark residue dissolved into 10 mL of 10% aqueous NaOH (wt/vol) and extracted with CH2Cl2. The combined organic extracts were washed with brine and then dried over anhydrous K2CO3. After filtration the solvent was removed in vacuo to furnish the crude diamines as dark liquids. The residue was purified by silica gel column (MeOH in DCM=0% to 5%) to give N1-(2-chlorophenyl)ethane-1,2-diamine (3) (3.4 g, 0.02 mol, 67% yield) as colorless oil. LCMS: m/z 171.0 [M+H]+.

Step 2. Synthesis of tert-butyl (2-((2-chlorophenyl)amino)ethyl)carbamate (1b)

1b

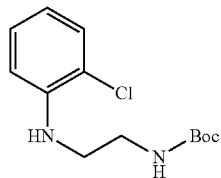

To a solution of N1-(2-chlorophenyl)ethane-1,2-diamine (3) (3.4 g, 0.02 mol), Et3N (6.06 g, 0.06 mol) in DCM (30 mL) was added (Boc)2O (5.23 g, 0.024 mol) at 0° C. and the mixture was stirred at room temperature for 2 h. The solvent was removed. The residue was purified by silica gel column (EA in PE=0% to 30%) to give tert-butyl (2-((2-chlorophenyl) amino)ethyl)carbamate (1b) (5 g, 0.018 mol, 93% yield) as a white solid. LCMS: m/z 271.0[M+H]+

Step 3. Synthesis of tert-butyl (2-((5-chloro-2-cyanobenzyl)(2-chlorophenyl)amino) ethyl)carbamate (4)

4

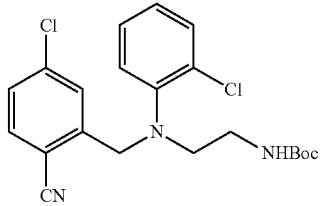

A solution of tert-butyl (2-((2-chlorophenyl)amino)ethyl) carbamate (1b) (170 mg, 0.74 mmol), 2-(bromomethyl)-4-chlorobenzonitrile from CPG-198-INT (200 mg, 0.74 mmol) and K2CO3 (200 mg, 1.48 mmol) in DMF (2 mL) and the mixture was stirred at 80° C. for 16 hrs. Water (1 mL) was added to the reaction mixture at room temperature and the mixture was extracted with EA (2 mL×3). The organic layer was dried over anhydrous Na2SO4, filtered and concentrated. The residue was purified by Prep-HPLC (eluted with 10 mM NH4HCO3 and ACN) to give 5-chloro-2-cyano-N-(2-((cyclopropylmethyl)amino)ethyl)-N-phenylbenzamide (4) (50 mg, 0.12 mmol, 16% yield) as white solid. LCMS: m/z 420.0 [M+H]+.

Step 4. Synthesis of 2-(((2-aminoethyl)(2-chlorophenyl)amino)methyl)-4-chlorobenzonitrile hydrochloride (CPG-199)

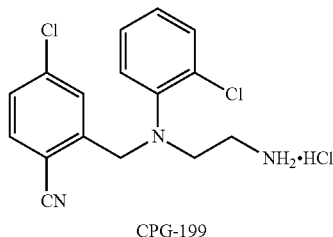

CPG-199

To a solution of 5-chloro-2-cyano-N-(2-((cyclopropylmethyl)amino)ethyl)-N-phenylbenzamide (4) (50 mg, 0.0054 mol), 4M HCl in 1,4-Dioxane (2 mL) was added and the mixture was stirred at room temperature for 2 h. When reaction was over, the white precipitate was appeared, it was collected by filtration and washed by EA, dried in vacuo, so to get 2-(((2-aminoethyl)(2-chlorophenyl)amino)methyl)-4-chlorobenzonitrile hydrochloride (25 mg, 0.078 mmol, 66% yield) as white solid. LCMS: m/z 320.0 [M+H]+. 1H NMR (400 MHz, MeOD) δ 7.67 (d, J=8.3 Hz, 1H), 7.48 (d, J=2.0 Hz, 1H), 7.43 (d, J=2.0 Hz, 1H), 7.40 (ddd, J=7.9, 3.4, 1.4 Hz, 2H), 7.30 (dd, J=12.3, 4.4 Hz, 1H), 7.20-7.11 (m, 1H), 4.50 (s, 2H), 3.44 (t, J=6.5 Hz, 2H), 3.16 (t, J=6.4 Hz, 2H).

Synthesis of 5-(2-chloroacetyl)-N-(2-chlorophenyl)-4,5,6,7-tetrahydropyrazolo[1,5-a]pyrazine-3-carboxamide (CPG-200)

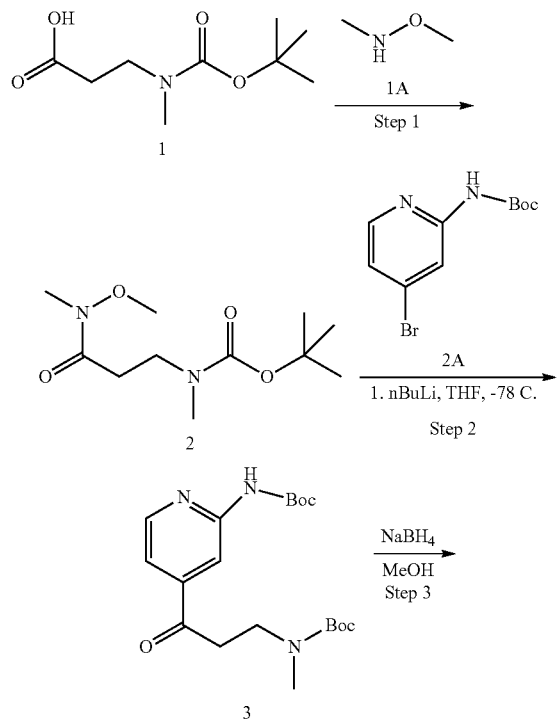

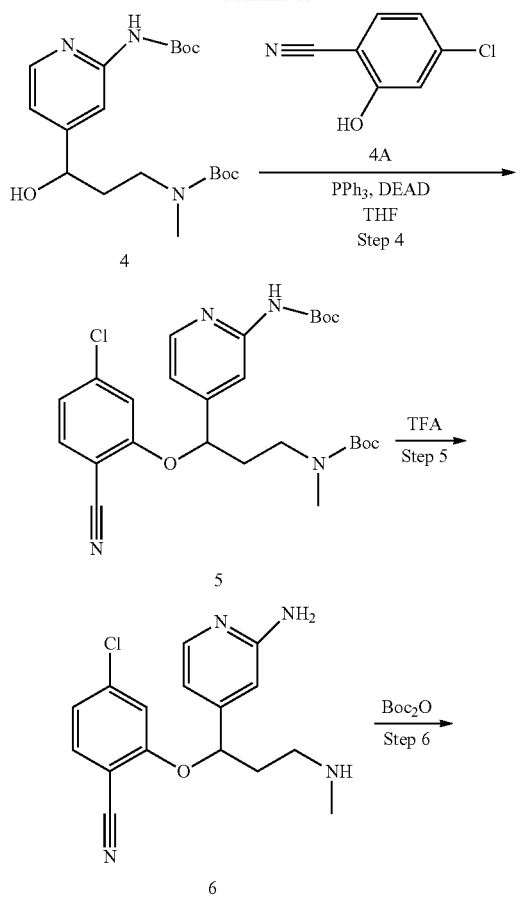

-continued

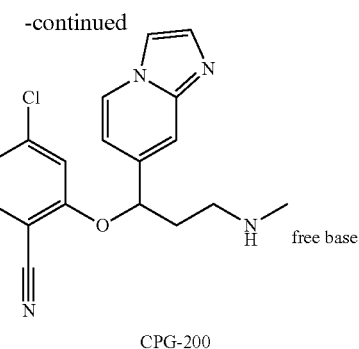

CPG-200 free base

Step 1. Synthesis of tert-butyl (3-(methoxy(methyl)amino)-3-oxopropyl)(methyl) carbamate (2)

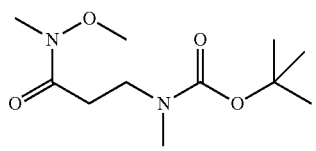

2

To a mixture of 3-((tert-butoxycarbonyl)(methyl)amino) propanoic acid (1.0 g, 4.92 mmol) and N,O-Dimethylhydroxylamine hydrochloride (479 mg, 4.92 mmol) and DIPEA (1.9 g, 14.7 mmol) in DMF (30 mL) was added HATU (2.8 g, 7.38 mmol) at room temperature and the mixture was stirred at room temperature for 3 hrs. The mixture was quenched with by adding water (50 mL). The mixture was extracted with EtOAc (100 mL×3). The combined organic layer was washed with 0.5 M HCl solution (100 mL) and then sat. NaHCO3 (50 mL) and brine (50 mL), dried over anhydrous Na2SO4, filtered and concentrated to give tert-butyl (3-(methoxy (methyl)amino)-3-oxopropyl) (methyl)carbamate (2) (2.3 g, 64% yield) as colorless oil. 1H NMR (400 MHz, CDCl₃) δ 3.70 (d, J=8.0 Hz, 3H), 3.52 (s, 2H), 3.19 (s, 3H), 2.89 (s, 3H), 2.67 (s, 2H), 1.46 (s, 9H).

Step 2. Synthesis of tert-butyl (3-(2-((tert-butoxycarbonyl)amino)pyridin-4-yl)-3-oxopropyl)(methyl) carbamate (3)

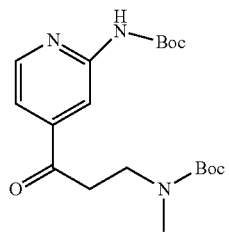

3

To a solution of tert-butyl (4-bromopyridin-2-yl)carbamate (1.66 g, 6.08 mmol) in THF (30 mL) was added dropwise n-BuLi (2.5M, 4.9 mL, 12.18 mmol) at −78° C. and the mixture was stirred at −78° C. for 30 min. Then a solution of tert-butyl (3-(methoxy(methyl)amino)-3-oxopropyl) (methyl)carbamate (1.5 g, 6.08 mmol) in THF (5 mL) was added dropwise to the above mixture at −78° C. and the mixture was stirred at −78° C. for 1 hr. The saturated NaCl solution (20 mL) was added to the mixture and the mixture was extracted with EtOAc (20 mL×3). The organic layer was washed with brine (10 mL), dried over anhydrous Na2SO4, filtered and concentrated to give desired product (2.1 g crude) as pale-yellow oil, which will be used in next step without further purification. LCMS: m/z 380.3 [M+H]+.

Step 3. Synthesis of tert-butyl (3-(2-((tert-butoxycarbonyl)amino)pyridin-4-yl)-3-hydroxypropyl) (methyl)carbamate (4)

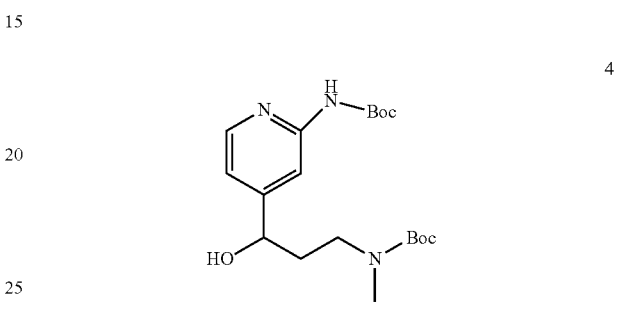

4

To a mixture of tert-butyl (3-(2-((tert-butoxycarbonyl) amino)pyridin-4-yl)-3-oxopropyl) (methyl)carbamate (2.1 g, 5.53 mmol) in methanol (20 mL) was added NaBH4 (209 mg, 5.53 mmol) at 0° C. and the mixture was stirred at 0° C. for 10 min. The solvent was removed, and the residue was purified by column chromatography (MeOH in DCM=0% to 18%) to give tert-butyl (3-(2-((tert-butoxycarbonyl)amino) pyridin-4-yl)-3-hydroxypropyl)(methyl) carbamate (4) (1.1 g, crude) as a yellow oil. LCMS: m/z 382.3 [M+H]+. 1H NMR (400 MHz, DMSO) δ 9.66 (s, 1H), 8.13 (d, J=4.8 Hz, 1H), 7.80 (s, 1H), 6.95 (d, J=4.0 Hz, 1H), 5.44 (d, J=4.4 Hz, 1H), 4.53-4.51 (m, 1H), 3.20-3.14 (m, 2H), 2.77 (s, 3H), 1.82-1.75 (m, 2H), 1.46 (s, 9H), 1.38 (s, 9H).

Step 4. Synthesis of tert-butyl (3-(2-((tert-butoxycarbonyl)amino)pyri din-4-yl)-3-(5-chloro-2-cyanophenoxy)propyl)(methyl)carbamate (5)

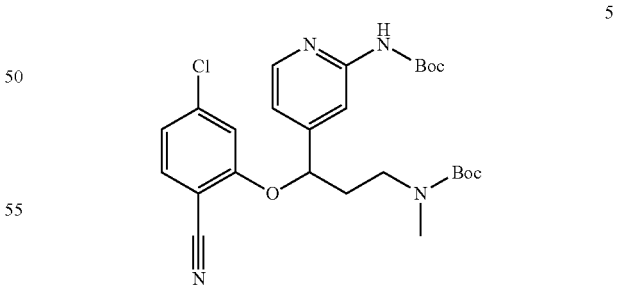

5

To a mixture of tert-butyl (3-(2-((tert-butoxycarbonyl) amino)pyridin-4-yl)-3-hydroxypropyl)(methyl)carbamate (1.1 g, 2.88 mmol), 4-chloro-2-hydroxybenzonitrile (660 mg, 5.68 mmol) in THF (30 mL) was added triphenylphosphine (1.36 g, 5.18 mmol) and then dropwise DEAD (902 mg, 5.18 mmol) at 0° C. and the mixture was stirred at room temperature for 12 hrs. The mixture was quenched with water (15 mL) and extracted with EtOAc (30 mL×2). The organic layers were washed with brine (10 mL), dried over anhydrous Na2SO4, filtered, concentrated. The residue was purified by column chromatography with a gradient of EtOAc/petroleum ether (0 to 50 percent) to give tert-butyl (3-(2-((tert-butoxycarbonyl)amino) pyridin-4-yl)-3-(5-chloro-2-cyanophenoxy)propyl)(methyl)carbamate (5) (420 mg, 0.814 mmol, 28.2% yield) as yellow oil. LCMS: m/z 517.1[M+H]+. 1H NMR (400 MHz, MeOD) δ 8.21 (d, J=5.2 Hz, 1H), 7.91 (s, 1H), 7.64 (d, J=8.0 Hz, 1H), 7.11-6.96 (m, 3H), 5.53-5.49 (m, 1H), 3.58-3.55 (m, 1H), 3.51-3.48 (m, 1H), 2.86 (s, 3H), 2.28-2.23 (m, 2H), 1.53 (s, 9H), 1.43 (s, 9H).

Step 5. Synthesis of 2-(1-(2-aminopyridin-4-yl)-3-(methylamino)propoxy)-4-chlorobenzonitrile (6)

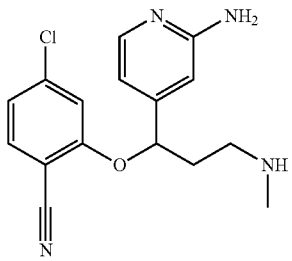

6

To a mixture of tert-butyl (3-(2-((tert-butoxycarbonyl)amino)pyridin-4-yl)-3-(5-chloro-2-cyanophenoxy)propyl)(methyl)carbamate (357 mg, 0.69 mmol) in DCM (10 mL) was added Trifluoroacetic acid (10 mL) at 0° C. and the mixture was stirred at room temperature for 1.5 hrs. The solvent was removed under reduced pressure to give 2-(1-(2-aminopyridin-4-yl)-3-(methylamino)propoxy)-4-chlorobenzonitrile (6) (218.6 mg, 100% yield) as yellow oil. LCMS: m/z 317.1[M+H]+.

Step 6. Synthesis of tert-butyl (3-(2-aminopyridin-4-yl)-3-(5-chloro-2-cyanophenoxy) propyl)(methyl) carbamate (7)

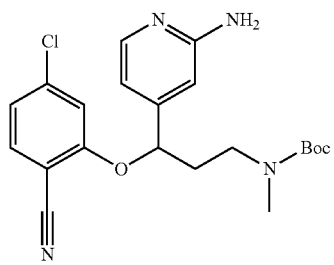

7

To a mixture of 2-(1-(2-aminopyridin-4-yl)-3-(methylamino)propoxy)-4-chloro benzonitrile (174.86 mg, 0.552 mmol (80% purity)) in THF (10 mL) was added triethylamine to adjust the pH of the mixture to 8-9. Then Boc2O (120 mg, 0.552 mmol) was added at room temperature and the mixture was stirred at room temperature for 2 hrs. The mixture was purified on silica flash chromatography with a gradient of MeOH/DCM (0 to 10 percent) to give tert-butyl (3-(2-aminopyridin-4-yl)-3-(5-chloro-2-cyanophenoxy) propyl)(methyl)carbamate (7) [500 mg, 0.6 mmol, 89.5% yield, (LCMS purity >93%)] as yellow oil. LCMS: m/z 417.0[M+H]+. 1H NMR (400 MHz, MeOD) δ 7.87 (d, J=6.4 Hz, 1H), 7.68 (d, J=8.4 Hz, 1H), 7.15 (s, 1H), 7.11-7.02 (m, 1H), 6.92-6.90 (m, 2H), 5.54-5.52 (m, 1H), 3.76-3.52 (m, 2H), 2.89 (s, 3H), 2.22-2.20 (m, 2H), 1.33 (s, 9H).

Step 7. Synthesis of tert-butyl (3-(5-chloro-2-cyanophenoxy)-3-(imidazo[1,2-a]pyridin-7-yl)propyl)(methyl)carbamate (8)

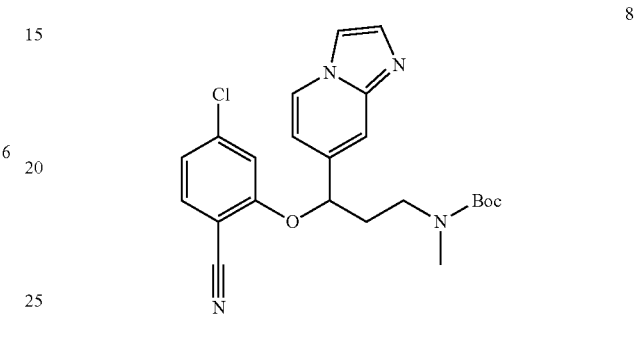

8

A mixture of tert-butyl (3-(2-aminopyridin-4-yl)-3-(5-chloro-2-cyanophenoxy) propyl)(methyl)carbamate (180 mg, 0.432 mmol) and aqueous of 2-chloroacetaldehyde (6.1 Mol/L, 0.085 mL, 0.518 mmol) in EtOH (10 mL) in a sealed tube was stirred at 70° C. for 12 hrs. The solvent was removed and the residue was purified on silica flash chromatography with a gradient of EtOAc in Petroleum ether (0% to 100%) and then MeOH/DCM (0 to 10 percent) to give of tert-butyl (3-(5-chloro-2-cyanophenoxy)-3-(imidazo[1,2-a]pyridin-7-yl)propyl) (methyl)carbamate (150 mg, 0.341 mmol, 78.9% yield) (8) as yellow oil. LCMS: m/z 441.1[M+H]+. 1H NMR (400 MHz, MeOD) δ 8.49 (d, J=7.2 Hz, 1H), 7.86 (s, 1H), 7.67-7.58 (m, 3H), 7.18-7.16 (m, 1H), 7.07-7.05 (m, 2H), 5.65-5.60 (m, 1H), 3.60-3.52 (m, 2H), 2.90 (s, 3H), 2.34-2.32 (m, 1H), 2.19-2.16 (m, 1H), 1.36-1.31 (m, 9H).

Step 8. Synthesis of 4-chloro-2-(1-(imidazo[1,2-a] pyridin-7-yl)-3-(methylamino) propoxy)benzonitrile hydrogen chloride (CPG-200)

CPG-200

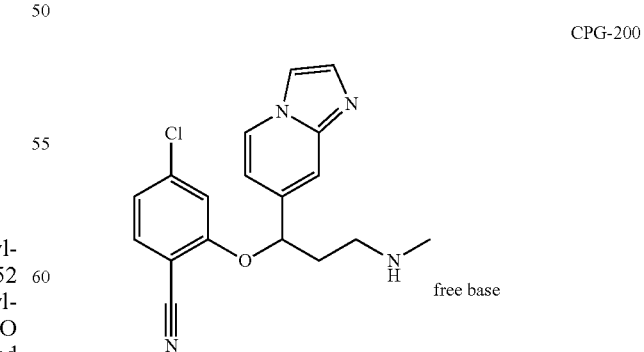

free base

To a solution of tert-butyl (3-(5-chloro-2-cyanophenoxy)-3-(imidazo[1,2-a]pyridin-7-yl) propyl)(methyl)carbamate (140 mg, 0.318 mmol) in MeOH (5 mL) was added a solution of HCl in dioxane (4M, 10 mL, 40 mmol) at 0° C. and the mixture was stirred at room temperature for 1 hr. The solvent was removed and the residue was purified by prep-HPLC (Fluent with 10 mM NH4HCO3 and ACN) to give 4-chloro-2-(1-(imidazo[1,2-a]pyridin-7-yl)-3-(methylamino) propoxy)benzonitrile as yellow syrup. LCMS: m/z 341.1.1[M+H]+. 1H NMR (400 MHz, MeOD) δ 8.50 (d, J=7.2 Hz, 1H), 7.85 (s, 1H), 7.63 (d, J=8.4 Hz, 1H), 7.60 (d, J=4.8 Hz, 2H), 7.17 (d, J=1.6 Hz, 1H), 7.09 (dd, J=8.4, 1.6 Hz, 1H), 7.00 (dd, J=7.2, 1.6 Hz, 1H), 5.74 (dd, J=8.4, 4.4 Hz, 1H), 3.08-2.96 (m, 2H), 2.57 (s, 3H), 2.47-2.35 (m, 1H), 2.31-2.22 (m, 1H).

Synthesis of (R)—N-methyl-3-(6-methylpyridin-2-yl)oxy)-3-phenylpropan-1-amine (CPG-201)

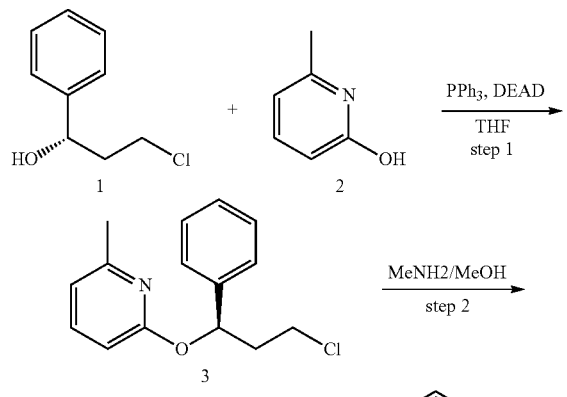

Step 1. Synthesis of (R)-2-(3-chloro-1-phenyl-propoxy)-6-methylpyridine (3)

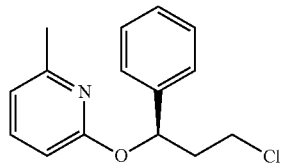

To a solution of (S)-3-chloro-1-phenylpropan-1-ol (2 g, 11.8 mmol), 6-methyl pyridin-2-ol (1.29 g, 11.8 mmol) and PPh3 (3.1 g, 11.8 mmol) in THF (50 mL) was added DEAD (2.05 g, 11.8 mmol) dropwise at 0° C. under N₂ balloon. The reaction was allowed to warm to room temperature and stirred overnight. The reaction solution was purified by column chromatography on silica gel (EA/PE=1/10) to afford the pure (R)-2-(3-chloro-1-phenyl propoxy)-6-methylpyridine (2.36 g, 77% yield) as a viscous oil. LCMS: m/z 262.1 [M+H]+.

Step 2. Synthesis of (R)—N-methyl-3-((6-methylpyridin-2-yl)oxy)-3-phenylpropan-1-amine (CPG-201)

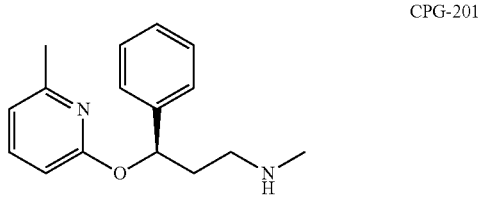 [SMILES: CNCC[C@@H](Oc1cccc(C)n1)c1ccccc1]

A mixture of (R)-2-(3-chloro-1-phenylpropoxy)-6-methylpyridine (183 mg, 0.7 mmol) and NaI (10 mg, 0.07 mmol) and MeNH2/MeOH (30%, 0.35 g, 3.5 mmol) in MeOH (5 mL) was stirred at 60° C. overnight. LCMS was used to monitor this reaction. The solvent was evaporated, and the residue was purified by Prep-HPLC (0.1% NH4HCO3/ MECN) to get (R)—N-methyl-3-((6-methylpyridin-2-yl)oxy)-3-phenylpropan-1-amine (60 mg, 33% yield) as colorless oil. LCMS: m/z 257.2 [M+H]+. 1H NMR (400 MHz, MeOD) δ 7.62 (dd, J=9.0, 7.2 Hz, 1H), 7.45-7.29 (m, 4H), 7.25 (t, J=7.2 Hz, 1H), 6.84 (d, J=9.1 Hz, 1H), 6.59 (d, J=7.1 Hz, 1H), 4.75 (dd, J=9.5, 3.4 Hz, 1H), 4.43-4.18 (m, 2H), 3.03 (s, 3H), 2.57-2.44 (m, 3H), 2.28-2.14 (m, 1H), 2.01 (dtd, J=13.9, 9.1, 4.5 Hz, 1H).

Synthesis of (R)-3-((3-bromo-6-methylpyridin-2-yl)oxy)-N-methyl-3-phenylpropan-1-amine (CPG-202)

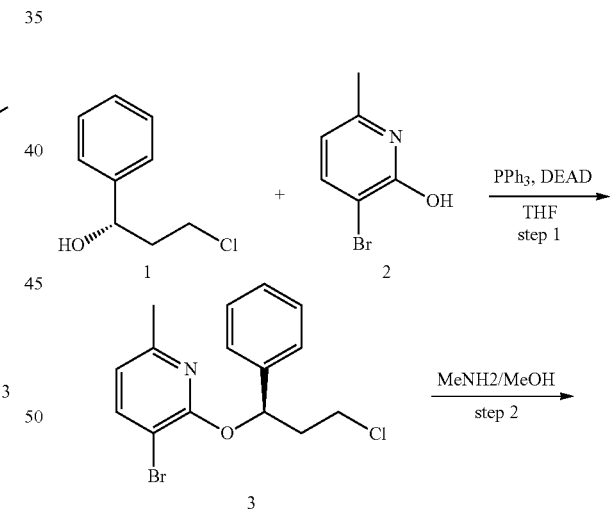

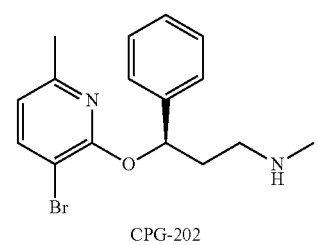

Step 1. Synthesis of (R)-3-bromo-2-(3-chloro-1-phenylpropoxy)-6-methylpyridine (3)

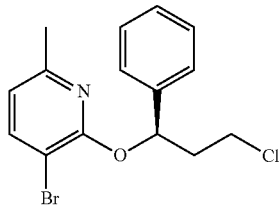

To a solution of (S)-3-chloro-1-phenylpropan-1-ol (2 g, 11.8 mmol), 3-bromo-6-methyl pyridin-2-ol (2.2 g, 11.8 mmol) and PPh3 (3.1 g, 11.8 mmol) in THF (50 mL) was added DEAD (2.05 g, 11.8 mmol) dropwise at 0° C. under N₂ balloon. The reaction was allowed to warm to room temperature and stirred overnight. The reaction solution was purified by column chromatography on silica gel (EA/PE=1/10) to afford the pure (R)-3-bromo-2-(3-chloro-1-phenyl-propoxy)-6-methylpyridine (2.36 g, 59% yield) as a viscous oil. LCMS: m/z 340.0 [M+H]+.

Step 2. Synthesis of (R)-3-((3-bromo-6-methylpyridin-2-yl)oxy)-N-methyl-3-phenylpropan-1-amine (CPG-202)

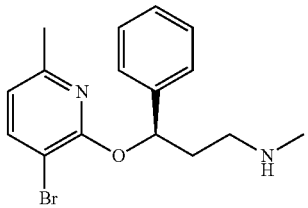

A mixture of (R)-3-bromo-2-(3-chloro-1-phenyl-propoxy)-6-methylpyridine (237 mg, 0.7 mmol) and NaI (10 mg, 0.07 mmol) and MeNH2/MeOH (30%, 0.35 g, 3.5 mmol) in MeOH (5 mL) was stirred at 60° C. overnight. LCMS was used to monitor this reaction. The solvent was evaporated and the residue was purified by Prep-HPLC (0.1% NH4HCO3/MECN) to get (R)-3-((3-bromo-6-methylpyridin-2-yl)oxy)-N-methyl-3-phenylpropan-1-amine (60 mg, 26% yield) as colorless oil. LCMS: m/z 335.1 [M+H]+. 1H NMR (400 MHz, MeOD) δ 7.80 (t, J=9.7 Hz, 1H), 7.51-7.08 (m, 6H), 6.21 (s, 1H), 3.32 (dt, J=3.2, 1.6 Hz, 1H), 2.91-2.47 (m, 5H), 2.42 (s, 3H), 2.35-1.80 (m, 2H).

Synthesis of (R)-2-(3-(methylamino)-1-phenyl-propoxy)-6-(trifluoromethyl)nicotine nitrile (CPG-203)

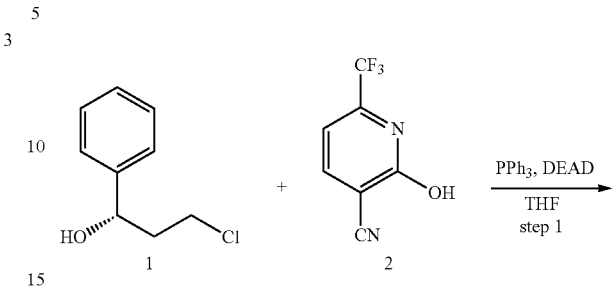

Step 1. Synthesis of (R)-2-(3-chloro-1-phenyl-propoxy)-6-(trifluoromethyl) nicotinonitrile (3)

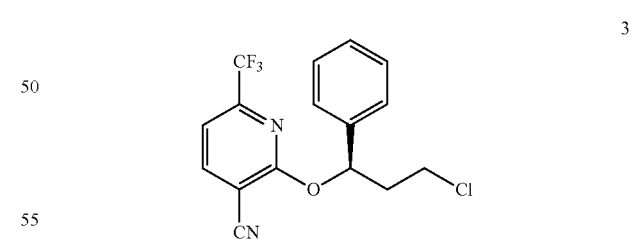

To a solution of (S)-3-chloro-1-phenylpropan-1-ol (2 g, 11.8 mmol), 2-hydroxy-6-(trifluoromethyl)nicotinonitrile (2.2 g, 11.8 mmol) and PPh3 (3.1 g, 11.8 mmol) in THF (50 mL) was added DEAD (2.05 g, 11.8 mmol) dropwise at 0° C. under N₂ balloon. The reaction was allowed to warm to room temperature and stirred overnight. The reaction solution was purified by column chromatography on silica gel (EA/PE=1/10) to afford the pure (R)-2-(3-chloro-1-phenyl-propoxy)-6-(trifluoromethyl)nicotinonitrile (2.36 g, 59% yield) as a viscous oil. LCMS: m/z 341.1 [M+H]+.

Step 2. Synthesis of ((R)-2-(3-(methylamino)-1-phenylpropoxy)-6-(trifluoromethyl) nicotinonitrile (CPG-203)

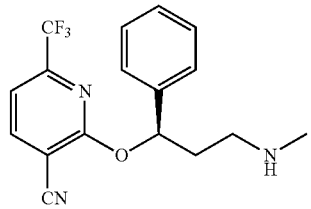

CPG-203

A mixture of (R)-2-(3-chloro-1-phenylpropoxy)-6-(trifluoromethyl) nicotinonitrile (237 mg, 0.7 mmol) and NaI (10 mg, 0.07 mmol) and MeNH2/MeOH (30%, 0.35 g, 3.5 mmol) in MeOH (5 mL) was stirred at 60° C. overnight. LCMS was used to monitor this reaction. The solvent was evaporated, and the residue was purified by Prep-HPLC (0.1% NH4HCO3/MeCN to get (R)-2-(3-(methylamino)-1-phenylpropoxy)-6-(trifluoromethyl) nicotinonitrile (60 mg, 26% yield) as colorless oil. LCMS: m/z 336.1 [M+H]+. 1H NMR (400 MHz, MeOD) δ 8.03 (d, J=7.8 Hz, 1H), 7.41-7.27 (m, 4H), 7.27-7.18 (m, 1H), 7.01 (d, J=7.8 Hz, 1H), 4.72 (dd, J=7.7, 5.7 Hz, 1H), 3.96-3.80 (m, 1H), 3.74 (ddd, J=14.3, 8.6, 5.8 Hz, 1H), 3.33 (s, 3H), 2.24-2.01 (m, 2H).

Synthesis of N-(2-aminoethyl)-2-bromo-5-chloro-N-phenylbenzamide (CPG-207)

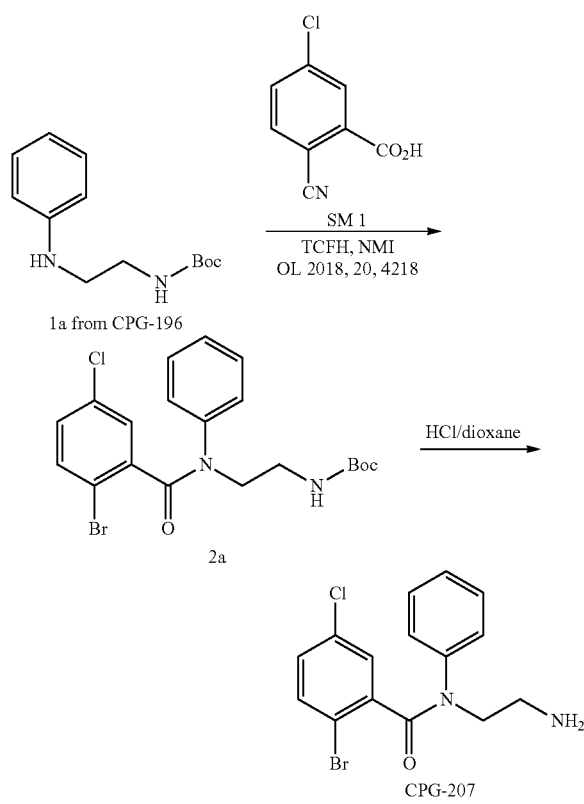

Step 1. Synthesis of tert-butyl (2-(2-bromo-5-chloro-N-phenylbenzamido) ethyl)carbamate (2a)

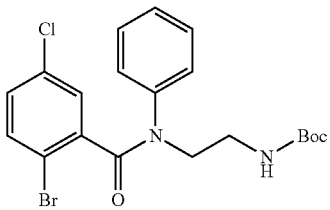

2a

To a solution of tert-butyl (2-(phenylamino)ethyl)carbamate (600 mg, crude, 214 nm:90%), 2-bromo-5-chlorobenzoic acid (700 mg, 3.0 mmol), in ACN (5 mL) was added TCFH (770 mg, 2.7 mmol), NMI (650 mg, 8.0 mmol), the mixture was stirred at room temperature for 16 hrs. Sat. NaCl solution (5 mL) was added to the mixture and the mixture was extracted with EA (5 mL×3). The organic layer was washed with brine (5 mL), dried over anhydrous Na2SO4, filtered and concentrated. The residue was purified by silica gel column (EA in PE=0% to 30%) to give tert-butyl (2-(2-bromo-5-chloro-N-phenylbenzamido)ethyl) carbamate (2a) (1.0 g, 2.0 mmol, 88% yield) as colorless oil. LCMS: m/z 353.0 [M+H]+.

Step 2. Synthesis of N-(2-aminoethyl)-2-bromo-5-chloro-N-phenyl benzamide (CPG-207)

CPG-207

To a solution of tert-butyl (2-(2-bromo-5-chloro-N-phenylbenzamido)ethyl)carbamate (2a) (200 mg, 0.44 mmol), 4M HCl in 1,4-Dioxane (2.0 mL) was added and the mixture was stirred at room temperature for 2 h. When reaction was over, added aqueous saturated NaHCO3 solution, and the product was extracted with EA. The EA extract was dried (MgSO4). The solvent was removed. The residue was purified by Prep-HPLC (eluted with 10 mM NH4HCO3 and ACN) to give N-(2-aminoethyl)-2-bromo-5-chloro-N-phenylbenzamide (CPG-207) (60 mg, 0.17 mmol, 39% yield) as colorless oil. LCMS: m/z 353.0 [M+H]+. 1H NMR (400 MHz, MeOD) δ 7.39 (d, J=1.5 Hz, 1H), 7.38 (d, J=4.4 Hz, 1H), 7.36-7.31 (m, 2H), 7.28 (dd, J=9.9, 4.9 Hz, 2H), 7.23 (dd, J=4.9, 3.6 Hz, 1H), 7.11 (dd, J=8.6, 2.5 Hz, 1H), 4.04 (t, J=6.8 Hz, 2H), 2.96 (t, J=6.8 Hz, 2H).

Synthesis of 2-(((2-aminoethyl)(2-chlorophenyl)amino)methyl)-4-chloro benzonitrile hydrochloride (CPG-2081)

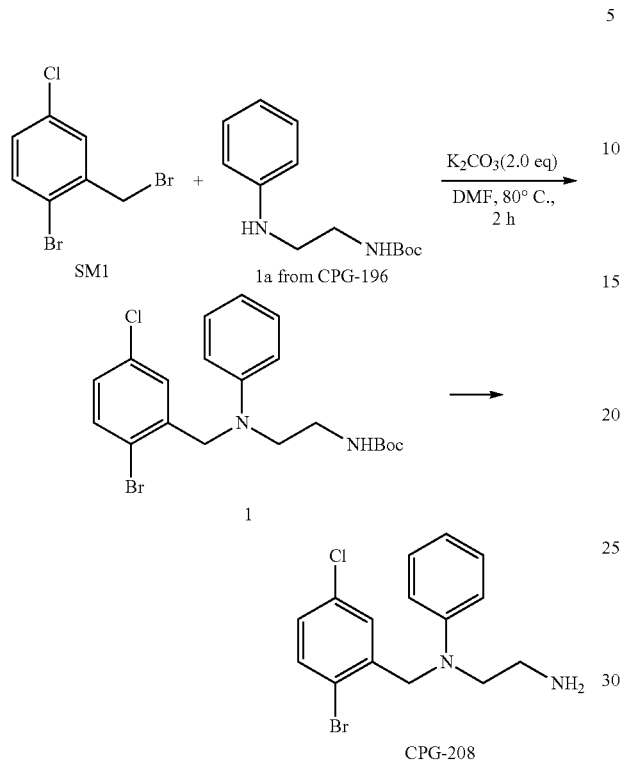

Step 1. Synthesis of tert-butyl (2-((5-chloro-2-cyanobenzyl)(2-chlorophenyl) amino)ethyl)carbamate (1)

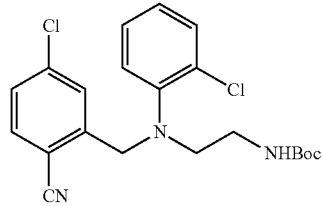

A solution of tert-butyl (2-(phenylamino)ethyl)carbamate (200 mg, 0.85 mmol), 1-bromo-2-(bromomethyl)-4-chlorobenzene (240 mg, 0.85 mmol) and K2CO3 (200 mg, 1.70 mmol) in DMF (2 mL) and the mixture was stirred at 80° C. for 16 hrs. Water (1 mL) was added to the reaction mixture at room temperature and the mixture was extracted with EA (2 mL×3). The organic layer was dried over anhydrous Na2SO4, filtered and concentrated. The residue was purified by Prep-HPLC (Fluent with 10 mM NH4HCO3 and ACN) to give tert-butyl (2-((5-chloro-2-cyanobenzyl)(2-chlorophenyl)amino)ethyl)carbamate (1)(325 mg, 0.74 mmol, 90% yield, 214 nm:90%) as white solid. LCMS: m/z 438.8 [M+H]+.

Step 2. Synthesis of N1-(2-bromo-5-chlorobenzyl)-N1-phenylethane-1,2-diamine (CPG-208)

To a solution of tert-butyl (2-((5-chloro-2-cyanobenzyl)(2-chlorophenyl)amino)ethyl) carbamate (1) (325 mg, crude), 4M HCl in 1,4-Dioxane (3 mL) was added and the mixture was stirred at room temperature for 2 h. When reaction was over, added aqueous saturated NaHCO3 solution, and the product was extracted with EA. The EA extract was dried (MgSO4). The solvent was removed. The residue was purified by Prep-HPLC (eluted with 10 mM NH4HCO3 and ACN) to give N1-(2-bromo-5-chlorobenzyl)-N1-phenylethane-1,2-diamine (CPG-208) (110 mg, 0.325 mmol, 48% yield) as a white solid. LCMS: m/z 338.8 [M+H]+. 1H NMR (400 MHz, DMSO) δ 7.70 (d, J=8.5 Hz, 1H), 7.30 (dd, J=8.5, 2.5 Hz, 1H), 7.15 (dd, J=8.5, 7.4 Hz, 2H), 6.98 (d, J=2.5 Hz, 1H), 6.63 (m, 3H), 4.54 (s, 2H), 3.55 (t, J=7.0 Hz, 2H), 2.86 (t, J=7.0 Hz, 2H).

Synthesis of N-(2-aminoethyl)-2-bromo-5-chloro-N-(2-chlorophenyl) benzamide (CPG-209)

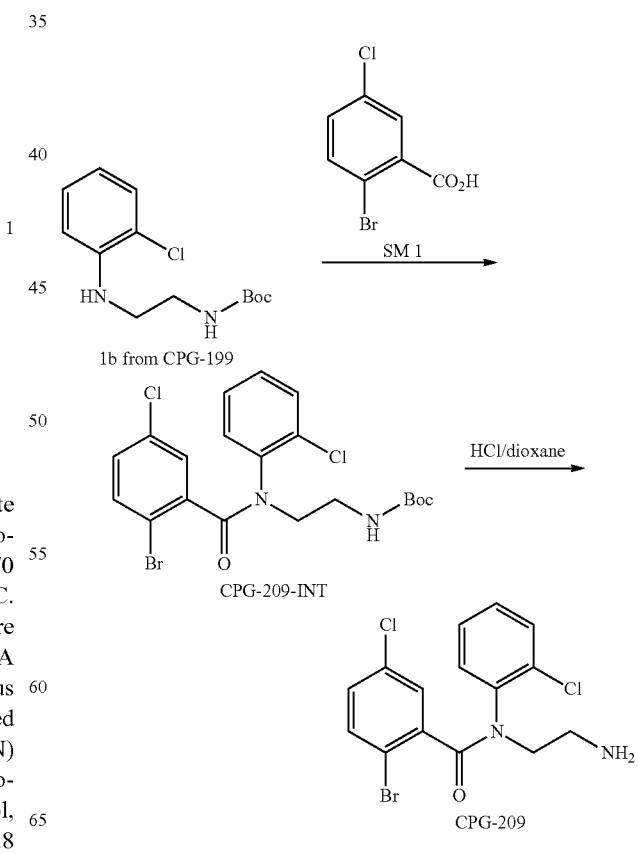

Step 1. Synthesis of tert-butyl (2-(2-bromo-5-chloro-N-(2-chlorophenyl)benzamido) ethyl)carbamate (CPG-209-INT)

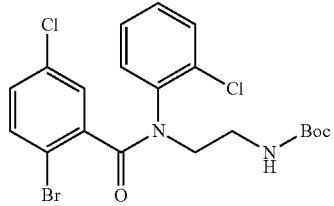

CPG-209-INT

To a solution of tert-butyl (2-((2-chlorophenyl)amino) ethyl)carbamate (1.5 g, 0.0075 mol), 2-bromo-5-chlorobenzoic acid (2.34 g, 0.0096 mol), in ACN (10 mL) was added TCFH (2.52 g, 0.009 mol), NMI (2.1 g, 0.026 mol). The mixture was stirred at room temperature for 16 hrs. Sat. NaCl solution (5.0 mL) was added to the mixture and the mixture was extracted with EA (10 mL×3). The organic layer was washed with brine (20 mL), dried over anhydrous Na2SO4, filtered and concentrated. The residue was purified by silica gel column (EA in PE=0% to 30%) to give tert-butyl (2-(2-bromo-5-chloro-N-(2-chlorophenyl)benzamido)ethyl) carbamate (CPG-209-INT) (1.7 g, 0.0035 mol, 47% yield) as white solid. LCMS: m/z 387.0 [M+H]+.

Step 2. Synthesis of N-(2-aminoethyl)-2-bromo-5-chloro-N-(2-chlorophenyl) benzamide (CPG-209)

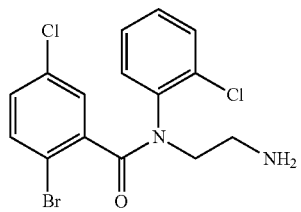

CPG-209

To a solution of tert-butyl (2-(2-bromo-5-chloro-N-(2-chlorophenyl) benzamido) ethyl) carbamate (500 mg, 1.0 mmol), 4M HCl in 1,4-Dioxane (3.0 mL) was added and the mixture was stirred at room temperature for 2 h. When reaction was over, added aqueous saturated NaHCO₃ solution, and the product was extracted with EA. The EA extract was dried (MgSO4). The solvent was removed. The residue was purified by Prep-HPLC (Fluent with 10 mM NH4HCO3 and ACN) to give N-(2-aminoethyl)-2-bromo-5-chloro-N-(2-chlorophenyl) benzamide (CPG-209) (350 mg, 0.9 mmol, 90% yield) as colorless oil. LCMS: m/z 389.0 [M+H]+. 1H NMR (400 MHz, MeOD) δ 7.54 (dd, J=7.9, 1.8 Hz, 1H), 7.49-7.43 (m, 2H), 7.30 (d, J=2.4 Hz, 1H), 7.27 (dd, J=7.9, 1.8 Hz, 1H), 7.14 (dd, J=8.6, 2.4 Hz, 1H), 4.41-4.29 (m, 1H), 3.57-3.45 (m, 1H), 3.06-2.87 (m, 2H).

Synthesis of N1-(2-bromo-5-chlorobenzyl)-N1-(2-chlorophenyl)ethane-1,2-diamine hydrochloride (CPG-210)

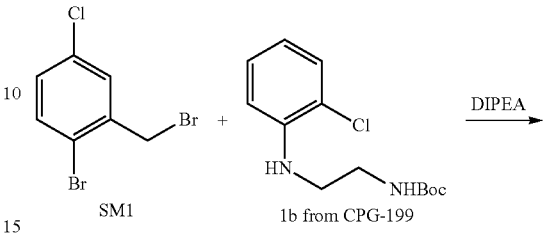

Step 1. Synthesis of tert-butyl (2-((2-bromo-5-chlorobenzyl)(2-chlorophenyl) amino) ethyl) carbamate (1)

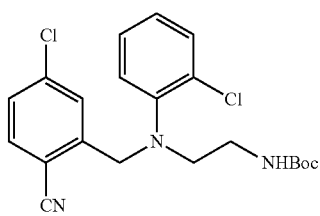

A solution of tert-butyl (2-((2-chlorophenyl)amino)ethyl) carbamate (400 mg, 1.48 mmol), 1-bromo-2-(bromomethyl)-4-chlorobenzene (420 mg, 1.48 mmol) and DIPEA (380 mg, 3.0 mmol) in DMF (2 mL) and the mixture was stirred at 100° C. for 16 hrs. When reaction was over, the white precipitate was appeared, it was collected by filtration and washed by EA, dried in vacuo to provide tert-butyl (2-((2-bromo-5-chlorobenzyl)(2-chlorophenyl) amino) ethyl) carbamate (1) (350 mg, 0.74 mmol, 50% yield) as white solid. LCMS: m/z 473.0 [M+H]+.

Step 2. Synthesis of N1-(2-bromo-5-chlorobenzyl)-N1-(2-chlorophenyl)ethane-1,2-diamine hydrochloride (CPG-210)

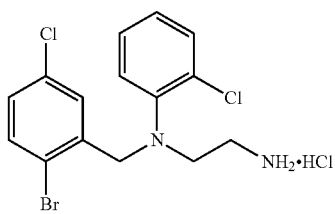
CPG-210

To a solution of tert-butyl (2-((2-bromo-5-chlorobenzyl)(2-chlorophenyl) amino)ethyl) carbamate (350 mg, 0.74 mmol), 4M HCl in 1,4-Dioxane (2 mL) was added and the mixture was stirred at room temperature for 2 h. When reaction was over, added aqueous saturated NaHCO₃ solution, and the product was extracted with EA. The EA extract was dried (MgSO4). The solvent was removed. The residue was purified by Prep-HPLC (Fluent with 10 mM NH4HCO3 and ACN) to give N1-(2-bromo-5-chlorobenzyl)-N1-(2-chlorophenyl)ethane-1,2-diamine hydrochloride (CPG-210) (200 mg, 0.078 mmol, 66% yield) as colorless oil. LCMS: m/z 373.0 [M+H]+.

Synthesis of (R)-2-(3-((2-hydroxyethyl)amino)-1-phenylpropoxy)-6-methylnicotine nitrile (CPG-211)

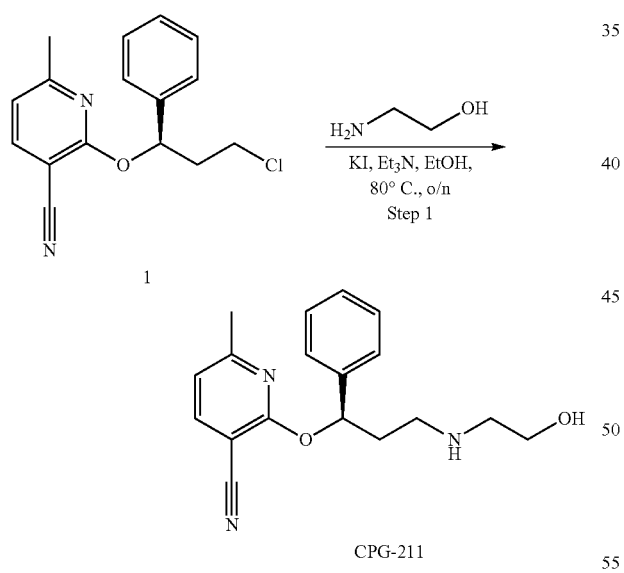

CPG-211

A mixture of (R)-2-(3-chloro-1-phenylpropoxy)-6-methylnicotinonitrile (100 mg, 0.349 mmol), potassium iodide (5.7 mg, 0.0349 mmol), 2-aminoethan-1-ol (106 mg, 1.74 mmol) in EtOH (2 mL) was stirred at 80° C. in a sealed tube for 12 hrs. The mixture was purified on prep-HPLC (Fluent with 10 mM NH4HCO3 and ACN) to give (R)-2-(3-((2-hydroxyethyl) amino)-1-phenylpropoxy)-6-methylnicotinonitrile (CPG-211) (42.8 mg, 0.138 mmol, 39.2% yield) as yellow gum. LCMS: m/z 312.1 [M+H]+. 1H NMR (400 MHz, MeOD) δ 7.91 (d, J=7.6 Hz, 1H), 7.46 (d, J=7.2 Hz, 2H), 7.36 (t, J=7.6 Hz, 2H), 7.29 (t, J=7.2 Hz, 1H), 6.93 (d, J=7.6 Hz, 1H), 6.34 (dd, J=8.4, 4.8 Hz, 1H), 3.76-3.71 (m, 2H), 3.13-3.01 (m, 4H), 2.45-2.43 (m, 1H), 2.41 (s, 3H), 2.33-2.31 (m, 1H).

Synthesis of 2-((R)-3-((S)-3-hydroxypyrrolidin-1-yl)-1-phenylpropoxy)-6-methyl nicotinonitrile (CPG-213)

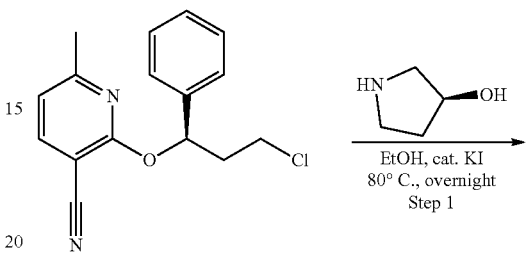

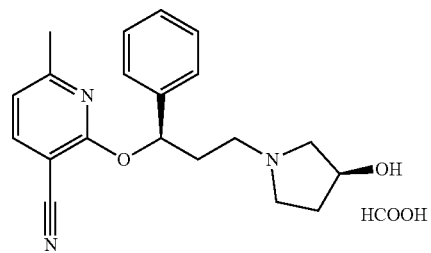

CPG-213

A mixture of (R)-2-(3-chloro-1-phenylpropoxy)-6-methylnicotinonitrile (200 mg, 0.687 mmol), potassium iodide (11.6 mg, 0.07 mmol) and (S)-pyrrolidin-3-ol (303.8 mg, 3.487 mmol) in EtOH (4 mL) was stirred at 80° C. in a sealed tube for 16 hrs. The mixture was purified on prep-HPLC (Fluent with 0.2 M Formic acid and ACN) to give 2-((R)-3-((S)-3-hydroxy pyrrolidin-1-yl)-1-phenylpropoxy)-6-methylnicotinonitrile (CPG-213) (114 mg, 0.297 mmol, 48.5% yield) as brown gum. LCMS: m/z 338.3[M+H]+. 1H NMR (400 MHz, MeOD) δ 8.51 (s, 1H), 7.91 (d, J=7.6 Hz, 1H), 7.47 (d, J=7.2 Hz, 2H), 7.36 (t, J=7.6 Hz, 2H), 7.29 (t, J=7.2 Hz, 1H), 6.93 (d, J=7.6 Hz, 1H), 6.32 (dd, J=8.4, 4.8 Hz, 1H), 4.49 (d, J=4.8 Hz, 1H), 3.45-3.40 (m, 1H), 3.30-3.11 (m, 6H), 2.55-2.43 (m, 1H), 2.41 (s, 3H), 2.40-2.15 (m, 2H), 2.02-1.90 (m, 1H).

Synthesis of 2-((R)-3-((R)-3-hydroxypyrrolidin-1-yl)-1-phenylpropoxy)-6-methyl nicotinonitrile (CPG-214)

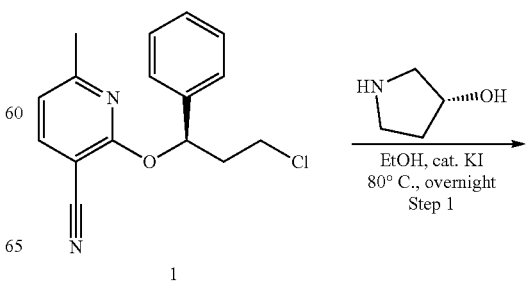

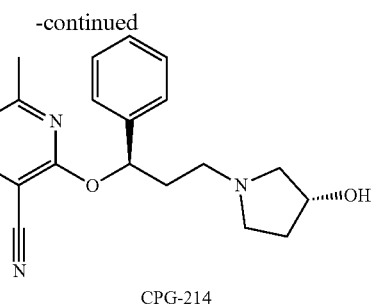

CPG-214

A mixture of (R)-2-(3-chloro-1-phenylpropoxy)-6-methylnicotinonitrile (200 mg, 0.687 mmol), potassium iodide (11.6 mg, 0.07 mmol) and (R)-pyrrolidin-3-ol (303.8 mg, 3.487 mmol) in EtOH (4 mL) was stirred at 80° C. in a sealed tube for 16 hrs. The mixture was purified on prep-HPLC (Fluent with 10 mM NH4HCO3 and ACN) to give 2-((R)-3-((R)-3-hydroxy pyrrolidin-1-yl)-1-phenylpropoxy)-6-methylnicotinonitrile (CPG-214) (98 mg, 0.29 mmol, 41.7% yield) as brown gum. LCMS: m/z 338.3[M+H]+. 1H NMR (400 MHz, MeOD) δ 7.88 (d, J=7.6 Hz, 1H), 7.45 (d, J=7.2 Hz, 2H), 7.34 (t, J=7.6 Hz, 2H), 7.26 (t, J=7.2 Hz, 1H), 6.90 (d, J=7.6 Hz, 1H), 6.29 (dd, J=7.6, 5.4 Hz, 1H), 4.41-4.33 (m, 1H), 2.97-2.90 (m, 2H), 2.90-2.62 (m, 5H), 2.40 (s, 3H), 2.39-2.31 (m, 1H), 2.22-2.07 (m, 2H), 1.77 (dd, J=8.0, 5.4 Hz, 1H).

Synthesis of 5-chloro-2-cyano-N-(2-((2-hydroxyethyl)amino)ethyl)-N-phenylbenzamide (CPG-215)

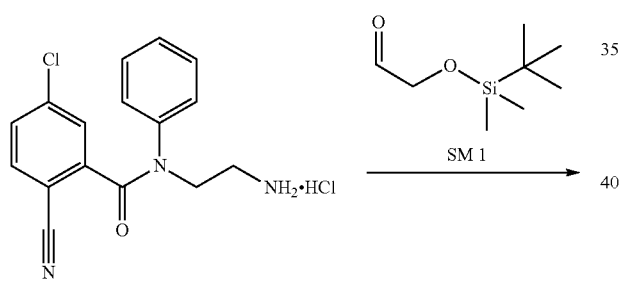

from CPG-196

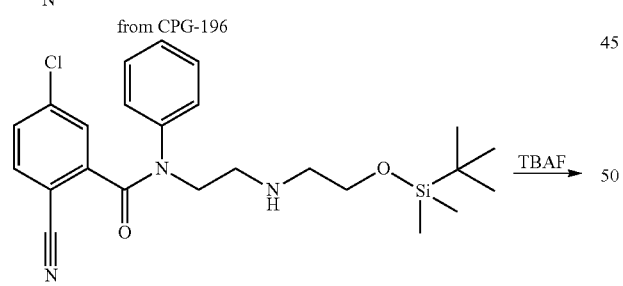

1

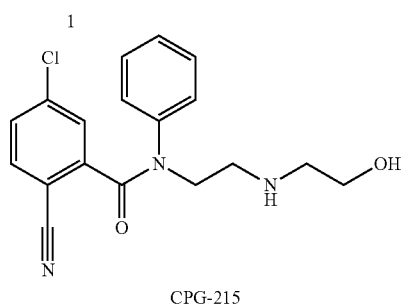

CPG-215

Step 1. Synthesis of N1N-(2-((2-((tert-butyldimethylsilyl)oxy)ethyl)amino)ethyl)-5-chloro-2-cyano-N-phenylbenzamide (1)

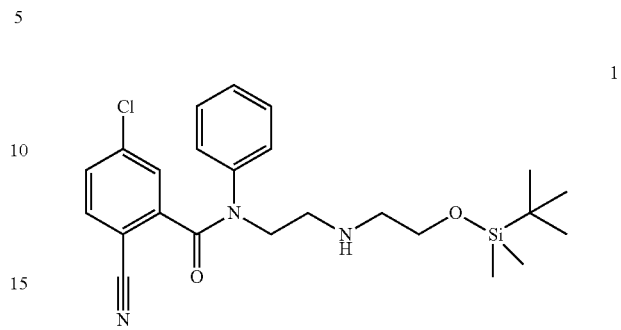

1

To a solution of N-(2-aminoethyl)-5-chloro-2-cyano-N-phenylbenzamide hydrochloride (200 mg, 0.6 mmol), 2-((tert-butyldimethylsilyl)oxy)acetaldehyde (156 mg, 0.9 mmol) in DCE (2 mL), glacial AcOH (54 mg, 0.9 mmol) was added and the mixture was stirred at room temperature for 4 h, then was added NaBH(OAc)$_3$ (190 mg, 0.9 mmol) and the mixture was stirred at room temperature for 16 h. The reaction mixture was quenched with aqueous saturated NaHCO$_3$ solution, and the product was extracted with EA. The EA extract was dried (MgSO4). The solvent was removed. The residue was purified by Prep-HPLC (eluted with 10 mM NH4HCO3 and ACN) to give N-(2-((2-((tert-butyldimethylsilyl)oxy)ethyl) amino)ethyl)-5-chloro-2-cyano-N-phenylbenzamide (1) (100 mg, 0.22 mmol, 37% yield) as a liquid. LCMS: m/z 458.2[M+H]+.

Step 2. Synthesis of 5-chloro-2-cyano-N-(2-((2-hydroxyethyl)amino)ethyl)-N-phenylbenzamide (CPG-215)

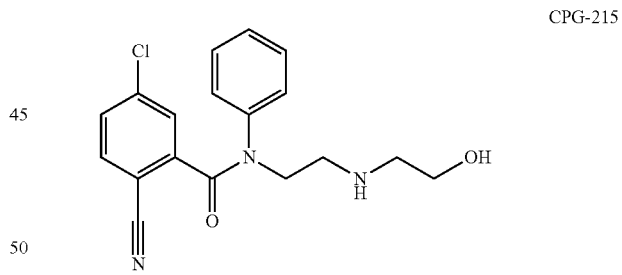

CPG-215

To a solution of N-(2-((2-((tert-butyldimethylsilyl)oxy) ethyl)amino)ethyl)-5-chloro-2-cyano-N-phenylbenzamide (1) (100 mg, 0.22 mmol), 3M TBAF in THF (30 mL) was added and the mixture was stirred at room temperature for 2 h. The solvent was removed. then added water (1 ml) and extracted with EA. The combined organic extracts were washed with brine and then dried over anhydrous MgSO4. After filtration the solvent was removed in vacuo. The residue was purified by Prep-HPLC (eluted with 10 mM NH4HCO3 and ACN) to give 5-chloro-2-cyano-N-(2-((2-hydroxyethyl)amino)ethyl)-N-phenylbenzamide (CPG-215) (45 mg, 0.13 mmol, 60% yield) as a liquid. LCMS: m/z 458.2[M+H]+. 1H NMR (400 MHz, DMSO) δ 10.18 (s, 1H), 8.15 (d, J=8.1 Hz, 1H), 7.84 (dd, J=8.1, 1.8 Hz, 1H), 7.78 (d, J=1.8 Hz, 1H), 7.10 (t, J=7.9 Hz, 2H), 6.81 (d, J=8.3

Hz, 2H), 6.54 (t, J=7.2 Hz, 1H), 4.57 (t, J=5.4 Hz, 1H), 3.94-3.85 (m, 2H), 3.57 (dt, J=11.8, 6.7 Hz, 5H), 3.39 (t, J=6.4 Hz, 2H).

Synthesis of 4-chloro-2-(((2-((2-hydroxyethyl)amino)ethyl)(phenyl)amino)methyl) benzonitrile (CPG-216)

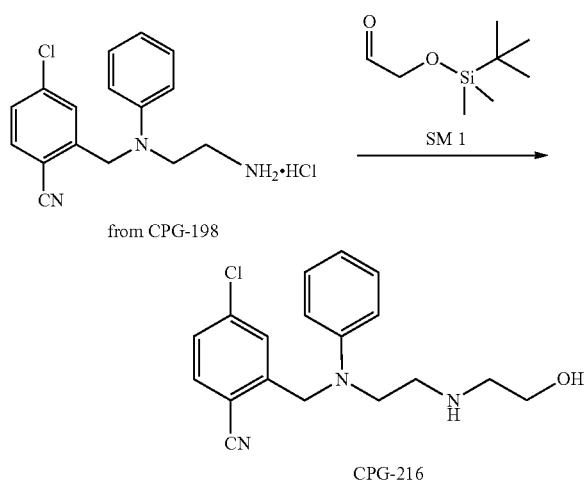

To a solution of 2-(((2-aminoethyl)(phenyl)amino) methyl)-4-chloro benzonitrile hydrochloride (300 mg, 0.93 mmol), 2-((tert-butyldimethylsilyl)oxy)acetaldehyde (240 mg, 1.4 mmol) in THF (2 mL), glacial AcOH (80 mg, 1.4 mmol) was added and the mixture was stirred at room temperature for 4 h, then was added NaBH(OAc)₃ (300 mg, 1.4 mmol) and the mixture was stirred at room temperature for 16 h. The reaction mixture was quenched with aqueous saturated NaHCO₃ solution, and the product was extracted with EA. The EA extract was dried (MgSO4). The solvent was removed. The residue was purified by Prep-HPLC (Fluent with 10 mM NH4HCO3 and ACN) to give 4-chloro-2-(((2-((2-hydroxyethyl)amino)ethyl)(phenyl) amino) methyl)benzonitrile (CPG-216) (17.5 mg, 0.053 mmol, 6% yield) as a liquid. LCMS: m/z 330.0 [M+H]+. 1H NMR (400 MHz, MeOD) δ 7.75 (d, J=8.3 Hz, 1H), 7.45 (dd, J=8.3, 1.8 Hz, 1H), 7.33 (d, J=1.8 Hz, 1H), 7.20 (dd, J=8.8, 7.3 Hz, 2H), 6.75 (dd, J=13.2, 7.3 Hz, 3H), 4.78 (s, 2H), 3.66 (dt, J=14.2, 6.3 Hz, 4H), 2.92 (t, J=7.1 Hz, 2H), 2.78 (t, J=7.1 Hz, 2H).

Synthesis of (R)-2-(3-(tert-butylamino)-1-phenyl-propoxy)-6-methylnicotinonitrile (CPG-217)

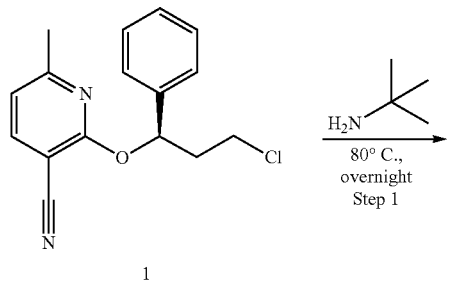

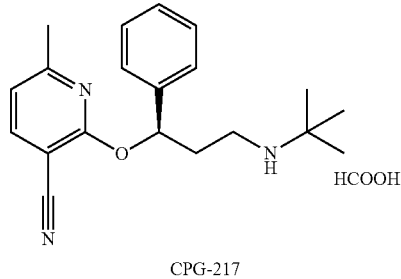

A mixture of (R)-2-(3-chloro-1-phenylpropoxy)-6-methylnicotinonitrile (200 mg, 0.697 mmol), potassium iodide (115 mg, 0.697 mmol) and 2-methylpropan-2-amine (152 mg, 2.091 mmol) in DMF (4 mL) was stirred at 80° C. in a sealed tube for 12 hrs. The solvent was removed, and the residue was purified by column chromatography (MeOH in DCM=0% to 40%) to give crude product (50 mg). Then the crude product was purified on prep-HPLC (Fluent with 0.2% Formic acid and ACN) to give (R)-2-(3-(tert-butylamino)-1-phenylpropoxy)-6-methyl nicotinonitrile (CPG-217) (25 mg, 0.068 mmol, 11.0% yield) as a white solid. LCMS: m/z 324.3[M+H]+. 1H NMR (400 MHz, MeOD) δ 8.55 (s, 1H), 7.94 (d, J=7.6 Hz, 1H), 7.48 (d, J=7.2 Hz, 2H), 7.39 (t, J=7.6 Hz, 2H), 7.32 (t, J=7.2 Hz, 1H), 6.96 (d, J=7.6 Hz, 1H), 6.34 (dd, J=8.8, 4.4 Hz, 1H), 3.21-3.11 (m, 2H), 2.50-2.43 (m, 1H), 2.41 (s, 3H), 2.28-2.26 (m, 1H), 1.36 (s, 9H).

Synthesis of (R)-2-(3-((2-(dimethylamino)ethyl)amino)-1-phenylpropoxy)-6-methyl nicotinonitrile (CPG-218)

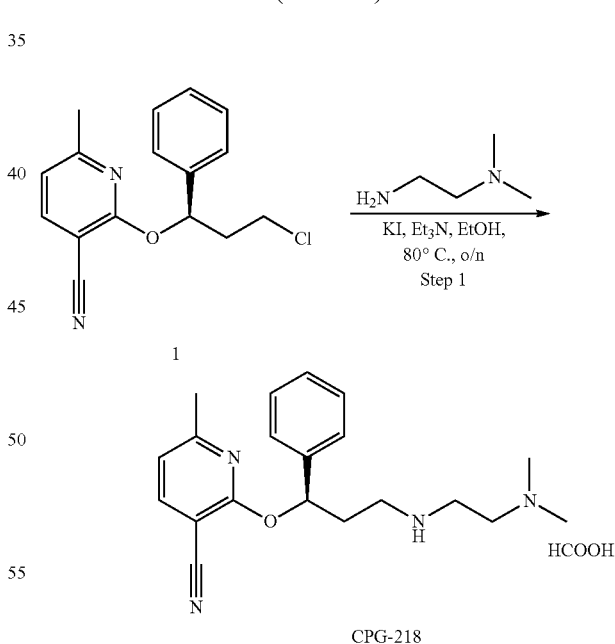

A mixture of (R)-2-(3-chloro-1-phenylpropoxy)-6-methylnicotinonitrile (138 mg, 0.481 mmol), potassium iodide (8.0 mg, 0.0481 mmol), N1,N1-dimethylethane-1,2-diamine (212 mg, 2.41 mmol) in EtOH (3 mL) was stirred at 80° C. in a sealed tube for 12 hrs. The mixture was purified on prep-HPLC (Fluent with 0.2% Formic acid and ACN) to give (R)-2-(3-((2-(dimethyl amino) ethyl)amino)-1-phenyl-propoxy)-6-methylnicotinonitrile (CPG-218) (14.9 mg, 0.044 mmol, 9.1% yield) as yellow gum. LCMS: m/z 339.1 [M+H]+. 1H NMR (400 MHz, MeOD) δ 8.43 (s, 1H), 7.92 (d, J=7.6 Hz, 1H), 7.45 (d, J=7.2 Hz, 2H), 7.36 (t, J=7.6 Hz, 2H), 7.30 (d, J=7.2 Hz, 1H), 6.94 (d, J=7.6 Hz, 1H), 6.34-6.32 (m, 1H), 3.11-3.06 (m, 4H), 2.72-2.68 (m, 2H), 2.43 (s, 1H), 2.40 (s, 3H), 2.39 (s, 6H), 2.32-2.28 (m, 1H).

Synthesis of (R)-6-methyl-2-(3-((2-morpholino-ethyl)amino)-1-phenylpropoxy) nicotinonitrile (CPG-219)

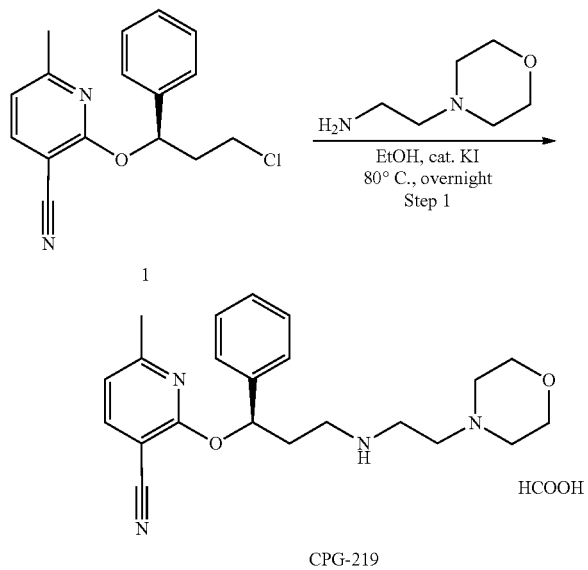

CPG-219

A mixture of (R)-2-(3-chloro-1-phenylpropoxy)-6-methylnicotinonitrile (200 mg, 0.697 mmol), potassium iodide (11.6 mg, 0.07 mmol) and 2-morpholinoethan-1-amine (454 mg, 3.487 mmol) in EtOH (4 mL) was stirred at 80° C. in a sealed tube for 16 hrs. The mixture was purified on prep-HPLC (Fluent with 0.2% Formic acid and ACN) to give (R)-6-methyl-2-(3-((2-morpholinoethyl)amino)-1-phenylpropoxy)nicotinonitrile (CPG-219) (82 mg, 0.192 mmol, 30.9% yield) as brown gum. LCMS: m/z 381.3[M+H]+. 1H NMR (400 MHz, MeOD) δ 8.52 (s, 1H), 7.92 (d, J=7.6 Hz, 1H), 7.50-7.43 (m, 2H), 7.37 (t, J=7.6 Hz, 2H), 7.29 (t, J=7.32 Hz, 1H), 6.94 (d, J=7.6 Hz, 1H), 6.34 (dd, J=8.0, 4.8 Hz, 1H), 3.69-3.62 (m, 4H), 3.19-3.07 (m, 4H), 2.63-2.57 (m, 2H), 2.46 (t, J=8.9 Hz, 5H), 2.40 (s, 3H), 2.38-2.28 (m, 1H).

Synthesis of (R)-2-(3-(((1H-imidazol-2-yl)methyl)amino)-1-phenylpropoxy)-6-methyl nicotinonitrile (CPG-220)

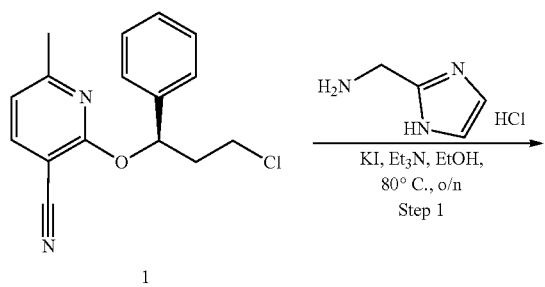

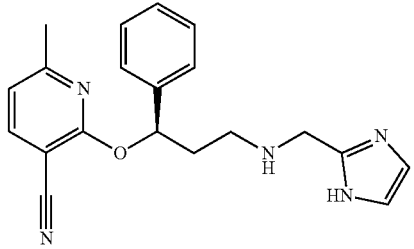

CPG-220

A mixture of (R)-2-(3-chloro-1-phenylpropoxy)-6-methylnicotinonitrile (100 mg, 0.349 mmol), potassium iodide (5.7 mg, 0.0349 mmol), 2-(aminomethyl)imidazole dihydrochloride (296 mg, 1.74 mmol) and Et3N (176 mg, 1.745 mmol) in EtOH (3 mL) was stirred at 80° C. in a sealed tube for 12 hrs. The mixture was purified on prep-HPLC (Fluent with 10 mM NH4HCO3 and ACN) to give (R)-2-(3-(((1H-imidazol-2-yl)methyl)amino)-1-phenylpropoxy)-6-methyl nicotinonitrile (CPG-220) (29.1 mg, 0.084 mmol, 24.0% yield) as yellow gum. LCMS: m/z 348.2 [M+H]+. 1H NMR (400 MHz, MeOD) δ 7.84 (d, J=7.6 Hz, 1H), 7.36 (dd, J=7.6, 6.0 Hz, 4H), 7.29 (dd, J=8.4, 3.2 Hz, 1H), 7.00 (s, 2H), 6.32 (d, J=7.6 Hz, 1H), 4.24-4.13 (m, 1H), 3.99-3.88 (m, 1H), 3.77-3.62 (m, 3H), 2.33 (s, 3H), 2.18-1.98 (m, 2H).

Synthesis of (R)-2-(3-((2-(1H-imidazol-1-yl)ethyl)amino)-1-phenylpropoxy)-6-methyl nicotinonitrile (CPG-221)

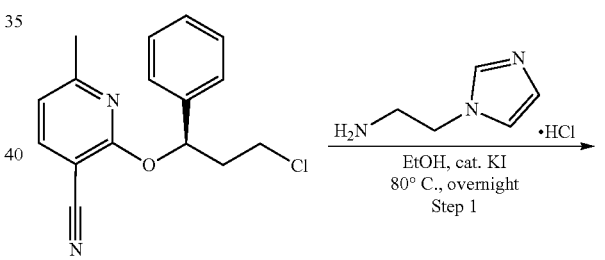

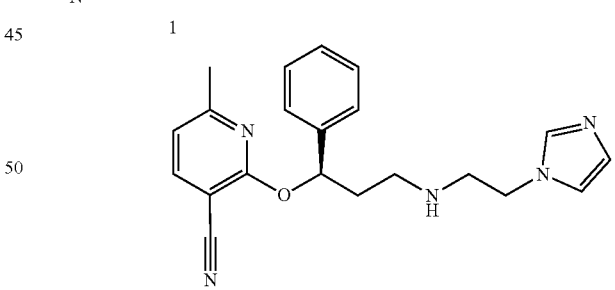

CPG-221

A mixture of (R)-2-(3-chloro-1-phenylpropoxy)-6-methylnicotinonitrile (110 mg, 0.384 mmol), potassium iodide (6.4 mg, 0.0384 mmol), 2-(1H-Imidazol-1-yl)ethanamine dihydrochloride (282 mg, 1.92 mmol) and Et3N (194 mg, 1.92 mmol) in EtOH (2 mL) was stirred at 80° C. in a sealed tube for 12 hrs. The mixture was purified on prep-HPLC (Fluent with 10 mM NH4HCO3 and ACN) to give (R)-2-(3-((2-(1H-imidazol-1-yl)ethyl)amino)-1-phenylpropoxy)-6-methylnicotinonitrile (CPG-221) (14.2 mg, 0.039 mmol, 10.3% yield) as yellow gum. LCMS: m/z 362.1 [M+H]+. 1H NMR (400 MHz, MeOD) δ 8.40 (d, J=7.6 Hz, 1H), 7.55 (s, 1H), 7.44 (d, J=4.4 Hz, 4H), 7.41-7.35 (m, 1H), 7.08 (s, 1H), 7.01 (s, 1H), 6.78 (d, J=8.0 Hz, 1H), 5.47 (dd, J=10.0, 3.2 Hz, 1H), 4.68-4.66 (m, 2H), 4.59-4.57 (m, 2H), 3.86-3.77 (m, 2H), 2.32-2.29 (m, 1H), 2.10-2.09 (m, 1H), 2.05 (s, 3H).

Synthesis of (R)-2-(3-((2-(1H-imidazol-4-yl)ethyl) amino)-1-phenylpropoxy)-6-methylnicotinonitrile (CPG-222)

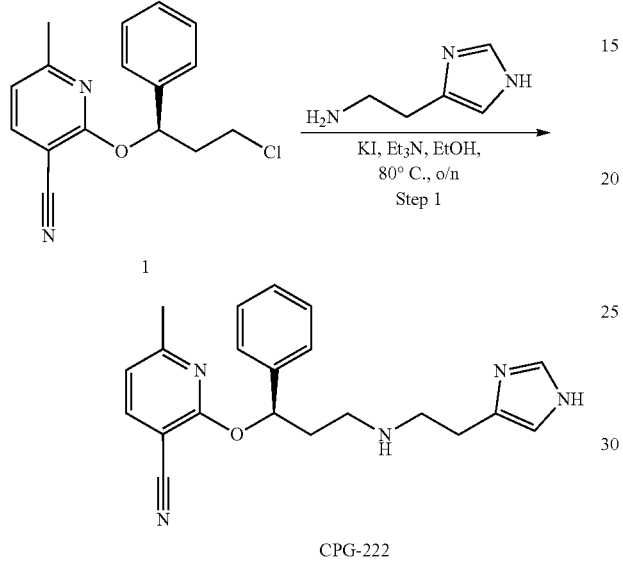

A mixture of (R)-2-(3-chloro-1-phenylpropoxy)-6-methylnicotinonitrile (50 mg, 0.174 mmol), potassium iodide (31.8 mg, 0.192 mmol), histamine (38.6 mg, 0.348 mmol) and Et3N (87.8 mg, 0.87 mmol) in DMSO (2 mL) was stirred at 80° C. in a sealed tube for 12 hrs. The mixture was purified on prep-HPLC (Fluent with 10 mM NH4HCO3 and ACN) to give (R)-2-(3-((2-(1H-imidazol-4-yl)ethyl)amino)-1-phenylpropoxy)-6-methyl nicotinonitrile (CPG-222) (14.7 mg, 0.041 mmol, 22.7% yield) as brown gum. LCMS: m/z 362.1 [M+H]+. 1H NMR (400 MHz, MeOD) δ 8.36 (d, J=7.6 Hz, 1H), 7.68 (s, 1H), 7.43 (d, J=4.4 Hz, 4H), 7.39 (dd, J=8.4, 4.4 Hz, 1H), 6.94 (s, 1H), 6.80 (d, J=8.0 Hz, 1H), 5.46-5.44 (m, 1H), 4.50 (t, J=7.2 Hz, 2H), 3.88-3.75 (m, 2H), 3.11 (t, J=7.2 Hz, 2H), 2.44 (s, 3H), 2.32-2.30 (m, 1H), 2.15-2.02 (m, 1H).

Synthesis of ((R)-3-((6-chloro-1H-benzo[d]imidazol-4-yl)oxy)-3-phenylpropan-1-amine (CPG-224)

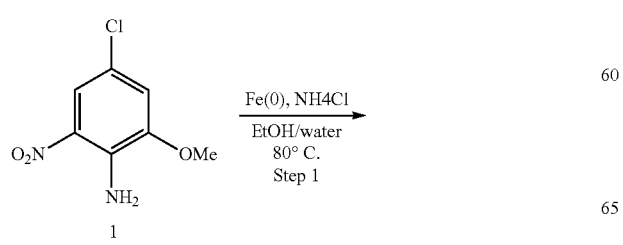

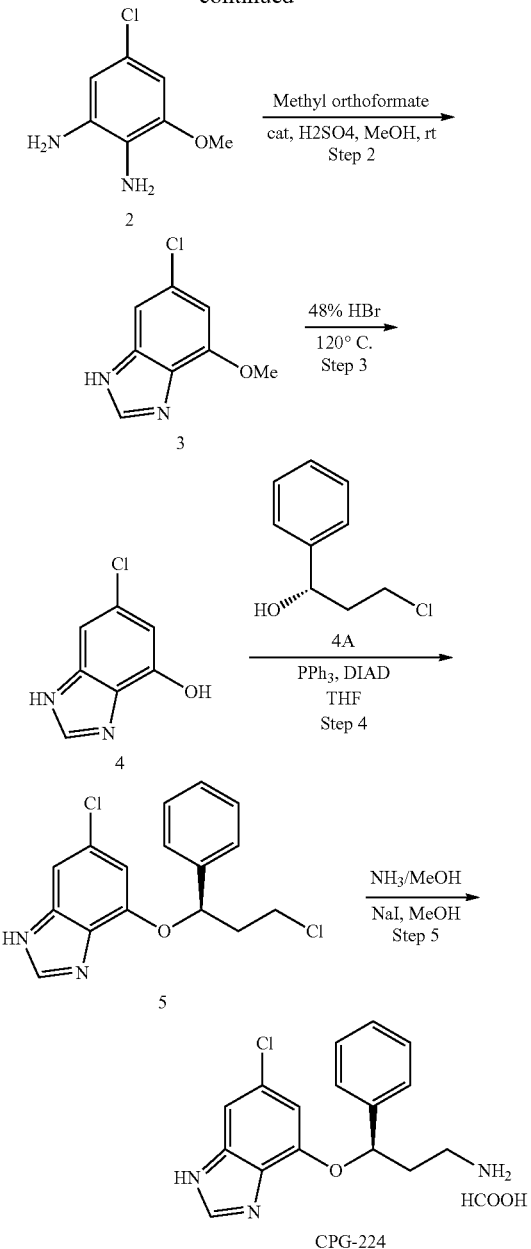

Step 1. Synthesis of 5-chloro-3-methoxybenzene-1,2-diamine (2)

A mixture of 4-chloro-2-methoxy-6-nitroaniline (10 g, 49.5 mmol), Fe powder (27.7 g, 495 mmol) and NH4Cl (26.5 g, 495 mmol) in 95% ethanol (250 mL) was stirred at 80° C. overnight carefully. LCMS was used to monitor this reaction. Filtered, the filtrate was purified by silica gel chromatography (EA/PE from 10% to 50%) to get 5-chloro-3-methoxy benzene-1,2-diamine (7 g, 82% yield) as brown solid. LCMS: m/z 173.1 [M+H]+.

Step 2. 6-chloro-4-methoxy-1H-benzo[d]imidazole-diamine (3)

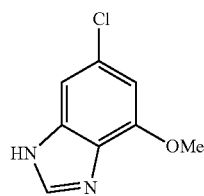 [SMILES: COc1cc(Cl)cc2[nH]cnc12]

A solution of 5-chloro-3-methoxybenzene-1,2-diamine (2 g, 11.6 mmol), methyl orthoformate (1.48 g, 14 mmol) and conc. H2SO4 (57 mg, 0.58 mmol) in methanol (50 mL) was stirred at room temperature for 1 h. LCMS was used to monitor this reaction. The solvent was evaporated, and the residue was partitioned between water (30 mL) and EtOAc (50 mL). The organic phase was separated, washed with water (30 mL) and brine (30 mL), dried over anhydrous Na2SO4 and concentrated, purified by column chromatography on silica gel (PE/EA from 0/1 to 1/1) to get 6-chloro-4-methoxy-1H-benzo[d]imidazole (1.9 g, 90% yield) as brown solid. LCMS: m/z 183.0 [M+H]+.

Step 3. 6-chloro-1H-benzo[d]imidazol-4-ol (4)

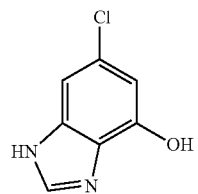 [SMILES: Oc1cc(Cl)cc2[nH]cnc12]

A mixture of 6-chloro-4-methoxy-1H-benzo[d]imidazole (1.5 g, 8.24 mmol) in HBr/H2O (48%, 30 mL) was stirred at 120° C. for 4 days. LCMS was used to monitor this NaHCO₃, and filtered. The filter cake was dried in vacuo to get 6-chloro-1H-benzo[d]imidazol-4-ol (1.2 g, 87% yield) as brown solid. LCMS: m/z 169.0 [M+H]+.

Step 4. (R)-6-chloro-4-(3-chloro-1-phenylpropoxy)-1H-benzo[d]imidazole (5)

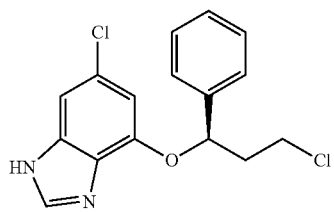

To a solution of 6-chloro-1H-benzo[d]imidazol-4-ol (1.98 g, 11.8 mmol), (S)-3-chloro-1-phenylpropan-1-ol (2.0 g, 11.8 mmol) and PPh3 (3.1 g, 11.8 mmol) in THF (50 mL) was added DEAD (2.05 g, 11.8 mmol) dropwise at 0° C. under N2 balloon. The reaction was allowed to warm to room temperature and stirred overnight. The reaction solution was purified by column chromatography on silica gel (EA/PE from 1/10 to 1/4) to afford the pure product (2.36 g, 62% yield) as a white solid. LCMS: m/z 321.1 [M+H]+.

Step 5. Synthesis of (R)-3-((6-chloro-1H-benzo[d]imidazol-4-yl)oxy)-3-phenyl propan-1-amine (CPG-224)

CPG-224

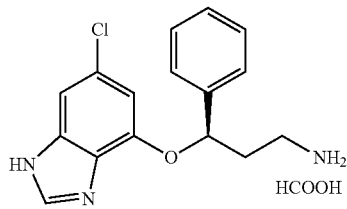

A mixture of (R)-6-chloro-4-(3-chloro-1-phenyl-propoxy)-1H-benzo[d]imidazole (100 mg, 0.311 mmol), sodium iodide (4.7 mg, 0.031 mmol) in NH3/EtOH (3 mL) was stirred at 70° C. in a sealed tube for 16 hrs. The mixture was purified on prep-HPLC (0.1% formic acid/MeCN) to give (R)-3-((6-chloro-1H-benzo[d]imidazol-4-yl)oxy)-3-phenylpropan-1-amine (31.2 mg, 0.103 mmol) as the brown oil. LCMS: m/z 302.10 [M+H]+. 1HMR (400 MHz, MeOD) δ 8.52 (s, 1H), 8.20 (s, 1H) 7.45-7.41 (d, J=7.2 Hz, 2H), 7.37 (t, J=7.6 Hz, 2H), 7.31 (t, J=7.2 Hz, 1H), 7.16 (d, J=1.6 Hz, 1H), 6.56 (s, 1H), 5.64 (m, 1H), 3.28-3.22 (m, 2H), 2.47-2.37 (m, 1H), 2.29-2.24 (m, 1H).

Synthesis of 5-chloro-2-cyano-N-(2-((3-hydroxypropyl)amino)ethyl)-N-phenyl benzamide (CPG-237)

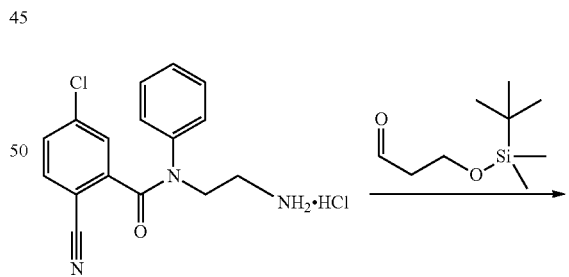

from CPG-196

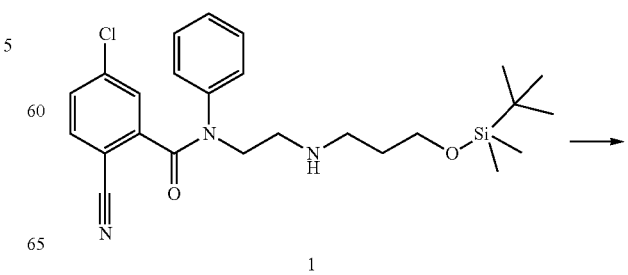

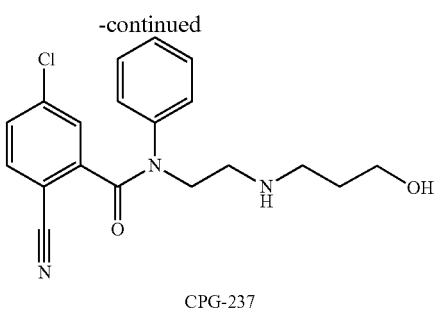

CPG-237

Step 1. Synthesis of N-(2-((3-((tert-butyldimethylsilyl)oxy)propyl)amino) ethyl)-5-chloro-2-cyano-N-phenylbenzamide (1)

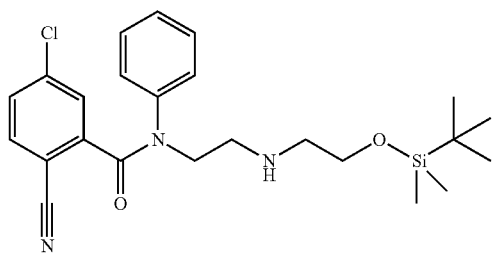

1

To a solution of N-(2-aminoethyl)-5-chloro-2-cyano-N-phenylbenzamide hydrochloride (200 mg, 0.6 mmol), 3-((tert-butyldimethylsilyl)oxy)propanal (170 mg, 0.9 mmol) in THF (2 mL), glacial AcOH (54 mg, 0.9 mmol) was added and the mixture was stirred at room temperature for 4 h, then was added NaBH(OAc)₃ (190 mg, 0.9 mmol) and the mixture was stirred at room temperature for 16 h. The reaction mixture was quenched with aqueous saturated NaHCO₃ solution, and the product was extracted with EA. The EA extract was dried (MgSO4). The solvent was removed. The residue was purified by Prep-HPLC (eluted with 10 mM NH4HCO3 and ACN) to give N-(2-((3-((tert-butyldimethylsilyl)oxy)propyl)amino) ethyl)-5-chloro-2-cyano-N-phenylbenzamide (1) (50 mg, 0.106 mmol, 18% yield) as a liquid. LCMS: m/z 458.2[M+H]+.

Step 2. Synthesis of 5-chloro-2-cyano-N-(2-((3-hydroxypropyl)amino)ethyl)-N-phenylbenzamide (CPG-237)

CPG-237

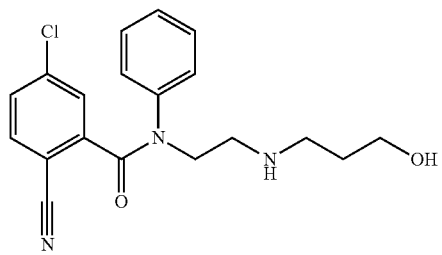

To a solution of N-(2-((3-((tert-butyldimethylsilyl)oxy) propyl) amino)ethyl)-5-chloro-2-cyano-N-phenylbenzamide (1) (50 mg, 0.106 mmol), 3M TBAF in THF (2 mL) was added and the mixture was stirred at room temperature for 2 h. The solvent was removed, then added water (1 ml) and extracted with EA. The combined organic extracts were washed with brine and then dried over anhydrous MgSO4. After filtration, the solvent was removed in vacuo. The residue was purified by Prep-HPLC (eluted with 10 mM NH4HCO3 and ACN) to give 5-chloro-2-cyano-N-(2-((3-hydroxypropyl)amino)ethyl)-N-phenylbenzamide (CPG-237) (2.6 mg, 0.0073 mmol, 7% yield) as a liquid. LCMS: m/z 358.0 [M+H]+. 1H NMR (400 MHz, MeOD) δ 7.83 (d, J=8.4 Hz, 0.6H), 7.63 (dd, J=8.4, 2.1 Hz, 0.6H), 7.57 (d, J=8.6 Hz, 1H), 7.42 (m, 2.6H), 7.13 (dd, J=8.5, 7.4 Hz, 1.2H), 6.96 (dd, J=8.5, 7.4 Hz, 2H), 6.72 (d, J=7.7 Hz, 1.2H), 6.64 (t, J=7.3 Hz, 0.6H), 6.53 (t, J=7.3 Hz, 1H), 6.32 (d, J=7.7 Hz, 2H), 3.73 (dt, J=15.8, 6.3 Hz, 5.2H), 3.52 (t, J=6.5 Hz, 1.2H), 3.43 (dt, J=16.7, 5.9 Hz, 3.2H), 2.03-1.93 (m, 2H), 1.68 (ddd, J=25.7, 15.3, 7.0 Hz, 3.2H), 1.41 (dq, J=14.6, 7.4 Hz, 2H), 1.02 (t, J=7.4 Hz, 2.4H).

Synthesis of 5-chloro-2-cyano-N-(2-((2-hydroxyethyl)amino)ethyl)-N-phenyl benzamide (CPG-242)

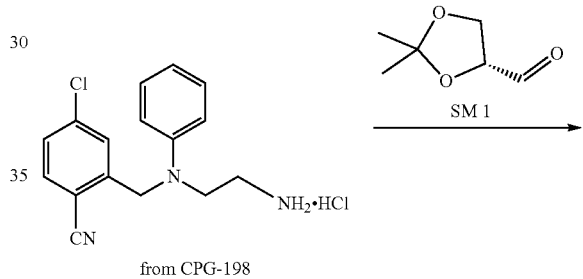

from CPG-198

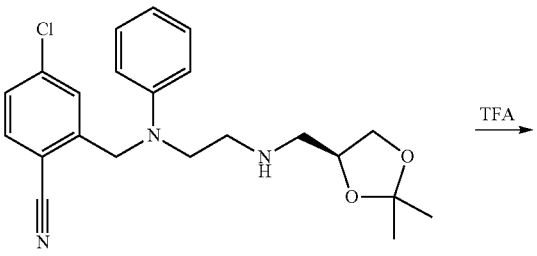

1

CPG-242

Step 1. Synthesis of (S)-4-chloro-2-(((2-(((2,2-dimethyl-1,3-dioxolan-4-yl) methyl) amino) ethyl)(phenyl)amino)methyl)benzonitrile (1)

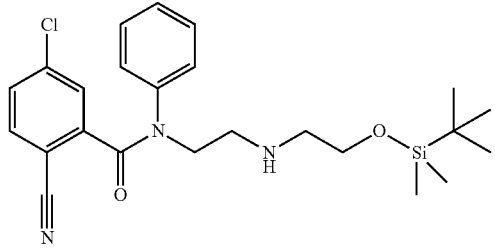

To a solution of 2-(((2-aminoethyl)(phenyl)amino)methyl)-4-chloro benzonitrile hydrochloride (300 mg, 0.93 mmol), (R)-2,2-dimethyl-1,3-dioxolane-4-carbaldehyde (180 mg, 1.40 mmol) in THF (2 mL), glacial AcOH (84 mg, 1.4 mmol) was added and the mixture was stirred at room temperature for 4 h; then was added NaBH(OAc)3 (296 mg, 1.4 mmol) and the mixture was stirred at room temperature for 16 h. The reaction mixture was quenched with aqueous saturated NaHCO₃ solution, and the product was extracted with EA. The EA extract was dried (MgSO4). The solvent was removed. The residue was purified by Prep-HPLC (Fluent with 10 mM NH4HCO3 and ACN) to give (S)-4-chloro-2-(((2-(((2,2-dimethyl-1,3-dioxolan-4-yl) methyl) amino)ethyl)(phenyl)amino)methyl)benzonitrile (1) (100 mg, 0.25 mmol, 27% yield) as a liquid. LCMS: m/z 400.0 [M+H]+.

Step 2. Synthesis of (R)-4-chloro-2-(((2-((2,3-dihydroxypropyl)amino)ethyl)(phenyl) amino)methyl)benzonitrile (CPG-242)

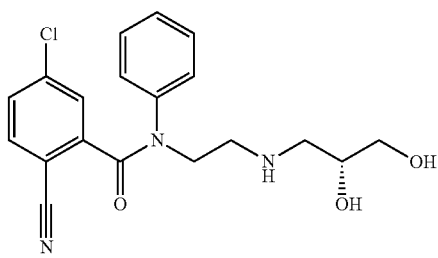 [SMILES: N#Cc1ccc(Cl)cc1C(=O)N(CCNC[C@@H](O)CO)c1ccccc1]

To a solution give (S)-4-chloro-2-(((2-(((2,2-dimethyl-1,3-dioxolan-4-yl)methyl) amino)ethyl)(phenyl)amino)methyl)benzonitrile (1) (100 mg, 0.25 mmol), TFA (3.0 ml) in DCM (3.0 mL) was added and the mixture was stirred at room temperature for 6 h. The solvent was removed. The residue was purified by Prep-HPLC (eluted with 10 mM NH4HCO3 and ACN) to give (R)-4-chloro-2-(((2-((2,3-dihydroxypropyl)amino)ethyl)(phenyl)amino)methyl)benzonitrile (8.0 mg, 0.022 mmol, 9% yield) as a liquid. LCMS: m/z 359.9[M+H]+. 1H NMR (400 MHz, MeOD) δ 7.67 (d, J=8.3 Hz, 1H), 7.36 (dd, J=8.3, 1.9 Hz, 1H), 7.25 (d, J=1.9 Hz, 1H), 7.11 (t, J=8.0 Hz, 2H), 6.66 (m, 3H), 4.70 (s, 2H), 3.68 (m, 1H), 3.57 (t, J=7.0 Hz, 2H), 3.44 (d, J=5.5 Hz, 2H), 2.83 (t, J=7.0 Hz, 2H), 2.71 (dd, J=12.2, 3.5 Hz, 1H), 2.56 (dd, J=12.1, 8.4 Hz, 1H).

Synthesis of 2-((R)-3-(((S)-2,3-dihydroxypropyl)amino)-1-phenylpropoxy)-6-methylnicotinonitrile (CPG-243)

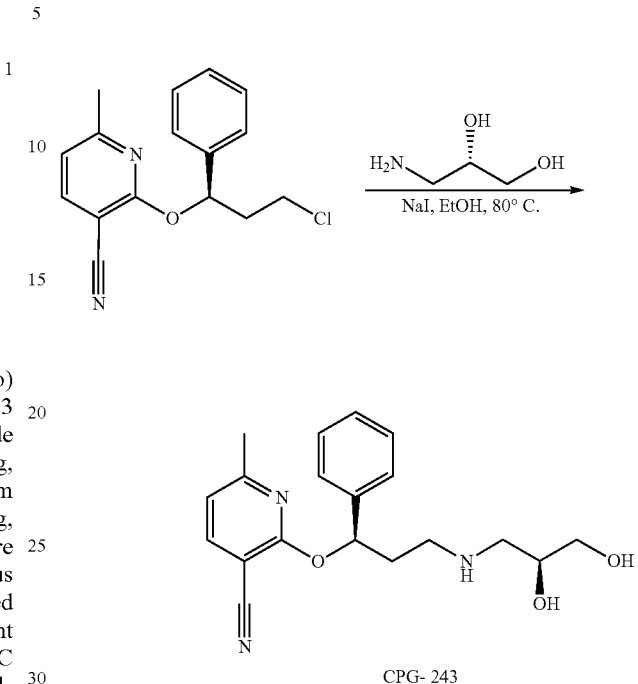

A mixture of (R)-2-(3-chloro-1-phenylpropoxy)-6-methylnicotinonitrile (200 mg, 0.697 mmol), sodium iodide (10.5 mg, 0.070 mmol), (S)-3-aminopropane-1,2-diol (317.7 mg, 3.487 mmol) in EtOH (3 mL) was stirred at 80° C. in a sealed tube for 16 hrs. The reaction solution was purified by column chromatography on silica gel (NH3 in MeOH/DCM=1/99) to afford the pure (130 mg, crude) as a yellow oil. The crude was purified on prep-HPLC (0.1% formic acid/MECN) to give 2-((R)-3-(((S)-2,3-dihydroxypropyl)amino)-1-phenyl propoxy)-6-methylnicotinonitrile (57.3 mg, 24.1% yield) as yellow oil. LCMS: m/z 342.17[M+H]+. H NMR (400 MHz, MeOD) δ 8.54 (s, 1H), 7.89 (d, J=7.6 Hz, 1H), 7.49 (d, J=7.2 Hz, 2H), 7.37 (t, J=7.6 Hz, 2H), 7.30 (m, 1H), 6.92 (d, J=7.6 Hz, 1H), 6.37 (m, 1H), 3.93 (m, 1H), 3.57 (m, 2H), 3.28-3.12 (m, 3H), 3.02 (m, 1H), 2.57-2.47 (m, 1H), 2.42 (s, 3H), 2.41-2.35 (m, 1H).

Synthesis of 2-((R)-3-(((R)-2,3-dihydroxypropyl)amino)-1-phenylpropoxy)-6-methylnicotinonitrile (CPG-244)

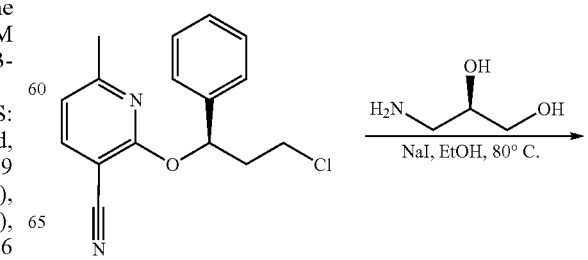

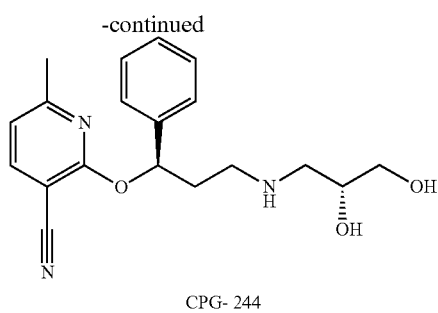

CPG-244

A mixture of (R)-2-(3-chloro-1-phenylpropoxy)-6-methylnicotinonitrile (200 mg, 0.697 mmol), sodium iodide (10.5 mg, 0.070 mmol), and (R)-3-aminopropane-1,2-diol (173 mg, 1.40 mmol) in EtOH (3 mL) was stirred at 80° C. in a sealed tube for 16 hrs. The mixture was purified on Prep-HPLC (0.1% formic acid/MeCN), then the crude was purified by prep-HPLC (Fluent with 10 mM NH4HCO3 and ACN) to give 2-((R)-3-(((R)-2,3-dihydroxypropyl)amino)-1-phenyl propoxy)-6-methylnicotinonitrile (26.0 mg, 0.076 mmol, 10.9% yield) as yellow oil. LCMS: m/z 342.17[M+H]+. 1H NMR (400 MHz, MeOD) δ 7.89 (d, J=7.6 Hz, 1H), 7.45 (d, J=7.2 Hz, 2H), 7.35 (t, J=7.6 Hz, 2H), 7.27 (t, J=7.2 Hz, 1H), 6.91 (d, J=7.8 Hz, 1H), 6.34 (m, 1H), 3.77 (m, 1H), 3.50 (m, 2H), 2.92-2.84 (m, 3H), 2.72 (m, 1H), 2.41 (s, 3H), 2.39-2.32 (m, 1H), 2.26-2.17 (m, 1H).

Synthesis of 2-((R)-3-(((1r,3R)-3-hydroxycyclobutyl)amino)-1-phenylpropoxy)-6-methylnicotinonitrile (CPG-245)

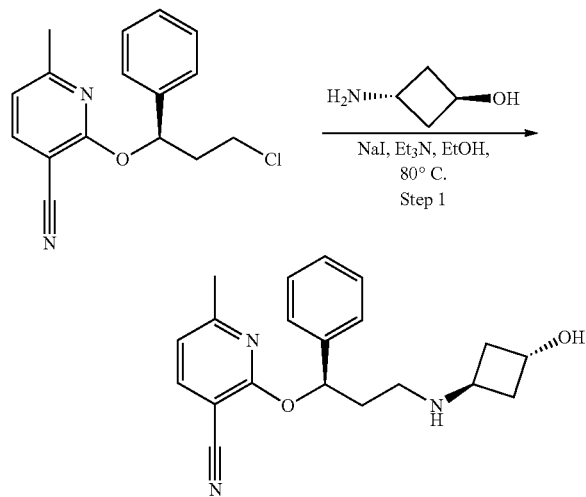

CPG-245

A mixture of (R)-2-(3-chloro-1-phenylpropoxy)-6-methylnicotinonitrile (200 mg, 0.697 mmol), sodium iodide (10.5 mg, 0.070 mmol), (1r,3r)-3-aminocyclobutan-1-ol (173 mg, 1.40 mmol) and triethylamine (141 mg, 1.395 mmol) in EtOH (3 mL) was stirred at 80° C. in a sealed tube for 16 hrs. The mixture was purified on prep-HPLC (0.1% formic acid/MeCN) to give 2-((R)-3-(((1r,3R)-3-hydroxycyclobutyl)amino)-1-phenylpropoxy)-6-methyl nicotinonitrile (CPG-245) (48 mg, 0.142 mmol, 20.0% yield) as yellow gum. LCMS: m/z 338.18[M+H]+. 1HNMR (400 MHz, MeOD) δ 7.88 (d, J=7.6 Hz, 1H), 7.52-7.50 (t, J=3.2 Hz, 5H), 6.35 (d, J=7.6 Hz, 1H), 4.39 (m, 2H), 4.17-4.06 (m, 1H), 3.93-3.81 (m, 1H), 3.77-3.68 (m, 1H), 2.55 (m, 1H), 2.45 (m, 2H), 2.36 (s, 3H), 2.31-2.20 (m, 2H), 2.07-1.98 (m, 1H).

Synthesis of 2-((R)-3-(((1s,3S)-3-hydroxycyclobutyl)amino)-1-phenyl propoxy)-6-methylnicotinonitrile (CPG-246)

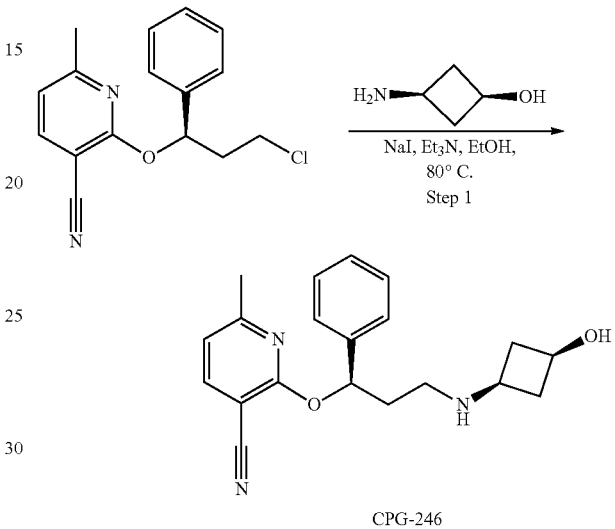

CPG-246

The exact method as described for the synthesis of (R)-2-(3-amino-1-phenyl propoxy)-6-methylnicotinonitrile (CPG-245) was applied with substitution of (1s,3s)-3-aminocyclobutan-1-ol for ammonia to provide the product 2-((R)-3-(((1s,3S)-3-hydroxycyclobutyl)amino)-1-phenylpropoxy)-6-methylnicotinonitrile (47 mg, 0.139 mmol, 20.0% yield) as yellow oil. LCMS: m/z 338.18[M+H]+. 1H NMR (400 MHz, DMSO) δ 8.20 (s, 1H), 7.95 (d, J=7.5 Hz, 1H), 7.39-7.17 (m, 5H), 6.29 (d, J=7.5 Hz, 1H), 4.08-3.98 (m, 1H), 3.84-3.73 (m, 2H), 3.30-3.53 (m, 2H), 2.40 (dd, J=13.7, 5.7 Hz, 1H), 2.34 (d, J=9.4 Hz, 4H), 2.07 (dt, J=17.0, 6.5 Hz, 1H), 1.96-1.75 (m, 3H), 1.52 (dd, J=18.3, 8.6 Hz, 1H), 1.41 (dd, J=18.7, 8.4 Hz, 1H).

Synthesis of (R)-2-(3-(bicyclo[1.1.1]pentan-1-ylamino)-1-phenylpropoxy)-6-methylnicotinonitrile (CPG-247)

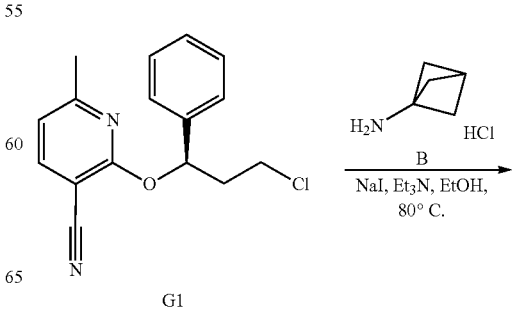

G1

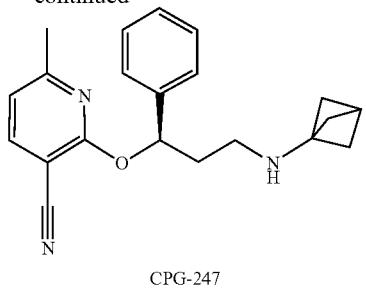

CPG-247

A mixture of (R)-2-(3-chloro-1-phenylpropoxy)-6-methylnicotinonitrile (500 mg, 1.744 mmol), triethylamine (671 mg, 6.631 mmol), sodium iodide (26.3 mg, 0.175 mmol), and bicyclo[1,1,1]pentan-1-amine (793 mg, 6.631 mmol) in EtOH (7 mL) was stirred at 80° C. in a sealed tube for 16 hrs. The reaction solution was purified by column chromatography on silica gel (NH3 in MeOH/DCM=1/99) to afford the pure (130 mg, crude) as a yellow oil. The crude was purified on prep-HPLC (0.1% TFA/MeCN) to give (R)-2-(3-(bicyclo[1.1.1]pentan-1-yl amino)-1-phenylpropoxy)-6-methylnicotinonitrile (83.9 mg, 14.4% yield) as brown solid. LCMS: m/z 334.18[M+H]+. 1H NMR (400 MHz, MeOD) δ 7.88 (d, J=7.6 Hz, 1H), 7.59-7.48 (m, 5H), 6.34 (d, J=7.6 Hz, 1H), 4.46 (m, 1H), 4.20-4.10 (m, 1H), 3.76 (m, 1H), 2.62 (s, 1H), 2.43 (m, 1H), 2.38-2.31 (m, 1H), 2.30 (d, J=7.6 Hz, 3H), 2.03 (m, 3H), 1.89 (m, 3H).

Synthesis of (R)-2-(3-(cyclopropylamino)-1-phenylpropoxy)-6-methyl nicotinonitrile (CPG-248)

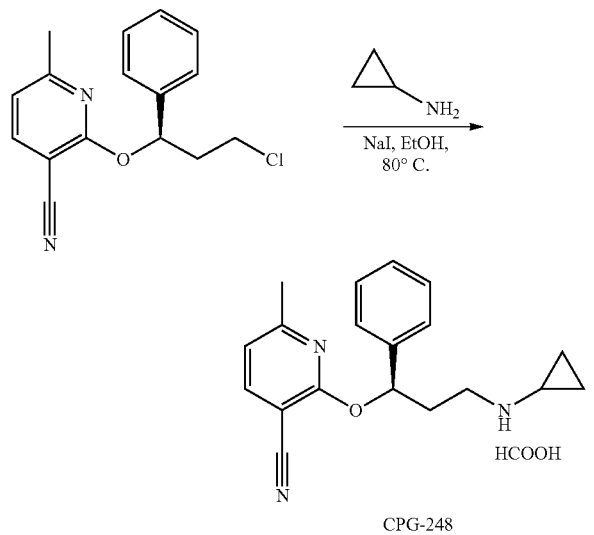

CPG-248

A mixture of (R)-2-(3-chloro-1-phenylpropoxy)-6-methylnicotinonitrile (200 mg, 0.697 mmol), sodium iodide (10.5 mg, 0.070 mmol), and cyclopropanamine (199 mg, 3.485 mmol) in EtOH (3 mL) was stirred at 80° C. in a sealed tube for 16 hrs. The mixture was purified on prep-HPLC (0.1% formic acid/MeCN) to give (R)-2-(3-(cyclopropylamino)-1-phenyl propoxy)-6-methylnicotinonitrile (40.4 mg, 0.153 mmol, 18.9% yield) as yellow oil. LCMS: m/z 308.17[M+H]+. 1H NMR (400 MHz, MeOD) δ 8.35 (s, 1H), 7.85 (d, J=7.5 Hz, 1H), 7.57-7.34 (m, 5H), 6.32 (d, J=7.6 Hz, 1H), 4.25-4.00 (m, 2H), 3.86 (ddd, J=13.7, 9.7, 6.5 Hz, 1H), 2.43-2.14 (m, 5H), 0.88-0.25 (m, 4H).

Synthesis of (R)-2-(3-((1,3-dihydroxypropan-2-yl)amino)-1-phenylpropoxy)-6-methylnicotinonitrile (CPG-249)

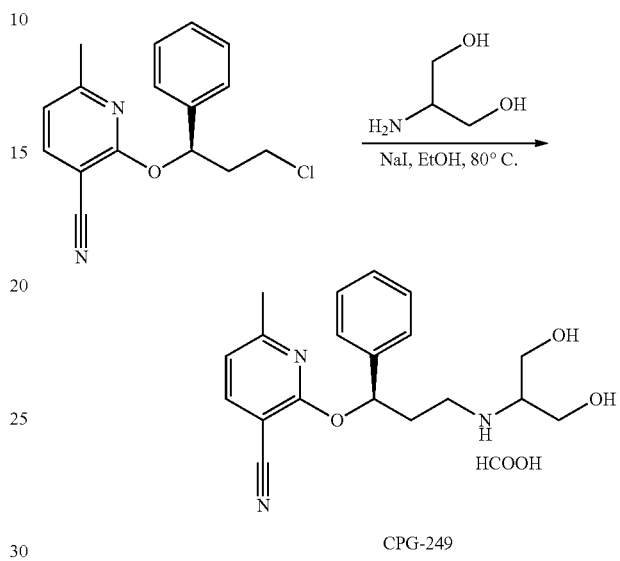

CPG-249

A mixture of (R)-2-(3-chloro-1-phenylpropoxy)-6-methylnicotinonitrile (200 mg, 0.697 mmol), sodium iodide (10.5 mg, 0.070 mmol), and 2-aminopropane-1,3-diol (318 mg, 3.490 mmol) in EtOH (3 mL) was stirred at 80° C. in a sealed tube for 16 hrs. The reaction solution was purified by column chromatography on silica gel (NH3 in MeOH/DCM=1/99) to afford the pure (60 mg, crude) as a yellow oil. The crude was purified on prep-HPLC (0.1% formic acid/MeCN) to give (R)-2-(3-((1,3-dihydroxypropan-2-yl)amino)-1-phenylpropoxy)-6-methyl nicotinonitrile (19.1 mg, 0.08% yield) as yellow gum. LCMS: m/z 342.17[M+H]+. 1H NMR (400 MHz, MeOD) δ 8.43 (s, 1H), 7.86 (d, J=7.6 Hz, 1H), 7.54-7.50 (m, 2H), 7.46 (t, J=7.2 Hz, 2H), 7.43-7.38 (m, 1H), 6.33 (d, J=7.6 Hz, 1H), 4.39 (m, 1H), 4.17 (m, 1H), 3.83 (m, 1H), 3.70 (m, 2H), 3.58 (m, 2H), 2.84 (m, 1H), 2.41-2.34 (m, 1H), 2.33 (s, 3H), 2.27 (m, 1H).

Synthesis of 5-chloro-2-cyano-N-(2-((1,3-dihydroxypropan-2-yl)amino)ethyl)-N-phenylbenzamide (CPG-250)

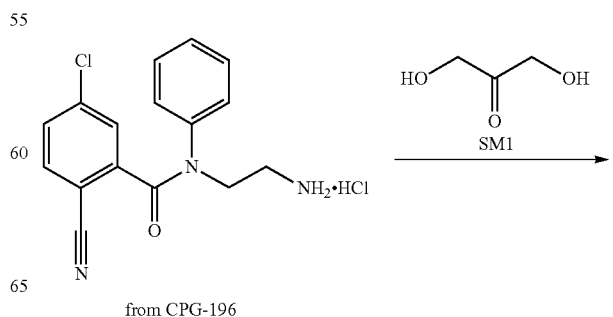

from CPG-196

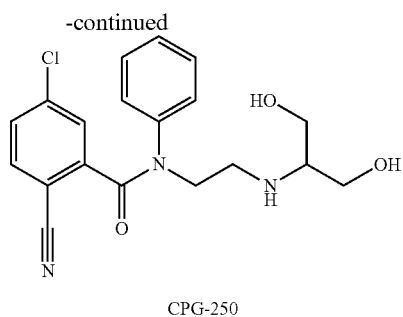

CPG-250

To a solution of N-(2-aminoethyl)-5-chloro-2-cyano-N-phenylbenzamide hydrochloride (150 mg, 0.45 mmol), 1,3-dihydroxypropan-2-one (60 mg, 0.67 mmol) in THF (2 mL), glacial AcOH (40 mg, 0.67 mmol) was added and the mixture was stirred at room temperature for 4 h; then was added NaBH(OAc)₃ (142 mg, 0.67 mmol) and the mixture was stirred at room temperature for 16 h. The reaction mixture was quenched with aqueous saturated NaHCO₃ solution, and the product was extracted with EA. The EA extract was dried (MgSO4). The solvent was removed. The residue was purified by Prep-HPLC (eluted with 10 mM NH4HCO3 and ACN) to give -chloro-2-cyano-N-(2-((1,3-dihydroxypropan-2-yl)amino)ethyl)-N-phenyl benzamide (CPG-250) (180 mg, 0.48 mmol, 72% yield) as a liquid. LCMS: m/z 374.1 [M+H]+. 1H NMR (400 MHz, MeOD) δ 7.60 (d, J=8.3 Hz, 1H), 7.56 (d, J=1.6 Hz, 1H), 7.42 (dd, J=8.3, 1.6 Hz, 1H), 7.32 (d, J=4.2 Hz, 4H), 7.26 (d, J=4.3 Hz, 1H), 4.13 (t, J=6.6 Hz, 2H), 3.63 (dd, J=11.0, 5.4 Hz, 2H), 3.55 (dd, J=11.0, 5.4 Hz, 2H), 2.97 (t, J=6.6 Hz, 2H), 2.78-2.67 (m, 1H).

Synthesis of 4-chloro-2-(((2-((1,3-dihydroxypropan-2-yl)amino)ethyl)(phenyl)amino) methyl)benzonitrile (CPG-251)

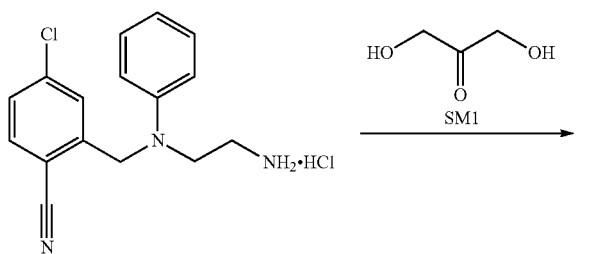

from CPG-198

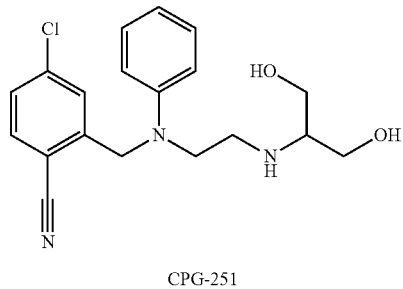

CPG-251

To a solution of 2-(((2-aminoethyl)(phenyl)amino) methyl)-4-chlorobenzonitrile hydrochloride (150 mg, 0.45 mmol), 1,3-dihydroxypropan-2-one (60 mg, 0.67 mmol) in THF (2 mL), glacial AcOH (40 mg, 0.67 mmol) was added and the mixture was stirred at room temperature for 4 h; then was added NaBH(OAc)₃ (142 mg, 0.67 mmol); and the mixture was stirred at room temperature for 16 h. The reaction mixture was quenched with aqueous saturated NaHCO₃ solution, and the product was extracted with EA. The EA extract was dried (MgSO4). The solvent was removed. The residue was purified by Prep-HPLC (Fluent with 10 mM NH4HCO3 and ACN) to give 4-chloro-2-(((2-((1,3-dihydroxypropan-2-yl)amino)ethyl)(phenyl) amino) methyl)benzonitrile (CPG-251) (160 mg, 0.45 mmol, 95% yield) as a liquid. LCMS: m/z 360.1 [M+H]+. 1H NMR (400 MHz, MeOD) δ 7.72 (d, J=8.3 Hz, 1H), 7.42 (dd, J=8.3, 1.9 Hz, 1H), 7.32 (s, 1H), 7.17 (t, J=8.0 Hz, 2H), 6.72 (m, 3H), 4.76 (s, 2H), 3.66-3.57 (m, 4H), 3.52 (dd, J=11.1, 5.7 Hz, 2H), 2.95 (t, J=7.0 Hz, 2H), 2.78-2.64 (m, 1H).

Synthesis of (R)-2-(3-((cyclopropylmethyl)amino)-1-phenylpropoxy)-6-methylnicotino nitrile (CPG-252)

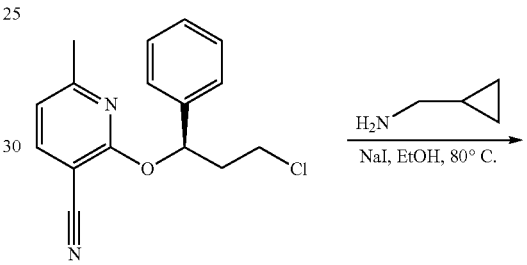

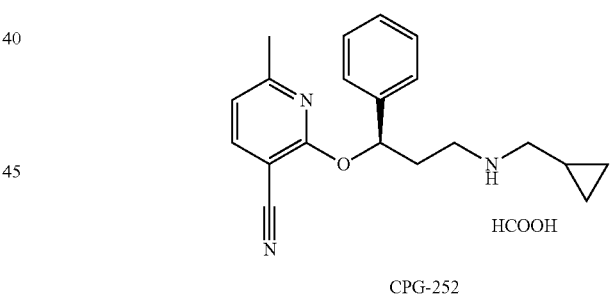

CPG-252

A mixture of (R)-2-(3-chloro-1-phenylpropoxy)-6-methylnicotinonitrile (200 mg, 0.697 mmol), sodium iodide (10.5 mg, 0.070 mmol), and cyclpropylmethanamine (248 mg, 3.487 mmol) in EtOH (3 mL) was stirred at 80° C. in a sealed tube for 16 hrs. The mixture was purified on prep-HPLC (0.1% formic acid/MeCN) to give ((R)-2-(3-((cyclopropylmethyl)amino)-1-phenylpropoxy)-6-methylnicotinonitrile (38.3 mg, 17.1% yield) as green gum. LCMS: m/z 322.18[M+H]+. 1H NMR (400 MHz, MeOD) δ 8.52 (s, 1H), 7.93 (t, J=8.9 Hz, 1H), 7.46 (d, J=7.4 Hz, 2H), 7.37 (t, J=7.5 Hz, 2H), 7.29 (t, J=7.3 Hz, 1H), 6.94 (d, J=7.7 Hz, 1H), 6.36-6.27 (m, 1H), 3.24-3.11 (m, 2H), 2.90 (d, J=7.5 Hz, 2H), 2.53-2.43 (m, 1H), 2.40 (s, 3H), 2.33 (dq, J=15.0, 5.3 Hz, 1H), 1.12-1.01 (m, 1H), 0.68 (q, J=5.9 Hz, 2H), 0.38 (q, J=4.8 Hz, 2H).

Synthesis of 5-chloro-2-cyano-N-(2-((cyclopropylmethyl)amino)ethyl)-N-phenyl benzamide (CPG-253)

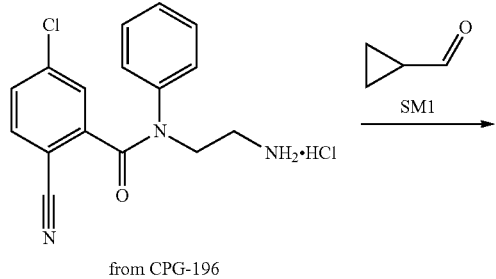

from CPG-196

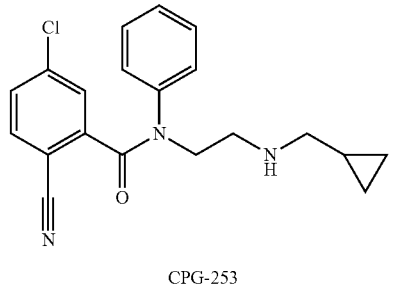

CPG-253

To a solution of N-(2-aminoethyl)-5-chloro-2-cyano-N-phenylbenzamide hydrochloride (300 mg, 0.90 mmol), cyclopropanecarbaldehyde (95 mg, 1.35 mmol) in THF (2 mL), glacial AcOH (84 mg, 1.40 mmol) was added; and the mixture was stirred at room temperature for 4 h; then was added NaBH(OAc)$_3$ (285 mg, 1.40 mmol) and the mixture was stirred at room temperature for 16 h. The reaction mixture was quenched with aqueous saturated NaHCO$_3$ solution, and the product was extracted with EA. The EA extract was dried (MgSO4). The solvent was removed. The residue was purified by Prep-HPLC (Fluent with 10 mM NH4HCO3 and ACN) to give 5-chloro-2-cyano-N-(2-((cyclopropylmethyl)amino)ethyl)-N-phenyl benzamide (CPG-253) (28.4 mg, 0.080 mmol, 9% yield) as a liquid. LCMS: m/z 354.1 [M+H]+. 1H NMR (400 MHz, MeOD) δ 7.81 (d, J=8.4 Hz, 1H), 7.62 (dd, J=8.4, 2.0 Hz, 1H), 7.57 (d, J=8.4 Hz, 1H), 7.44 (d, J=2.0 Hz, 1H), 7.41 (dd, J=8.4, 2.0 Hz, 1H), 7.37 (d, J=2.0 Hz, 1H), 7.11 (t, J=7.9 Hz, 2H), 6.95 (t, J=7.9 Hz, 2H), 6.71 (d, J=7.8 Hz, 2H), 6.63 (d, J=7.3 Hz, 1H), 6.52 (t, J=7.3 Hz, 1H), 6.30 (d, J=7.8 Hz, 2H), 3.85 (t, J=6.5 Hz, 2H), 3.52 (dd, J=10.8, 6.0 Hz, 6H), 3.27 (t, J=6.5 Hz, 2H), 3.06 (d, J=6.7 Hz, 2H), 1.24-1.13 (m, 1H), 0.90 (m, 1H), 0.63-0.56 (q, J=5.8 Hz, 2H), 0.49 (q, J=5.8 Hz, 2H), 0.37 (q, J=4.8 Hz, 2H), −0.01 (q, J=4.8 Hz, 2H).

Synthesis of 4-chloro-2-(((2-((cyclopropylmethyl)amino)ethyl)(phenyl)amino)methyl) benzonitrile (CPG-254)

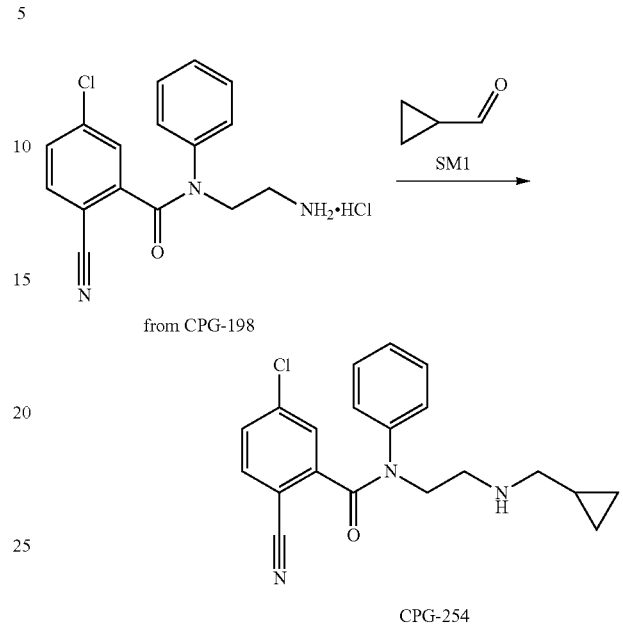

from CPG-198

CPG-254

To a solution of 2-(((2-aminoethyl)(phenyl)amino)methyl)-4-chloro benzonitrile hydrochloride (300 mg, 0.93 mmol), cyclopropanecarbaldehyde (98 mg, 1.4 mmol) in THF (2 mL), glacial AcOH (84 mg, 1.40 mmol) was added and the mixture was stirred at room temperature for 4 h; then was added NaBH(OAc)3 (298 mg, 1.40 mmol) and the mixture was stirred at room temperature for 16 h. The reaction mixture was quenched with aqueous saturated NaHCO$_3$ solution, and the product was extracted with EA. The EA extract was dried (MgSO4). The solvent was removed. The residue was purified by Prep-HPLC (Fluent with 10 mM NH4HCO3 and ACN) to give 4-chloro-2-(((2-((cyclopropylmethyl)amino)ethyl)(phenyl) amino) methyl) benzonitrile (CPG-254) (22.0 mg, 0.067 mmol, 7% yield) as a liquid. LCMS: m/z 340.0 [M+H]+. 1H NMR (400 MHz, MeOD) δ 7.74 (d, J=8.3 Hz, 1H), 7.44 (dd, J=8.3, 1.8 Hz, 1H), 7.31 (d, J=1.8 Hz, 1H), 7.24-7.14 (m, 2H), 6.81-6.68 (m, 3H), 4.75 (s, 2H), 3.62 (t, J=7.2 Hz, 2H), 2.89 (t, J=7.2 Hz, 2H), 2.50 (d, J=7.0 Hz, 2H), 1.01-0.80 (m, 1H), 0.62-0.41 (m, 2H), 0.20-0.13 (m, 2H).

Synthesis of (R)-3-((6-chloro-1H-benzo[d]imidazol-4-yl)oxy)-N-methyl-3-phenyl propan-1-amine (CPG-255)

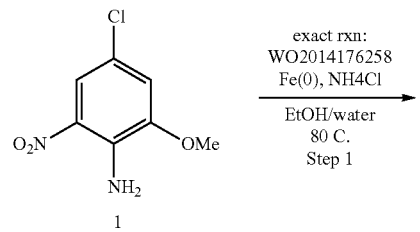

1

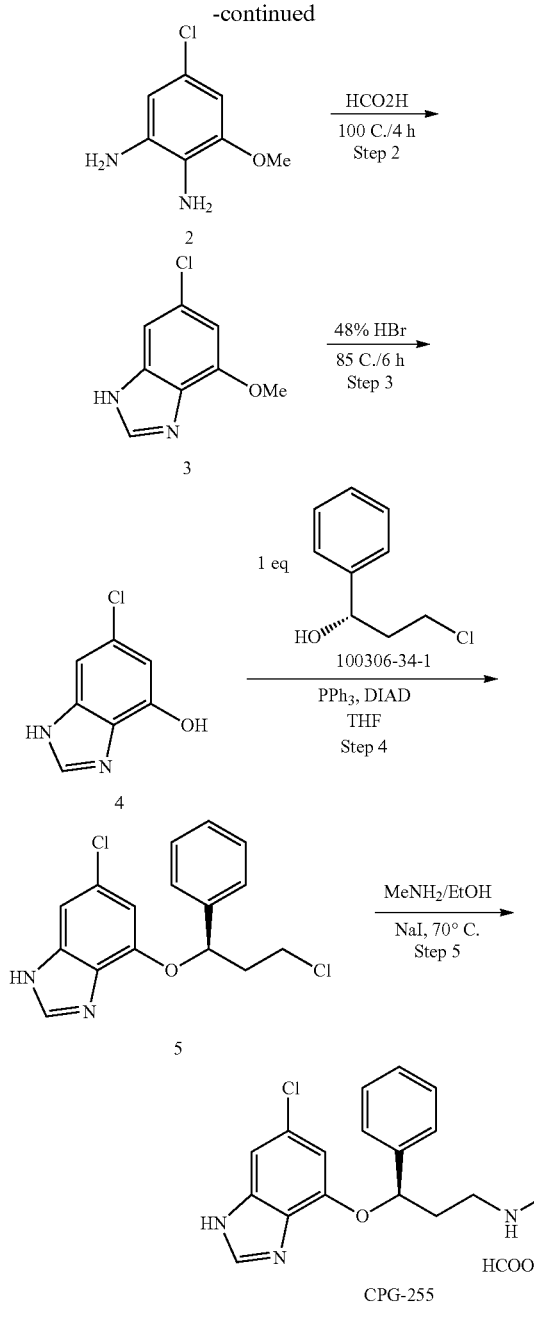

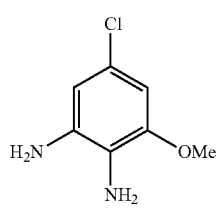

Step 1. Synthesis of 5-chloro-3-methoxybenzene-1,2-diamine (2)

A mixture of 4-chloro-2-methoxy-6-nitroaniline (10 g, 49.5 mmol), Fe powder (27.7 g, 495 mmol) and NH4Cl (26.5 g, 495 mmol) in 95% ethanol (250 mL) was stirred at 80° C. overnight carefully. LCMS was used to monitor this reaction. Filtered, the filtrate was purified by silica gel chromatography (EA/PE from 10% to 50%) to get 5-chloro-3-methoxy benzene-1,2-diamine (7 g, 82% yield) as brown solid. LCMS: m/z 173.1 [M+H]+.

Step 2. 6-chloro-4-methoxy-1H-benzo[d]imidazole-diamine (3)

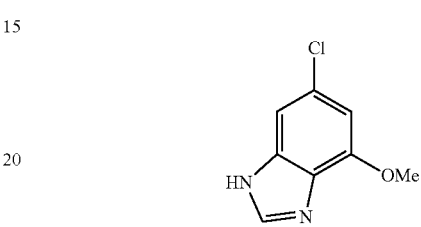

A solution of 5-chloro-3-methoxybenzene-1,2-diamine (2 g, 11.6 mmol), methyl orthoformate (1.48 g, 14 mmol) and conc. H2SO4 (57 mg, 0.58 mmol) in methanol (50 mL) was stirred at room temperature for 1 h. LCMS was used to monitor this reaction. The solvent was evaporated, and the residue was partitioned between water (30 mL) and EtOAc (50 mL). The organic phase was separated, washed with water (30 mL) and brine (30 mL), dried over anhydrous Na2SO4 and concentrated, purified by column chromatography on silica gel (PE/EA from 0/1 to 1/1) to get 6-chloro-4-methoxy-1H-benzo[d]imidazole (1.9 g, 90% yield) as brown solid. LCMS: m/z 183.0 [M+H]+.

Step 3. 6-chloro-1H-benzo[d]imidazol-4-ol (4)

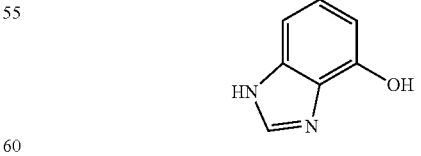

A mixture of 6-chloro-4-methoxy-1H-benzo[d]imidazole (1.5 g, 8.24 mmol) in HBr/H2O (48%, 30 mL) was stirred at 120° C. for 4 days. LCMS was used to monitor this reaction. NaHCO3. Filtered, the filter cake was dried in vacuo to get 6-chloro-1H-benzo[d]imidazol-4-ol (1.2 g, 87% yield) as brown solid. LCMS: m/z 169.0 [M+H]+.

Step 4. (R)-6-chloro-4-(3-chloro-1-phenylpropoxy)-1H-benzo[d]imidazole (5)

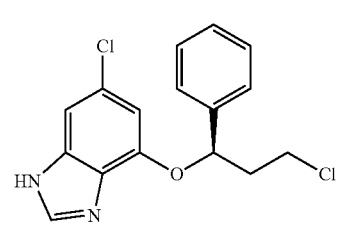

To a solution of 6-chloro-1H-benzo[d]imidazol-4-ol (1.98 g, 11.8 mmol), (S)-3-chloro-1-phenylpropan-1-ol (2.0 g, 11.8 mmol) and PPh3 (3.1 g, 11.8 mmol) in THF (50 mL) was added DEAD (2.05 g, 11.8 mmol) dropwise at 0° C. under N2 balloon. The reaction was allowed to warm to room temperature and stirred overnight. The reaction solution was purified by column chromatography on silica gel (EA/PE from 1/10 to 1/4) to afford the pure product (2.36 g, 62% yield) as a white solid. LCMS: m/z 321.1 [M+H]+.

Step 5. (R)-3-((6-chloro-1H-benzo[d]imidazol-4-yl)oxy)-N-methyl-3-phenylpropan-1-amine (CPG-255)

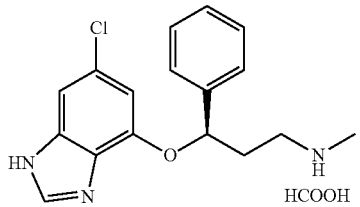

CPG-255

A mixture of (R)-6-chloro-4-(3-chloro-1-phenyl-propoxy)-1H-benzo[d]imidazole (100 mg, 0.311 mmol), sodium iodide (5 mg, 0.033 mmol) in MeNH2/EtOH (3 mL) was stirred at 70° C. in a sealed tube for 16 hrs. The mixture was purified on prep-HPLC (0.1% formic acid/MeCN) to give (R)-3-((6-chloro-1H-benzo[d]imidazol-4-yl)oxy)-N-methyl-3-phenylpropan-1-amine (CPG-255) (71.4 mg, 72.6% yield) as the brown oil. LCMS: m/z 316.11 [M+H]+. 1HNMR (400 MHz, MeOD) δ 8.53 (s, 1H), 8.22 (s, 1H), 7.45-7.43 (d, J=7.2 Hz, 2H), 7.40-7.36 (t, J=7.6 Hz, 2H), 7.33-7.30 (t, J=7.2 Hz, 1H), 7.18 (d, J=1.6 Hz, 1H), 6.55-6.54 (d, J=1.6 Hz, 1H), 5.62-5.59 (m, 1H), 3.39-3.28 (m, 2H), 2.77 (s, 3H), 2.49-2.40 (m, 1H), 2.33-2.24 (m, 1H).

Synthesis of (R)-3-((6-chloro-1H-indazol-4-yl)oxy)-N-methyl-3-phenylpropan-1-amine (CPG-256)

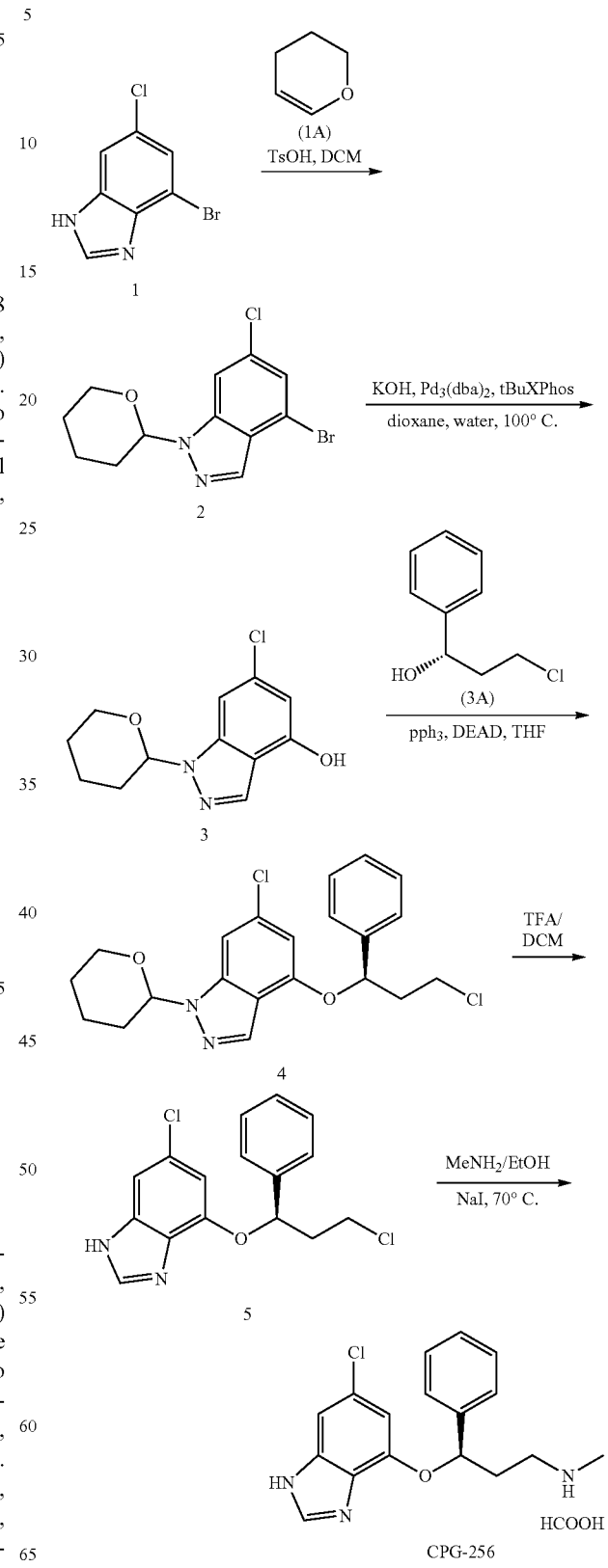

Step 1. Synthesis of 4-bromo-6-chloro-1-(tetrahydro-2H-pyran-2-yl)-1H-indazole (2)

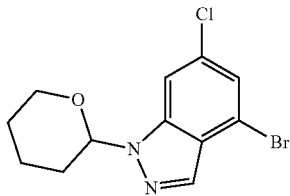

2

To a solution of 4-bromo-6-chloro-1H-indazole (3 g, 13 mmol) and TsOH (224 mg, 1.3 mmol) in DCM (30 mL) was added 3,4-dihydro-2H-pyran (2.18 g, 26 mmol) dropwise at ice-bath. Then, the reaction was stirred at room temperature for 4 h. LCMS was used to monitor this reaction. The reaction mixture was partitioned between sat. aq NaHCO$_3$ (30 mL) and EtOAc (100 mL). The organic phase was separated, washed with water (30 mL) and brine (30 mL), dried over anhydrous Na2SO4 and concentrated, purified by column chromatography on silica gel (PE/EA from 0/1 to 1/1) to get 4-bromo-6-chloro-1-(tetrahydro-2H-pyran-2-yl)-1H-indazole (3 g, 75% yield) as a pale solid. LCMS: m/z 315.0 [M+H]+.

Step 2. Synthesis of 6-chloro-1-(tetrahydro-2H-pyran-2-yl)-1H-indazol-4-ol (3)

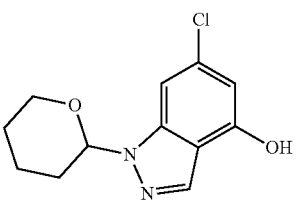

3

A mixture of 4-bromo-6-chloro-1-(tetrahydro-2H-pyran-2-yl)-1H-indazole (3.8 g, 12.1 mmol), Pd3(dba)2 (219 mg, 0.24 mmol), tBuXPhos (259 mg, 0.05 mmol) and KOH (2.71 g, 48.4 mmol) in dioxane (30 mL) and water (30 mL) was stirred at reflux for 2 h. LCMS was used to monitor this reaction. The reaction mixture neutralized with 1N HCl, extracted with EtOAc (30 mL*3). The organic phase was separated, washed with water (30 mL) and brine (30 mL), dried over anhydrous Na2SO4 and concentrated, purified by column chromatography on silica gel (PE/EA from 0/1 to 1/1) to get 6-chloro-1-(tetrahydro-2H-pyran-2-yl)-1H-indazol-4-ol (2.3 g, 80% yield) as pale solid. LCMS: m/z 253.1 [M+H]+.

Step 3. Synthesis of 6-chloro-4-((R)-3-chloro-1-phenylpropoxy)-1-(tetrahydro-2H-pyran-2-yl)-1H-indazole (4)

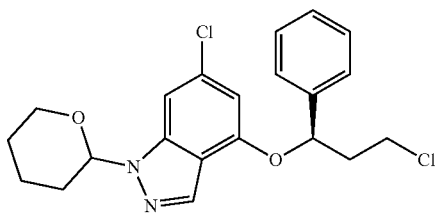

4

To a solution of 6-chloro-1-(tetrahydro-2H-pyran-2-yl)-1H-indazol-4-ol (2.97 g, 11.8 mmol), SM2 (2.0 g, 11.8 mmol) and PPh3 (3.1 g, 11.8 mmol) in THF (50 mL) was added DEAD (2.05 g, 11.8 mmol) dropwise at 0° C. under N$_2$ balloon. The reaction was allowed to warm to room temperature and stirred overnight. The reaction solution was purified by column chromatography on silica gel (EA/PE from 1/10 to 1/1) to afford 6-chloro-4-((R)-3-chloro-1-phenylpropoxy)-1-(tetrahydro-2H-pyran-2-yl)-1H-indazole (2.36 g, 50% yield) as a white solid. LCMS: m/z 405.1 [M+H]+.

Step 4. Synthesis of (R)-6-chloro-4-(3-chloro-1-phenylpropoxy)-1H-indazole (5)

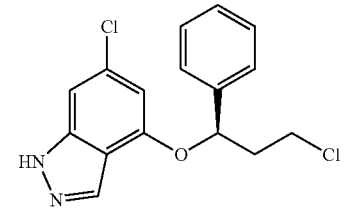

5

To a solution of 6-chloro-4-((R)-3-chloro-1-phenylpropoxy)-1-(tetrahydro-2H-pyran-2-yl)-1H-indazole (2.36 g, 9.374 mmol) in DCM (20 mL) was added TFA (10 mL) dropwise at 0° C. The reaction was allowed to warm to room temperature and stirred overnight. The solvent was evaporated to afford (R)-6-chloro-4-(3-chloro-1-phenylpropoxy)-1H-indazole (2.5 g, 100% yield) as brown oil. LCMS: m/z 321.1 [M+H]+.

Step 5. Synthesis of (R)-3-((6-chloro-1H-indazol-4-yl)oxy)-N-methyl-3-phenylpropan-1-amine (CPG-256)

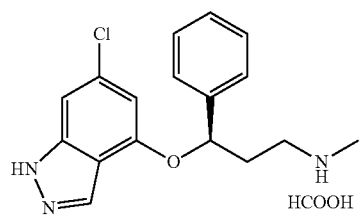

CPG-256

A mixture of (R)-6-chloro-4-(3-chloro-1-phenyl-propoxy)-1H-indazole (200 mg, 0.623 mmol), sodium iodide (10 mg, 0.067 mmol) in MeNH2/EtOH (4 mL) was stirred at 70° C. in a sealed tube for 16 hrs. The mixture was purified on prep-HPLC (0.1% formic acid/MeCN) to give synthesis of (R)-3-((6-chloro-1H-indazol-4-yl)oxy)-N-methyl-3-phenylpropan-1-amine (CPG-256). (59.9 mg, 30.5% yield) as the yellow oil. LCMS: m/z 316.11 [M+H]+. 1H NMR (400 MHz, DMSO) δ 8.37 (s, 1H), 8.16 (d, J=0.7 Hz, 1H), 7.45 (d, J=7.2 Hz, 2H), 7.37 (t, J=7.5 Hz, 2H), 7.28 (t, J=7.3 Hz, 1H), 7.11 (s, 1H), 6.43 (d, J=1.2 Hz, 1H), 5.71 (m, 1H), 2.83 (t, J=7.3 Hz, 2H), 2.42 (s, 3H), 2.25 (m, 1H), 2.09 (m, 1H).

Synthesis of (R)-2-((3-((6-chloro-1H-benzo[d]imidazol-4-yl)oxy)-3-phenylpropyl) amino)ethan-1-ol (CPG-257)

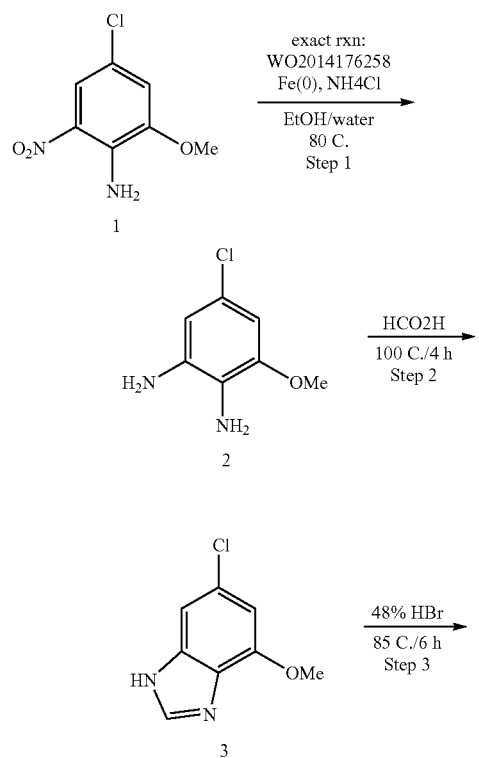

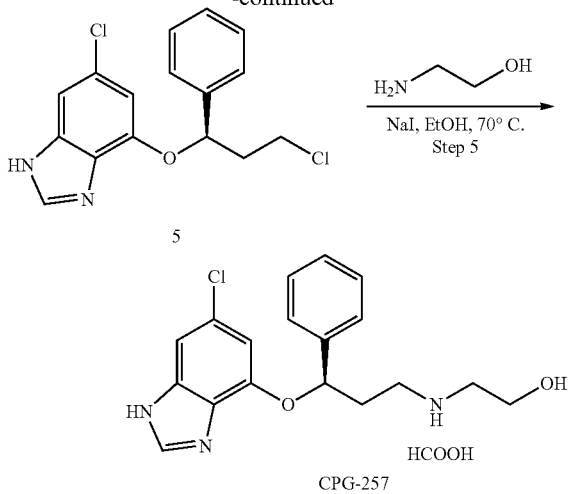

Step 1. Synthesis of 5-chloro-3-methoxybenzene-1,2-diamine (2)

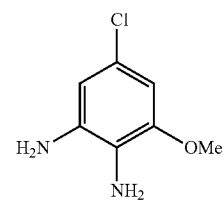

A mixture of 4-chloro-2-methoxy-6-nitroaniline (10 g, 49.5 mmol), Fe powder (27.7 g, 495 mmol) and NH4Cl (26.5 g, 495 mmol) in 95% ethanol (250 mL) was stirred at 80° C. overnight carefully. LCMS was used to monitor this reaction. Filtered, the filtrate was purified by silica gel chromatography (EA/PE from 10% to 50%) to get 5-chloro-3-methoxy benzene-1,2-diamine (7 g, 82% yield) as brown solid. LCMS: m/z 173.1 [M+H]+.

Step 2. 6-chloro-4-methoxy-1H-benzo[d]imidazole-diamine (3)

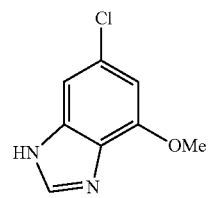 [SMILES: COc1cc(Cl)cc2[nH]cnc12]

A solution of 5-chloro-3-methoxybenzene-1,2-diamine (2 g, 11.6 mmol), methyl orthoformate (1.48 g, 14 mmol) and conc. H2SO4 (57 mg, 0.58 mmol) in methanol (50 mL) was stirred at room temperature for 1 h. LCMS was used to monitor this reaction. The solvent was evaporated, and the residue was partitioned between water (30 mL) and EtOAc (50 mL). The organic phase was separated, washed with

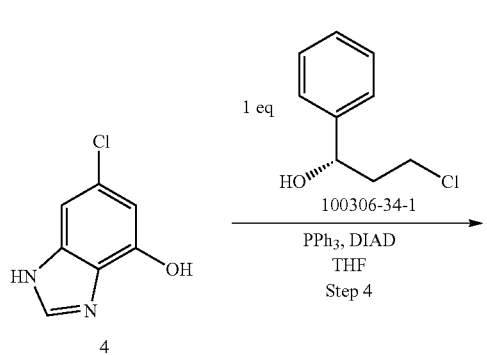

water (30 mL) and brine (30 mL), dried over anhydrous Na2SO4 and concentrated, purified by column chromatography on silica gel (PE/EA from 0/1 to 1/1) to get 6-chloro-4-methoxy-1H-benzo[d]imidazole (1.9 g, 90% yield) as brown solid. LCMS: m/z 183.0 [M+H]+.

Step 3. 6-chloro-1H-benzo[d]imidazol-4-ol (4)

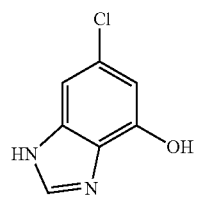 [SMILES: Oc1cc(Cl)cc2[nH]cnc12]

A mixture of 6-chloro-4-methoxy-1H-benzo[d]imidazole (1.5 g, 8.24 mmol) in HBr/H2O (48%, 30 mL) was stirred at 120° C. for 4 days. LCMS was used to monitor this NaHCO$_3$. Filtered, the filter cake was dried in vacuo to get 6-chloro-1H-benzo[d]imidazol-4-ol (1.2 g, 87% yield) as brown solid. LCMS: m/z 169.0 [M+H]+.

Step 4. (R)-6-chloro-4-(3-chloro-1-phenylpropoxy)-1H-benzo[d]imidazole (5)

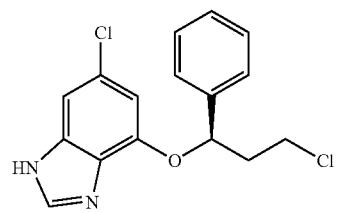

To a solution of 6-chloro-1H-benzo[d]imidazol-4-ol (1.98 g, 11.8 mmol), (S)-3-chloro-1-phenylpropan-1-ol (2.0 g, 11.8 mmol) and PPh3 (3.1 g, 11.8 mmol) in THF (50 mL) was added DEAD (2.05 g, 11.8 mmol) dropwise at 0° C. under N$_2$ balloon. The reaction was allowed to warm to room temperature and stirred overnight. The reaction solution was purified by column chromatography on silica gel (EA/PE from 1/10 to 1/4) to afford the pure product (2.36 g, 62% yield) as a white solid. LCMS: m/z 321.1 [M+H]+.

Step 5. (R)-2-((3-((6-chloro-1H-benzo[d]imidazol-4-yl)oxy)-3-phenylpropyl)amino) ethan-1-ol (CPG-257)

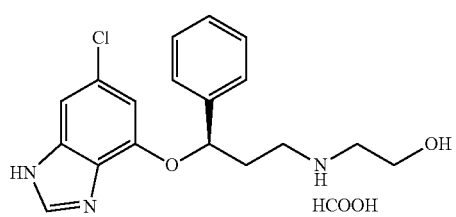

A mixture of (R)-6-chloro-4-(3-chloro-1-phenyl-propoxy)-1H-benzo[d]imidazole (100 mg, 0.311 mmol), 2-aminoethan-1-ol (95 mg, 1.555 mmol) and sodium iodide (5 mg, 0.033 mmol) in EtOH (2 mL) was stirred at 70° C. in a sealed tube for 16 hrs. The mixture was purified on prep-HPLC (0.1% formic acid/MeCN) to give (R)-2-((3-((6-chloro-1H-benzo[d]imidazol-4-yl)oxy)-3-phenylpropyl)amino)ethan-1-ol (CPG-257) (69.9 mg, 64.9% yield) as the yellow oil. LCMS: m/z 346.12 [M+H]+. 1H NMR (400 MHz, DMSO) δ 8.32 (s, 1H), 8.21 (s, 1H), 7.44 (d, J=7.3 Hz, 2H), 7.36 (t, J=7.5 Hz, 2H), 7.27 (t, J=7.2 Hz, 1H), 7.19 (d, J=1.6 Hz, 1H), 6.64 (d, J=1.5 Hz, 1H), 5.81 (dd, J=8.2, 4.5 Hz, 1H), 3.57 (t, J=5.4 Hz, 2H), 2.93 (s, 2H), 2.81 (t, J=5.5 Hz, 2H), 2.24 (dt, J=14.0, 7.8 Hz, 1H), 2.11 (dd, J=12.5, 7.6 Hz, 1H).

Synthesis of (R)-2-((3-(6-chloro-1H-indazol-4-yl)oxy)-3-phenylpropyl)amino) ethan-1-ol (CPG-258)

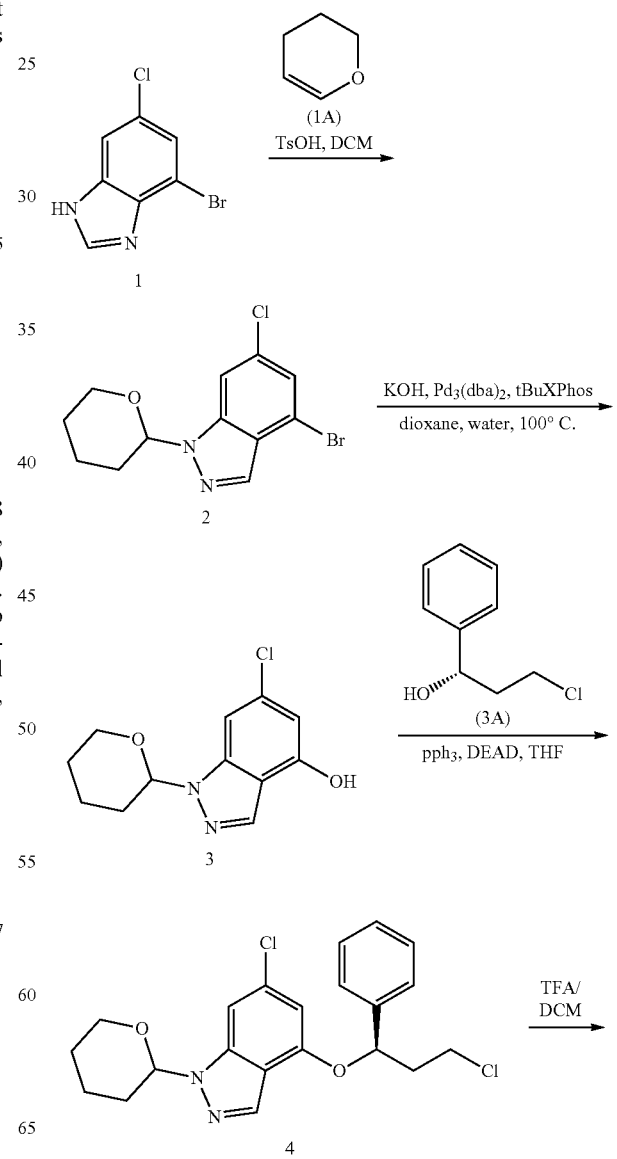

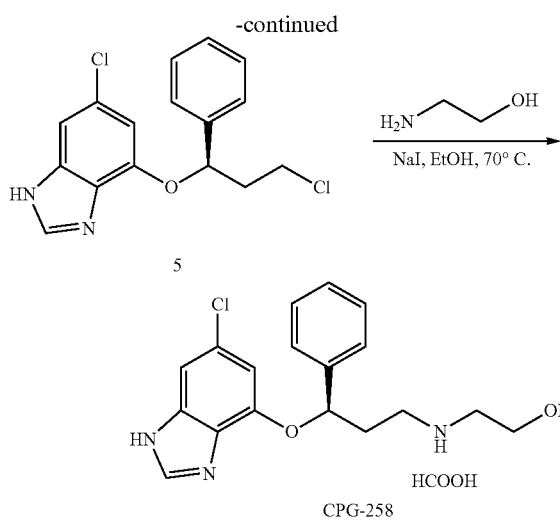

Step 1. Synthesis of 4-bromo-6-chloro-1-(tetra-hydro-2H-pyran-2-yl)-1H-indazole (2)

To a solution of 4-bromo-6-chloro-1H-indazole (3 g, 13 mmol) and TsOH (224 mg, 1.3 mmol) in DCM (30 mL) was added 3,4-dihydro-2H-pyran (2.18 g, 26 mmol) dropwise at ice-bath. Then, the reaction was stirred at room temperature for 4 h. LCMS was used to monitor this reaction. The reaction mixture was partitioned between sat. aq. NaHCO₃ (30 mL) and EtOAc (100 mL). The organic phase was separated, washed with water (30 mL) and brine (30 mL), dried over anhydrous Na2SO4 and concentrated, purified by column chromatography on silica gel (PE/EA from 0/1 to 1/1) to get 4-bromo-6-chloro-1-(tetrahydro-2H-pyran-2-yl)-1H-indazole (3 g, 75% yield) as a pale solid. LCMS: m/z 315.0 [M+H]+.

Step 2. Synthesis of 6-chloro-1-(tetrahydro-2H-pyran-2-yl)-1H-indazol-4-ol (3)

A mixture of 4-bromo-6-chloro-1-(tetrahydro-2H-pyran-2-yl)-1H-indazole (3.8 g, 12.1 mmol), Pd3(dba)2 (219 mg, 0.24 mmol), tBuXPhos (259 mg, 0.05 mmol) and KOH (2.71 g, 48.4 mmol) in dioxane (30 mL) and water (30 mL) was stirred at reflux for 2 h. LCMS was used to monitor this reaction. The reaction mixture neutralized with 1N HCl, extracted with EtOAc (30 mL*3). The organic phase was separated, washed with water (30 mL) and brine (30 mL), dried over anhydrous Na2SO4 and concentrated, purified by column chromatography on silica gel (PE/EA from 0/1 to 1/1) to get 6-chloro-1-(tetrahydro-2H-pyran-2-yl)-1H-indazol-4-ol (2.3 g, 80% yield) as pale solid. LCMS: m/z 253.1 [M+H]+.

Step 3. Synthesis of 6-chloro-4-((R)-3-chloro-1-phenylpropoxy)-1-(tetrahydro-2H-pyran-2-yl)-1H-indazole (4)

To a solution of 6-chloro-1-(tetrahydro-2H-pyran-2-yl)-1H-indazol-4-ol (2.97 g, 11.8 mmol), SM2 (2.0 g, 11.8 mmol) and PPh3 (3.1 g, 11.8 mmol) in THF (50 mL) was added DEAD (2.05 g, 11.8 mmol) dropwise at 0° C. under N₂ balloon. The reaction was allowed to warm to room temperature and stirred overnight. The reaction solution was purified by column chromatography on silica gel (EA/PE from 1/10 to 1/1) to afford 6-chloro-4-((R)-3-chloro-1-phenylpropoxy)-1-(tetrahydro-2H-pyran-2-yl)-1H-indazole (2.36 g, 50% yield) as a white solid. LCMS: m/z 405.1 [M+H]+.

Step 4. Synthesis of (R)-6-chloro-4-(3-chloro-1-phenylpropoxy)-1H-indazole (5)

To a solution of 6-chloro-4-((R)-3-chloro-1-phenylpropoxy)-1-(tetrahydro-2H-pyran-2-yl)-1H-indazole (2.36 g, 9.374 mmol) in DCM (20 mL) was added TFA (10 mL) dropwise at 0° C. The reaction was allowed to warm to room temperature and stirred overnight. The solvent was evaporated to afford (R)-6-chloro-4-(3-chloro-1-phenylpropoxy)-1H-indazole (2.5 g, 100% yield) as brown oil. LCMS: m/z 321.1 [M+H]+.

Step 5. Synthesis of (R)-2-((3-((6-chloro-1H-indazol-4-yl)oxy)-3-phenylpropyl) amino)ethan-1-ol (CPG-258)

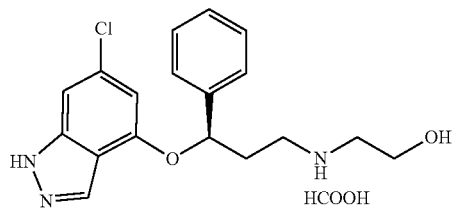

CPG-258

A mixture of (R)-6-chloro-4-(3-chloro-1-phenyl-propoxy)-1H-indazole (200 mg, 0.623 mmol), 2-amino-ethan-1-ol (190 mg, 3.111 mmol), and sodium iodide (10 mg, 0.067 mmol) in EtOH (3 mL) was stirred at 70° C. in a sealed tube for 16 hrs. The mixture was purified on prep-HPLC (0.1% formic acid/MeCN) to give (R)-2-((3-((6-chloro-1H-indazol-4-yl)oxy)-3-phenylpropyl)amino) ethan-1-ol (CPG-258) (71.3 mg, 33.1% yield) as the yellow oil. LCMS: m/z 346.12 [M+H]+. 1H NMR (400 MHz, MeOD) δ 8.52 (s, 1H), 8.17 (d, J=0.4 Hz, 1H), 7.46 (d, J=7.2 Hz, 2H), 7.39 (t, J=7.6 Hz, 2H), 7.31 (t, J=7.2 Hz, 1H), 7.08 (s, 1H), 6.37 (d, J=1.2 Hz, 1H), 5.62 (m, 1H), 3.80-3.76 (m, 2H), 3.37-3.32 (m, 1H), 3.28-3.21 (m, 1H), 3.17-3.12 (m, 2H), 2.53-2.43 (m, 1H), 2.34 (m, 1H).

Synthesis of 5-chloro-2-cyano-N-(2-(4-hydroxycyclohexyl)amino)ethyl)-N-phenyl benzamide (CPG-259/260)

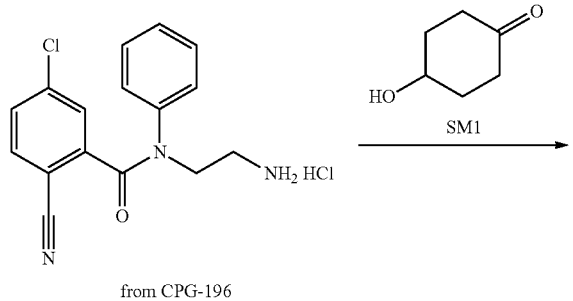

from CPG-196

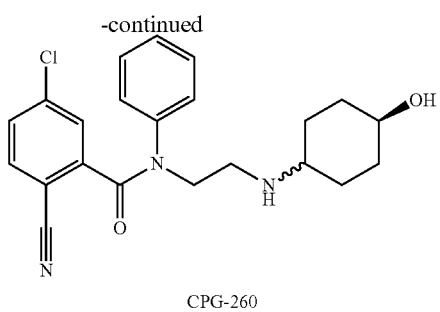

CPG-260

To a solution of N-(2-aminoethyl)-5-chloro-2-cyano-N-phenylbenzamide hydrochloride (250 mg, 0.746 mmol), 4-hydroxycyclohexan-1-one (127 mg, 1.112 mmol) in THF (2 mL), glacial AcOH (67 mg, 1.11 mmol) was added and the mixture was stirred at room temperature for 4 h; then was added NaBH(OAc)$_3$ (235 mg, 1.11 mmol) and the mixture was stirred at room temperature for 16 h. The reaction mixture was quenched with aqueous saturated NaHCO$_3$ solution, and the product was extracted with EA. The EA extract was dried (MgSO4). The solvent was removed. The residue was purified by Prep-HPLC (eluted with 10 mM NH4HCO3 and ACN) to give 5-chloro-2-cyano-N-(2-(4-hydroxycyclohexyl)amino)ethyl)-N-phenyl benzamide (CPG-259: 16 mg, 0.04 mmol; CPG-260: 40 mg, 0.1 mmol, 19% total yield) as a white solid. CPG-259: 1H NMR (400 MHz, MeOD) δ 7.87 (d, J=8.4 Hz, 1H), 7.68 (dd, J=8.4, 1.9 Hz, 1H), 7.62 (d, J=8.4 Hz, 0.5H), 7.60 (d, J=1.9 Hz, 1H), 7.54 (d, J=1.9 Hz, 1H), 7.48 (dd, J=8.4, 1.9 Hz, 1H), 7.18-7.06 (t, J=7.9 Hz, 2H), 6.93 (t, J=7.9 Hz, 1H), 6.73 (d, J=7.8 Hz, 2H), 6.62 (t, J=7.3 Hz, 1H), 6.53 (d, J=7.3 Hz, 0.5H), 6.20 (d, J=7.8 Hz, 1H), 3.60 (m, 3H), 3.52-3.35 (m, 4H), 3.20 (m, 2H), 2.10-1.88 (m, 5H), 1.86-1.66 (m, 4H), 1.43 (m, 1H), 1.05 (m, 2H). LCMS: m/z 398.0 [M+H]+. CPG-260: 1H NMR (400 MHz, MeOD) δ 7.86 (d, J=8.4 Hz, 1H), 7.70-7.62 (m, 1.5H), 7.59 (m, 1.5H), 7.50 (d, J=8.4 Hz, 0.5H), 7.11 (dd, J=8.4, 7.4 Hz, 2H), 6.93 (t, J=7.9 Hz, 1H), 6.74 (d, J=7.7 Hz, 2H), 6.61 (t, J=7.3 Hz, 1H), 6.52 (t, J=7.3 Hz, 0.5H), 6.19 (d, J=7.7 Hz, 1H), 4.34 (t, J=12.2 Hz, 0.5H), 4.01 (s, 0.5H), 3.82 (s, 1H), 3.66 (s, 2H), 3.49 (s, 2H), 3.41 (d, J=7.1 Hz, 1H), 3.28-3.15 (m, 2H), 2.06 (ddd, J=42.6, 34.1, 13.2 Hz, 4H), 1.86-1.51 (m, 6H), 1.30 (t, J=13.6 Hz, 2H). LCMS: m/z 398.0 [M+H]+.

Synthesis of 2-(3-amino-1-(2-aminopyridin-4-yl)propoxy)-4-chlorobenzonitrile (CPG-263)

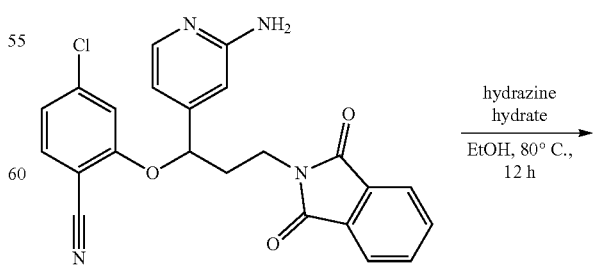

From CPG-196

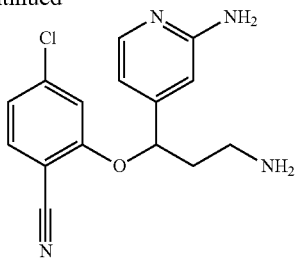

CPG-263

A mixture of 2-(1-(2-aminopyridin-4-yl)-3-(1,3-dioxoisoindolin-2-yl)propoxy)-4-chlorobenzonitrile (150 mg, 0.347 mmol), hydrazine hydrate (0.5 mL, 10.3 mmol) in EtOH (10 mL) was stirred at 80° C. for 12 hrs. The solvent was removed and the residue was purified by Prep-HPLC (Fluent with 10 mM NH4HCO3 and ACN) to give 2-(3-amino-1-(2-amino pyridin-4-yl)propoxy)-4-chlorobenzonitrile (CPG-263) (27.5 mg, 0.091 mmol, 26.2% yield) as a white solid. LCMS: m/z 303.0 [M+H]+ 1HNMR (400 MHz, MeOD) δ 7.89 (d, J=5.6 Hz, 1H), 7.63 (d, J=8.4 Hz, 1H), 7.09 (dd, J=8.4, 1.6 Hz, 1H), 6.99 (d, J=1.6 Hz, 1H), 6.62 (dd, J=5.6, 1.6 Hz, 1H), 6.57 (s, 1H), 5.47 (dd, J=8.4, 4.4 Hz, 1H), 2.94 (t, J=7.2 Hz, 2H), 2.27-2.18 (m, 1H), 2.14-2.04 (m, 1H).

Synthesis of (R)-2-(3-((6-chloro-1H-indazol-4-yl) oxy)-3-phenylpropyl) isoindoline-1,3-dione (CPG-265)

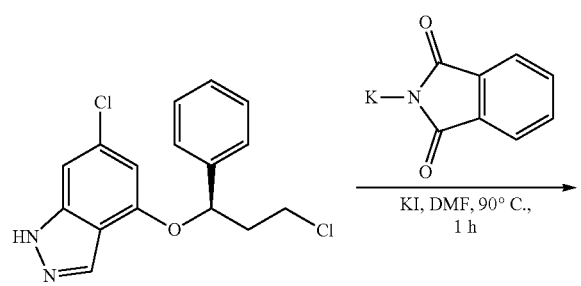

CPG-265

A mixture of (R)-6-chloro-4-(3-chloro-1-phenylpropoxy)-1H-indazole (321.2 mg, 1.0 mmol) in DMF (5 mL) in a sealed tube was stirred at 90° C. for 1 h. The mixture was purified on prep-HPLC (Fluent with 0.2% Formic acid and ACN) to give (R)-2-(3-((6-chloro-1H-indazol-4-yl)oxy)-3-phenylpropyl)isoindoline-1,3-dione (CPG-265) (22.3 mg, 0.052 mmol, 5.2% yield) as a white solid. LCMS: m/z 432.1 [M+H]+. 1HNMR (400 MHz, MeOD) δ 7.81 (s, 1H), 7.75-7.68 (m, 4H), 7.41 (d, J=7.2 Hz, 2H), 7.31 (t, J=7.6 Hz, 2H), 7.22 (t, J=7.2 Hz, 1H), 6.98 (s, 1H), 6.28 (d, J=1.2 Hz, 1H), 5.55 (dd, J=8.8, 3.6 Hz, 1H), 4.08-3.99 (m, 1H), 3.98-3.88 (m, 1H), 2.52-2.48 (m, 1H), 2.35-2.16 (m, 1H).

Synthesis of 4-chloro-2-(((2-((4-hydroxycyclohexyl) amino)ethyl)(phenyl)amino)methyl) benzonitrile (CPG-266/267)

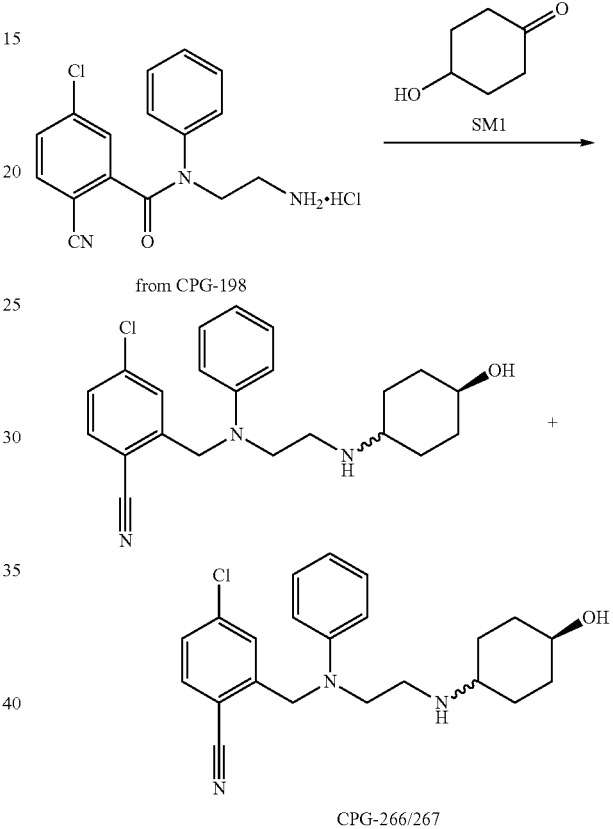

CPG-266/267

To a solution of 2-(((2-aminoethyl)(phenyl)amino) methyl)-4-chlorobenzonitrile hydrochloride (250 mg, 0.77 mmol), 4-hydroxycyclohexan-1-one (130 mg, 1.15 mmol) in THF (2 mL), glacial AcOH (70 mg, 1.15 mmol) was added and the mixture was stirred at room temperature for 4 h; then was added NaBH(OAc)3 (240 mg, 1.15 mmol); and the mixture was stirred at room temperature for 16 h. The reaction mixture was quenched with aqueous saturated NaHCO3 solution, and the product was extracted with EA. The EA extract was dried (MgSO4). The solvent was removed. The residue was purified by Prep-HPLC (eluted with 10 mM NH4HCO3 and ACN) to give 4-chloro-2-(((2-((4-hydroxycyclohexyl)amino)ethyl)(phenyl) amino) methyl)benzonitrile (CPG-266: 18.5 mg, 0.048 mmol; CPG-267 (15.6 mg, 0.040 mmol, 11% total yield) as a liquid. CPG-266: 1H NMR (400 MHz, MeOD) δ 7.74 (d, J=8.3 Hz, 1H), 7.44 (dd, J=8.3, 2.0 Hz, 1H), 7.33 (d, J=2.0 Hz, 1H), 7.20 (dd, J=8.6, 7.4 Hz, 2H), 6.75 (dd, J=12.7, 7.8 Hz, 3H), 4.73 (s, 2H), 3.58 (t, J=7.2 Hz, 2H), 3.55-3.48 (m, 1H), 2.85 (t, J=7.2 Hz, 2H), 2.43 (ddd, J=10.9, 7.7, 3.4 Hz, 1H), 1.94 (dd, J=10.3, 2.0 Hz, 4H), 1.39-1.07 (m, 4H). LCMS: m/z 384.0 [M+H]+. CPG-267: 1H NMR (400 MHz, MeOD) δ 7.74 (d, J=8.3 Hz, 1H), 7.43 (dd, J=8.3, 1.8 Hz, 1H), 7.32 (d, J=1.8 Hz, 1H), 7.19 (dd, J=8.7, 7.4 Hz, 2H), 6.74 (dd, J=15.3, 7.4 Hz, 3H), 4.74 (s, 2H), 3.86 (m, 1H), 3.60 (t, J=7.2 Hz, 2H), 2.87 (t, J=7.2 Hz, 2H), 2.53 (m, 1H), 1.85-1.47 (m, 8H). LCMS: m/z 384.0 [M+H]+.

IC50 of Compounds of Formula (I)

The IC50 of some compounds of the invention was determined using the abcam NOS Inhibitor Screening Kit. The procedure includes the following steps: (1) Dissolved a test compound to 10 mM in DMSO; (2) Diluted the test compound to 1 mM in NOS Assay Buffer; (3) Diluted 1 mM of the test compound stocks to 200 µM, 50 µM, 12.5 µM, 3.125 µM, 0.781 µM, and 0.195 µM in NOS Assay Buffer; (4) Diluted 1 mM DPI Control to 50.0 µM, 12.5 µM, 3.125 µM, 0.781 µM, 0.195 µM, and 0.0488 µM in NOS Assay Buffer; (5) Diluted NOS enzyme with 400 µL of NOS Assay Buffer; (6) Combined Diluted NOS Enzyme with 1.6 mL of NOS Assay buffer then transferred 20 µL of enzyme solution to all wells of 96-well Fluorescence plate except background wells. Added 20 µL of NOS Assay buffer to background wells. (7) Transferred 10 uL of each test compound dilution to the enzyme buffer mix according to the plate map (see addendum for plate map and raw data values). (8) Incubated 15 minutes at room temperature. (9) Added 11 µL of NOS reaction mix (according to manufacturer's protocol) to each well, mixed, and incubated at 37° C. for 1 hour. (10) Added 110 µL of NOS Assay Buffer to each well followed by 5 µL of Enhancer to each well, mixed, and incubated 10 minutes at room temperature; (11) Added 10 µL of Probe to each well, mixed, and incubated 10 minutes at room temperature; and (12) Added 5 µL of NaOH to each well, mixed, and incubated 10 minutes at room temperature. Measure Fluorescence at 360 nm excitation/450 nm emission.

The IC50 results of Formula (I) compounds are tabulated in Table C-1 below.

TABLE C-1

| GT-ID | IC50 (µM) | GT-ID | IC50 (µM) | GT-ID | IC50 (µM) |
|---|---|---|---|---|---|
| GT-5001 | 1.59 | GT-6041 | 0.156 | GT-7002 | 0.112 |
| GT-5002 | 1.35 | GT-6045 | 0.231 | GT-7003 | 0.064 |
| GT-5012 | 12600 | GT-6058 | 0.457 | GT-7004 | 5.79 |
| GT-5013 | 23.3 | GT-6059 | 0.252 | GT-7006 | 157 |
| GT-5014 | 2.17 | GT-6060 | 0.444 | GT-7007 | 0.0955 |
| GT-5015 | 1.74 | GT-6064 | 0.0285 | GT-7008 | 5.56 |
| GT-5016 | 4.04 | GT-6065 | 0.0678 | GT-7009 | 0.148 |
| GT-5017 | 6.75 | GT-6066 | 0.27 | GT-7010 | 9.18 |
| GT-5018 | 5.04 | | | GT-7011 | 0.29 |
| GT-5019 | 9.62 | | | GT-7016 | 8.52 |
| GT-5020 | 7.29 | | | GT-7017 | 3.66 |
| GT-5023 | 5.43 | | | GT-7018 | 20.3 |
| GT-5024 | 2.34 | | | GT-7019 | 0.438 |
| GT-5025 | 3.56 | | | GT-7020 | 15.5 |
| GT-5031 | 4.54 | | | GT-7023 | 10.5 |
| | | | | GT-7024 | 14.4 |

Given that Compound AZ 6b has an IC50 of 0.0488 µM, the following compounds of the invention in Table C-2 demonstrate promising result for prophylaxis and/or treatment of a disorder or disease mediated by iNOS or associated with aberrant iNOS activity.

TABLE C-2

| GT-ID | IC50 (uM) | Fold (GT-xxxx)/AZ 6b |
|---|---|---|
| GT-6064 | 0.0285 | 0.58 |
| GT-6065 | 0.0678 | 1.39 |

TABLE C-2-continued

| GT-ID | IC50 (uM) | Fold (GT-xxxx)/AZ 6b |
|---|---|---|
| GT-6041 | 0.156 | 3.20 |
| GT-6045 | 0.231 | 4.73 |
| GT-6059 | 0.252 | 5.16 |
| GT-6066 | 0.27 | 5.53 |
| GT-6060 | 0.444 | 9.10 |
| GT-6058 | 0.457 | 9.36 |
| GT-7002 | 0.112 | 2.30 |
| GT-7003 | 0.064 | 1.31 |
| GT-7007 | 0.0955 | 1.96 |
| GT-7009 | 0.148 | 3.03 |
| GT-7011 | 0.29 | 5.94 |
| GT-7019 | 0.438 | 8.98 |

In the foregoing specification, embodiments of the present invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicant to be the scope of the invention, is the literal and equivalent scope of the set of claims that issue from this application, in the specific form in which such claims issue, including any subsequent correction.

The invention claimed is:

1. A method of inhibiting one or more members selected from the family of nitric oxide synthases (NOS) including three isoforms inducible NOS (iNOS), endothelial NOS (eNOS), and neuronal NOS (nNOS), comprising:

contacting the NOS with an effective amount of N-aminoethyl N-phenyl amine derivatives as represented by Formula (I-7)

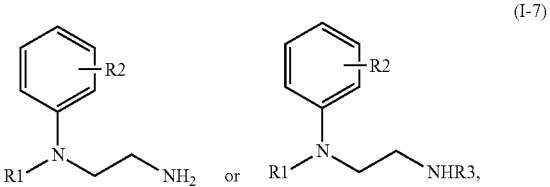

(I-7)

wherein R1 is selected from

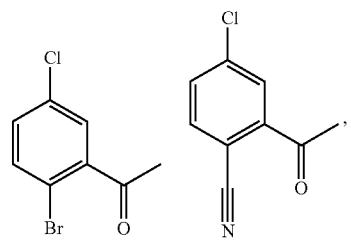

and benzyl substituted with two groups selected from —F, —Cl, —Br, —I and —CN; R2 is —H, —F, —Cl, —Br or —I; and R3 is hydroxyl substituted C1-C6 alkyl, cyclopropyl methyl, or hydroxyl cyclohexyl; or a pharmaceutically acceptable salt, solvate, or hydrate thereof, in any crystalline form or in amorphous form.

2. The method according to claim 1, wherein said N-aminoethyl N-phenyl amine derivative as represented by Formula (I-7) is:

(GT-7003)
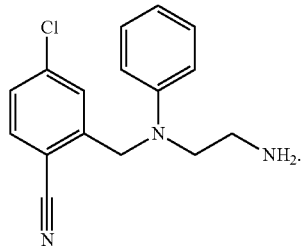

3. The method according to claim 1, wherein said N-aminoethyl N-phenyl amine derivative as represented by Formula (I-7) is:

(GT-7007)
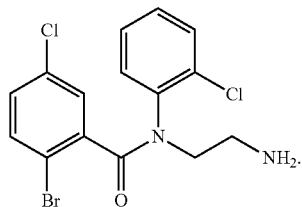

4. The method according to claim 1, wherein said N-aminoethyl N-phenyl amine derivative as represented by Formula (I-7) is:

(GT-7002)
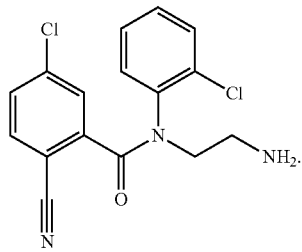

5. The method according to claim 1, wherein said N-aminoethyl N-phenyl amine derivative as represented by Formula (I-7) is:

(GT-7009)
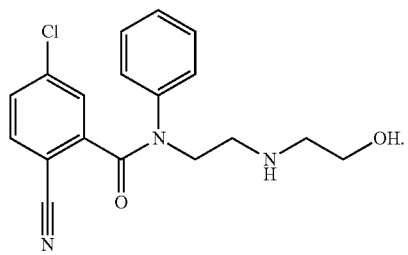

6. The method according to claim 1, wherein said N-aminoethyl N-phenyl amine derivative as represented by Formula (I-7) is:

(GT-7011)
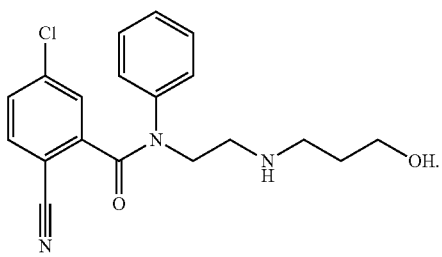

7. The method according to claim 1, said N-aminoethyl N-phenyl amine derivative as represented by Formula (I-7) is:

(GT-7019)
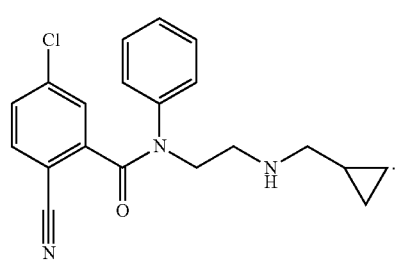

8. The method according to claim 1, wherein said N-aminoethyl N-phenyl amine derivative as represented by Formula (I-7) is:

(GT-7017)
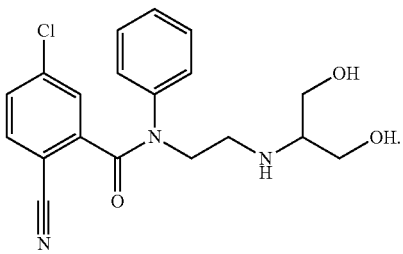

9. The method according to claim 1, said N-aminoethyl N-phenyl amine derivative as represented by Formula (I-7) is:

(GT-7008)
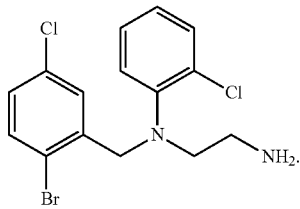

10. The method according to claim 1, said N-aminoethyl N-phenyl amine derivative as represented by Formula (I-7) is:

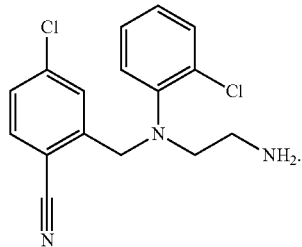

(GT-7004)

11. The method according to claim 1, wherein said N-aminoethyl N-phenyl amine derivative as represented by Formula (I-7) is:

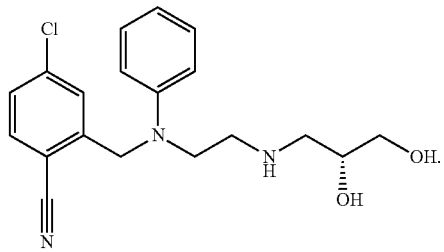

(GT-7016)

12. The method according to claim 1, said N-aminoethyl N-phenyl amine derivative as represented by Formula (I-7) is:

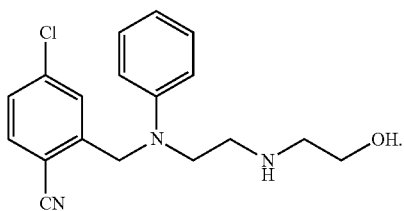

(GT-7010)

13. The method according to claim 1, wherein said N-aminoethyl N-phenyl amine derivative as represented by Formula (I-7) is:

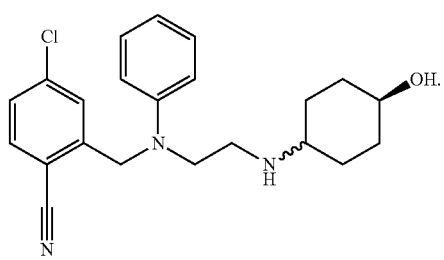

(GT-7023)

14. The method according to claim 1, wherein said N-aminoethyl N-phenyl amine derivative as represented by Formula (I-7) is:

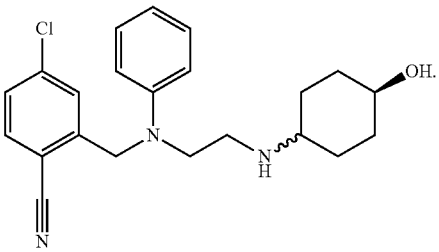

(GT-7024)

15. The method according to claim 1, wherein said N-aminoethyl N-phenyl amine derivative as represented by Formula (I-7) is:

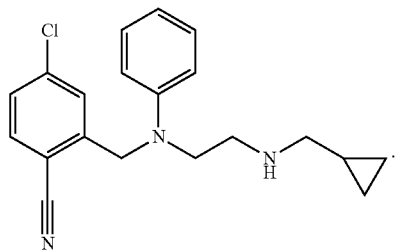

(GT-7020)

16. The method according to claim 1, wherein said N-aminoethyl N-phenyl amine derivative as represented by Formula (I-7) is:

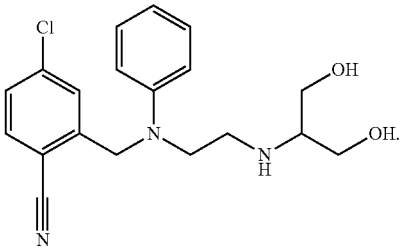

(GT-7018)

17. The method according to claim 1, wherein said N-aminoethyl N-phenyl amine derivative as represented by Formula (I-7) is selected from:

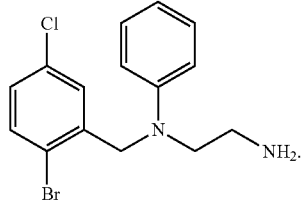

(GT-7006)

18. The method according to claim 1, which is for selectively inhibiting (iNOS) over eNOS and/or nNOS.

19. A method for treatment of a disorder or disease mediated by one or more members in the family of nitric oxide synthases (NOS), comprising administering to a subject in need thereof a therapeutically effective amount of N-aminoethyl N-phenyl amine derivatives as represented by Formula (I-7)

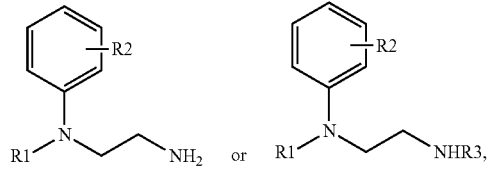

(I-7)

wherein R1 is selected from

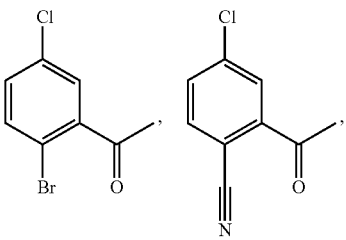

and benzyl substituted with two groups selected from —F, —Cl, —Br, —I and —CN; R2 is —H, —F, —Cl, —Br or —I; and R3 is hydroxyl substituted C1-C6 alkyl, cyclopropyl methyl, or hydroxyl cyclohexyl; or a pharmaceutically acceptable salt, solvate, or hydrate thereof, in any crystalline form or in amorphous form; or a pharmaceutical composition thereof; and wherein the disorder or disease is selected from inflammatory diseases, and proliferative diseases including cancer, wherein the cancer comprises gastro-intestinal, colorectal, gynecological, pancreatic, head and neck, esophageal, breast, lung, and central nervous system tumors.

* * * * *